(12) United States Patent
Waldstreicher et al.

(10) Patent No.: US 11,324,543 B2
(45) Date of Patent: May 10, 2022

(54) METHODS, APPARATUSES, AND SYSTEMS FOR THE TREATMENT OF DISEASES STATES AND DISORDERS

(71) Applicant: Galary, Inc., San Carlos, CA (US)

(72) Inventors: Jonathan Reuben Waldstreicher, West Orange, NJ (US); William Sanford Krimsky, Forest Hill, MD (US); Denise M. Zarins, Saratoga, CA (US); Robert J. Beetel, Sunnyvale, CA (US); Paul Brian Friedrichs, Belmont, CA (US); Kevin James Taylor, San Mateo, CA (US); Roman Turovskiy, San Francisco, CA (US); Robert E. Neal, II, Palo Alto, CA (US)

(73) Assignee: Galvanize Therapeutics, Inc., San Carlos, CA (US)

( * ) Notice: Subject to any disclaimer, the term of this patent is extended or adjusted under 35 U.S.C. 154(b) by 0 days.

(21) Appl. No.: 17/214,688

(22) Filed: Mar. 26, 2021

(65) Prior Publication Data

US 2021/0236816 A1 Aug. 5, 2021

Related U.S. Application Data

(63) Continuation of application No. 16/914,072, filed on Jun. 26, 2020, which is a continuation of application No. PCT/US2018/067501, filed on Dec. 26, 2018.
(Continued)

(51) Int. Cl.
*A61N 1/362* (2006.01)
*A61B 18/12* (2006.01)
(Continued)

(52) U.S. Cl.
CPC ............ *A61B 18/1206* (2013.01); *A61N 1/06* (2013.01); *A61B 1/2676* (2013.01);
(Continued)

(58) Field of Classification Search
CPC .......................... A61N 1/36002; A61N 1/326
See application file for complete search history.

(56) References Cited

U.S. PATENT DOCUMENTS

| 6,038,478 A * | 3/2000 | Yuen ...................... A61N 1/326 128/898 |
| 6,733,485 B1 * | 5/2004 | Whitehurst ......... A61M 31/002 604/20 |

(Continued)

FOREIGN PATENT DOCUMENTS

| EP | 2736432 B1 | 3/2016 |
| EP | 2661236 B1 | 8/2016 |
| WO | WO-2019133606 A1 | 7/2019 |

OTHER PUBLICATIONS

A. Valipour et Al. Bronchial Rheoplasty Treatment for Chronic Bronchitis Using the Rheox System, 2020 American Thoracic Society, Abstract, Aug. 5, 2020.
(Continued)

*Primary Examiner* — George R Evanisko
(74) *Attorney, Agent, or Firm* — Wilson Sonsini Goodrich & Rosati

(57) ABSTRACT

Apparatuses, systems and methods are provided for treating pulmonary tissues via delivery of energy, generally characterized by high voltage pulses, to target tissue using a pulmonary tissue modification system (e.g., an energy delivery catheter system). Example pulmonary tissues include, without limitation, the epithelium (the goblet cells, ciliated pseudostratified columnar epithelial cells, and basal cells), lamina propria, submucosa, submucosal glands, basement membrane, smooth muscle, cartilage, nerves, pathogens
(Continued)

resident near or within the tissue, or a combination of any of these. The system may be used to treat a variety of pulmonary diseases or disorders such as or associated with COPD (e.g., chronic bronchitis, emphysema), asthma, interstitial pulmonary fibrosis, cystic fibrosis, bronchiectasis, primary ciliary dyskinesia (PCD), acute bronchitis and/or other pulmonary diseases or disorders.

11 Claims, 59 Drawing Sheets

Related U.S. Application Data

(60) Provisional application No. 62/610,430, filed on Dec. 26, 2017.

(51) Int. Cl.
| | | |
|---|---|---|
| *A61N 1/06* | (2006.01) | |
| *A61B 1/267* | (2006.01) | |
| *A61B 18/14* | (2006.01) | |
| *A61N 1/32* | (2006.01) | |
| *A61B 18/00* | (2006.01) | |

(52) U.S. Cl.
CPC ............... *A61B 18/1492* (2013.01); *A61B 2018/0022* (2013.01); *A61B 2018/00351* (2013.01); *A61B 2018/00541* (2013.01); *A61N 1/326* (2013.01); *A61N 1/362* (2013.01)

(56) References Cited

U.S. PATENT DOCUMENTS

| | | | |
|---|---|---|---|
| 9,125,666 B2 | 9/2015 | Steinke et al. | |
| 10,702,337 B2 | 7/2020 | Waldstreicher et al. | |
| 2002/0103483 A1* | 8/2002 | Edwards | A61B 18/1477 606/41 |
| 2002/0115991 A1* | 8/2002 | Edwards | A61B 18/148 606/41 |
| 2005/0222646 A1* | 10/2005 | Kroll | A61N 1/326 607/72 |
| 2008/0319372 A1* | 12/2008 | Palti | A61N 1/326 604/20 |
| 2011/0152855 A1 | 6/2011 | Mayse et al. | |
| 2012/0220998 A1 | 8/2012 | Long et al. | |
| 2015/0045788 A1 | 2/2015 | Litscher et al. | |
| 2015/0119879 A1 | 4/2015 | Jameson et al. | |
| 2015/0289923 A1 | 10/2015 | Davalos et al. | |
| 2015/0342669 A1 | 12/2015 | Flanagan et al. | |
| 2016/0000499 A1 | 1/2016 | Lennox et al. | |
| 2016/0128767 A1 | 5/2016 | Azamian et al. | |
| 2017/0215939 A1 | 8/2017 | Palti et al. | |
| 2018/0221078 A1 | 8/2018 | Howard et al. | |
| 2018/0344378 A1 | 12/2018 | Wolf et al. | |
| 2021/0146126 A1 | 5/2021 | Jonathan et al. | |

OTHER PUBLICATIONS

A. Valipour, et Al.*First-in-Human Results of Bronchial Rheoplasty: An Endobronchial Treatment for Chronic Bronchitis (CB)*, Epidemiology and Therapy, Mini Symposium, May 22, 2019, Abstract.
Arschang Valipour et al.*Bronchial Rheoplasty for Treatment of Chronic Bronchitis*, American Journal of Respritoryand Critical Care Medicine, vol. 202, No. 5, Sep. 1, 2020, pp. 681-689.
Arschang Valipour et al. Bronchial Rheoplasty for Treatment of Chronic Bronchitis. Twelve-Month Results from a Multicenter Clinical Trial, American Journal of Respiratory and Critical Care Medicine, vol. 202, Issue 5, 2019.
Arschang Valipour, et al. Late Breaking Abstract—Bronchial Rheoplasty for Treatment of Chronic Bronchitis: 6 Month Results from a Prospective Multi-Center Study, Abstract, European Respiratory Journal2019, pp. 1-5.
EP18845335.1 Office Action dated Jun. 8, 2021.
International Preliminary Report on Patentability for PCT/US2018/067501 dated Jun. 30, 2020.
Pallav L Shah, et al. *Epithelial Resurfacing: The Bronchial Skin Peel*, American Thoracic Society, May 22, 2020, pp. 1-8.
PCT/US2018/067501 International Search Report and Written Opinion dated Mar. 13, 2019.
S. Fernandez-Bussy, et Al.*Histopathologic Results Post Bronchial Rheoplasty*, Epidemiology and Therapy, Mini Symposium, May 22, 2019, Abstract.
V. Kim et al.*Bronchial Rheoplasty Increases Distal Airway Volume in Chronic Bronchitis*, European Respiratory Journal 2019, vol. 54, Suppl. 63, PA2040 Abstract.
Valipour, A., Ing, A., Williamson, J., et al. *Late BreakingAbstract— First-in-Human Results of Bronchial Rheoplasty: An EndobronchialTreatment for Chronic Bronchitis (CB)* .European Respiratory Journal 2018 52: Suppl. 62, OA2162.
U.S. Appl. No. 16/914,072 Office Action dated Nov. 26, 2021.

\* cited by examiner

Example:
Larger Cell Targets  $\lambda = 1\,\mu s$ $f = 250$ kHz $f = 1$ MHz

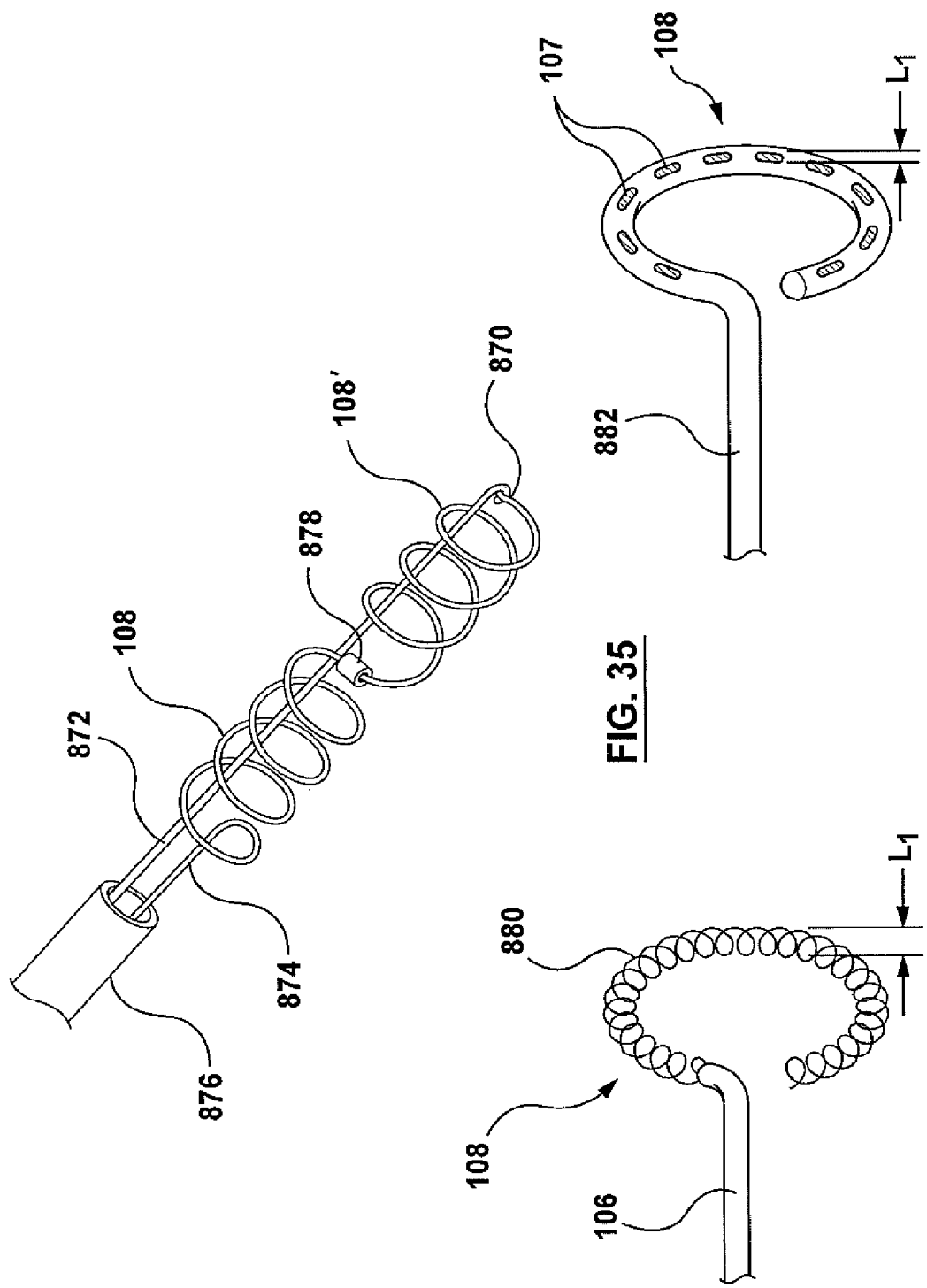

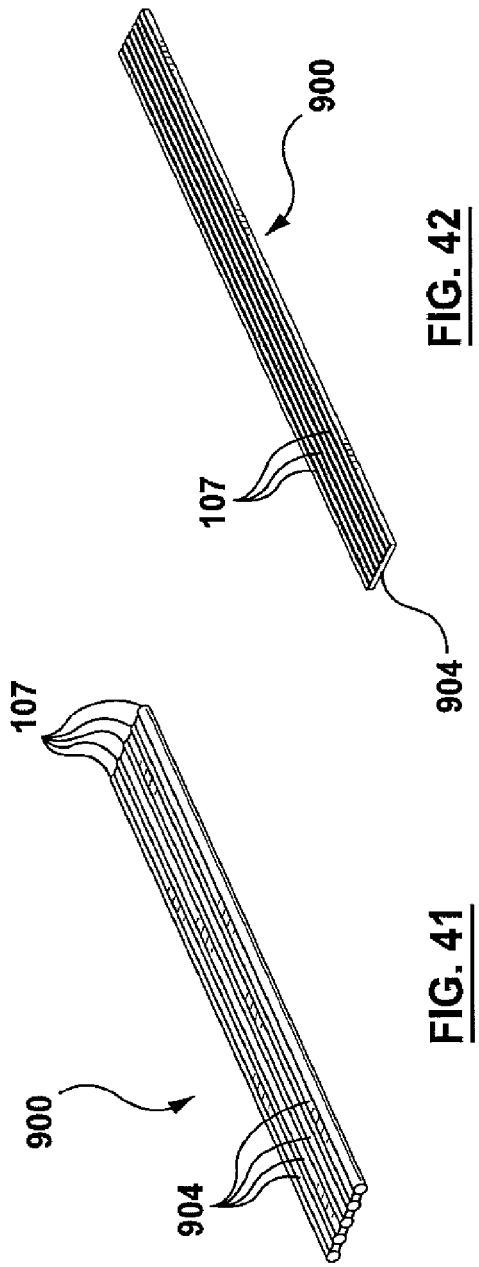
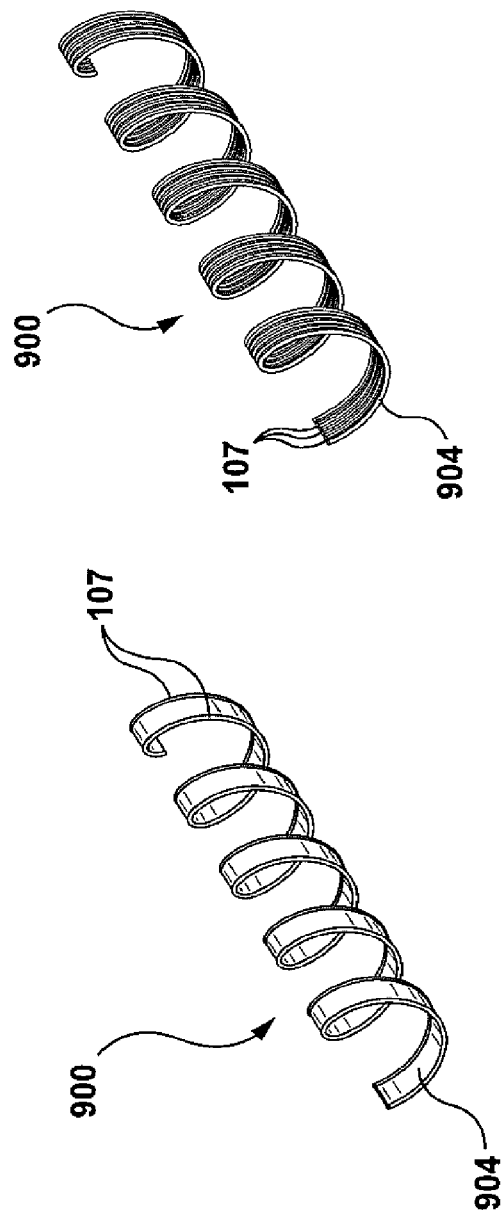

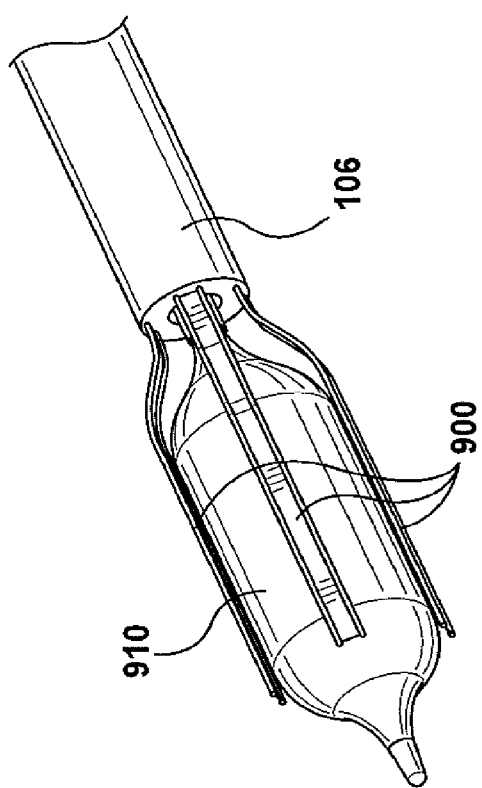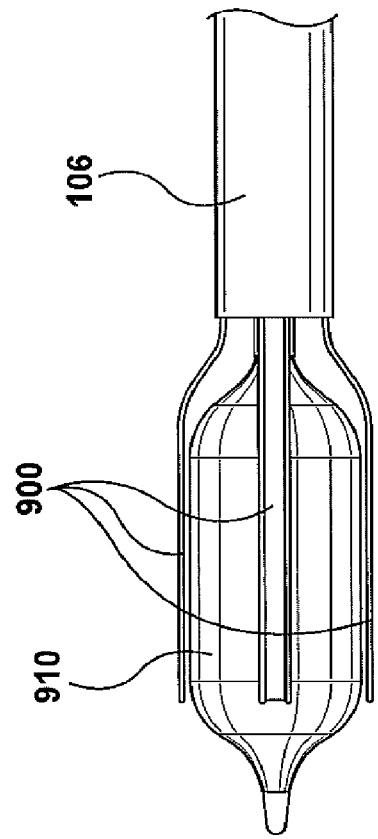
FIG. 45A
FIG. 45B

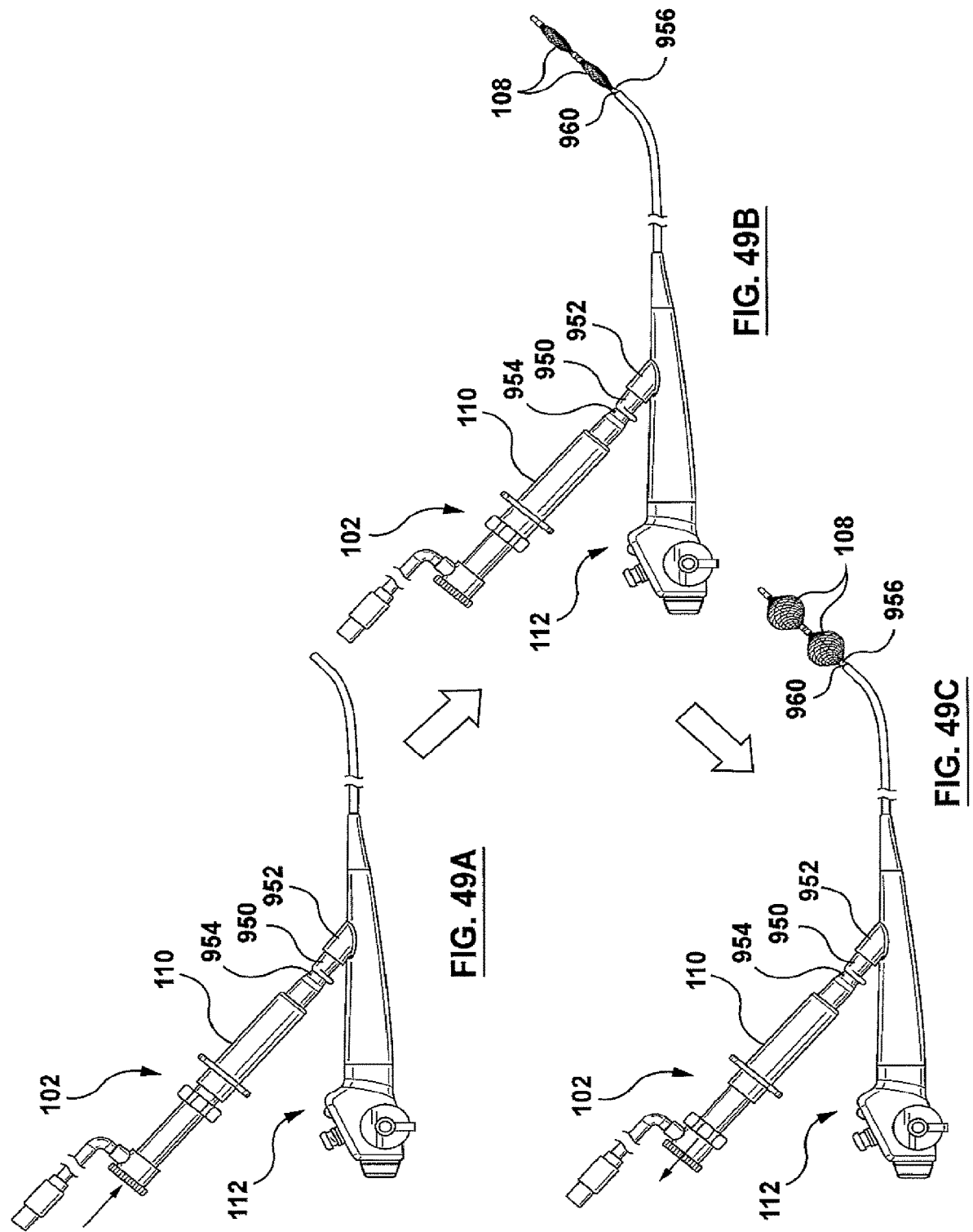

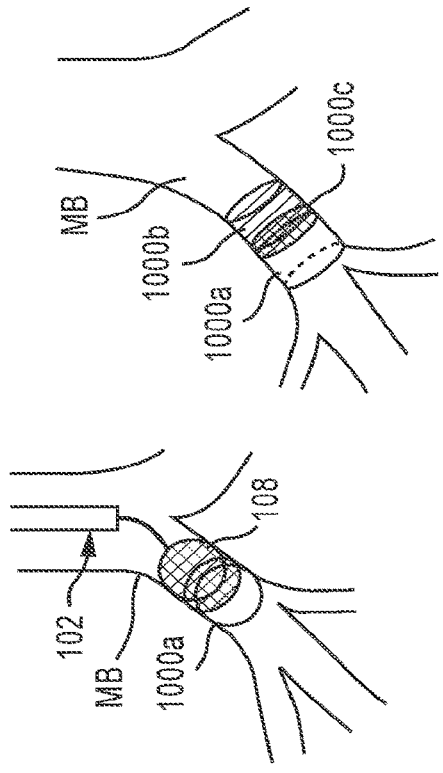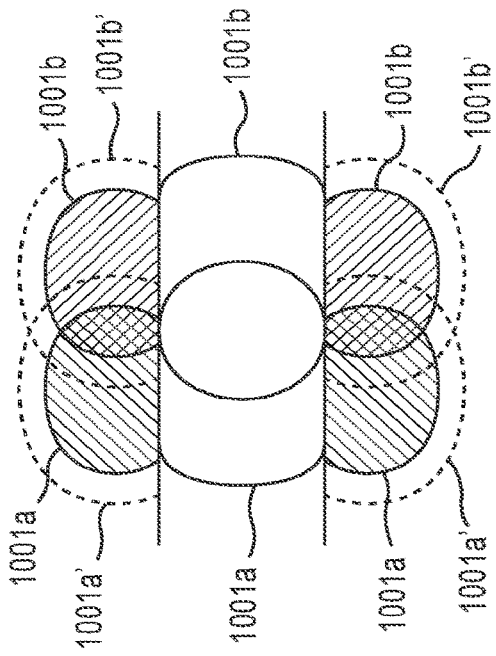

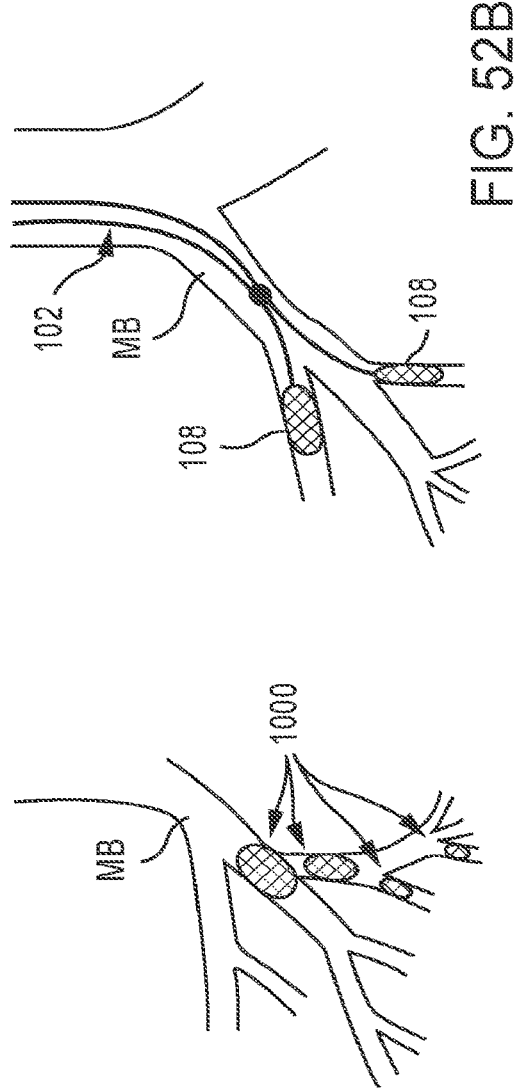
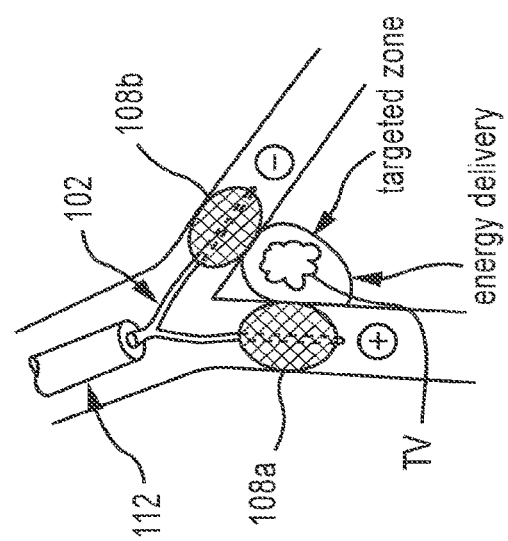
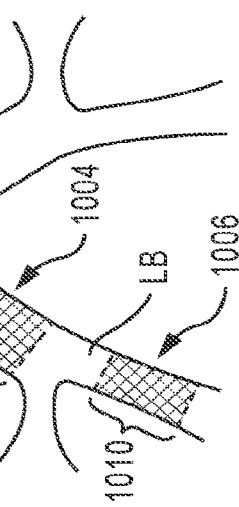
FIG. 52B
FIG. 52C
FIG. 52A
FIG. 52

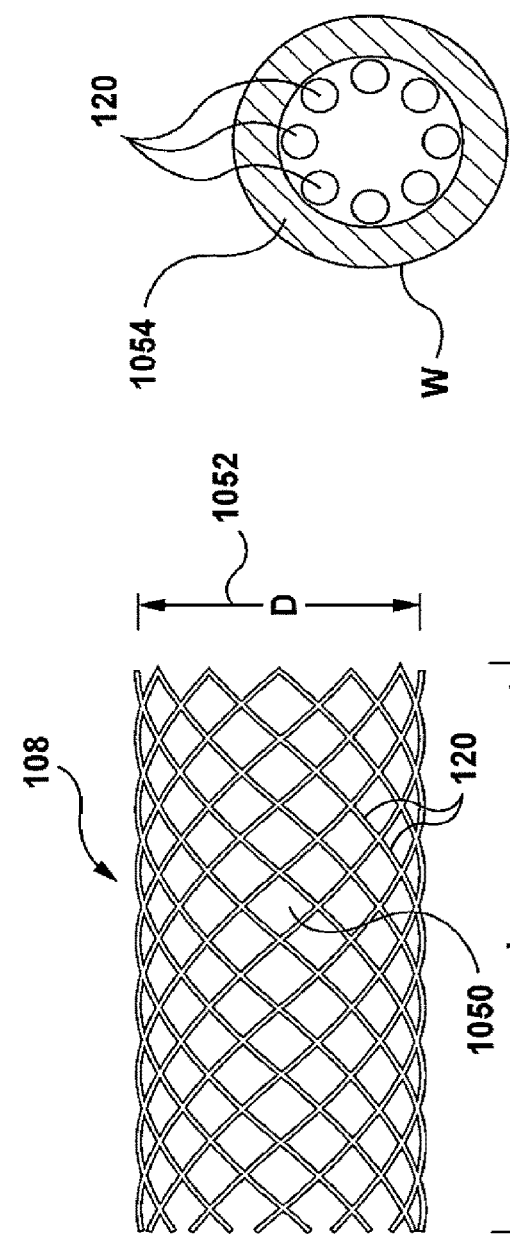
FIG. 53A
FIG. 53B
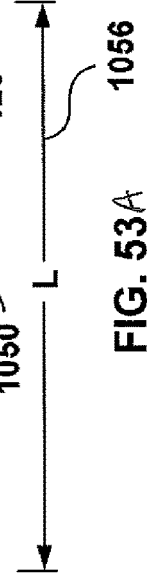
FIG. 54
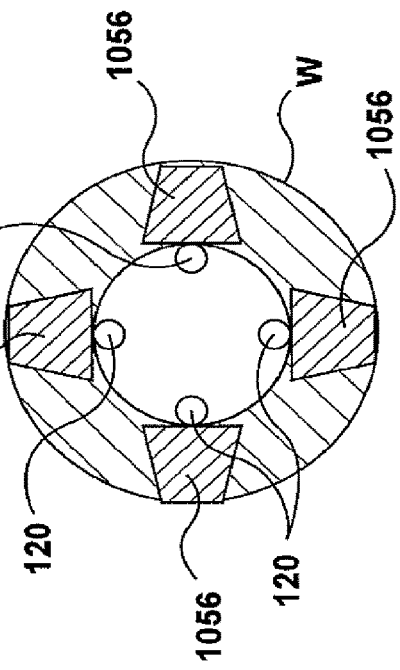
FIG. 55

METHODS, APPARATUSES, AND SYSTEMS FOR THE TREATMENT OF DISEASES STATES AND DISORDERS

CROSS-REFERENCE TO RELATED APPLICATIONS

This application is a continuation of U.S. patent application Ser. No. 16/914,072, filed Jun. 25, 2020, which is continuation of PCT No. PCT/US2018/067501, filed Dec. 26, 2018, which claims priority to U.S. Provisional Patent Application No. 62/610,430, filed Dec. 26, 2017, the entire content of which are incorporated herein by reference for all purposes.

BACKGROUND

I. Anatomy

FIG. 1 provides an illustration of the pulmonary anatomy. Air travels down the trachea T and into the lungs L where the trachea T branches into a plurality of airways that extend throughout the lungs L. The trachea T first bifurcates into the right and left mainstem bronchi MB at the carina CA. These main bronchi MB further divide into the lobar bronchi LB, segmental bronchi SB, sub-segmental bronchi SSB, and terminate with the alveoli A. The diameters of the airways decrease as they bifurcate. The trachea T can have a luminal diameter ranging from about 15 mm to 22 mm, the mainstem bronchi MB can have a luminal diameter ranging from about 12 mm to 16 mm, the lobar bronchi LB can have a luminal diameter ranging from about 9 mm to 12 mm, and the diameter of subsequent bronchi continue to become smaller. The length of the airway also varies with each segment. In some patients, the trachea T has a length of about 12 cm, the mainstem bronchi MB has a length of about 4.8 cm, the lobar bronchi LB has a length of about 1.9 cm, and the length of subsequent bronchi continue to become shorter. In addition, the airway walls become thinner and have less supporting structure as they move more distally into the lung tissue.

The airways of the lung L are comprised of various layers, each with one or several types of cells. FIG. 2 illustrates a cross-sectional view representative of an airway wall W having a variety of layers and structures. The inner-most cellular layer of the airway wall W is the epithelium or epithelial layer E which includes pseudostratified columnar epithelial cells PCEC, goblet cells GC and basal cells BC. Goblet cells GC are responsible for the secretion of mucus M, which lines the inner wall of the airways forming a mucus blanket. The pseudostratified columnar epithelial cells PCEC include cilia C which extend into the mucus blanket. Cilia C that are attached to the epithelium E beat towards the nose and mouth, propelling mucus M up the airway in order for it to be expelled.

The basal cells BC attach to the basement membrane BM, and beneath the basement membrane BM resides the submucosal layer or lamina propria LP. The lamina propria LP includes a variety of different types of cells and tissue, such as smooth muscle SM. Smooth muscle is responsible for bronchoconstriction and bronchodilation. The lamina propria LP also include submucosal glands SG. Submucosal glands SG are responsible for much of the inflammatory response to pathogens and foreign material. Likewise, nerves N are present. Nerve branches of the vagus nerve are found on the outside of the airway walls or travel within the airway walls and innervate the mucus glands and airway smooth muscle, connective tissue, and various cell types including fibroblasts, lymphocytes, mast cells, in addition to many others. And finally, beneath the lamina propria LP resides the cartilaginous layer CL.

FIG. 3 provides a cross-sectional illustration of the epithelium E of an airway wall W showing types of cellular connections within the airway. Pseudostratified columnar epithelial cells PCEC and goblet cells GC are connected to each other by tight junctions TJ and adherens junctions AJ. The pseudostratified columnar epithelial cells PCEC and goblet cells GC are connected to the basal cells BC by desmosomes D. And, the basal cells BC are connected to the basement membrane BM by hemidesmosomes H.

II. Pulmonary Disorders

FIGS. 4A-4B depict bronchial airways B in healthy and diseased states, respectively. FIG. 4A illustrates a bronchial airway B in a healthy state wherein there is a normal amount of mucus M and no inflammation. FIG. 4B illustrates a bronchial airway B in a diseased state, such as chronic obstructive pulmonary disease, particularly chronic bronchitis. Chronic bronchitis is characterized by a persistent airflow obstruction, chronic cough, and sputum production for at least three months per year for two consecutive years. FIG. 4B illustrates both excess mucus M and inflammation I which leads to airway obstruction. The airway inflammation I is consistent with a thickened epithelial layer E.

A variety of pulmonary disorders and diseases lead to airway obstruction. A few of these disorders and diseases will be described briefly herein.

A. Chronic Obstructive Pulmonary Disease (COPD)

Chronic Obstructive Pulmonary Disease (COPD) is a common disease characterized by chronic irreversible airflow obstruction and persistent inflammation as a result of noxious environmental stimuli, such as cigarette smoke or other pollutants. COPD includes a range of diseases with chronic bronchitis and asthma primarily affecting the airways; whereas, emphysema affects the alveoli, the air sacs responsible for gas exchange. Some individuals have characteristics of both.

In chronic bronchitis, the airway structure and function is altered. In chronic bronchitis, noxious stimuli such as cigarette smoke or pollutants are inhaled and recognized as foreign by the airways, initiating an inflammatory cascade. Neutrophils, lymphocytes, macrophages, cytokines and other markers of inflammation are found in the airways of people with prolonged exposure, causing chronic inflammation and airway remodeling. Goblet cells can undergo hyperplasia, in which the cells increase in number, or hypertrophy, in which the goblet cells increase in size. Overall, the goblet cells produce more mucus as a response to the inflammatory stimulus and to remove the inhaled toxins. The excess mucus causes further airway luminal narrowing, leading to more obstruction and the potential for mucus plugging at the distal airways. Cilia are damaged by the noxious stimuli, and therefore the excess mucus remains in the airway lumen, obstructing airflow from proximal to distal during inspiration, and from distal to proximal during the expiratory phase. Smooth muscle can become hypertrophic and thicker, causing bronchoconstriction. Submucosal glands can also become hyperplastic and hypertrophic, increasing their mucus output, as well as the overall thickness of the airway wall and, which further constricting the diameter of the lumen. All of these mechanisms together contribute to chronic cough and expectoration of copious mucus. In severe cases of mucus plugging, the plugs prevent airflow to the alveoli, contributing to chronic hypoxia and respiratory acidosis.

In addition to a reduction in the luminal diameter or complete plugging of the airway, mucus hypersecretion can also lead to an exacerbation, or general worsening of health. As a consequence of the excess mucus and damaged cilia, pathogens such as bacteria (e.g., *Haemophilus influenzae, Streptococcus pneumoniae, Moraxella catarrhalis, Staphylococcus aureus, Pseudomonas aeruginosa, Burkholderia cepacia*, opportunistic gram-negatives, *Mycoplasma pneumoniae*, and *Chlamydia pneumoniae*), viruses (rhinoviruses, influenze/parainfluenza viruses, respiratory syncytial virus, coronaviruses, herpes simplex virus, adenoviruses), and other organisms (e.g., fungi) can flourish, causing an exacerbation, resulting in a set of symptoms. These include worsening cough, congestion, an increase in sputum quantity, a change in sputum quality, and/or shortness of breath. Treatment for an acute exacerbation can include oral or intravenous steroids, antibiotics, oxygen, endotracheal intubation and the need for mechanical ventilation via a ventilator.

B. Asthma

Asthma is a disease of the airways characterized by airway hyper-responsiveness. In asthma, the epithelium can be thickened, mucus hypersecretion can be present as a result of excess production from goblet cells and submucosal glands, and smooth muscle can be thickened. As discussed herein, mucus hypersecretion or excess mucus can allow pathogens to flourish, leading to an infection. In addition, mucus plugging at the distal bronchi and bronchioles can be a direct contributor to asthma exacerbations, increasing their severity by completely blocking airflow to the distal bronchioles and alveoli.

C. Interstitial Pulmonary Fibrosis

Interstitial pulmonary fibrosis is thought to be initiated with acute injury to the lung tissue that leads to chronic and aberrant inflammation. Fibroblasts are activated in response to the inflammation, which causes pulmonary fibrosis, scarring, and worsening lung function. Only 20 to 30% of patients are alive at five years after the diagnosis.

D. Cystic Fibrosis (CF)

Cystic Fibrosis (CF) is a systemic disease with pulmonary manifestations defined by a genetic defect, wherein the Cystic Fibrosis Transmembrane Conductance Regulator (CFTR) gene is mutated, leading to thickened secretions that cannot be expelled. Chronic inflammation leads to airway remodeling and hypersecretion via the goblet cells and submucosal glands, which lead to airway constriction and infections that are difficult to fully resolve.

E. Bronchiectasis

Bronchiectasis is a condition that leads to the airways to dilate, become thickened and scarred. It usually occurs due to an infection or other condition that injures the airway walls, prevents the airway from clearing mucus, or both. With this condition, the airways lose their ability to clear mucus, which can lead to repeated infections. Each infection causes additional damage, eventually leading to moderate airflow obstruction. Bronchiectasis can be caused by genetic disorders such as primary ciliary dyskinesia or can be of idiopathic origin.

III. Pulmonary Treatments

In some instances, the most effective treatment for a pulmonary disorder is a lifestyle change, particularly smoking cessation. This is particularly the case in COPD. However, many patients are unable or unwilling to cease smoking. A variety of treatments are currently available to reduce symptoms of pulmonary disorders.

A. Medication

COPD can be managed with one or several medications, such as Short Acting Beta Agonists (SABAs), Long Acting Beta Agonists (LABAs), Long Acting Muscarinic Antagonists (LAMAs), steroids, chronic antibiotic therapy, or PDE4 inhibitors such as Roflumilast. SABAs and LABAs act on the beta receptor of smooth muscle in the airway to cause bronchodilation. LAMAs act via anticholinergic pathways, inhibiting the release of acetylcholine causing bronchodilation. LABAs and LAMAs have been demonstrated to decrease breathlessness, reduce frequency of exacerbations and improve quality of life but have not been shown to decrease mortality. Tiotropium, a LAMA, can slow the rate of decline of lung function and increase the time until an exacerbation Inhaled corticosteroids directly target inflammation Inhaled corticosteroids have been demonstrated to decrease exacerbations but have little effect on lung function and mortality. Combinations of LABAs, LAMAs and inhaled corticosteroid drugs have been formulated Inhaled oxygen is known to decrease breathlessness and improve mortality but these results are only associated with advanced disease represented by strict criteria and require chronic administration via nasal cannula or alternative apparatuses.

COPD can also be managed with one or several oral medications, such as PDE4 inhibitors, steroids, and antibiotics. Roflumilast is an oral medication that is a selective long acting inhibitor of the enzyme PDE4. It has very strong anti-inflammatory effects but is not well tolerated, with adverse effects including diarrhea, weight loss, nausea, decreased appetite and abdominal pain among others. Oral steroids such as prednisone can be prescribed to a patient in order to treat acute inflammation during an exacerbation. Patients have been known to continue on oral steroids for long periods of time if withdrawal leads to another exacerbation. Oral steroids have many side effects such as weight gain, insomnia, thyroid dysfunction, and osteoporosis, among others. Azithromycin or long term administration of antibiotics has been shown to reduce the frequency of COPD exacerbations. Antibiotics can achieve this via an antimicrobial effect by killing the pathogens responsible for the exacerbation or by other mechanisms such as a reduction in mucus secretion as has been shown with macrolide antibiotics. Side effects of long-term administration of antibiotics include hearing loss and antibiotic resistance.

Oftentimes patients are non-compliant with prescribed respiratory medications Inhaled therapies require deep inspiration as well as synchronization with inspiration, which many patients, especially the elderly, cannot perform. Patients can skip doses secondary to cost, experience side effects, or both. Together, all of these factors contribute to inadequate and inconsistent dosing.

Asthma can range in severity in adults, from mild disease to persistent. Milder disease can be adequately managed with trigger avoidance and Short Acting Beta Agonists (SABAs) whereas the mainstay of therapy for persistent asthma is inhaled glucocorticoids. Regular use of inhaled glucocorticoids has been shown in clinical trials to reduce the need for rescue inhalers, improve lung function, decrease symptoms, and prevent exacerbations. Some patients benefit from the addition of a leukotriene modifying agent or LABA. Tiotropium can be another option to improve lung function, more so than inhaled glucocorticoids alone. Very severe cases can require temporary or long term treatment with oral corticosteroids.

There is no known cure for interstitial pulmonary fibrosis (IPF). The mainstay of treatment is supplemental oxygen when required and preventive measures, such as vaccination. Pirfenidone is an anti-fibrotic agent that is approved for IPF, attempting to slow the fibroblast foci, collagen deposition and inflammatory cell infiltration of the disease. In clinical trials, Pirfenidone has been shown to reduce the decline in vital capacity (a measure of pulmonary function) and demonstrated a reduction in all-cause mortality. Nintedanib is another agent approved for IPF and acts via a receptor blocker for multiple tyrosine kinases that mediate elaboration of fibrogenic growth factors (e.g., platelet-derived growth factor, vascular endothelial growth factor, fibroblast growth factor). It appears to slow the rate of disease progression in IPF. No device therapy is approved for IPF.

Treatment for cystic fibrosis has rapidly evolved from chest physiotherapy and supplemental oxygen to therapies that target the underlying defect in the CFTR gene. Ivacaftor is a CFTR potentiator, improving the transport of chloride through the ion channel, which is FDA approved for several CFTR gene mutations. In clinical trials it has been shown to improve FEV1 and reduce the frequency of exacerbations. It also improves mucociliary and cough clearance. It does not, however, improve outcomes when used alone in patients with the most common delta F508 deletion. Other targeted therapies are in clinical trials. Chronic antibiotics are commonly prescribed for CF, including azithromycin, which likely has anti-inflammatory benefits, and inhaled tobramycin to treat *Pseudomonas aeruginosa*. As with other obstructive diseases, CF patients benefit from bronchodilators including LABAs and LAMAs. Agents to promote airway secretion clearance include inhaled DNase to decrease the viscosity of mucus, inhaled hypertonic saline to draw water from the airway in the mucus, and inhaled N-acetylcysteine that cleaves disulfide bonds within mucus glycoproteins. Guidelines recommend against chronic use of inhaled corticosteroids although oral steroids can be used in cases of exacerbations.

Bronchiectasis is the anatomic manifestation of a host injury response resulting in the excess dilatation of airway luminal caliber and thus therapy is often directed at the cause of the primary disease. These can be non-tuberculous mycobacteria infection, primary immunodeficiencies, allergic bronchopulmonary and aspergillosis among others. Treatment of acute exacerbation is focused on treating the offending bacterial pathogens with antibiotics. Macrolide and non-macrolide antibiotics have been shown to reduce the frequency of exacerbations. The use of inhaled antibiotics in the absence of CF is unclear as are the use of mucolytic agents. Bronchodilators can be used in patients with signs of airway obstruction on spirometry.

Primary Ciliary Dyskinesia (PCD) interventions aim to improve secretion clearance and reduce respiratory infections with daily chest physiotherapy and prompt treatment of respiratory infections. The role of nebulized DNase and other mucolytic drugs is less clear.

Respiratory tract infections caused by pathogens in the airway can occur with any of these maladies, and are typically treated with antibiotics. Unfortunately, drug development in this area is in decline and current therapies have significant limitations. One issue is that there is no one agent capable of treating the spectrum of pathogens found in these patients. While sputum testing can be performed to determine the resident pathogen or pathogens, this sometimes requires that specimens be obtained by bronchoscopy with special techniques to avoid sample contamination that typically effect other methods and modalities of collection.

Another issue is that currently-available medicines are not always effective, due to pathogens developing a resistance to these therapies.

B. Interventional Procedures

More recently, several groups have developed interventional procedures for COPD. Surgical Lung Volume Reduction (LVR) has been proven to be an effective therapy, although the morbidity and mortality rates are high in this frail population. Bronchoscopic Lung Volume Reduction (BLVR) can be achieved by the placement of one-way valves, coils, vapor steam ablation, or by delivering biologic or polymer based tissue glues into target lobes. The physiologic target for LVR/BLVR is emphysema, which specifically addresses the hyperinflation that these patients experience. In several studies, BLVR has been demonstrated to improve pulmonary function and quality of life. Volume reducing therapies are not effective in patients with chronic bronchitis, which is a disease of the airways, not the alveoli.

Another emerging therapy is lung denervation in which the parasympathetic nerves that innervate the airways are ablated, theoretically leading to chronic bronchodilation by disabling the reactive airway smooth muscle. The effect can be similar to the bronchodilator drugs like LABAs and LAMAs, but provide for long-term effect without the typical peaks and troughs seen with medication dosing. Due to only proximal treatment with this modality, it can be limited in effect to the upper airways whereas the higher resistance airways are lower in the respiratory tract.

A variety of thermal ablation approaches have also been described as therapies to treat diseased airways, but all have limitations and challenges associated with controlling the ablation and/or targeting specific cell types. Spray cryotherapy is applied by spraying liquid nitrogen directly onto the bronchial wall with the intent of ablating superficial airway cells and initiating a regenerative effect on the bronchial wall. Since the operator (e.g. physician) is essentially 'spray painting' the wall, coverage, dose and/or depth of treatment can be highly operator dependent without appropriate controllers. This can lead to incomplete treatment with skip areas that were not directly sprayed with nitrogen. Lack of exact depth control can also lead to unintended injury to tissues beyond the therapeutic target such as lamina propria and cartilage, especially since airway wall thickness can vary. Radiofrequency and microwave ablation techniques have also been described wherein energy is delivered to the airway wall in a variety of locations to ablate diseased tissue. Due to uncontrolled thermal conduction, an inability to measure actual tissue temperature to control energy delivery, risk of overlapping treatments, and variable wall thickness of the bronchi, these therapies can cause unintended injury to tissues beyond the therapeutic target, as well. In addition, since they all require repositioning of the catheter for multiple energy applications, incomplete treatment can also occur. All of these thermal ablative technologies non-selectively ablate various layers of the airway wall, often undesirably ablating non-target tissues beyond the epithelium or submucosa. As a consequence of damage to tissues beyond the therapeutic targets of the epithelium, an inflammatory cascade can be triggered, resulting in inflammation, which can lead to an exacerbation, and remodeling. As a result, the airway lumen can be further reduced. Thus, continued improvements in interventional procedures are needed which are more controlled, targeted to specific depths and structures that match the physiologic malady, while limiting the amount of inflammatory response and remodeling.

Asthmatx has previously developed a radiofrequency ablation system to conduct Bronchial Thermoplasty. The operator deploys a catheter in the airways and activates the electrode, generating heat in the airway tissue in order to thermally ablate smooth muscle. Because of the acute inflammation associated with the heat generated in the procedure, many patients experience acute exacerbations. In the AIR2 clinical study, patients did not experience a clinically significant improvement in the Asthma Quality of Life Questionnaire at 12 months as compared to a sham group. However, the treatment group had fewer exacerbations and a decrease in emergency room visits. The FDA approved the procedure, but it is not commonly used due to the side effects and the designation by insurers as an investigational procedure.

There is hence an unmet need for interventional procedures which are more controlled, targeted to specific structures and/or pathogens that match the pathophysiologic aberrancy or aberrancies, able to treat relatively large surface areas at the appropriate depth, and limit the amount of inflammatory response and remodeling. Embodiments of the present disclosure meet at least some of these objectives.

SUMMARY

Described herein are embodiments of apparatuses, systems and methods for treating or manipulating tissues and/or treating diseases or disorders, particularly those related to pulmonary disease and disorders such as or associated with COPD (e.g., chronic bronchitis, emphysema), asthma, interstitial pulmonary fibrosis, cystic fibrosis, bronchiectasis, primary ciliary dyskinesia (PCD), acute bronchitis and/or other pulmonary diseases or disorders, wherein one or more features from any of these embodiments can be combined with one or more features from one or more other embodiments to form a new embodiment within the scope of this disclosure. Example pulmonary tissues include, without limitation, the epithelium (the goblet cells, ciliated pseudostratified columnar epithelial cells, and basal cells), lamina propria, submucosa, submucosal glands, basement membrane, smooth muscle, cartilage, nerves, pathogens resident near or within the tissue, or a combination of any or all of the foregoing. Other treatable body passageways include a blood vessel, a lymphatic vessel, a bile duct, a kidney tubule, an esophagus, a stomach, a small intestine, a large intestine, an appendix, a rectum, a bladder, a ureter, a pharynx, a mouth, a vagina, a urethra, or a duct of a gland, to name a few.

The methods, apparatuses, and systems disclosed herein can treat tissues via delivery of energy, generally characterized by high voltage pulses, to target tissue using a tissue modification system (e.g., an energy delivery catheter system). In some embodiments, the nature of the energy delivery allows for removal of target tissue without a clinically significant inflammatory healing response, while in other embodiments, some inflammatory healing response is considered acceptable. This further allows for regeneration of healthy new target tissue within days of the procedure.

The disclosure also relates to following numbered clauses:

1. A system for treating a body lumen having at least one side branch comprising:
a catheter comprising a shaft having a proximal end, a distal end and at least one energy delivery body disposed near its distal end, wherein the distal end is configured to be advanced into the body lumen near the at least one side branch; and
a generator in electrical communication with the at least one energy delivery body, wherein the generator includes at least one energy delivery algorithm configured to provide an electric signal of non-thermal energy transmittable by the at least one energy delivery body to a wall of the body lumen which treats particular cells up to a depth of 2.5 cm within the wall.

2. A system as in claim 1, wherein the distal end of the shaft comprises a Y shape having a first arm configured to be advanced into the body lumen and a second arm configured to be advanced into one of the at least one side branches, and wherein the at least one energy delivery comprises a first energy delivery body disposed on the first arm of the Y shape and a second energy delivery disposed on the second arm of the Y shape.

3. A system as in claim 2, wherein the first energy delivery body and the second energy delivery body function as a bipolar pair.

4. A system as in any of claims 1-3, wherein the shaft has a pre-bend configured to direct the distal end into the at least one side branch.

5. A system as in any of the above claims, further comprising a delivery device having at least one lumen for passage of at least the catheter therethrough.

6. A system as in claim 5, further comprising a second catheter configured for passage within the at least one lumen of the delivery device, wherein the second catheter has at least one energy delivery body disposed near its distal end, and wherein the system is configured to allow positioning of the at least one energy delivery body of the catheter into the body lumen while allowing positioning of the at least one energy body of the second catheter into one of the at least one side branch.

7. A system as in any of the above claims, wherein the at least one energy delivery body includes at least one penetrating element configured to extend into the wall and deliver energy thereto.

8. A system as in any of the above claims, wherein the at least one energy delivery body comprises an inflatable member configured to expand within the body lumen covering and extending at least partially into the at least one side branch.

9. A system as in claim 8, wherein the inflatable member comprises at least one finger-like projection configured to extend into the at least one side branch.

10. A system as claim 8, wherein the catheter further comprises an internal lumen within the shaft, and wherein the inflatable member has an elongate balloon shape which is attached to the distal end of the catheter so that the inflatable member is positionable within the internal lumen of the shaft.

11. A system as in claim 10, wherein the inflatable member has an interior surface, and wherein the inflatable member is positionable within the internal lumen so that the interior surface of the inflatable member faces a surface of the internal lumen.

12. A system as in claim 8, wherein the inflatable member comprises at least one electrode trace.

13. A system as in claim 12, wherein the at least one electrode trace includes at least two activation points which function in a bipolar manner or in a multipolar manner in combination with a dispersive external electrode.

14. A system as in claim 1, wherein the at least one energy delivery body comprises an inflatable member configured to expand within the body lumen covering the at least one side branch, wherein the at least one energy delivery body includes a first set of electrodes having a first center spine which extends longitudinally along the inflatable member and a first series of ribs wherein each of the first series of ribs extends at least partially around a circumference of the inflatable member.

15. A system as in claim 14, wherein the at least one energy delivery body includes a second set of electrodes having a second center spine which extends longitudinally along the inflatable member and a second series of ribs wherein each of the second series of ribs extends at least partially around a circumference of the inflatable member.

16. A system as in claim 15, wherein the each of the first series of ribs interlaces with each of the second series of ribs.

17. A system as in claim 16, wherein the first and second series of ribs have opposite polarities.

18. A system as in claim 15, wherein the first set of electrodes and the second set of electrodes generate overlapping treatment zones along the body lumen.

19. A system as in any of the above claims, further comprising a liquid electrode positionable within the body lumen so as to extend into the at least one side branch.

20. A system as in claim 19, wherein the liquid electrode comprises a conductive solution.

21. A system for treating a body passageway of a patient, the system comprising:
a catheter comprising at least one electrode disposed near its distal end, wherein the distal end of the catheter is configured to be positioned within the body passageway so that the at least one electrode is able to transmit energy to a wall of the lung passageway; and
a generator in electrical communication with the at least one electrode, wherein the generator includes at least one energy delivery algorithm configured to provide an electric signal of the energy transmittable to the wall which selectively treats particular cells at least on a surface of the wall, wherein the electric signal comprises biphasic pulses.

22. A system as in claim 21, wherein the electric signal comprises a frequency and a voltage, and wherein an effect of the frequency inversely balances an effect of the voltage so as to target the particular cells.

23. A system as in any of claims 21-22, wherein the biphasic pulses have identical duration and voltage.

24. A system as in any of claims 21-22, wherein at least two of the biphasic pulses have different voltages.

25. A system as in any of claims 21-22, wherein at least two of the biphasic pulses have different durations.

26. A system as in any of claims 21-25, wherein at least some of the biphasic pulses are separated by a dead time so as to reduce biphasic cancellation.

27. A system as in any of any of claims 21-26, wherein the particular cells comprise actionable contracting cells.

28. A system as in claim 27, wherein the actionable contracting cells comprise smooth muscle cells.

29. A system as in any of claims 21-28, wherein each of the biphasic pulses has a voltage between approximately 100 V to 10 kV.

30. A system as in claim 29, wherein each of the biphasic pulses has a voltage between approximately 500-4000 V.

31. A system as in any of claims 21-30, wherein the electric signal has a frequency in the range of approximately 100-1000 kHz.

32. A system for providing therapy to a body passageway of a patient, the system comprising:
at least one energy delivery body positionable within the body passageway and configured to deliver energy to a wall of the body passageway;
at least one sensor positionable on or within the patient, wherein the at least one sensor is configured to receive sensed information from the patient; and
a generator having at least one energy delivery algorithm configured to provide electric signals of the energy to the at least one energy delivery body, wherein the electric signals includes a test signal configured to generate the sensed information and a therapeutic electrical signal configured to provide therapy to the body passageway.

33. A system as in claim 32, wherein the at least one energy delivery algorithm comprises an energy delivery algorithm that generates the therapeutic electrical signal based on the sensed information.

34. A system as in claim 32, wherein the sensed information indicates that the at least one energy delivery body is desirably positioned within the body passageway.

35. A system as in claim 32, wherein the sensed information indicates that the therapeutic electrical signal configured to provide the therapy to the body passageway corresponds to a desired therapeutic electrical signal.

36. A system as in claim 35, wherein the at least one energy delivery algorithm is configured to withhold the therapeutic electrical signal unless the sensed information indicates that the therapeutic electrical signal corresponds to the desired therapeutic electrical signal.

37. A system as in any of claims 32-36, wherein the at least one sensor is disposed on or is part of the at least one energy delivery body.

38. A system as in any of claims 32-36, wherein the at least one sensor is disposed on or is part of a dispersive electrode.

39. A system as in any of claims 32-38, wherein the test signal has a lower voltage than the therapeutic electric signal.

40. A system as in any of claims 32-39, wherein the at least one energy delivery algorithm is configured to deliver the test signal before the therapeutic electric signal is delivered.

41. A system as in claim 40, wherein the at least one energy delivery algorithm is configured to deliver the test signal at least one heartbeat before the therapeutic electric signal is delivered.

42. A system as in claim 40, wherein the at least one energy delivery algorithm is configured to deliver the test signal 500 ms before the therapeutic electric signal is delivered.

43. A system as in any of claims 32-42, wherein the test signal comprises a brief pulse having a duration of 1 us, 100 us, 1 ms or 100 ms.

44. A system as in any of claims 32-43, wherein the test signal comprises a continuous low voltage waveform having a voltage of 0.5V, 1V, 5V, 10V, 50V or 500V.

45. A system as in any of claims 32-44, wherein the sensed information comprises impedance.

46. A system as in claim 45, wherein the at least one energy delivery algorithm is configured to withhold the therapeutic electrical signal if the sensed information indicates an impedance measurement of >200?.

47. A system as in any of claims 32-46, wherein the sensed information comprises temperature.

48. A system for treating a lumen in a body comprising:
at least one energy delivery body positionable within the lumen and configured to deliver energy to a wall of the lumen; and
a generator having at least one energy delivery algorithm configured to provide an electric signal of the energy to the at least one energy delivery body, wherein the electric signal selectively targets particular cells of the lumen while avoiding collateral cells.

49. A system as in claim 48, wherein the electric signal selectively targets the particular cells based at least on its frequency.

50. A system as in any of claim 49, wherein the frequency is in the range of 400-800 kHz.

51. A system as in claim 48, wherein the particular cells are targeted based on their size.

52. A system as in claim 51, wherein the particular cells have a diameter of greater than or equal to 15 µm.

53. A system as in claim 48, wherein the lumen comprises an airway and wherein the particular cells comprise cells involved in mucus hypersecretion.

54. A system as in claim 52, wherein the particular cells comprise goblet cells, dysfunctional pseudostratified columnar epithelial cells and/or submucosal glands.

55. A system as in claim 52, wherein the collateral cells comprise basal cells and/or chondrocytes.

56. A system as in claim 48, wherein the particular cells are targeted based on their location within the wall of the lumen.

57. A system as in claim 56, wherein the electric signal selectively targets the particular cells based on the number of packets delivered.

58. A system as in claim 57, wherein the particular cells are on or near a surface of the lumen and the number of packets delivered is up to 5 packets.

59. A system as in claim 48, wherein the lumen comprises an airway where the particular cells comprise goblet cells and/or submucosal glands and the collateral cells comprise chondrocytes, wherein the electric signal has a frequency of 600 kHz, a packet duration of 100 us, a voltage of 2500-3000V and one to five packets.

60. A system as in claim 48, wherein the lumen comprises a blood lumen, and wherein the particular cells comprise cardiomyocytes and the collateral cells comprise cells in the sinoatrial node or atrioventricular node that generate normal heart rhythms.

61. A system as in claim 48, wherein the particular cells comprise precancerous cells or cancerous cells and the collateral cells comprise noncancerous cells.

62. A method for treating one or more target cells of a cellular lining of a body passageway comprising:
conditioning the one or more target cells; and
transmitting energy to a surface of the cellular lining so as to treat the one or more target cells for a duration that is below a threshold for thermal ablation of the one or more target cells and that treats the one or more target cells up to and not beyond a depth of 2.5 cm from the surface of the cellular lining.

63. A method as in claim 62, wherein conditioning comprises delivering a conditioning solution.

64. A method as in claim 63, wherein the conditioning solution comprises a drug, genetic material, a bioactive compound, or an antimicrobial agent.

65. A method as in any of claims 63-64, wherein the conditioning solution comprises a cell.

66. A method as in claim 65, wherein the cell comprises a stem cell, an autograft cell, or an allograft cell.

67. A method as in claim 65, wherein the cell is of a type suitable to repopulate the cellular lining with desirable cells.

68. A method as in claim 67, further comprising washing or mechanically stimulating the cellular lining of the body passageway prior to the conditioning step.

69. A method as in any of claims 63-68, further comprising warming the conditioning solution prior to delivering.

70. A method as in any of claims 63-68, further comprising chilling the conditioning solution prior to delivering.

71. A method as in any of claims 62-70, wherein conditioning comprises delivering a conditioning therapy that increases the likelihood of the one or more target cells to expire after receiving the energy.

72. A method as in claim 71, wherein the conditioning therapy comprises a conditioning solution comprising a chemotherapy drug, calcium, an antibiotic, or a toxin.

73. A method as in any of claims 62-72, wherein conditioning comprises delivering a conditioning therapy that alters a response from non-targeted cells to the energy.

74. A method as in claim 73, wherein the conditioning therapy comprises a conditioning solution comprising a cytokine, an immunostimulant, an interleukin, a gene, VEGF, or a cellular differentiating factor.

75. A method as in any of claims 62-74, wherein conditioning comprises delivering a conditioning therapy that selectively alters an electrical property of one or more target cells.

76. A method as in claim 62, wherein conditioning comprises delivering a conditioning therapy, wherein the conditioning therapy includes radiation therapy, radiotherapy, or proton beam therapy.

77. A method as in any of claims 62-76, wherein the conditioning step invokes a targeted immune response.

78. A method as in any of claims 62-77, further comprising advancing an energy delivery catheter into the body passageway, wherein the energy delivery catheter comprises at least one energy delivery body configured to provide the transmitting step.

79. A method as in claim 78, wherein the energy delivery catheter includes at least one port, and wherein the conditioning step comprises delivering a conditioning solution through the at least one port, wherein the conditioning solution provides the conditioning step.

80. A method as in claim 79, wherein delivering the conditioning solution comprises delivering a predetermined volume of the conditioning solution.

81. A system for reducing hypersecretion of mucus in a lung passageway of a patient, the system comprising:
a catheter comprising at least one electrode disposed near its distal end, wherein the distal end of the catheter is configured to be positioned within a lung passageway so that the at least one electrode is able to transmit non-thermal energy to an airway wall of the lung passageway; and
a generator in electrical communication with the at least one electrode, wherein the generator includes at least one energy delivery algorithm configured to provide an electric signal of the non-thermal energy transmittable to the airway wall which selectively treats particular cells associated with hypersecretion of mucus within the airway wall causing reduced hypersecretion of mucus by the airway wall.

82. A system as in claim 81, wherein selectively treats comprises altering organelle and cellular transmembrane potential.

83. A system as in claim 81, wherein selectively treats comprises increasing organelle and cellular membrane permeability.

84. A system as in claim 81, wherein selectively treats comprises removing the particular cells.

85. A system as in claim 84, wherein removing comprises immune cell phagocytosis.

86. A system as in claim 84, wherein selectively treats comprises removing by cell death caused by apoptosis.

87. A system as in claim 84, wherein selectively treats comprises removing by cell death caused by necrosis.

88. A system as in claim 84, wherein selectively treats comprises removing by cell death caused by immune cell interaction.

89. A system as in claim 81, wherein the particular cells comprise actionable contracting cells.

90. A system as in claim 89, wherein the actionable contracting cells comprise smooth muscle cells.

91. A system as in claim 81, wherein selectively treats comprises selectively mitigates cell contractile ability.

92. A system as in claim 81, wherein the reduced hypersecretion causes the elimination of mucus plugging.

93. A system as in claim 81, wherein the particular cells comprise actionable contracting cells and wherein selectively treats comprises selectively mitigates cell contractile ability which contributes to the elimination of mucus plugging.

94. A system as in claim 81, wherein the non-thermal energy has a frequency selected to inversely balance with a voltage selection causing targeting of a specific cell population.

95. A system as in claim 81, wherein the non-thermal energy has opposing polarity pulses which have identical duration and voltage.

96. A system as in claim 81, wherein the non-thermal energy has opposing polarity pulses which have different voltages.

97. A system as in claim 81, wherein the non-thermal energy has opposing polarity pulses which have different duration.

98. A system as in claim 81, wherein the non-thermal energy has opposing polarity pulses which are separated by a dead time to reduce bipolar cancellation.

99. A system as in claim 81, wherein the non-thermal energy is comprised of pulses, wherein each pulse is between approximately 100 V to 10 kV.

100. A system as in claim 99, wherein each pulse is between approximately 500-4000 V.

101. A system as in claim 81, wherein the non-thermal energy is comprised of at least one energy packet which has a frequency in the range of approximately 100-1000 kHz.

102. A system as in claim 101, where the frequency is selected to inversely balance with a voltage to specifically target different cell populations.

103. A system as in an of claim 81, wherein the non-thermal energy is comprised of pulses, wherein each pulse is the same polarity.

104. A system as in claim 81, wherein the catheter attaches to an accessing device and/or a visualization device.

105. A system as in claim 104, wherein the catheter comprises a mechanism to permit small placement changes including advancement and retraction relative to the accessing and/or visualization device while attached to the accessing and/or visualization device.

106. A system as in claim 81, wherein the catheter comprises at least two protrusions expandable to contact the airway wall of the lung passageway and wherein the at least two protrusions are configured to deploy and contact the airway walls with assistance by an internal dielectric inflatable device.

107. A system as in claim 106, wherein the dielectric inflatable device uses liquid or gas fluids to inflate.

108. A system as in claim 81, wherein the catheter comprises at least two protrusions expandable to contact the airway wall of the lung passageway and wherein the at least two protrusions are configured to deploy and contact the airway walls with assistance by an internal electrically conductive continuous inflatable device.

109. A system as in claim 108, wherein the conductive continuous inflatable device uses liquid or gas fluids to inflate.

110. A system as in claim 81, wherein the generator includes a processor that reduces the voltage, pulse duration, or dead time, or increases packet delivery delays if an impedance decays below an impedance threshold.

111. A system as in claim 110, wherein the impedance is derived from a low-voltage impedance determination, from an alternating current complex impedance, from a sweep of alternating current frequencies and resulting complex impedance, or from impedance derived directly from a therapy pulse delivery energy.

112. A system for treating a body passageway, the system comprising:
a catheter comprising at least one energy delivery body disposed near its distal end, wherein the distal end is configured to be positioned within the body passageway so that the at least one energy delivery body is able to transmit non-thermal energy to a wall of the body passageway; and
a generator in electrical communication with the at least one energy delivery body, wherein the generator includes at least one energy delivery algorithm configured to provide an electric signal of the non-thermal energy transmittable to the body passageway which selectively treats a targeted cell population in the body passageway.

113. A system as in claim 112, wherein the body passageway comprises a blood vessel, a lymphatic vessel, a bile duct, a kidney tubule, an esophagus, a stomach, a small intestine, a large intestine, an appendix, a rectum, a bladder, a ureter, a pharynx, a mouth, a vagina, a urethra, or a duct of a gland.

114. A system as in claim 112, wherein selectively treats comprises altering organelle and cellular transmembrane potential.

115. A system as in claim 112, wherein selectively treats comprises increasing organelle and cellular membrane permeability.

116. A system as in claim 112, wherein selectively treats comprises selectively removes the particular cells from the airway wall.

117. A system as in claim 116, wherein removes comprises cell detachment.

118. A system as in claim 117, wherein cell detachment is achieved by dielectrophoresis.

119. A system as in claim 116, wherein removes comprises cell death.

120. A system as in claim 119, wherein removes comprises immune cell phagocytosis.

121. A system as in claim 119, wherein cell death is caused by apoptosis.

122. A system as in claim 119, wherein cell death is caused by necrosis.

123. A system as in claim 119, wherein cell death is caused by immune cell interaction.

124. A system as in any of claim 112, wherein the cell population comprises epithelial cells and not basal cells.

125. A system as in claim 124, wherein the epithelial cells comprise abnormal or hyperplastic goblet cells.

126. A system as in claim 124, wherein the epithelial cells comprise abnormal ciliated pseudostratified columnar epithelial cells.

127. A system as in claim 112, wherein the cell population comprise cells of a basement membrane, and wherein selectively treats comprises modifying the cells of the basement membrane so as to modify the permeability of the basement membrane.

128. A system as in claim 112, wherein the cell population comprises submucosal glands, and wherein selectively treats comprises causing cell death of the submucosal glands.

129. A system as in any of claim 112, wherein the cell population comprises pathogens, and wherein selectively treats comprises causing cell death of the pathogens.

130. A system as in claim 112, wherein selectively treats comprises selectively modifies the cell population to alter mucus production.

131. A system as in claim 112, wherein cell population comprises actionable contracting cells.

132. A system as in claim 131, wherein actionable contracting cells comprise smooth muscle cells.

133. A system as in claim 112, wherein selectively treats comprises mitigating cell contractile ability.

134. A system as in claim 112, wherein selectively treats allows regeneration of the wall with normative healthy tissue.

135. A method for treating a body passageway of a patient comprising:

positioning at least one electrode within the body passageway so that the at least one electrode is disposed near or against a portion of a wall of the body passageway; and energizing the at least one electrode so as to deliver non-thermal energy to the portion of the wall, wherein the non-thermal energy selectively treats particular cells within the portion of the wall.

136. A method as in claim 135, further comprising administering a physical property-altering solution within the body passageway prior to energizing.

137. A system as in claim 136, wherein the physical property-altering solution comprises a hypertonic saline, isotonic saline, hypotonic saline, or dextrose buffer solution.

138. A system as in claim 135, further comprising administering prior to energizing or following energizing a cell-level bioactive solution comprising hypertonic calcium, a solution with a drug, a solution with a gene, or a solution with other effect-inducing properties on the cells.

139. A system as in claim 135, further comprising administering prior to energizing or following energizing a tissue-level bioactive solution comprising hypertonic calcium, a solution with a drug, a solution with a gene, or a solution with other effect-inducing properties.

140. A system as in claim 135, further comprising systemically administering prior to energizing or following energizing a bioactive solution comprising hypertonic calcium, a solution with a drug, a solution with a gene, or a solution with other effect-inducing properties.

141. A system as in claim 135, further comprising systemically administering prior to energizing or following energizing a tissue-level bioactive solution comprising hypertonic calcium, a solution with a drug, a solution with a gene, solutions with cytokines, or a solution with other effect-inducing properties.

142. A system as in claim 135, further comprising introducing prior to energizing or following energizing at least one cell population comprising stem cells, healthy normal cells, or genetically modified cells.

143. A system as in claim 135, further comprising administering prior to energizing or following energizing a physical property-altering solution comprising hypertonic saline, isotonic saline, hypotonic saline, or dextrose buffer solution.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of embodiments of the present disclosure are set forth with particularity in the appended claims. A better understanding of the features and advantages made possible by some embodiments will be obtained by reference to the following detailed description that sets forth illustrative embodiments, and the accompanying drawings of which:

FIG. 35 illustrates an embodiment of a catheter having two energy delivery bodies, each energy delivery body having the shape of an expandable coil.

FIG. 36 illustrates an embodiment of an energy delivery body comprising a coil having a width and a length, wherein the length of the coil is pre-shaped into a substantially circular pattern.

FIG. 37 illustrates an embodiment of an energy delivery body comprising a rod having electrodes, wherein the length of the rod is pre-shaped into a substantially circular pattern.

FIG. 41 illustrates an embodiment of a prong having yet narrower insulating substrates and greater than two electrodes.

FIG. 42 illustrates a plurality of electrodes mounted on an insulating substrate.

FIG. 43 illustrates the insulating substrate with electrodes as shown in FIGS. 36-37 configured as a helix.

FIG. 44 illustrates the insulating substrate with electrodes as shown in FIG. 38 configured as a helix.

FIGS. 45A-45B illustrate expanding an expandable member until a desired interface between the prongs and bronchial wall is achieved.

FIGS. 49A-49C illustrate introduction of a catheter having two energy delivery bodies through a bronchoscope.

FIGS. 51A-51D illustrate a method of generating two target segments intentionally overlapped, where some overlapped region of tissue will receive the therapy more than once, so as to ensure complete contiguous treatment effects FIGS. 51E-51F illustrate compounding effect intensity of overlapping treatment segments.

FIG. 52 is a schematic illustration of two target zones within a patient.

FIG. 52A illustrates a variety of target segments along various branching lung passageways, including within an ostium and along various smaller branches.

FIG. 52B illustrates treatment of differing lung passageways, such as branching from the same mainstem bronchi.

FIG. 52C illustrates a catheter having a Y-shaped distal end which splits into a first end having a first energy delivery body and a second distal end having a second energy delivery body.

FIG. 53A is a schematic side view illustration of a portion of an energy delivery body comprised of a braided basket.

FIG. 53B is a schematic cross-sectional view of the energy delivery body of FIG. 50 positioned within a lung passageway having an airway wall.

FIG. 54 is a schematic illustration of the effect of continuous full circumference treatment of an airway along a length of the energy delivery body.

FIG. 55 is a schematic illustration of a discontinuous tissue effect in a lung passageway.

FIG. 57A illustrates a section from an untreated airway, FIG. 57B illustrates a section from treated airway.

FIG. 58A illustrates a section of an untreated airway, FIG. 58B illustrates a section of a treated airway.

DETAILED DESCRIPTION

Figure 1:
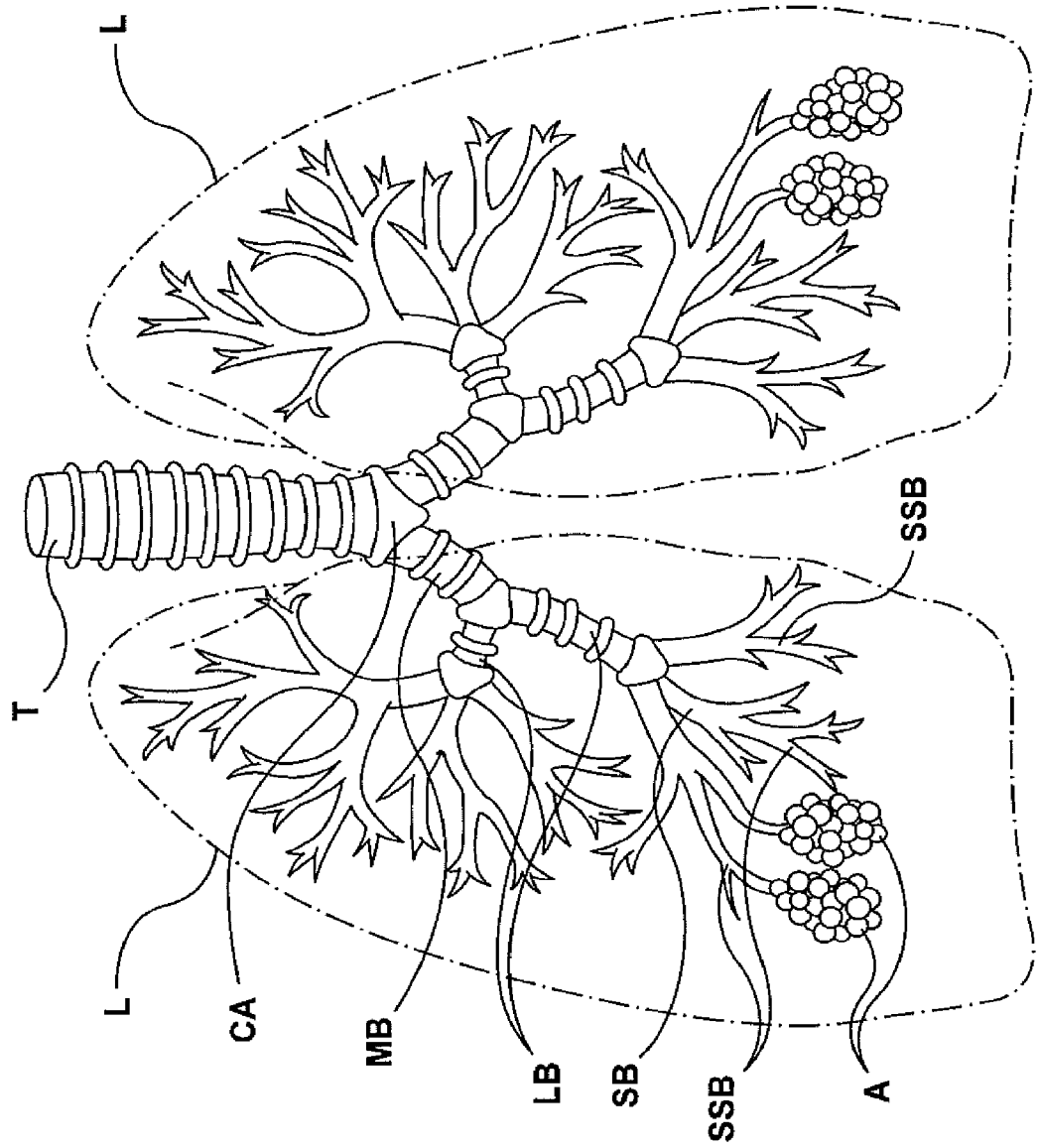
FIG. 1 provides an illustration of the pulmonary anatomy.
Figure 2:
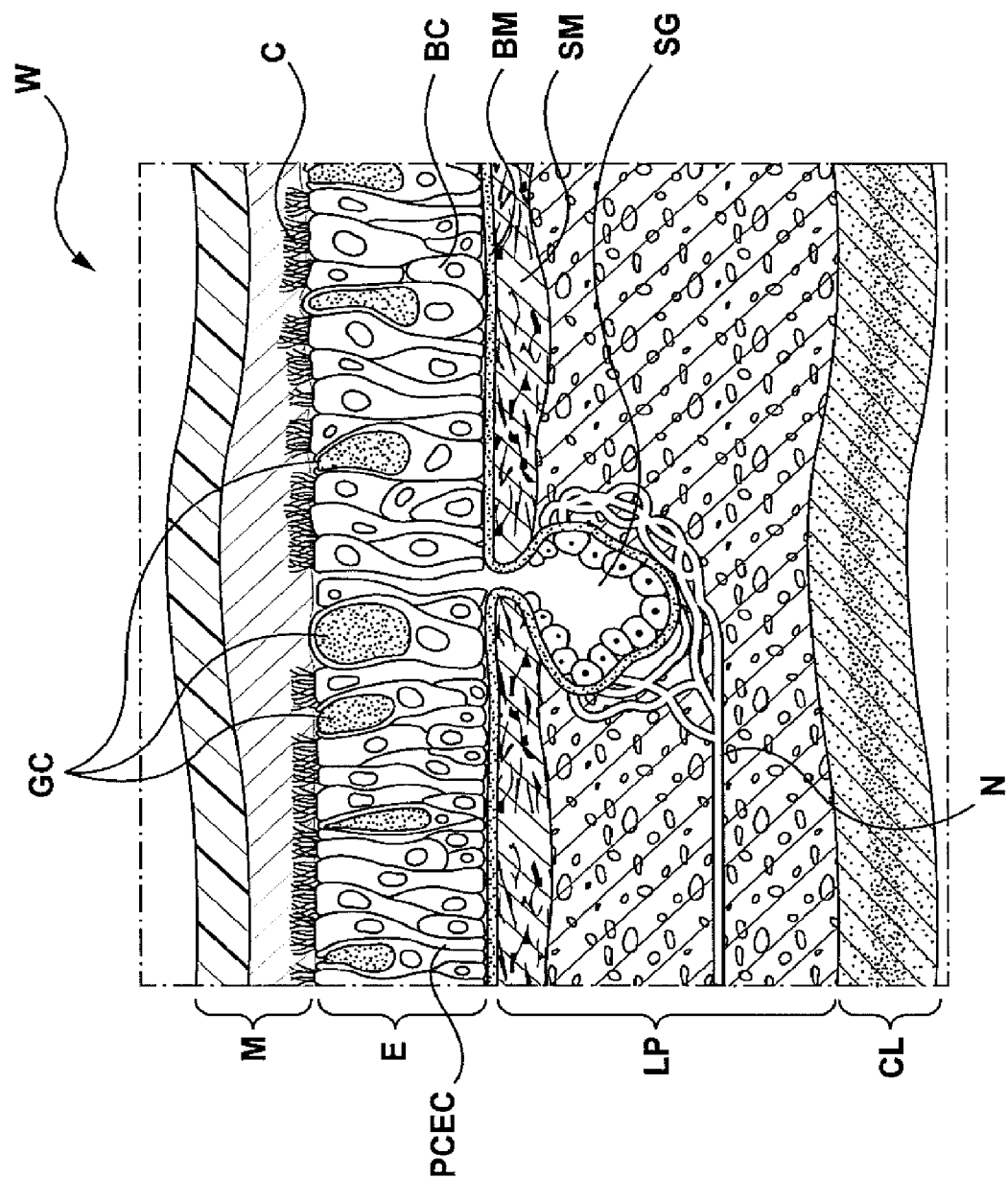
FIG. 2 illustrates a cross-sectional view representative of an airway wall having a variety of layers and structures.

Specific embodiments of the disclosed device, delivery system, and methods will now be described with reference to the drawings. Nothing in this detailed description is intended to imply that any particular component, feature, or step is essential to the implementation of any embodiment.

I. Overview

The secretion of mucus in the bronchial airways is an inherent part of the defense of the lungs, protecting the interior membranes and assisting in fighting off infections. The amount of mucus secretion varies with a range of stimuli, including bacteria, particles and chemical irritants. Normal secretion levels rise and fall depending on the transient conditions of the environment. Mucus on the epithelial layer of the bronchial airways traps particles and the ciliated cells permits moving of the mucus out of the lower airways so that it can ultimately be cleared by coughing or swallowing. Mucus also contains antibacterial agents to aid in its defense function. Pathogens and harmless inhaled proteins are thus removed from the respiratory tract and have a limited encounter with other immune components. In the bronchial airways, mucus is produced by goblet cells. Goblet cells produce mucins that are complexed with water in secretory granules and are released into the airway lumen. In the large airways, mucus is also produced by mucus glands. After infection or toxic exposure, the airway epithelium upregulates its mucus secretory ability to cause coughing and release of sputum. Subsequently, the airway epithelium recovers and returns to its normal state, goblet cells disappear, and coughing abates.

However, in some instances, such as in the development of many pulmonary disorders and diseases, the body does not recover, chronically producing too much mucus and causing it to accumulate in the lungs and plug the distal airways. This creates symptoms such as chronic coughing, difficulty breathing, fatigue and chest pain or discomfort. Such hypersecretion of mucus occurs in many disease states and is a major clinical and pathological feature in cystic fibrosis (CF) related bronchiectasis, non-CF bronchiectasis, chronic obstructive pulmonary disease and asthma, to name a few.

These disorders are all associated with an impaired innate lung defense and considerable activation of the host inflammatory response. Abnormal levels of antimicrobial peptides, surfactant, salivary lysozyme, sputum secretory leukocyte protease inhibitor, and macrophages in addition to signaling of toll-like receptors (TLRs), trigger pathways for mucin transcription and NF-KB (nuclear factor kappa-light-chain-enhancer of activated B cells). The increased mucus production and decreased clearance causes decreased ventilation, increased exacerbations and airway epithelial injury. Ciliary activity is disrupted and mucin production is upregulated. There is expansion of the goblet cell population. Epithelial cell proliferation with differentiation into goblet cells increases. Likewise, inflammation is elevated during exacerbations which activates proteases, destroying the elastic fibers that allow air and $CO_2$ to flow in and out of alveoli. In response to injury, the airway epithelium produces even more mucus to clear the airways of inflammatory cells. This progresses the disorder. Pathogens invade the mucus, which cannot be cleared. This primes the airways for another exacerbation cycle. As exacerbation cycles continue, the excessive mucus production leads to a pathological state with increased risk of infection, hospitalization and morbidity.

To interrupt or prevent the cycle of disease progression, the airways are treated with a pulmonary tissue modification system useful for impacting one or more cellular structures in the airway wall such that the airway wall structures are restored from a diseased/remodeled state to a relatively normal state of architecture, function and/or activity. The pulmonary tissue modification system treats pulmonary tissues via delivery of energy, generally characterized by high voltage pulses. In some embodiments, the energy delivery allows for modification or removal of target tissue without a clinically significant inflammatory response, while in other embodiments, some inflammatory response is permissible. This allows for regeneration of healthy new tissue within days of the procedure.

In one method, the energy output from the pulmonary tissue modification system induces a separation in the epithelial layer E in which abnormal and dysfunctional ciliated pseudostratified columnar epithelial cells PCEC and hyperplastic and abnormal goblet cells GC are separated from the basal cells BC and pulled into the airway lumen, where they are expelled from the lumen of the airway. In another method, the energy output induces cell death of the epithelial cells in which abnormal and non-functioning ciliated epithelial cells and hyperplastic or abnormal goblet cells expire. The expired cells are either resorbed into the airway tissue via immune cell infiltration and phagocytosis or they are expelled into the lumen of the airway, after which they are removed by normal airway debris removal processes.

As a result, the basal cells BC are left on the basement membrane BM to regenerate normal goblet cells GC and normal ciliated pseudostratified columnar epithelial cells PCEC, thereby inducing reverse remodeling of the disease to reduce the mucus hypersecretion. The newly regenerated goblet cells GC are significantly less productive of mucus and the newly regenerated ciliated pseudostratified columnar epithelial cells PCEC regrow normally functioning cilia C, which more easily expel mucus M. The reduction in mucus volume is felt directly by the patient, whose cough and airway obstruction are reduced. Alveoli are better ventilated and therefore hypoxia and respiratory acidosis improve. If the patient has hyperinflation at baseline, the reduction in mucus plugging may reduce the volume of trapped air, improving the low inspiratory to expiratory ratio. Other subjects may suffer from low lung volumes at baseline which may increase when mucus obstruction is relieved. Over the ensuing weeks, this translates into a reduction in exacerbations and an improved quality of life.

Figure 3:
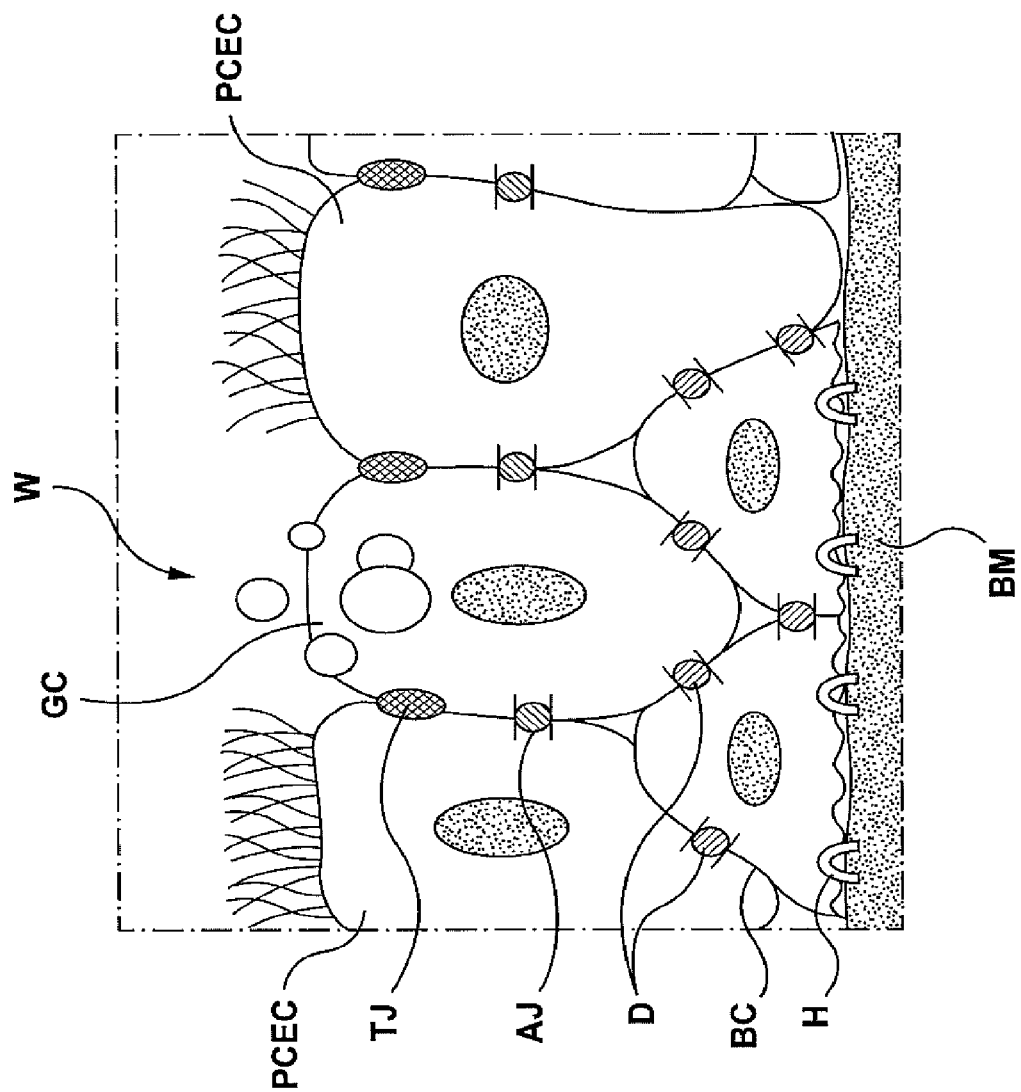
FIG. 3 provides a cross-sectional illustration of the epithelium of an airway wall showing types of cellular connection within the airway.
Figure 4B:
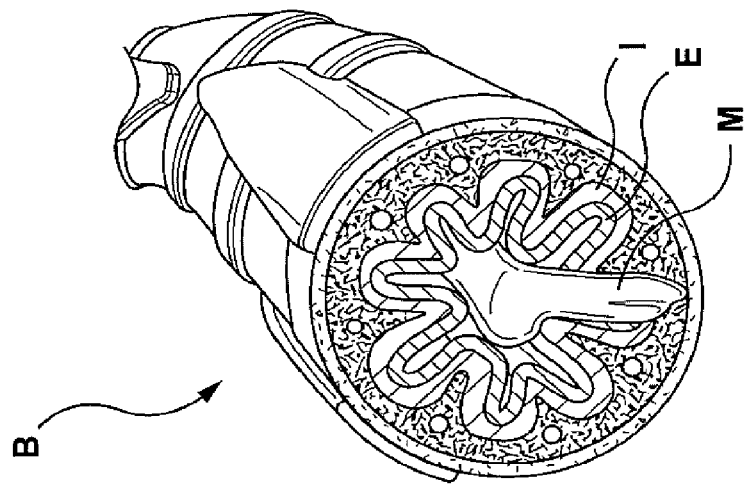
FIGS. 4A-4B depict bronchial airways in healthy and diseased states, respectively.
Figure 4A:
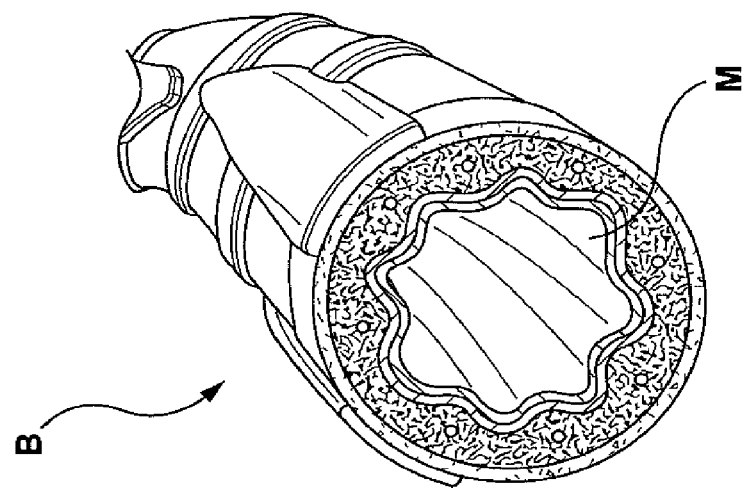

In some embodiments, the energy induces epithelial separation between the basal cells BC and more superficial goblet GC and ciliated pseudostratified columnar epithelial cells PCEC because of the relative strength of the cell-cell connections. The basal cells BC are connected to the basement membrane BM by hemidesmosomes H (illustrated in FIG. 3) whereas the basal cells BC connect to the goblet cells GC and ciliated pseudostratified columnar epithelial cells PCEC via desmosomes D (illustrated in FIG. 3). The energy parameters and electrode configurations of the pulmonary tissue modification system can be designed such that the desmosomes connections D separate but the hemidesmosomes H remain intact, thereby removing the surface cells, leaving the basal cells BC substantially intact, and ready to regenerate epithelium. The regenerative process is faster than would normally occur in trauma or with a thermal ablative modality where the basement membrane BM is disrupted and necrosis ensues. Basement membrane disruption and necrosis, such as in thermal ablation procedures, can cause activation of inflammatory pathways including T cells, macrophages, IL-13, IL-4, monocytes, proteases, cytokines, and chemokines among others. With methods disclosed herein, there is no substantial disruption of the basement membrane BM, and little or no acute inflammation. This allows for regeneration of healthy new target tissue within days of the procedure. It may be appreciated that in other embodiments the energy output from the pulmonary tissue modification system may induce other or additional changes to the airway wall W, leading to regeneration of healthy target tissue.

Figure 5:
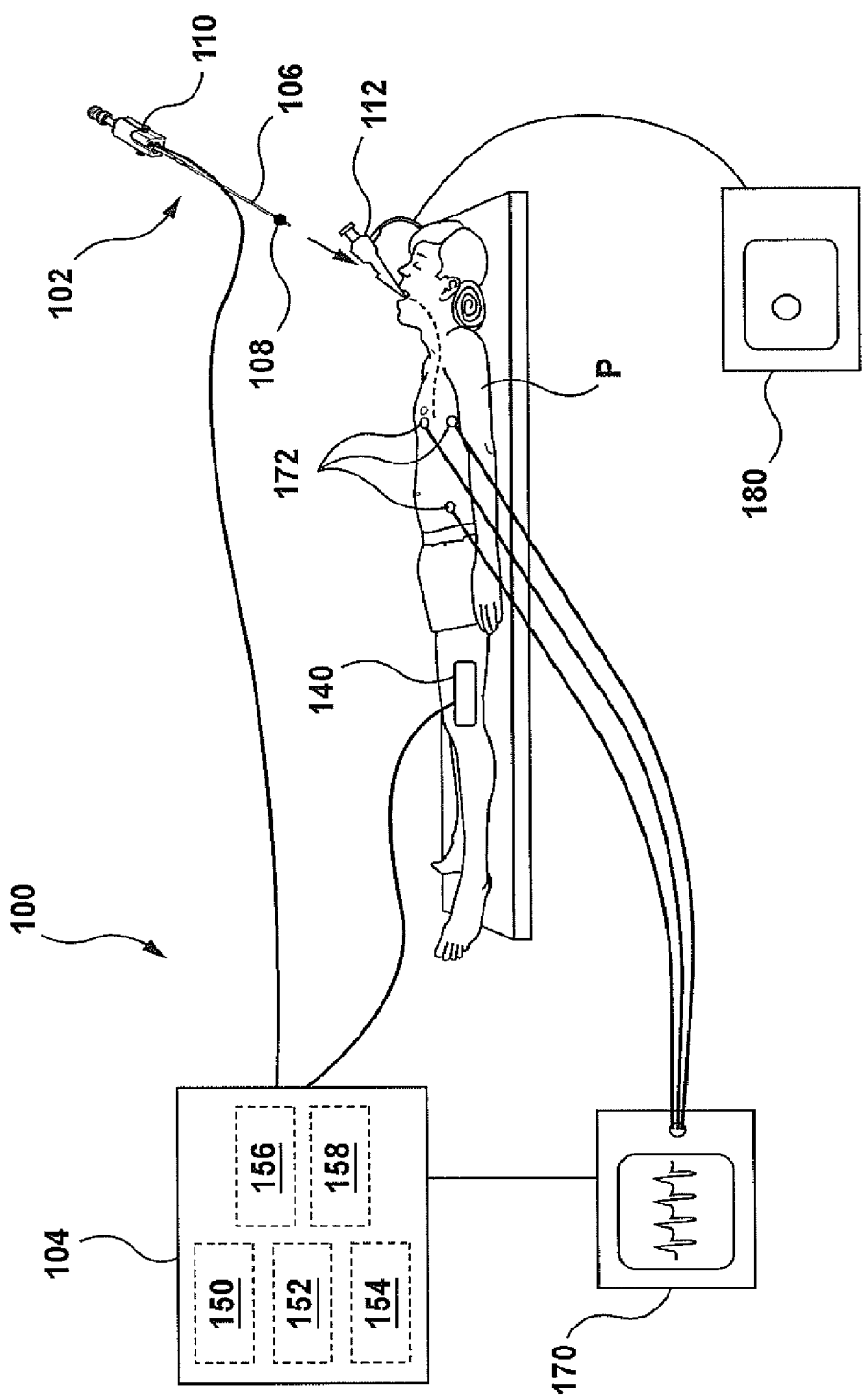
FIG. 5 illustrates an embodiment of a pulmonary tissue modification system used in treatment of a patient.

FIG. 5 illustrates an embodiment of a pulmonary tissue modification system 100 used in treatment of a patient P. In this embodiment, the system 100 comprises a therapeutic energy delivery catheter 102 connectable to a generator 104. The catheter 102 comprises an elongate shaft 106 having at least one energy delivery body 108 near its distal end and a handle 110 at its proximal end. Connection of the catheter 102 to the generator 104 provides electrical energy to the energy delivery body 108, among other features. The catheter 102 is insertable into the bronchial passageways of the patient P by a variety of methods, such as through a lumen in a bronchoscope 112, as illustrated in FIG. 5.

Figure 6:
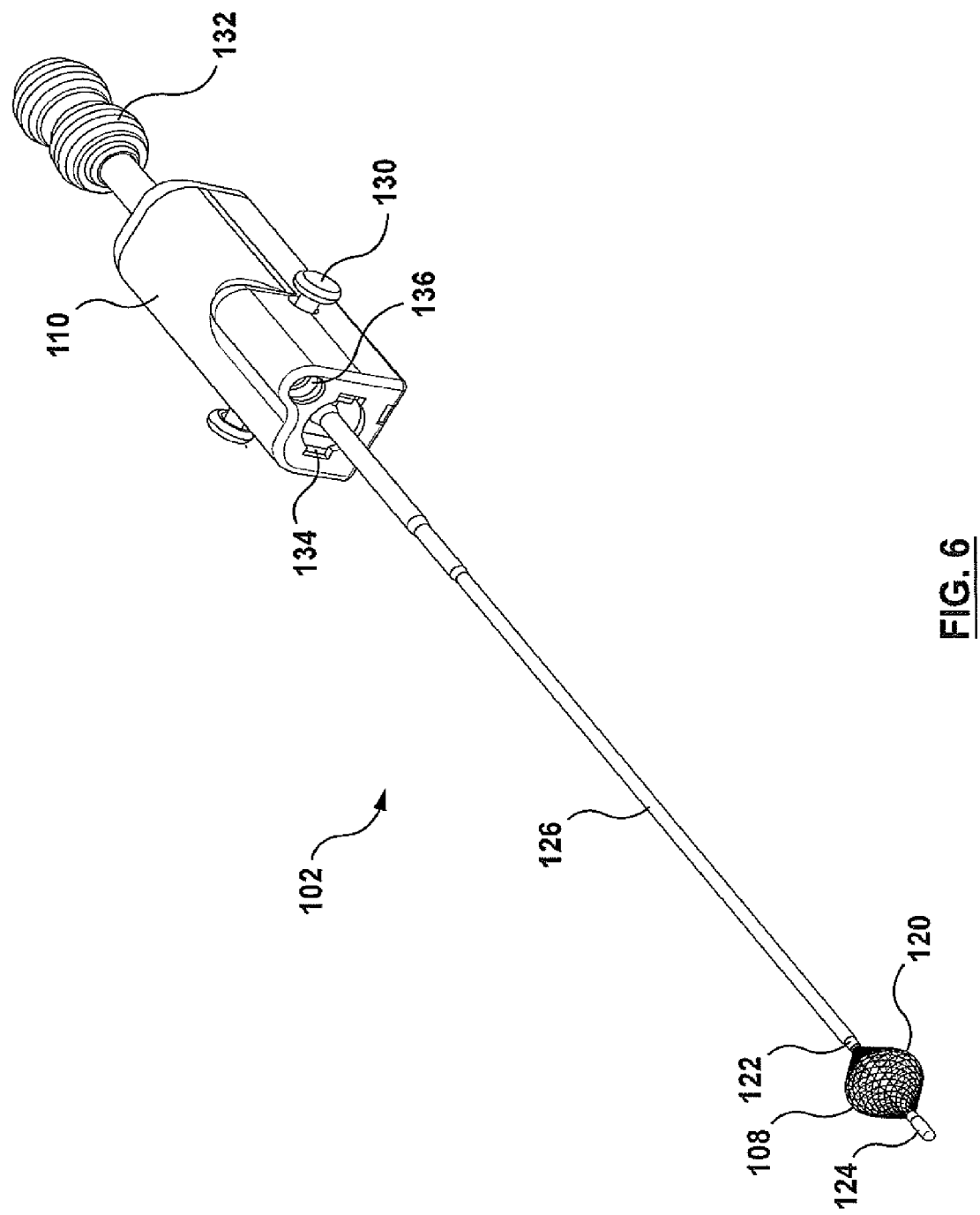
FIG. 6 provides a closer view of the embodiment of the therapeutic energy delivery catheter illustrated in FIG. 5.

FIG. 6 provides a closer view of the embodiment of the therapeutic energy delivery catheter 102 illustrated in FIG. 5. In this embodiment, the energy delivery body 108 comprises a single monopolar delivery electrode, however it may be appreciated that other types, numbers and arrangements may be used, further examples of which will be provided herein. In this embodiment, the energy delivery body 108 is comprised of a plurality of wires or ribbons 120 constrained by a proximal end constraint 122 and a distal end constraint 124 forming a spiral-shaped basket serving as an electrode. In an alternative embodiment, the wires or ribbons are straight instead of formed into a spiral-shape (i.e., configured to form a straight-shaped basket). In still another embodiment, the energy delivery body 108 is laser cut from a tube. In some embodiments, the energy delivery body 108 is self-expandable and delivered to a targeted area in a collapsed configuration. This collapsed configuration can be achieved, for example, by placing a sheath 126 over the energy delivery body 108. In FIG. 6, the catheter shaft 106 (within the sheath 126) terminates at the proximal end constraint 122, leaving the distal end constraint 124 essentially unconstrained and free to move relative to the shaft 106 of the catheter 102. Advancing the sheath 126 over the energy delivery body 108 allows the distal end constraint 124 to move forward, thereby lengthening/collapsing and constraining the energy delivery body 108.

The catheter 102 includes a handle 110 at its proximal end. In some embodiments, the handle 110 is removable, such as by pressing a handle removal button 130. In this embodiment, the handle 110 includes an energy delivery body manipulation knob 132 wherein movement of the knob 132 causes expansion or retraction/collapse of the basket-shaped electrode. In this example, the handle 110 also includes a bronchoscope working port snap 134 for connection with the bronchoscope 112 and a cable plug-in port 136 for connection with the generator 104.

Referring back to FIG. 5, in this embodiment, the therapeutic energy delivery catheter 102 is connectable with the generator 104 along with a dispersive (return) electrode 140 applied externally to the skin of the patient P. Thus, in this embodiment, monopolar energy delivery is achieved by supplying energy between the energy delivery body 108 disposed near the distal end of the catheter 102 and the return electrode 140. It may be appreciated that bipolar energy delivery and other arrangements may alternatively be used, as will be described in further detail herein. In this embodiment, the generator 104 includes a user interface 150, one or more energy delivery algorithms 152, a processor 154, a data storage/retrieval unit 156 (such as a memory and/or database), and an energy-storage sub-system 158 which generates and stores the energy to be delivered. In some embodiments, one or more capacitors are used for energy storage/delivery, but as new technology is developed any suitable element may be used. In addition, one or more communication ports are included.

It may be appreciated that in some embodiments, the generator 104 is comprised of three sub-systems; 1) a high energy storage system, 2) a high voltage, medium frequency switching amplifier, and 3) the system control, firmware, and user interface. The system controller includes a cardiac synchronization trigger monitor that allows for synchronizing the pulsed energy output to the patient's cardiac rhythm. The generator takes in AC (alternating current) mains to power multiple DC (direct current) power supplies. The generator's controller instructs the DC power supplies to charge a high-energy capacitor storage bank before energy delivery is initiated. At the initiation of therapeutic energy delivery, the generator's controller, high-energy storage banks and a bi-phasic pulse amplifier operate simultaneously to create a high-voltage, medium frequency output.

The processor 154 can be, for example, a general-purpose processor, a field programmable gate array (FPGA), an application specific integrated circuit (ASIC), a digital signal processor (DSP), and/or the like. The processor 154 can be configured to run and/or execute application processes and/or other modules, processes and/or functions associated with the system 100, and/or a network associated with the system 100.

As used herein the term "module" refers to any assembly and/or set of operatively-coupled electrical components that can include, for example, a memory, a processor, electrical traces, optical connectors, software (executing in hardware), and/or the like. For example, a module executed in the processor can be any combination of hardware-based module (e.g., a FPGA, an ASIC, a DSP) and/or software-based module (e.g., a module of computer code stored in memory and/or executed at the processor) capable of performing one or more specific functions associated with that module.

The data storage/retrieval unit 156 can be, for example, a random access memory (RAM), a memory buffer, a hard drive, a database, an erasable programmable read-only memory (EPROM), an electrically erasable read-only memory (EEPROM), a read-only memory (ROM), flash memory, and/or so forth. The data storage/retrieval unit 156 can store instructions to cause the processor 154 to execute modules, processes and/or functions associated with the system 100.

Some embodiments the data storage/retrieval unit 156 comprises a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) can be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as ASICs, Programmable Logic Devices (PLDs), Read-Only Memory (ROM) and Random-Access Memory (RAM) devices. Other embodiments described herein relate to a computer program product, which can include, for example, the instructions and/or computer code discussed herein.

Examples of computer code include, but are not limited to, micro-code or micro-instructions, machine instructions, such as produced by a compiler, code used to produce a web service, and files containing higher-level instructions that are executed by a computer using an interpreter. For example, embodiments can be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

In some embodiments, the system 100 can be communicably coupled to a network, which can be any type of network such as, for example, a local area network (LAN), a wide area network (WAN), a virtual network, a telecommunications network, a data network, and/or the Internet, implemented as a wired network and/or a wireless network. In some embodiments, any or all communications can be secured using any suitable type and/or method of secure communication (e.g., secure sockets layer (SSL)) and/or encryption. In other embodiments, any or all communications can be unsecured.

The user interface 150 can include a touch screen and/or more traditional buttons to allow for the operator to enter patient data, select a treatment algorithm (i.e. energy delivery algorithm 152), initiate energy delivery, view records stored on the storage/retrieval unit 156, or otherwise communicate with the generator 104.

Any of the systems disclosed herein can include a user interface 150 configured to allow operator-defined inputs. The operator-defined inputs can include duration of energy delivery or other timing aspects of the energy delivery pulse, power, target temperature, mode of operation, or a combination thereof. For example, various modes of operation can include system initiation and self-test, operator input, algorithm selection, pre-treatment system status and feedback, energy delivery, post energy delivery display or feedback, treatment data review and/or download, software update, or a combination thereof.

In some embodiments, the system 100 also includes a mechanism for acquiring an electrocardiogram (ECG), such as an external cardiac monitor 170. Example cardiac monitors are available from AccuSync Medical Research Corporation. In some embodiments, the external cardiac monitor 170 is operatively connected to the generator 104 Here, the cardiac monitor 170 is used to continuously acquire the ECG. External electrodes 172 may be applied to the patient P and to acquire the ECG. The generator 104 analyzes one or more cardiac cycles and identifies the beginning of a time period where it is safe to apply energy to the patient P, thus providing the ability to synchronize energy delivery with the cardiac cycle. In some embodiments, this time period is within milliseconds of the R wave to avoid induction of an arrhythmia which may occur if the energy pulse is delivered on a T wave. It may be appreciated that such cardiac synchronization is typically utilized when using monopolar energy delivery, however it may be utilized in other instances.

In some embodiments, the processor 154, among other activities, modifies and/or switches between the energy-delivery algorithms, monitors the energy delivery and any sensor data, and reacts to monitored data via a feedback loop. It may be appreciated that in some embodiments the processor 154 is configured to execute one or more algorithms for running a feedback control loop based on one or more measured system parameters (e.g., current), one or more measured tissue parameters (e.g., impedance), and/or a combination thereof. In these embodiments, the sensing of signals to gather data can be provided by using the energy delivery body, or dedicated, energetically-isolated sensors located on or near the energy delivery body.

The data storage/retrieval unit 156 stores data related to the treatments delivered and can optionally be downloaded by connecting a device (e.g., a laptop or thumb drive) to a communication port. In some embodiments, the device has local software used to direct the download of information, such as, for example, instructions stored on the data storage/retrieval unit 156 and executable by the processor 154. In some embodiments, the user interface 150 allows for the operator to select to download data to a device and/or system such as, but not limited to, a computer device, a tablet, a mobile device, a server, a workstation, a cloud computing apparatus/system, and/or the like. The communication ports, which can permit wired and/or wireless connectivity, can allow for data download, as just described but also for data upload such as uploading a custom algorithm or providing a software update.

As described herein, a variety of energy delivery algorithms 152 are programmable, or can be pre-programmed, into the generator 104, such as stored in memory or data storage/retrieval unit 156. Alternatively, energy delivery algorithms can be added into the data storage/retrieval unit to be executed by processor 154. Each of these algorithms 152 may be executed by the processor 154. Examples algorithms will be described in detail herein below. In some embodiments, the catheter 102 includes one or more sensors 160 that can be used to determine temperature, impedance, resistance, capacitance, conductivity, permittivity, and/or conductance, to name a few. Sensor data can be used to plan the therapy, monitor the therapy and/or provide direct feedback via the processor 154, which can then alter the energy-delivery algorithm 152. For example, impedance measurements can be used to determine not only the initial dose to be applied but can also be used to determine the need for further treatment, or not.

It may be appreciated that any of the systems disclosed herein can include an automated treatment delivery algorithm that could dynamically respond and adjust and/or terminate treatment in response to inputs such as temperature, impedance, treatment duration or other timing aspects of the energy delivery pulse, treatment power and/or system status.

In some embodiments, imaging is achieved with the use of a commercially-available system, such as a bronchoscope 112 connected with a separate imaging screen 180, as illustrated in FIG. 5. It may be appreciated that imaging modalities can be incorporated into the catheter 102 or used alongside or in conjunction with the catheter 102. The imaging modality can be mechanically, operatively, and/or communicatively coupled to the catheter 102 using any suitable mechanism.

Figure 7:
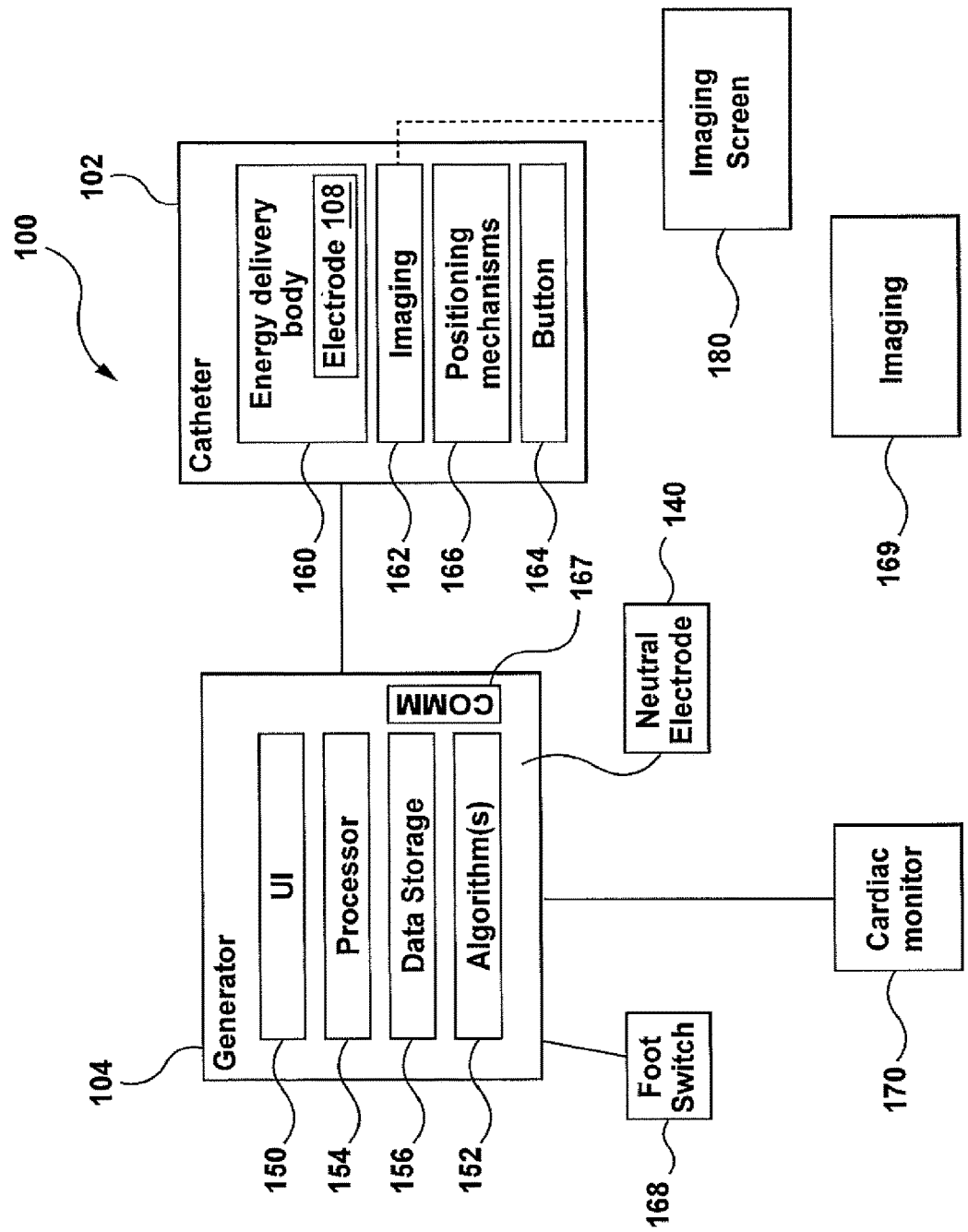
FIG. 7 is a schematic illustration of an embodiment of a pulmonary tissue modification system.

FIG. 7 is a schematic illustration of an embodiment of a pulmonary tissue modification system 100. In this embodiment, the catheter 102 is configured for monopolar energy delivery. As shown, a dispersive (neutral) or return electrode 140 is operatively connected to the generator 104 while affixed to the patient's skin to provide a return path for the energy delivered via the catheter 102. The energy-delivery catheter 102 includes one or more energy delivery bodies 108 (comprised of electrode(s)), one or more sensors 160, one or more imaging modalities 162, one or more buttons 164, and/or positioning mechanisms 166 (e.g., such as, but not limited to, levers and/or dials on a handle with pull wires, telescoping tubes, a sheath, and/or the like) the one or more energy delivery bodies 108 into contact with the tissue. In some embodiments, a foot switch 168 is operatively connected to the generator 104 and used to initiate energy delivery.

As mentioned previously, the user interface 150 can include a touch screen and/or more traditional buttons to allow for the operator to enter patient data, select a treatment algorithm 152, initiate energy delivery, view records stored on the storage/retrieval unit 156, or otherwise communicate with the generator 104. The processor 154 manages and executes the energy-delivery algorithm, monitors the energy delivery and any sensor data, and reacts to monitored data via a feedback loop. The data storage/retrieval unit 156 stores data related to the treatments delivered and can be downloaded by connecting a device (e.g., a laptop or thumb drive) to a communication port 167.

The catheter 102 is operatively connected to the generator 104 and/or a separate imaging screen 180. Imaging modalities 162 can be incorporated into the catheter 102 or used alongside or in conjunction with the catheter 102. Alternatively or in addition, a separate imaging modality or apparatus 169 can be used, such as a commercially-available system (e.g., a bronchoscope). The separate imaging apparatus 169 can be mechanically, operatively, and/or communicatively coupled to the catheter 102 using any suitable mechanism.

Figure 8A:
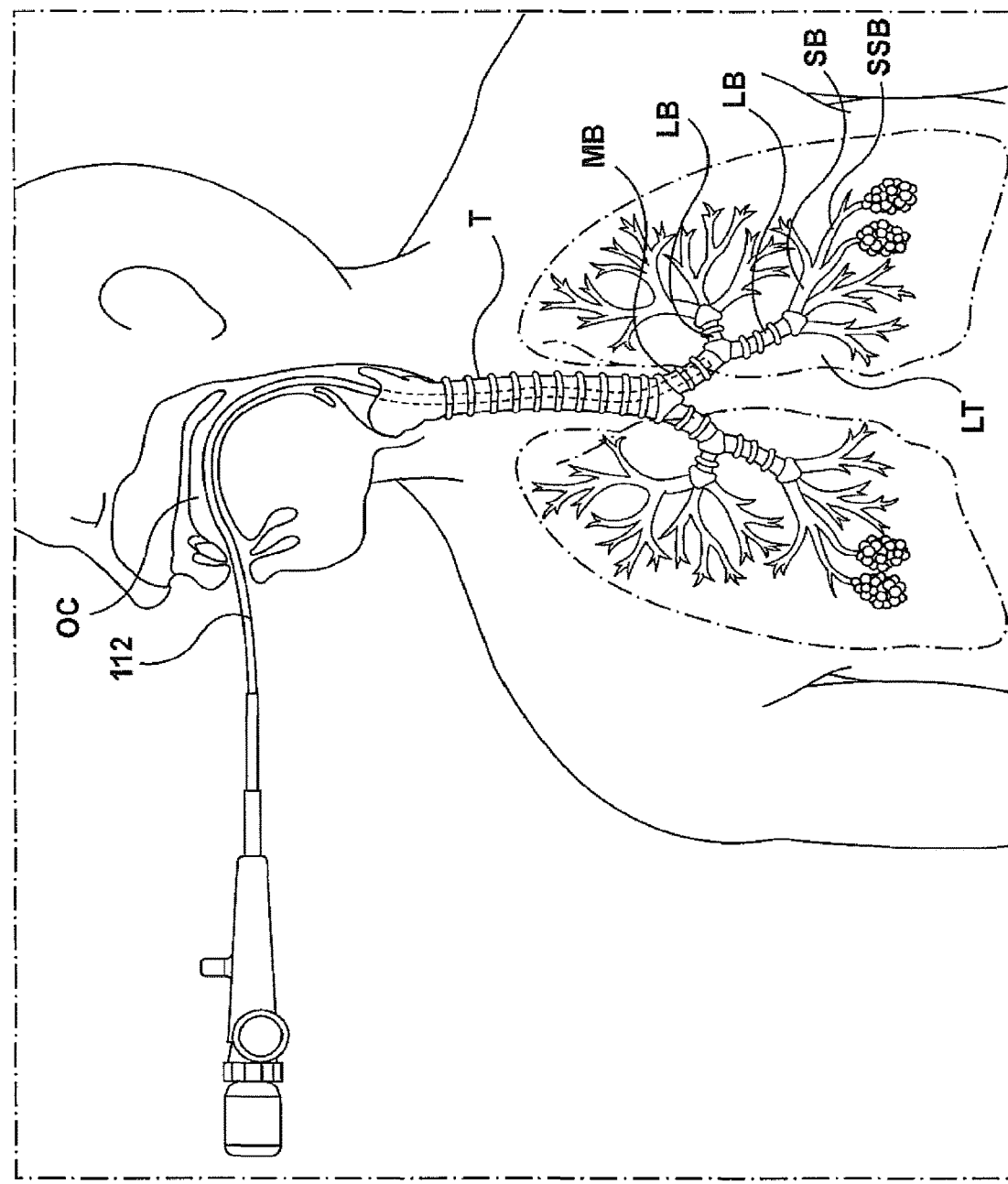
FIGS. 8A-8B illustrate a bronchoscope inserted in the mouth/oral cavity of the patient and the nose/nasal cavity of the patient, respectively.
Figure 8B:
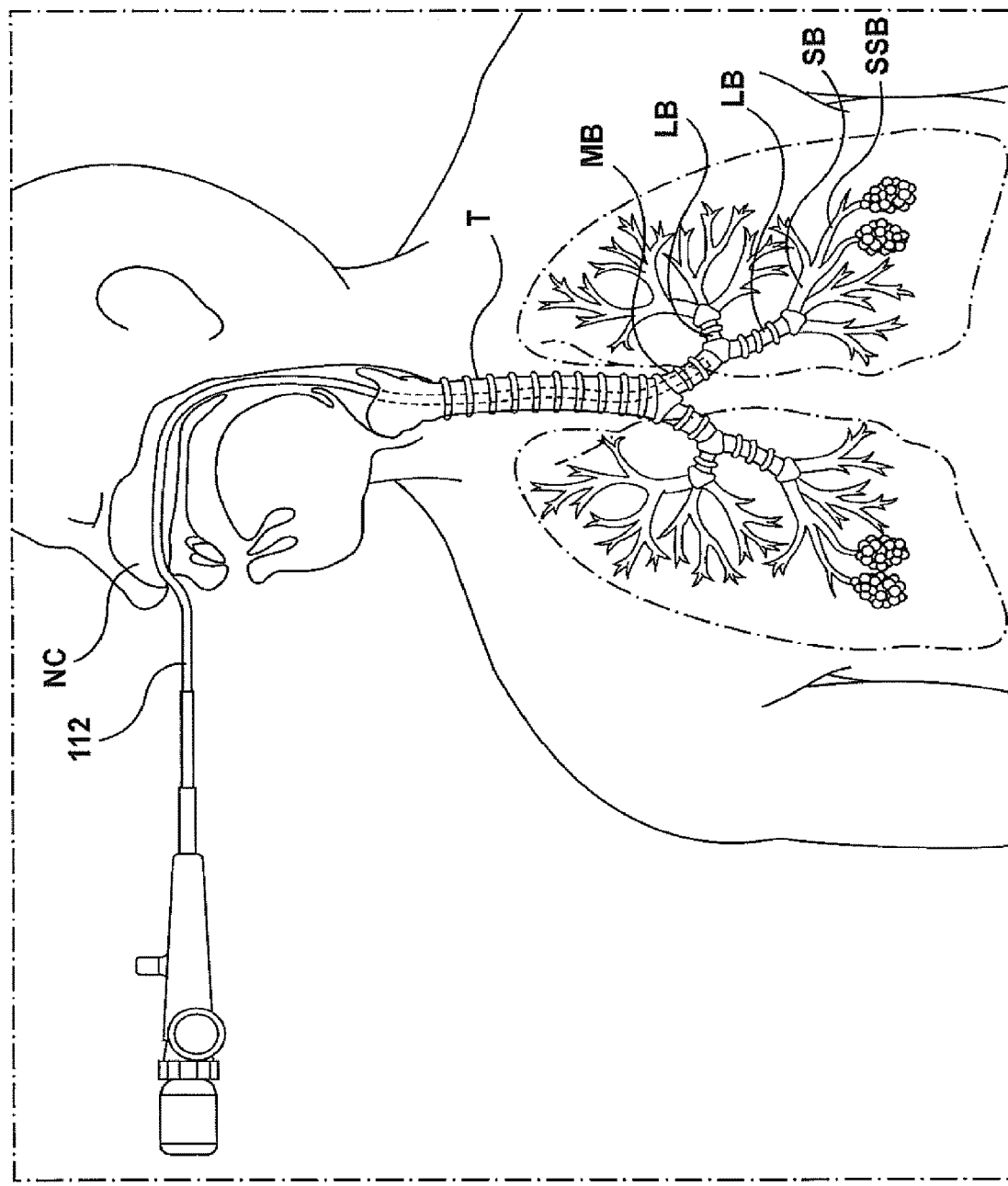

Referring to FIG. 8A, a bronchoscope 112 is inserted in the mouth or oral cavity OC of the patient P. It may be appreciated that methods for accessing the airway can include use of other natural orifices such as the nose or nasal cavity NC (illustrated in FIG. 8B). Alternatively, a suitable artificial orifice may be used (not shown e.g., stoma, tracheotomy). Use of the bronchoscope 112 allows for direct visualization of the target tissues and the working channel of the bronchoscope 112 can be used to deliver the catheter 102 as per the apparatuses and systems disclosed herein, allowing for visual confirmation of catheter placement and deployment. FIGS. 8A-8B illustrate advancement of the distal end of the catheter 102 into the trachea T and the mainstem bronchi MB, though it may be appreciated that the catheter 102 may be advanced into the lobar bronchi LB, more distal segmental bronchi SB and sub-segmental bronchi SSB if desired.

Figure 9:
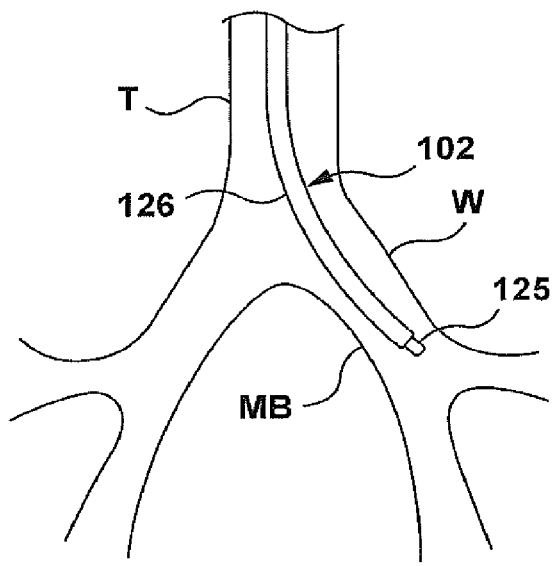
FIGS. 9, 10, 11 illustrate positioning of the distal end of the catheter into the mainstem bronchi for treatment of the airway.
Figure 10:
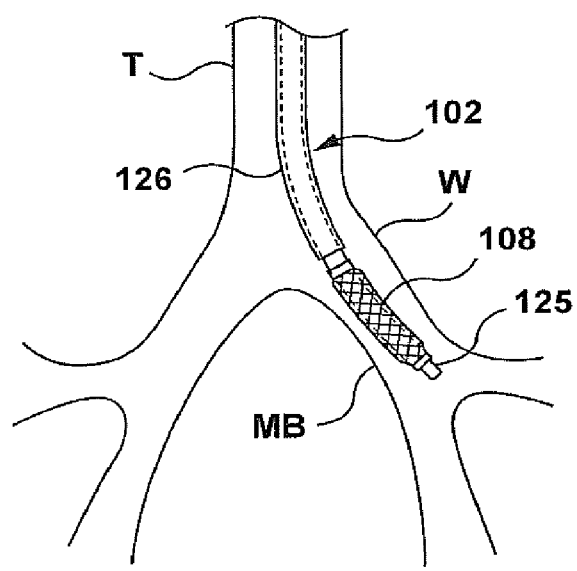
Figure 11:
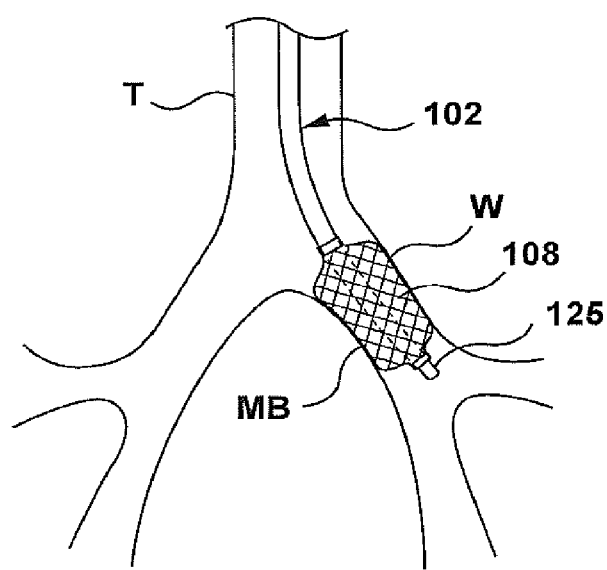

FIGS. 9-11 illustrate positioning of the distal end of the catheter 102 into the mainstem bronchi MB for treatment of the airway. In some embodiments, the catheter 102 has an atraumatic tip 125 to allow advancement through the airways without damaging or the airway walls W. FIG. 9 illustrates the catheter 102 advanced into the mainstem bronchi MB while the sheath 126 is covering the energy delivery body 108. Positioning of the catheter 102 may be assisted by various imaging techniques. For example, the bronchoscope 112 may be used to provide real-time direct visual guidance to the target site and may be used to observe accurate positioning of the catheter 102 before, during and after the delivery of treatment. FIG. 10 illustrates withdrawal of the sheath 126, exposing the energy delivery body 108. It may be appreciated that in some embodiments, the energy delivery body 108 is self-expanding so that the sheath 126 holds the energy delivery body 108 in a collapsed configuration. In such embodiments, withdrawal of the sheath 126 releases the energy delivery body 108, allowing self-expansion. In other embodiments, the energy delivery body 108 is expanded by other mechanisms, such as movement of the knob 132, which may occur after the sheath 126 is withdrawn. FIG. 11 illustrates the basket-shaped energy delivery body 108 in an expanded configuration, wherein the energy delivery body 108 contacts the airway walls W. Additional imaging can be used to verify positioning and/or make additional measurements (e.g., depth).

Once the energy delivery body 108 is desirably positioned, treatment energy is provided to the airway wall W by the energy delivery body 108. The treatment energy is applied according to at least one energy delivery algorithm.

In some embodiments, the user interface 150 on the generator 104 is used to select the desired treatment algorithm 152. In other embodiments, the algorithm 152 is automatically selected by the generator 104 based upon information obtained by one or more sensors on the catheter 102, which will be described in more detail in later sections. A variety of energy delivery algorithms may be used. In some embodiments, the algorithm 152 generates a signal having a waveform comprising a series of energy packets with rest periods between each packet, wherein each energy packet comprises a series of high voltage pulses. In some embodiments, each high voltage pulse is between about 500 V to 10 kV, or about 500 V to about 5,000 V, including all values and subranges in between. In some embodiments, the energy provided is within the frequency range of about 10 kHz to about 10 MHz, or about 100 kHz to about 1 MHz, including all values and subranges in between.

The algorithm 152 delivers energy to the walls of the airway so as to provide the desired treatment with minimal or no tissue heating. In some embodiments, a temperature sensor is used to measure electrode and/or tissue temperature during treatment to ensure that energy deposited in the tissue does not result in any clinically significant tissue heating. For example, a temperature sensor can monitor the temperature of the tissue and/or electrode, and if a pre-defined threshold temperature is exceeded (e.g., 65° C.), the generator can alter the algorithm to automatically cease energy delivery or modify the algorithm to reduce temperature to below the pre-set threshold. For example, if the temperature exceeds 65° C., the generator can reduce the pulse width or increase the time between pulses and/or packets in an effort to reduce further cumulative temperature rise. This can occur in a pre-defined step-wise approach, as a percentage of the parameter, or by other methods.

Conventional radiofrequency ablation (RFA) kills cells by application of high frequency alternating current in the 350-550 kHz range, generating heat in the tissue to product thermal necrosis of the cells. Many RFA devices have been developed to treat cardiac arrhythmias, solid tumors, renal nerves, and others. Microwave ablation is another thermal ablation modality in which 300 MHz to 300 GHz alternating current is used, also leading to thermal necrosis. This energy source is employed to target solid tumors because of the large ablation zones and uniform heating. In general, heat-related thermal ablation denatures the proteins within the tissue, causes a significant inflammatory response and can be difficult to control, often leading to injury to non-target tissues. For certain types of treatments (e.g., tumor treatments), inflammation is acceptable, but when focused within the pulmonary airways, substantive inflammation can lead to serious complications (e.g., exacerbation). While the denaturation of proteins alone may or may not produce clinical morbidity, more intact, less denatured proteins allow for the opportunity to enhance the host response to various challenges to the immune system, whether that is to affect pathogens, tumor, etc. These limitations especially make heat-related thermal ablation in the airways less desirable.

In contrast, the algorithm 152 prescribes energy delivery to the airway walls W which is non-thermal (e.g. below a threshold for thermal ablation; below a threshold for inducing coagulative thermal damage), thereby reducing or avoiding inflammation. In some embodiments, the algorithm 152 is tailored to affect tissue to a pre-determined depth and/or to target specific types of cells within the airway wall. Typically, depths of up to 0.01 mm, up to 0.02 mm, 0.01-0.02 mm, up to 0.03 mm, 0.03-0.05 mm, up to 0.05 mm, up to 0.08 mm, up to 0.09 mm, up to 0.1 mm, up to 0.2 mm, up to 0.5 mm, up to 0.7 mm, up to 1.0 mm, up to 1.5 mm, up to 2.0 mm, or up to 2.3 mm or less than 2.3 mm can be targeted, particularly when treating a lining of an airway or lung passageway. In some instances, the targeted pre-determined depth is 0.5 mm, such as when targeting airway epithelium and submucosal glands, with significant margin of safety to prevent any morbidity-associated cartilage effects at depths of 2.3 mm. In other instances, the targeted effect depth is more assertive to treat all of the airway epithelial cells and submucosal glands to a depth of up to 1.36 mm, while still preventing safety-associated effects to cartilage at depths of 2.3 mm. In other embodiments, such as when applying such treatment to another clinical application, such as a cardiac application, the algorithm 152 is tailored to affect tissue to deeper pre-determined depths such as of up to 0.1 cm, up to 0.2 cm, up to 0.3 cm, up to 0.5 cm, up to 0.8 cm, up to 0.9 cm, up to 1 cm or 0.5 cm to 1cm. In yet other embodiments, such as when applying such treatment to clinical applications involving even deeper targets, the algorithm 152 is tailored to affect tissue to even deeper pre-determined depths such as of up to 2 cm or up to 2.5 cm.

In some embodiments, the generator has several fixed algorithm settings whereby the targeted cell depth is reflected in each setting. For instance, when treating a lung passageway, one setting/algorithm may primarily affect the pathogens resident in the mucus layer, another setting/algorithm may target the epithelium, another setting/algorithm may primarily target the epithelium, basement membrane, submucosa and/or smooth muscle, while yet another setting/algorithm may primarily target the epithelium, basement membrane, submucosa, smooth muscle, submucosal glands and/or nerves. In some embodiments, treatment is performed at the same location, but in others, the operator may choose to affect certain cell types at different locations. The setting utilized by the operator may be dependent on the physiologic nature of the patient's condition.

The biological mechanisms and cellular processes by which the energy removes the cells will be described in more detail in later sections. The energy treats the airway wall W at the target location in a manner which allows the regeneration of healthy tissue. For example, normal goblet cells GC and normal ciliated pseudostratified columnar epithelial cells PCEC are able to regenerate, thereby inducing reverse remodeling of the disease to reduce the mucus hypersecretion. The newly regenerated goblet cells GC are significantly less productive of mucus and the newly regenerated ciliated pseudostratified columnar epithelial cells PCEC regrow normally functioning cilia C, which more easily expel mucus M. Thus, healthy new target tissue can be regenerated within days of the procedure. This dramatically reduces symptoms of cough, mucus hypersecretion and mucus plugging in patients which results in fewer and less severe exacerbations and improvement in quality of life.

Figure 12:
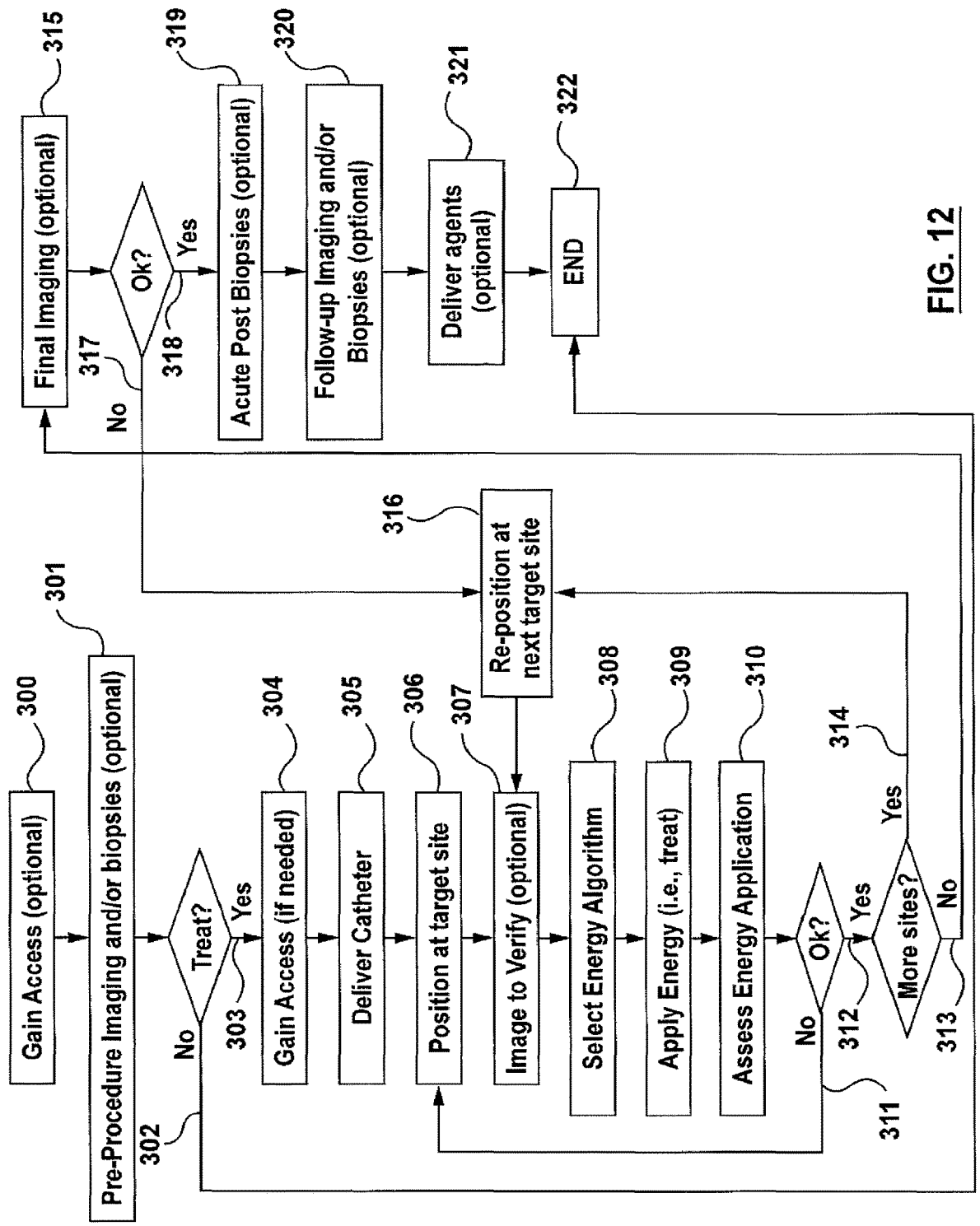
FIGS. 12, 12A, 12B are flowcharts illustrating methods described herein in a step-wise approach to treating patients.

FIG. 12 is a flowchart illustrating methods described herein in a step-wise approach to treating patients, wherein the methods are executed by a practitioner, therapeutic energy-delivery catheter, or generator as appropriate. In some embodiments, one or more of the steps disclosed herein can be optional. The first series of steps can be used to assess patient anatomy and/or suitability for the procedure to decide whether or not to treat. In some embodiments, this assessment can be optional, but can include one or more of the following steps. First, gain access 300 to the airway (if needed). Second, perform any suitable pre-procedural imaging, sputum sampling and/or biopsies that can be necessary and/or desired 301. Pre-procedural imaging can include a non-invasive CT scan, bronchoscopy, confocal laser endomicroscopy (CLE), optical coherence tomography (OCT) or any other appropriate technique along with any measurements that can be taken (e.g., depth). Sputum sampling can include nasal mucosa brushing, nasal washing, bronchial brushing, bronchial washing, and/or bronchoalveolar lavage. Then, decide whether or not to treat the patient. If the decision is 'No' 302, go to END 322. If the decision is 'Yes' 303, gain access, if needed 304. In some embodiments, the treatment can be performed one or more days after the pre-procedure assessment. In this embodiment, it would be required to gain access 304.

In some embodiments, the treatment can be performed immediately after the pre-procedure assessment. In this embodiment, it may not be necessary to gain access again. In this embodiment, the next step 305 of the procedure is to deliver the catheter. As described above, the catheter can be delivered by various methods, however, for the purposes of providing an example, the catheter is delivered via a working channel of a bronchoscope. In the next step 306, the catheter is positioned at a target site. Again, as an example, the bronchoscope can be used to provide real-time direct visual guidance to the target site and be used to observe accurate positioning of the catheter. This can include placement of one or more energy delivery bodies into contact with the airway wall. Additional imaging 307 can then be used to verify positioning and/or make additional measurements (e.g., depth). At the next step 308, the operator can optionally select the desired energy delivery algorithm 152. As described in detail above, this can include for example, selecting an algorithm based on target depth of treatment. Alternatively, the generator is configured to apply a pre-defined algorithm suitable for most patients. In this embodiment, the next step 309 is to execute or apply the energy delivery algorithm. This can be accomplished via a foot pedal or other mechanism described herein.

Figure 12A:
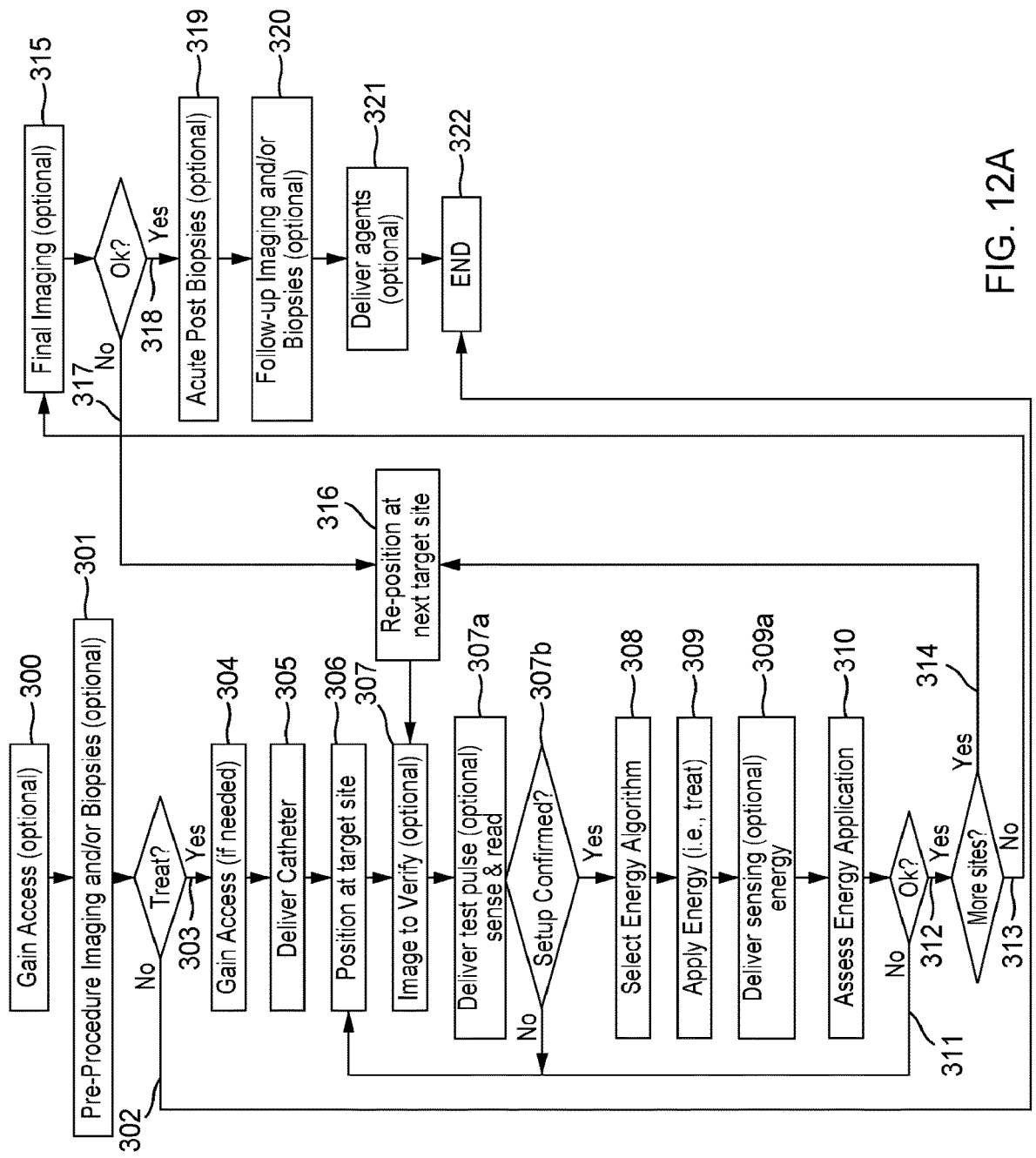
Figure 12B:
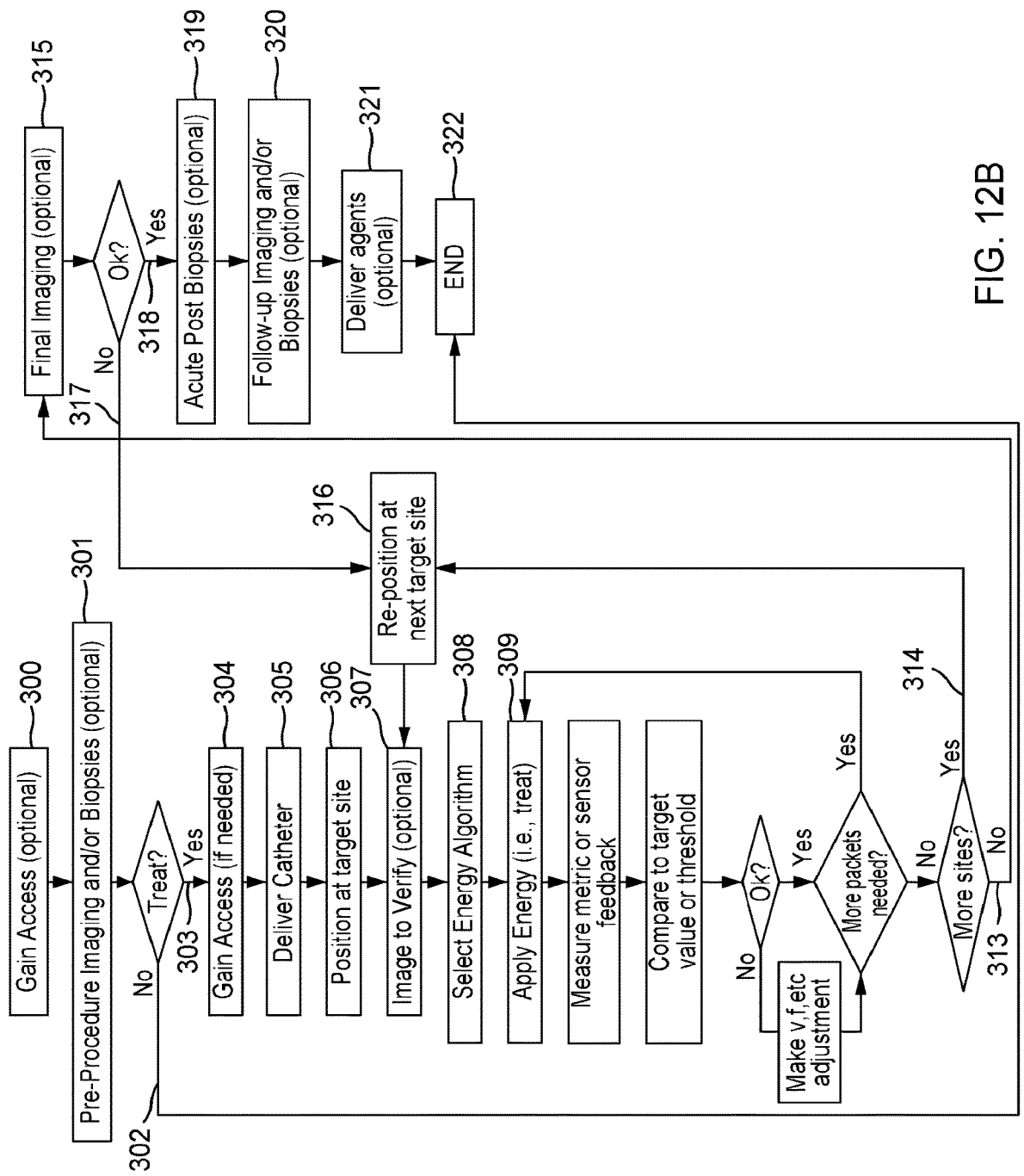

In some embodiments, as illustrated in FIG. 12A, a test pulse is delivered 307a after the step of positioning at the target site 306. After sensing and reading, set up is confirmed 307b. If the decision is 'Yes', the energy algorithm is selected 308. If the decision is 'No', the step of positioning at the target site 306 is repeated along with the steps that follow. After a 'Yes' confirmation and the application of energy 309, sensing energy may optionally be delivered 309a. Sensing is used with energy source other than therapy pulses (e.g. low voltage sense pulses, AC spectroscopy).

Referring to FIGS. 12-12A, after the energy is applied, the operator can assess the energy application 310. This can include performing additional imaging with or without measurements and/or reacting to messages communicated by the generator (e.g., an error with the energy delivery that can have led to incomplete treatment). If the treatment is not acceptable 311, then operator would go back to the Position at Target Site step 306. If the treatment is acceptable 312, then operator would proceed. The next step in the procedure can be to determine if more treatment sites are to be treated. If 'No' 313, the operator would then move on to Final Imaging 315 and the remaining steps until END 322. If 'Yes' 314, the operator would then re-position at the next target site 316 and repeat the steps for applying a treatment. Once all treatments are complete, the operator then moves on to optional Final Imaging 315, where the operator can perform additional confirmatory imaging to ensure all targeting areas were treated to his/her satisfaction. If 'No' 317, the operator would proceed back to 'Re-position at next target site' 316 and perform additional treatments. If 'Yes' 318, the operator can then decide to perform one or more acute biopsies and/or sputum samples 319 to compare to any pre-procedure biopsies and/or sputum samples 301 that can have been taken. At a later date, follow-up imaging and/or, biopsies, and/or sputum samples 320 can be taken and compared to any other images or, biopsies, and/or sputum samples to help assess and/or document the outcome of the therapy. The operator can then decide to deliver materials, active agents, etc. 321 to assist in the normative healing process and as such further reduce the potential for pen-procedural issues or complications. Moreover, this might further reduce the degree or frequency of exacerbations, especially in the short term. Some examples of these agents include isotonic saline gel, medicated films, antibacterials, antivirals, antifungals, anti-inflammatories, genetic material, stem cells, autograft cells, or allograft cells, to name a few. As a result of exposing the tissue(s) to high-energy fields, the treated tissue(s) can be conditioned for improved agent uptake. The procedure then ends 322. In some embodiments, the agents are delivered prior to pulsed electric field delivery. The patient can then continue to be followed by a physician and can undergo this entire procedure again, should the disease or disorder recur and/or continue.

Thus, it is contemplated that in certain embodiments where the desired clinical effect was not achieved or where it was achieved but then subsequently the condition re-occurred, repeat procedures may be desired. In these embodiments, it might be desired not only to re-treat certain areas but also to target a different portion of the pulmonary anatomy. Thus, the system 100 may be used to specifically re-treat the same portion of tissue as the original treatment or a distinctly different portion of tissue from the first intervention.

While various embodiments have been described above, it should be understood that they have been presented by way of example, and not limitation. Where methods described above indicate certain events occurring in certain order, the ordering of certain events can be modified. Additionally, certain of the events can be performed concurrently in a parallel process when possible, as well as performed sequentially as described above.

II. Energy Delivery Algorithms

As mentioned previously, one or more energy delivery algorithms 152 are programmable, or can be pre-programmed, into the generator 104 for delivery to the patient P. The one or more energy delivery algorithms 152 specify electric signals which provide energy delivered to the airway walls W which are non-thermal (e.g. below a threshold for thermal ablation; below a threshold for inducing coagulative thermal damage), reducing or avoiding inflammation, and preventing denaturation of stromal proteins. In general, the algorithm 152 is tailored to affect tissue to a pre-determined depth and/or to target specific types of cellular responses to the energy delivered. It may be appreciated that depth and/or targeting may be affected by parameters of the energy signal prescribed by the one or more energy delivery algorithms 152, the design of the catheter 102 (particularly the one or more energy delivery bodies 108), and/or the choice of monopolar or bipolar energy delivery. In some instances, bipolar energy delivery allows for the use of a lower voltage to achieve the treatment effect, as compared to monopolar energy delivery. In a bipolar configuration, the positive and negative poles are close enough together to provide a treatment effect both at the electrode poles and in-between the electrode poles. This can concentrate the treatment effect over a specific tissue area thus involving a lower voltage to achieve the treatment effect compared to monopolar. Likewise, this focal capability using lower voltages, may be used to reduce the depth of penetration, such as to affect the epithelial cells rather than the submucosal cells. In other instances, this reduced effect penetration depth may be used to focus the energy such as to target epithelial and submucosal layers, while sparing the deeper cartilage tissue. In addition, lower voltage requirements may obviate the use of cardiac synchronization if the delivered voltage is low enough to avoid stimulation of the cardiac muscle cells.

It may be appreciated that a variety of energy delivery algorithms 152 may be used. In some embodiments, the algorithm 152 prescribes a signal having a waveform comprising a series of energy packets wherein each energy packet comprises a series of high voltage pulses. In such embodiments, the algorithm 152 specifies parameters of the signal such as energy amplitude (e.g., voltage) and duration of applied energy, which is comprised of the number of packets, number of pulses within a packet, and the fundamental frequency of the pulse sequence, to name a few. Additional parameters may include switch time between polarities in biphasic pulses, dead time between biphasic cycles, and rest time between packets, which will be described in more detail in later sections. There may be a fixed rest period between packets, or packets may be gated to the cardiac cycle and are thus variable with the patient's heart rate. There may be a deliberate, varying rest period algorithm or no rest period may also be applied between packets. A feedback loop based on sensor information and an auto-shutoff specification, and/or the like, may be included.

Figure 13:
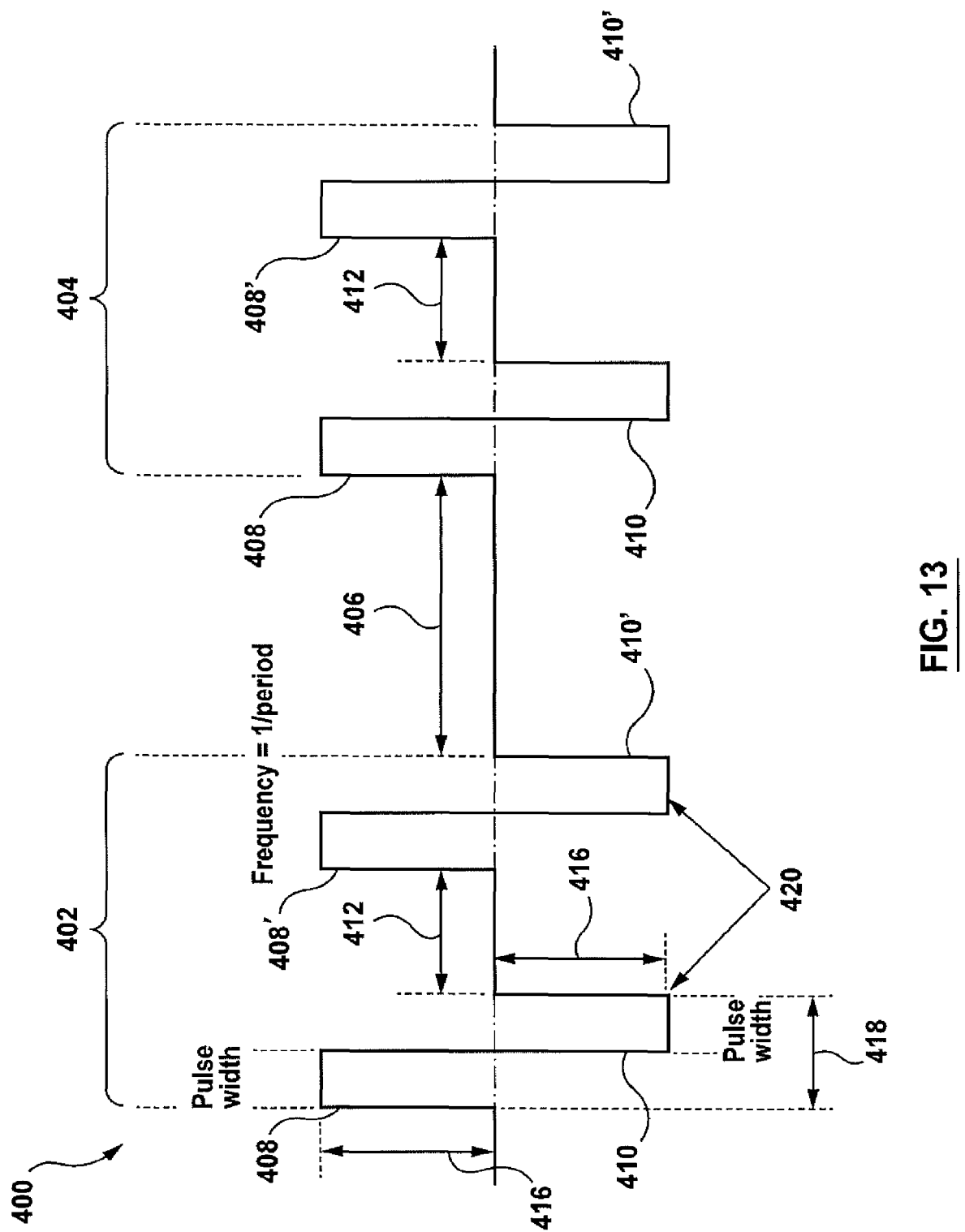
FIG. 13 illustrates an embodiment of a waveform of a signal provided by an energy delivery algorithm.

FIG. 13 illustrates an embodiment of a waveform 400 of a signal prescribed by an energy delivery algorithm 152. Here, two packets are shown, a first packet 402 and a second packet 404, wherein the packets 402, 404 are separated by a rest period 406. In this embodiment, each packet 402, 404 is comprised of a first biphasic cycle (comprising a first positive pulse peak 408 and a first negative pulse peak 410) and a second biphasic cycle (comprising a second positive pulse peak 408' and a second negative pulse peak 410'). The first and second biphasic pulses are separated by dead time 412 (i.e., a pause) between each pulse. In this embodiment, the biphasic pulses are symmetric so that the set voltage 416 is the same for the positive and negative peaks. Here, the biphasic, symmetric waves are also square waves such that the magnitude and time of the positive voltage wave is approximately equal to the magnitude and time of the negative voltage wave. When using a bipolar configuration, portions of the airway wall W cells facing the negative voltage wave undergo cellular depolarization in these regions, where a normally negatively charged cell membrane region briefly turns positive. Conversely, portions of the airway wall W cells facing the positive voltage wave undergo hyperpolarization in which the cell membrane region's electric potential becomes extremely negative. It may be appreciated that in each positive or negative phase of the biphasic pulse, portions of the airway wall W cells will experience the opposite effects. For example, portions of cell membranes facing the negative voltage will experience depolarization, while the portions 180° to this portion will experience hyperpolarization. In some embodiments, the hyperpolarized portion faces the dispersive or return electrode 140.

A. Voltage

The voltages used and considered may be the tops of square-waveforms, may be the peaks in sinusoidal or sawtooth waveforms, or may be the RMS voltage of sinusoidal or sawtooth waveforms. In some embodiments, the energy is delivered in a monopolar fashion and each high voltage pulse or the set voltage 416 is between about 500 V to 10,000 V, particularly about 500 V to 5000 V, about 500 V to 4000 V, about 1000 V to 4000 V, about 2500 V to 4000V, about 2000 to 3500, about 2000 V to 2500V, about 2500 V to 3500 V, including all values and subranges in between including about 500 V, 1000 V, 1500 V, 2000 V, 2500 V, 3000 V, 3500 V, 4000 V. In some embodiments, each high voltage pulse is in range of approximately 1000 V to 2500 V which can penetrate the airway wall W in particular parameter combinations so as to treat or affect particular cells somewhat shallowly, such as epithelial cells. In some embodiments, each high voltage pulse is in the range of approximately 2500 V to 4000 V which can penetrate the airway W in particular parameter combinations so as to treat or affect particular cells somewhat deeply positioned, such as submucosal cells or smooth muscle cells.

It may be appreciated that the set voltage 416 may vary depending on whether the energy is delivered in a monopolar or bipolar fashion. In bipolar delivery, a lower voltage may be used due to the smaller, more directed electric field. In some embodiments, the energy is delivered in a bipolar fashion and each pulse is in the range of approximately 100 V to 1900 V, particularly 100 V to 999 V, more particularly approximately 500 V to 800 V, such as 500 V, 550 V, 600 V, 650 V, 700 V, 750 V, 800 V. In other embodiments, the energy is delivered in a bipolar fashion and each pulse is between approximately 50 and 5000 volts, including 250 to 1500 volts.

The bipolar voltage selected for use in therapy is dependent on the separation distance of the electrodes, whereas the monopolar electrode configurations that use a distant dispersive pad electrode may be delivered with less consideration for exact placement of the catheter electrode and dispersive electrode placed on the body. In monopolar electrode embodiments, larger voltages are typically used due to the dispersive behavior of the delivered energy through the body to reach the dispersive electrode, on the order of 10 cm to 100 cm effective separation distance. Conversely, in bipolar electrode configurations, the relatively close active regions of the electrodes, on the order of 0.5 mm to 10 cm, including 1 mm to 1 cm, results in a greater influence on electrical energy concentration and effective dose delivered to the tissue from the separation distance. For instance, if the targeted voltage-to-distance ratio is 3000 V/cm to evoke the desired clinical effect at the appropriate tissue depth (1.3 mm), if the separation distance is changed from 1 mm to 1.2 mm, this would result in a necessary increase in treatment voltage from 300 to about 360 V, a change of 20%.

B. Frequency

The number of biphasic cycles per second of time is the frequency. In some embodiments, biphasic pulses are utilized to reduce undesired muscle stimulation, particularly cardiac muscle stimulation. In other embodiments, the pulse waveform is monophasic, and there is no clear inherent frequency, and instead a fundamental frequency may be considered by doubling the monophasic pulse length to derive the frequency. In some embodiments, the signal has a frequency in the range 100 kHz-1 MHz, more particularly 100 kHz-1000 kHz. In some embodiments, the signal has a frequency in the range of approximately 100-600 kHz which typically penetrates the airway W so as to treat or affect particular cells somewhat deeply positioned, such as submucosal cells or smooth muscle cells. In some embodiments, the signal has a frequency in range of approximately 600 kHz-1000 kHz or 600 kHz-1 MHz which typically penetrates the airway wall W so as to treat or affect particular cells somewhat shallowly, such as epithelial cells. It may be appreciated that at some voltages, frequencies at or below 300 kHz may cause undesired muscle stimulation. Therefore, in some embodiments, the signal has a frequency in the range of 400-800 kHz or 500-800 kHz, such as 500 kHz, 550 kHz, 600 kHz, 650 kHz, 700 kHz, 750 kHz, 800 kHz. In particular, in some embodiments, the signal has a frequency of 600 kHz. In addition, cardiac synchronization is typically utilized to reduce or avoid undesired cardiac muscle stimulation during sensitive rhythm periods. It may be appreciated that even higher frequencies may be used with components which minimize signal artifacts.

C. Voltage-Frequency Balancing

The frequency of the waveform delivered may vary relative to the treatment voltage in synchrony to retain adequate treatment effect. Such synergistic changes would include the decrease in frequency, which evokes a stronger effect, combined with a decrease in voltage, which evokes a weaker effect. For instance, in some cases the treatment may be delivered using 3000 V in a monopolar fashion with a waveform frequency of 800 kHz, while in other cases the treatment may be delivered using 2000 V with a waveform frequency of 400 kHz.

When used in opposing directions, the treatment parameters may be manipulated in a way that makes it too effective, which may increase muscle contraction likelihood or risk effects to undesirable tissues, such as cartilage for airway treatments. For instance, if the frequency is increased and the voltage is decreased, such as the use of 2000 V at 800 kHz, the treatment may not have sufficient clinical therapeutic benefit. Opposingly, if the voltage was increased to 3000 V and frequency decreased to 400 kHz, there may be undesirable treatment effect extent to cartilage tissues or other collateral sensitive tissues. In some cases, the overtreatment of these undesired tissues could result in morbidity or safety concerns for the patient.

D. Packets

As mentioned, the algorithm 152 prescribes a signal having a waveform comprising a series of energy packets wherein each energy packet comprises a series of high voltage pulses. The cycle count 420 is half the number of pulses within each biphasic packet. Referring to FIG. 13, the first packet 402 has a cycle count 420 of two (i.e. four biphasic pulses). In some embodiments, the cycle count 420 is set between 1 and 100 per packet, including all values and subranges in between. In some embodiments, the cycle count 420 is up to 5 pulses, up to 10 pulses, up to 25 pulses, up to 40 pulses, up to 60 pulses, up to 80 pulses, up to 100 pulses, up to 1,000 pulses or up to 2,000 pulses, including all values and subranges in between.

The packet duration is determined by the cycle count. The higher the cycle count, the longer the packet duration and the larger the quantity of energy delivered. In some embodiments, packet durations are in the range of approximately 50 to 100 microseconds, such as 50 µs, 60 µs, 70 µs, 80 µs, 90 µs or 100 µs. In other embodiments, the packet durations are in the range of approximately 100 to 1000 microseconds, such as 150 µs, 200 µs, 250 µs, 500 µs, or 1000 µs.

The number of packets delivered during treatment, or packet count, may include 1 packet, 2 packets, 3 packets, 4 packets, 5 packets, 10 packets, 15 packets, 20 packets, 50 packets, 100 packets, 1,000 packets, up to 5 packets, up to 10 packets, up to 15 packets, up to 20 packets, up to 100 packets, or up to 1000 packets, including all values and subranges in between. In some embodiments, 5 packets are delivered, wherein each packet has a packet duration of 100 microseconds and a set voltage of 2500 V. In some embodiments, 5 to 10 packets are delivered, wherein each packet has a packet duration of 100 microseconds and a set voltage of 2500 V, which results in a treatment effect that has increased intensity and uniformity. In some embodiments, less than 20 packets, wherein each packet has a packet duration of 100 microseconds and a set voltage of 2500 V, are delivered to avoid affecting the cartilage layer CL. In some embodiments, a total energy-delivery duration between 0.5 to 100 milliseconds at a set voltage of 2500 V can be optimal for the treatment effect.

E. Rest Period

In some embodiments, the time between packets, referred to as the rest period 406, is set between about 0.1 seconds and about 5 seconds, including all values and subranges in between. In other embodiments, the rest period 406 ranges from about 0.001 seconds to about 10 seconds, including all values and subranges in between. In some embodiments, the rest period 406 is approximately 1 second. In particular, in some embodiments the signal is synced with the cardiac rhythm so that each packet is delivered synchronously within a designated period relative to the heartbeats, thus the rest periods coincide with the heartbeats. In other embodiments wherein cardiac synchronization is utilized, the rest period 406 may vary, as the rest period between the packets can be influenced by cardiac synchronization, as will be described in later sections.

F. Switch Time and Dead Time

Figure 13A:
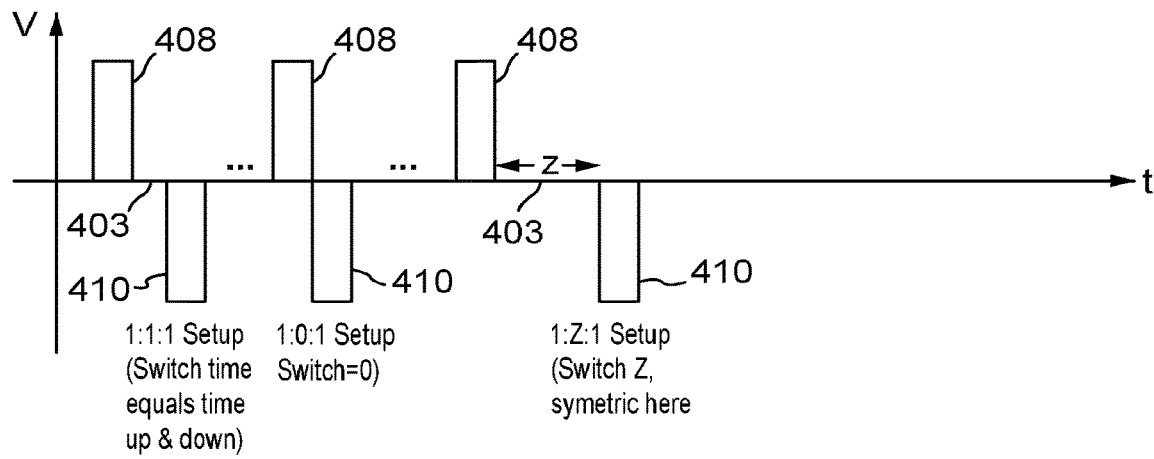
FIG. 13A illustrates various examples of biphasic pulses (comprising a positive peak and a negative peak) having a switch time therebetween.
Figure 13B:
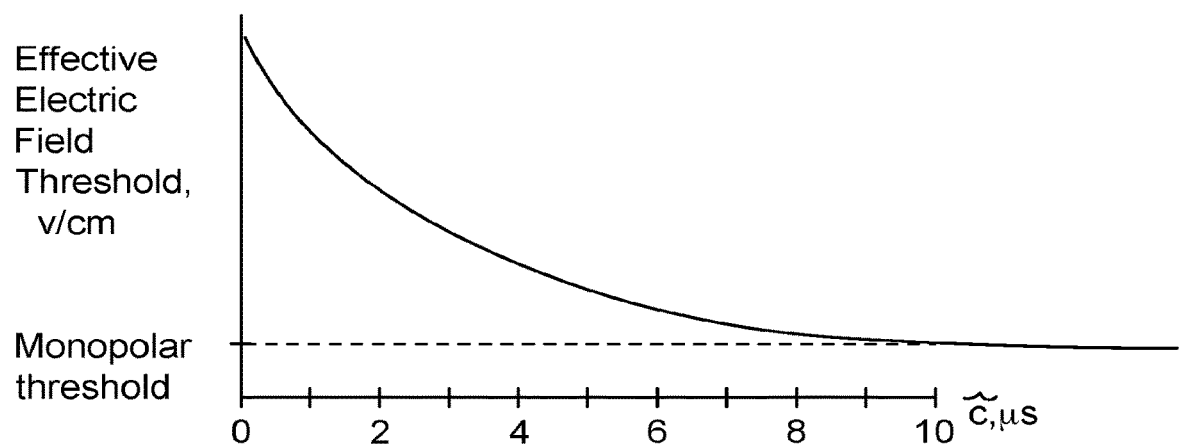
FIG. 13B illustrates the relationship between effective electric field threshold and switch time.

A switch time is a delay or period of no energy that is delivered between the positive and negative peaks of a biphasic pulse, as illustrated in FIGS. 13A-13B. FIG. 13A illustrates various examples of biphasic pulses (comprising a positive peak 408 and a negative peak 410) having a switch time 403 therebetween (however when the switch time 403 is zero, it does not appear). In some embodiments, the switch time ranges between about 0 to about 1 microsecond, including all values and subranges in between. In other embodiments, the switch time ranges between 1 and 20 microseconds, including all values and subranges in between. FIG. 13B illustrates the relationship between effective electric field threshold and switch time.

Delays may also be interjected between each cycle of the biphasic pulses, referred as "dead-time". Dead time occurs within a packet, but between biphasic pulses. This is in contrast to rest periods which occur between packets. In some embodiments, the dead time 412 is set between about 0 and about 500 nanoseconds, including 0 to 20 microseconds, including all values and subranges in between. In other embodiments, the dead time 412 is in a range of approximately 0 to 10 microseconds, or about 0 to about 100 microseconds, or about 0 to about 100 milliseconds, including all values and subranges in between. In some embodiments, the dead time 412 is in the range of 0.2 to 0.3 microseconds. Dead time may also be used to define a period between separate, monophasic, pulses within a packet.

Delays, such as switch times and dead times, are introduced to a packet to reduce the effects of biphasic cancellation within the waveform. Biphasic cancellation or bipolar cancellation is a term used to refer to the reduced induction of cellular modulation in response to biphasic waveforms versus monophasic waveforms, particularly when switch times and dead times are small, such as below 10 µs. One explanation for this phenomenon is provided here, though it may be appreciated that there are likely other biological, physical, or electrical characteristics or alterations that result in the reduced modulation from biphasic waveforms. When cells are exposed to the electromotive force induced by the electric field presence, there is electrokinetic movement of ions and solutes within the intracellular and extracellular fluids. These charges accumulate at dielectric boundaries such as cell and organelle membranes, altering the resting transmembrane potentials (TMPs). When the electric field is removed, the driving force that generated the manipulated TMPs is also eliminated, and the normal biotransport and ionic kinetics operating with concentration gradients begin to restore normative distributions of the solutes. This induces a logarithmic decay of the manipulated TMP on the membranes. However, if rather than eliminating the electric field, the electric field polarity is retained but with a reversed polarity, then there is a new electromotive force actively eliminating the existing TMP that was induced, followed by the accumulation of a TMP in the opposite polarity. This active depletion of the initially manipulated TMP considerably restricts the downstream effects cascade that may occur to the cell, weakening the treatment effect from the initial electric field exposure. Further, where the subsequent electric field with reversed polarity must first "undo" the original TMP manipulation generated, and then begin accumulating its own TMP in the opposite polarity; the final TMP reached by the second phase of the electric field is not as strong as the original TMP, assuming identical durations of each phase of the cycle. This reduces the treatment effects generated from each phase of the waveform resulting in a lower treatment effect than that generated by either pulse in the cycle would achieve alone. This phenomenon is referred as biphasic cancellation. For packets with many cycles, this pattern is repeated over the entire set of cycles and phase changes within the cycles for the packet. This dramatically limits the effect from the treatment. When cell behavior is modulated as a result of the pulsed electric fields by mechanisms other than purely transmembrane potential manipulation, it may be appreciated that the effects of biphasic cancellation are less pronounced, and thus the influence of switch times and dead times on treatment outcome are reduced.

Thus, in some embodiments, the influence of biphasic cancellation is reduced by introducing switch time delays and dead time. In some instances, the switch time and dead time are both increased together to strengthen the effect. In other instances, only switch time or only dead time are increased to induce this effect.

It may be appreciated that typically appropriate timing is for the relaxation of the TMP to complete after 5× the charging time-constant, τ. For most cells, the time constant may be approximated as 1 µs. Thus, in some embodiments the switch time and the dead time are both set to at least 5 µs to eliminate biphasic cancellation. In other embodiments, the reduction in biphasic cancellation may not require complete cell relaxation prior to reversing the polarity, and thus the switch time and the dead time are both set at 0.5 µs to 2 µs. In other embodiments, the switch time and the dead time are set to be the same length as the individual pulse lengths, since further increases in these delays may only offer diminishing returns in terms of increased treatment effect and the collateral increase in muscle contraction. In this way, the combination of longer-scale pulse durations (>500 ns) and stacked pulse cycles with substantial switch time and dead time delays, it is possible to use biphasic waveforms without the considerably reduced treatment effect that occurs due to biphasic cancellation. In some cases, the tuning of these parameters may be performed to evoke stronger treatment effects without a comparably proportional increase in muscle contraction. For example, using 600 kHz waveform with switch time=dead time=1.66 us (2× the duration as the pulses), may be used to retain the reduction in muscle contraction versus monophasic pulse waveforms, but with the retention of stronger treatment effects.

In some embodiments, the switch time duration is adjusted such that the degree of therapy effect relative to distant cell effects is optimized for the target of the therapy. In some embodiments, the switch time duration is minimized to decrease distant muscle cell contractions, with lesser local therapy effect. In other embodiments, the switch time duration is extended to increase the local therapy effect, with potential additional distant muscle cell contractions. In some embodiments, the switch time or dead time duration are extended to increase the local therapy effect, and the use of neuromuscular paralytics are employed to control the resulting increase in muscle contraction. In some embodiments, switch time duration is 10 ns to 2 µs, while in other embodiments, the switch time duration is 2 µs to 20 µs. In some instances, when cell modulation is targeted in a way where transmembrane potential manipulation is not the primary mechanism needed to evoke the targeted treatment effects, the switch time and dead time delays are minimized to less than 0.1 µs or to 0 µs. This elimination of delays minimizes the peripheral, non-targeted treatment effects such as skeletal muscle contraction or cardiac muscle action potential and contraction, but will not alter the treatment effect intensity at the targeted site.

Another benefit of utilizing switch time and the dead time delays to increase treatment effects for biphasic waveforms is a reduction in generator demands, whereby the introduction of pauses will enable stronger treatment effects without requiring asymmetric/unbalanced pulse waveforms. In this case, unbalanced waveforms are described as those that are monophasic, or have an unbalanced duration or voltage or combination in one polarity relative to the other. In some cases, unbalanced means that the integral of the positive portions of the waveform are not equal to the integral of the negative portions of the waveform. Generators capable of delivering unbalanced waveforms have a separate set of design considerations that are accounted for thereby increasing potential generator complexity.

G. Waveforms

Figure 14:
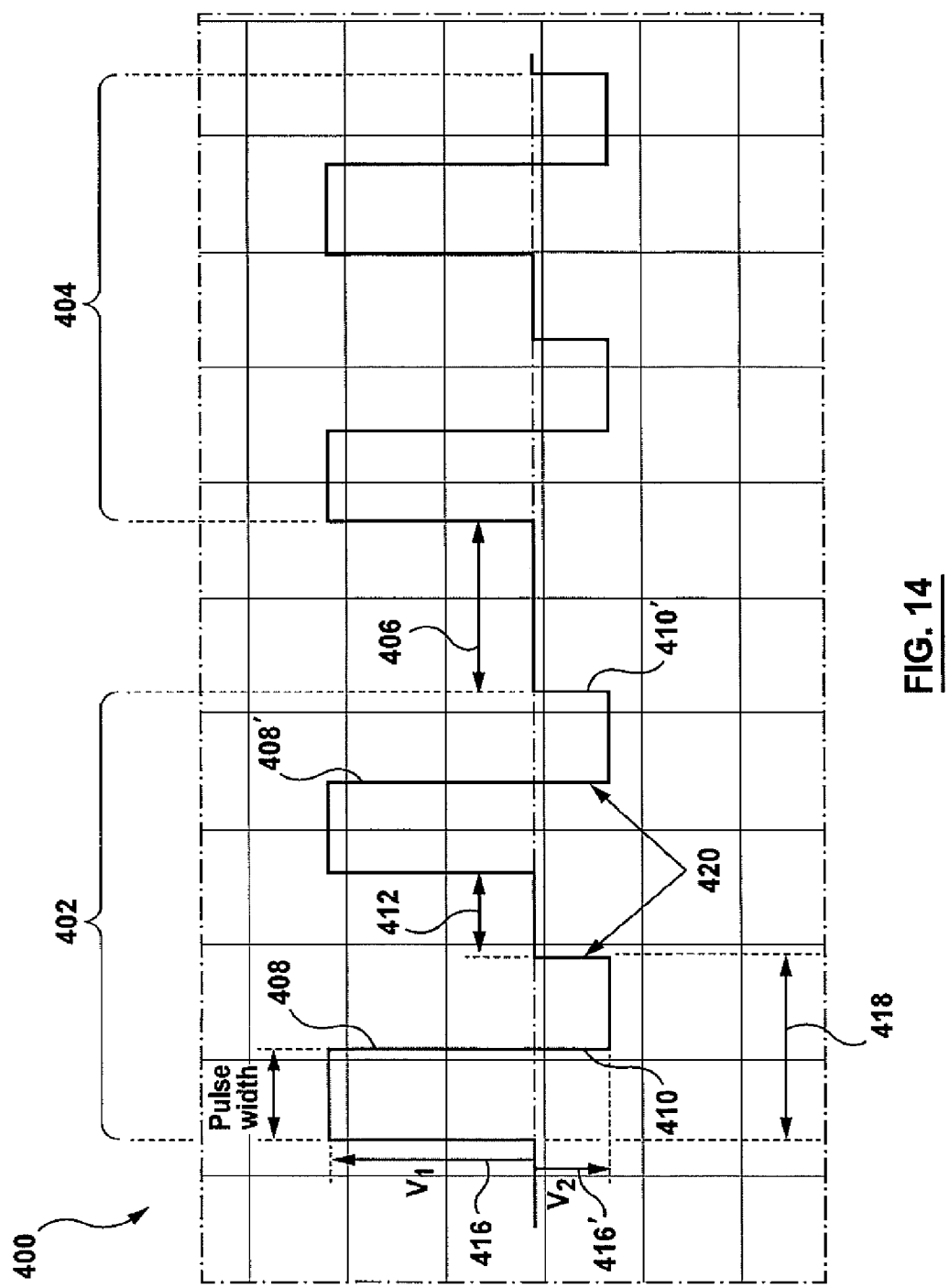
FIG. 14 illustrates an example waveform of another energy delivery algorithm.
Figure 14A:
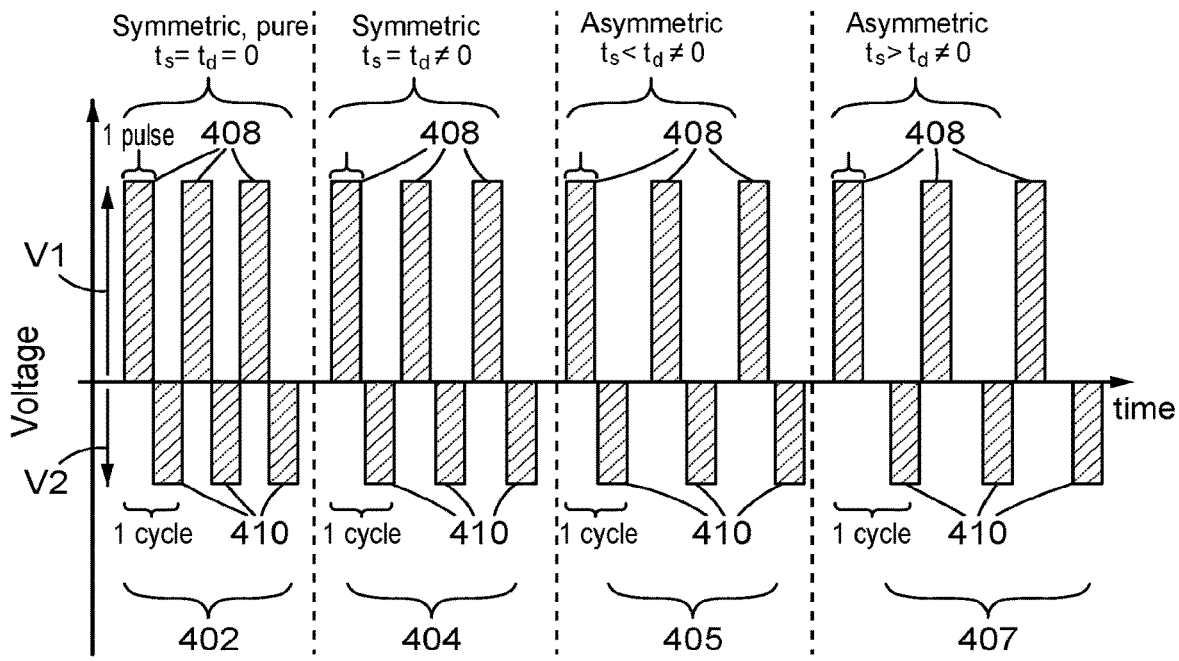
FIGS. 14A-14B illustrates further examples of waveforms having unequal voltages.

FIG. 13 illustrates an embodiment of a waveform 400 having symmetric pulses such that the voltage and duration of pulse in one direction (i.e., positive or negative) is equal to the voltage and duration of pulse in the other direction. FIG. 14 illustrates an example waveform 400 prescribed by another energy delivery algorithm 152 wherein the waveform 400 has voltage imbalance. Here, two packets are shown, a first packet 402 and a second packet 404, wherein the packets 402, 404 are separated by a rest period 406. In this embodiment, each packet 402, 404 is comprised of a first biphasic cycle (comprising a first positive pulse peak 408 having a first voltage V1 and a first negative pulse peak 410 having a second voltage V2) and a second biphasic cycle (comprising a second positive pulse peak 408' having first voltage V1 and a second negative pulse peak 410' having a second voltage V2). Here the first voltage V1 is greater than the second voltage V2. The first and second biphasic cycles are separated by dead time 412 between each pulse. Thus, the voltage in one direction (i.e., positive or negative) is greater than the voltage in the other direction so that the area under the positive portion of the curve does not equal the area under the negative portion of the curve. This unbalanced waveform may result in a more pronounced treatment effect as the dominant positive or negative amplitude leads to a longer duration of same charge cell membrane charge potential. In this embodiment, the first positive peak 408 has a set voltage 416 (V1) that is larger than the set voltage 416' (V2) of the first negative peak 410. FIG. 14A illustrates further examples of waveforms having unequal voltages. Here, four different types of packets are shown in a single diagram for condensed illustration. The first packet 402 is comprised of pulses having unequal voltages but equal pulse widths, along with no switch times and dead times. Thus, the first packet 402 is comprised of four biphasic pulses, each comprising a positive peak 408 having a first voltage V1 and a negative peak 410 having a second voltage V2). Here the first voltage V1 is greater than the second voltage V2. The second packet 404 is comprised of pulses having unequal voltages but symmetric pulse widths (as in the first pulse 402), with switch times equal to dead times. The third packet 405 is comprised of pulses having unequal voltages but symmetric pulse widths (as in the first pulse 402), with switch times that are shorter than dead times. The fourth packet 407 is comprised of pulses having unequal voltages but symmetric pulse widths (as in the first pulse 402), with switch times that are greater than dead times. It may be appreciated that in some embodiments, the positive and negative phases of biphasic waveform are not identical, but are balanced, where the voltage in one direction (i.e., positive or negative), is greater than the voltage in the other direction but the length of the pulse is calculated such that the area under the curve of the positive phase equals the area under the curve of the negative phase.

In some embodiments, imbalance includes pulses having pulse widths of unequal duration. In some embodiments, the biphasic waveform is unbalanced, such that the voltage in one direction is equal to the voltage in the other direction, but the duration of one direction (i.e., positive or negative) is greater than the duration of the other direction, so that the area under the curve of the positive portion of the waveform does not equal the area under the negative portion of the waveform.

Figure 14B:
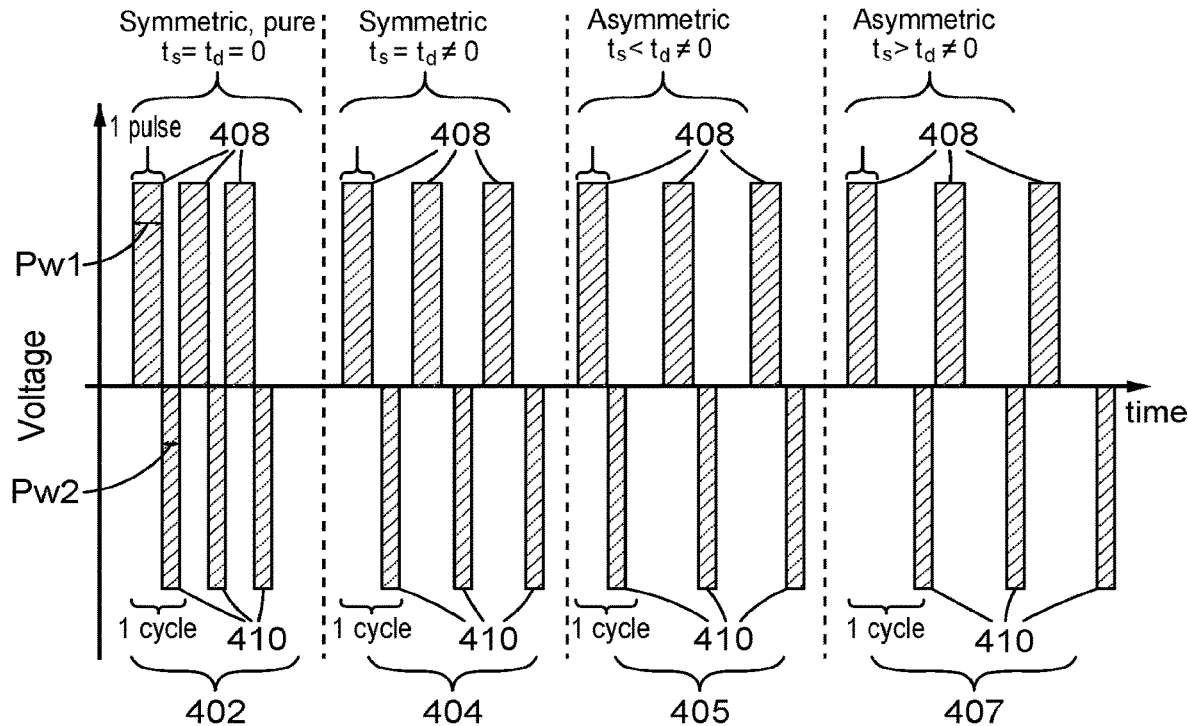

FIG. 14B illustrates further examples of waveforms having unequal pulse widths. Here, four different types of packets are shown in a single diagram for condensed illustration. The first packet 402 is comprised of pulses having equal voltages but unequal pulse widths, along with no switch times and dead times. Thus, the first packet 402 is comprised of four biphasic pulses, each comprising a positive peak 408 having a first pulse width PW1 and a negative peak 410 having a second pulse width PW2). Here the first pulse width PW1 is greater than the second pulse width PW2. The second packet 404 is comprised of pulses having equal voltages but unequal pulse widths (as in the first pulse 402), with switch times equal to dead times. The third packet 405 is comprised of pulses having equal voltages but unequal pulse widths (as in the first pulse 402), with switch times that are shorter than dead times. The fourth packet 407 is comprised of pulses having equal voltages but unequal pulse widths (as in the first pulse 402), with switch times that are greater than dead times.

Figure 15:
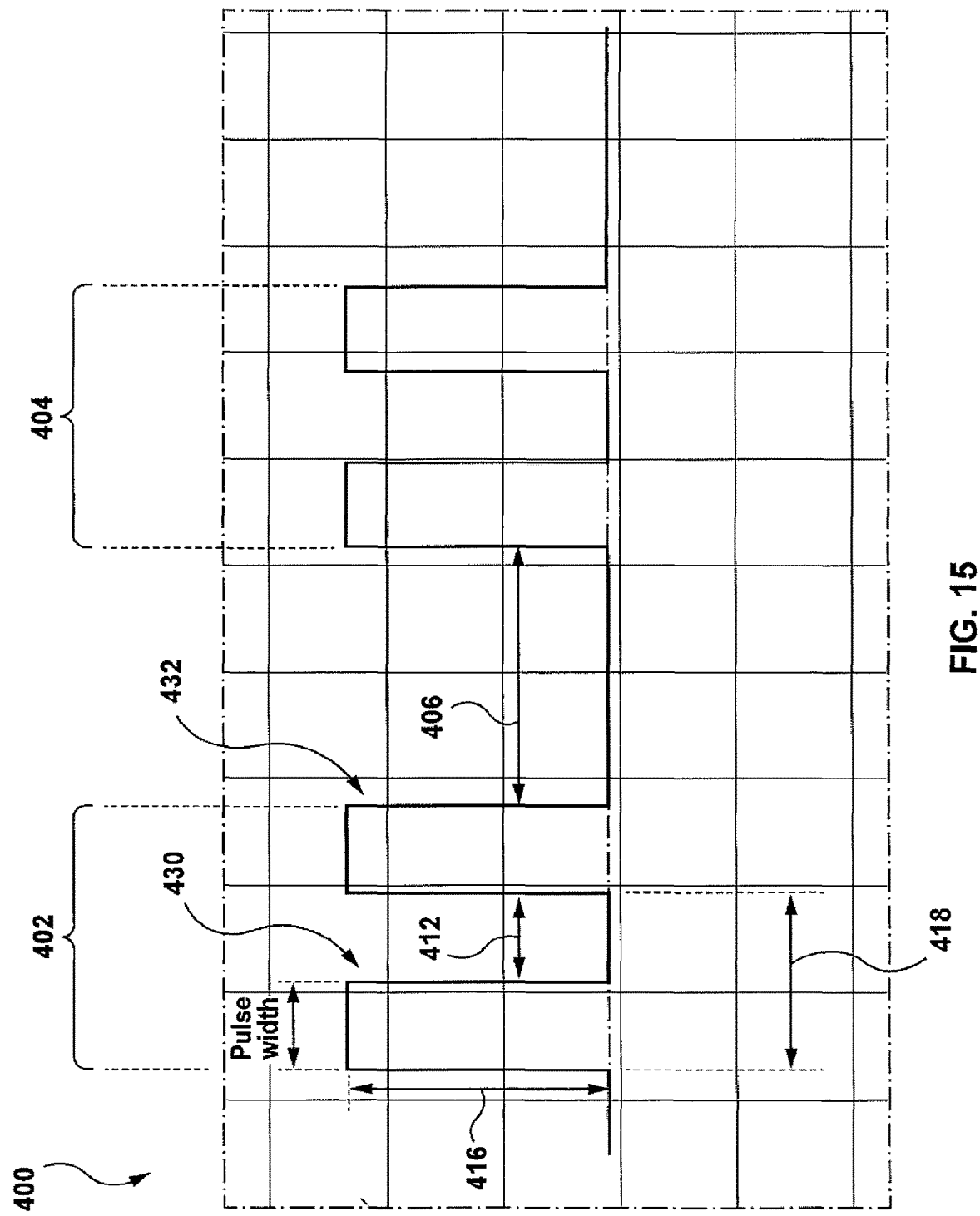
FIG. 15 illustrates an example waveform of another energy delivery algorithm.

FIG. 15 illustrates an example waveform 400 prescribed by another energy delivery algorithm 152 wherein the waveform is monophasic, a special case of imbalance whereby there is only a positive or only a negative portion of the waveform. Here, two packets are shown, a first packet 402 and a second packet 404, wherein the packets 402, 404 are separated by a rest period 406. In this embodiment, each packet 402, 404 is comprised of a first monophasic pulse 430 and a second monophasic pulse 432. The first and second monophasic pulses 430, 432 are separated by dead time 412 between each pulse. This monophasic waveform could lead to a more desirable treatment effect as the same charge cell membrane potential is maintain for longer durations. However, adjacent muscle groups will be more stimulated by the monophasic waveform, compared to a biphasic waveform.

Figure 15A:
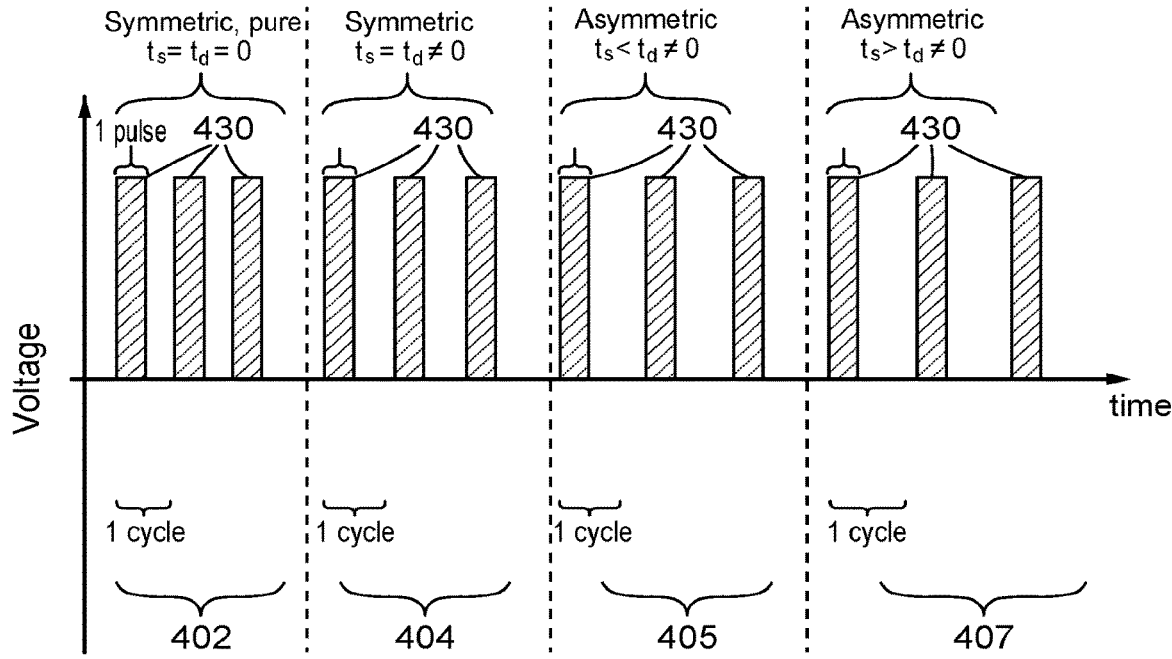
FIG. 15A illustrates further examples of waveforms having monophasic pulses.

FIG. 15A illustrates further examples of waveforms having monophasic pulses. Here, four different types of packets are shown in a single diagram for condensed illustration. The first packet 402 is comprised of pulses having identical voltages and pulse widths, with no switch times (because the pulses are monophasic) and a dead time equal to the active time. In some cases, there may be less dead time duration than the active time of a given pulse. Thus, the first packet 402 is comprised of three monophasic pulses 430, each comprising a positive peak. In instances where the dead time is equal to the active time, the waveform may be considered unbalanced with a fundamental frequency representing a cycle period of 2× the active time and no dead time. The second packet 404 is comprised of monophasic pulses 430 having equal voltages and pulse widths (as in the first packet 402), with larger dead times. The third packet 405 is comprised of monophasic pulses 430 having equal voltages and pulse widths (as in the first packet 402), and even larger dead times. The fourth packet 407 is comprised of monophasic pulses 430 having equal voltages and pulse widths (as in the first packet 402), with yet larger dead times.

Figure 15B:
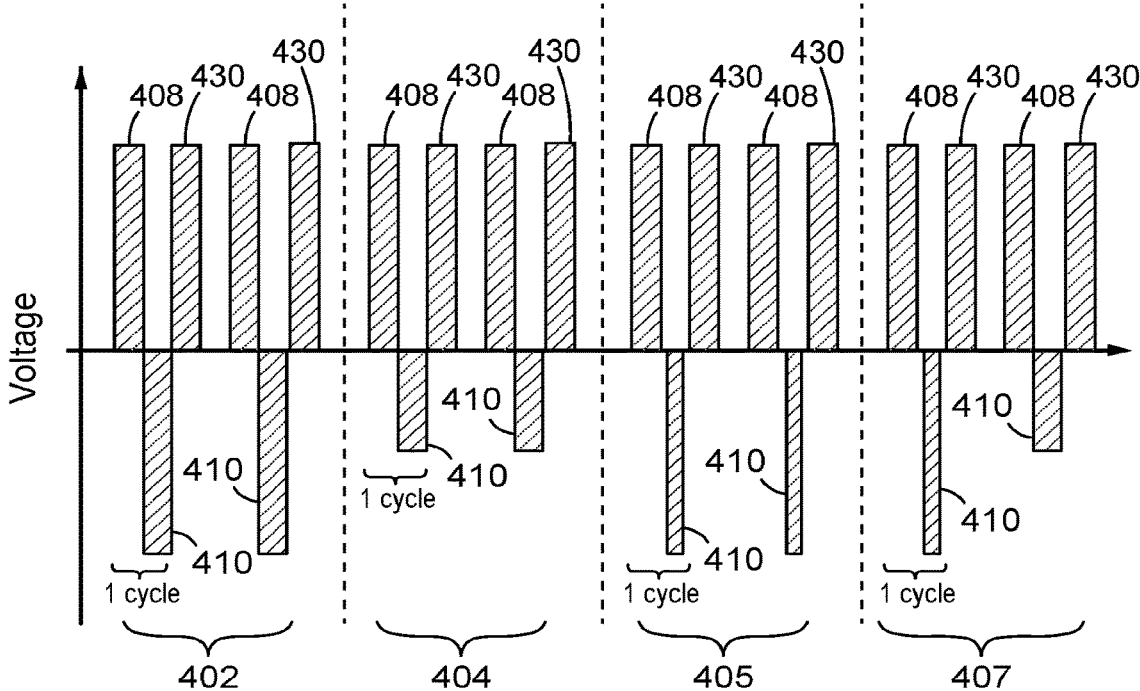
FIG. 15B illustrates examples of waveforms having phase imbalances achieved by delivering more than one pulse in one polarity before reversing to an unequal number of pulses in the opposite polarity.

In some embodiments, an unbalanced waveform is achieved by delivering more than one pulse in one polarity before reversing to an unequal number of pulses in the opposite polarity. FIG. 15B illustrates further examples of waveforms having such phase imbalances. Here, four different types of packets are shown in a single diagram for condensed illustration. The first packet 402 is comprised of four cycles having equal voltages and pulse widths, however, opposite polarity pulses are intermixed with monophasic pulses. Thus, the first cycle comprises a positive peak 408 and a negative peak 410. The second cycle is monophasic, comprising a single positive pulse with no subsequent negative pulse 430. This then repeats. The second packet 404 is comprised of intermixed biphasic and monophasic cycles (as in the first packet 402), however the pulses have unequal voltages. The third packet 405 is comprised of intermixed biphasic and monophasic cycles (as in the first packet 402), however the pulses have unequal pulse widths. The fourth packet 407 is comprised of intermixed biphasic and monophasic pulses (as in the first packet 402), however the pulses have unequal voltages and unequal pulse widths. Thus, multiple combinations and permutations are possible.

It should be noted that in each positive or negative phase of the biphasic cycle, portions of the airway wall W cells facing opposite sides of the energy will experience the opposite effects. In some embodiments, the hyperpolarized portion faces the dispersive or return electrode 140. It may further be appreciated that cells have a native negative resting electric transmembrane potential (TMP). Thus, changes to the native TMP on the side of the cell that promote a negative TMP will have an exaggerated absolute TMP. Conversely, the side of the cells that induce a positive TMP will have a lower reached absolute TMP induced. In either case, invocation of the desired therapeutic result may be reached by disturbing the native cell TMP, altering the cell behavior regardless of the final absolute TMP. Further, this difference may vary when considering the TMPs induced on the intracellular organelles.

Regarding the utility of unequal waveforms, the unbalanced TMP manipulation achieved reduces the implications of biphasic cancellation. There is a correlative relationship between the degree of imbalance, approaching a monopolar waveform as fully unbalanced, and the intensity of TMP manipulation. This will result in proportional relationship between the extent of treatment effect as well as the degree of muscle contraction. Thus, approaching more unbalanced waveforms will enable stronger treatment effects at the same voltage and frequency (if applicable) for biphasic waveforms than those produced from purely balanced biphasic waveforms. For example, the treatment effect evoked by a 830 ns-415 ns-830 ns-etc pulse length sequence within a packet will have the pulse constituting the second half of the cycle being half the duration of the original phase. This will restrict the induction of TMP manipulation by the second phase of the cycle, but will also generate less reversed TMP, enabling a stronger effect from the original polarity in the subsequent cycle at the original length. In another example, the "positive" portion of the waveform may be 2500V, with the "negative" portion being 1500V (2500-1250-2500-etc V), which will induce comparable effects on TMP polarization as that which was described for the pulse duration imbalance. In both of these cases, the manipulation of the opposing polarity intensity will result in cumulative stronger TMP manipulation for the positive pulse in the cycle. This will thus reduce the effects of biphasic cancellation and will generate stronger treatment effects than a protocol of 830-830-830 ns or 2500-2500-2500V, despite the deposition of less total energy delivered to the tissue. In this way, it is possible to deliver less total energy to the tissue but evoke the desired treatment effect when TMP manipulations are integral to the treatment mechanism of action.

Extended further, the fully unbalanced waveforms would not include any opposite polarity component but may still include brief portions of pulses delivered in just the positive phase. An example of this is a packet that contains 830 ns of positive polarity, an 830 ns pause with no energy delivered, followed by another 830 ns of positive polarity, and so forth. The same approach is true whether considering the pulse length imbalance or the voltage imbalance, as the absence of a negative pulse is equivalent to setting either of these parameters to zero for the "negative" portion.

However, appropriate treatment delivery considers that the advantages offered by biphasic waveforms, namely the reduction of muscle contraction, resulting from biphasic cancellation will likewise be reduced. Therefore, the appropriate treatment effect extent is balanced against the degree of acceptable muscle contraction. For example, an ideal voltage imbalance may be 2500-1000-2500- . . . V, or 2500-2000-2500- . . . V; or 830-100-830- . . . ns, or 830-500-830- . . . ns.

H. Waveform Shapes

Figure 16:
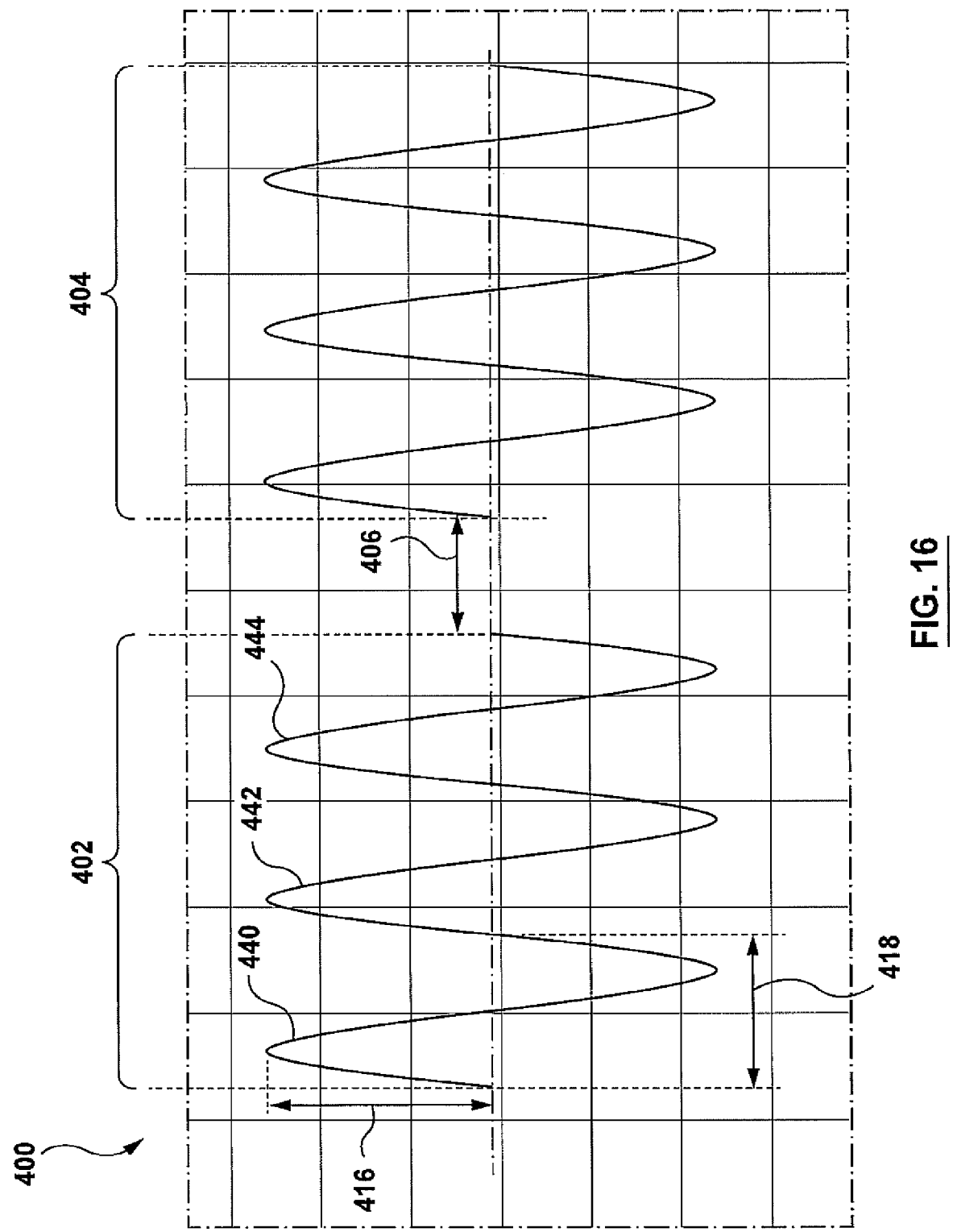
FIG. 16 illustrates an example waveform of another energy delivery algorithm.

FIG. 16 illustrates an example waveform 400 prescribed by another energy delivery algorithm 152 wherein the pulses are sinusoidal in shape rather than square. Again, two packets are shown, a first packet 402 and a second packet 404, wherein the packets 402, 404 are separated by a rest period 406. In this embodiment, each packet 402, 404 is comprised three biphasic pulses 440, 442, 444. And, rather than square waves, these pulses 440, 442, 444 are sinusoidal in shape. One benefit of a sinusoidal shape is that it is balanced or symmetrical, whereby each phase is equal in shape. Balancing may assist in reducing undesired muscle stimulation.

Energy delivery may be actuated by a variety of mechanisms, such as with the use of a button 164 on the catheter 102 or a foot switch 168 operatively connected to the generator 104. Such actuation typically provides a single energy dose. The energy dose is defined by the number of packets delivered and the voltage of the packets. Each energy dose delivered to the airway wall W maintains the temperature at or in the wall W below a threshold for thermal ablation, particularly thermal ablation of the basement membrane BM which comprises denaturing stromal proteins in the basement membrane or deeper submucosal extracellular protein matrices. In addition, the doses may be titrated or moderated over time so as to further reduce or eliminate thermal build up during the treatment procedure. Instead of inducing thermal damage, defined as protein coagulation, the energy dose provide energy at a level which induces biological mechanisms and cellular effects which ultimately lead to the regeneration of healthy tissue.

III. Biological Mechanisms & Cellular Effects

As mentioned previously, the algorithm provides energy to the airway walls W at a level which induces biological mechanisms and cellular effects while reducing or avoiding inflammation. Example biological mechanisms and cellular process are described herein but are not so limited.

The energy provided to the airway walls W may cause a variety of cellular effects which ultimately lead to the regeneration of healthy lung airway tissue. Example cellular effects include removal of particular cell types, such as by detachment of the cells from the airway wall W (so that the detached cells can be carried away by natural or induced methods) or by cell death (e.g. lysis and apoptosis). Other cellular effects include modification of particular cell types without removal, such as reprogramming the cells or conditioning the cells for improved agent uptake.

Figure 17:
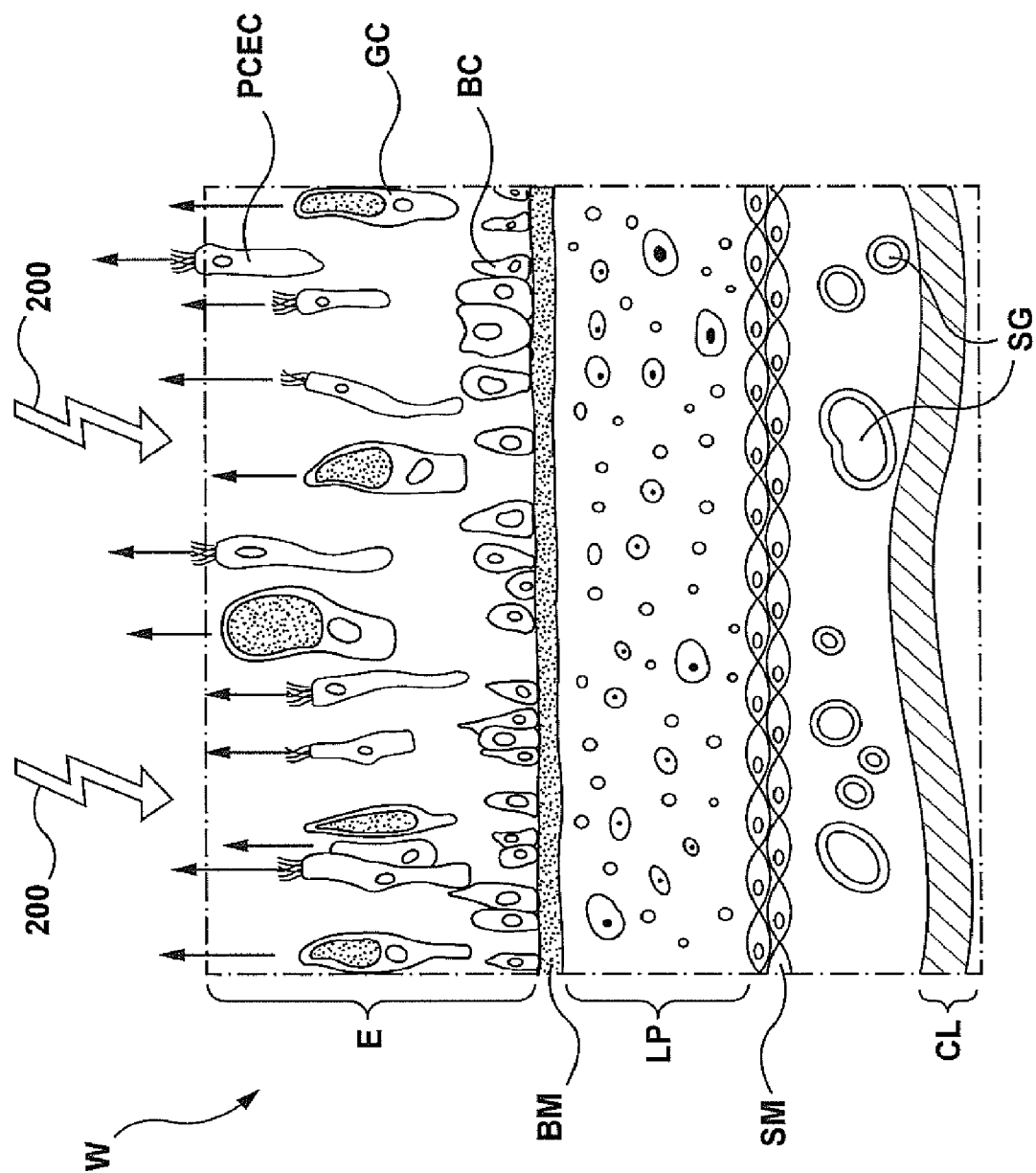
FIG. 17 illustrates an embodiment wherein delivered energy causes cells to be removed by detachment of the cells from the airway wall.

In some embodiments, particular cells are removed by detachment of the cells from the airway wall W. FIG. 17 illustrates an embodiment wherein energy (indicated by arrows 200) is provided to the airway wall W by the one or more energy delivery bodies. In this embodiment, the energy 200 has a targeted cell depth set to affect the epithelial layer E without extending beyond the basement membrane BM. The energy 200 is configured to cause particular epithelial cells, in this instance ciliated pseudostratified columnar epithelial cells PCEC and goblet cells GC, to detach from the remaining epithelial layer (e.g. basal cells BC) and/or the basement membrane BM. The detached cells are then free within the lung passageway, able to be removed by the natural process of expulsion or by interventional methods such as suction.

Figure 18:
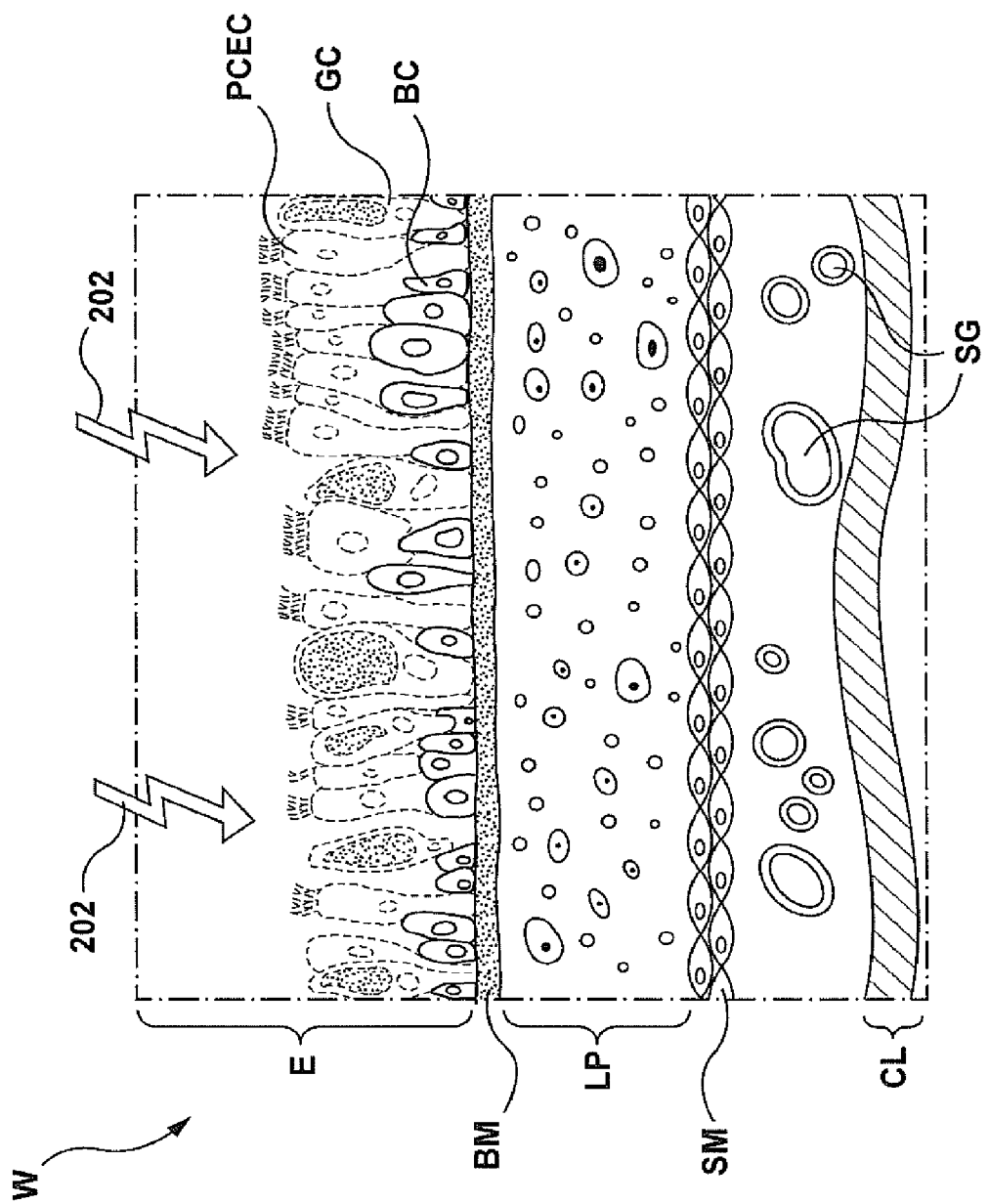
FIG. 18 illustrates an embodiment wherein delivered energy causes cells die, ultimately removing the cells from the airway wall.

In other embodiments, particular cells are removed by cell death, wherein the affected cells die by lysis or apoptosis, ultimately removing the cells from the airway wall W. FIG. 18 illustrates an embodiment wherein energy 202 is provided to the airway wall W by one or more energy delivery bodies and again, the energy 202 has a targeted cell depth set to affect the epithelial layer E without extending beyond the basement membrane BM. However, in this embodiment, the energy 202 is configured to cause particular epithelial cells, in this instance ciliated pseudostratified columnar epithelial cells PCEC and goblet cells GC, to die (as indicated by dashed line) while other cells (e.g. basal cells BC) remain. Cell death can be achieved by a variety of mechanisms. For example, in some embodiments, cell death occurs by destruction of the cell membrane. In such embodiments, the delivered energy may destroy the lipid bi-layer of the cell membrane such that the cell membrane is unable to maintain the barrier function of the cell. Without a plasma membrane, the cell cannot maintain proper intracellular concentrations of sodium, potassium, calcium and adenosine triphosphate (ATP). Consequently, the cell loses homeostasis and dies. In some embodiments, cell death occurs by disruption of intracellular organelles. In such embodiments, the delivered energy may permanently impede intracellular organelles from functioning. These organelles include endoplasmic reticulum, golgi apparatus, mitochondria, nucleus, nucleolus or others. Without the normal function of these intracellular organelles, the cell dies. It may be appreciated that in some instances, both the cell membrane and intracellular organelles are targeted by the delivered energy. Thus, if the delivered energy has only a partial effect on the cell membrane or intracellular organelles, the cumulative effect on both targets will ultimately yield cell death.

After cell death, the inflammatory cascade ensues. Cell fragments and intracellular contents signal leukocytes and macrophages to enter the affected area of the airway wall W. Over the course of hours to days, the dead cells are cleared from the area via phagocytosis. Unlike thermal ablation which damages the extracellular matrix, phagocytosis is limited to the cellular remains and not the collagen or matrix components of the extracellular matrix.

In some embodiments, particular cells are not removed, rather the targeted cells are modified or affected, such as reprogrammed. For example, in some embodiments, the ability of the goblet cells GC to secrete stored mucus or produce mucus at all is altered. Or, modification causes the cilia C on ciliated pseudostratified columnar epithelial cells PCEC to regain their function and better expel mucus up the airway. In other embodiments, ciliated pseudostratified columnar epithelial cells PCEC and goblet cells GC are unchanged but deeper structures are primarily affected such as a reduction in smooth muscle hypertrophy or neutralization of chronic inflammatory cells and eosinophils.

Whether the cells are removed or modified, the airway wall W regenerates and restores normal function. It may be appreciated that in some instances the epithelial cells may regenerate to their pre-treated state but the deeper cells, including the smooth muscle SM, eosinophils, submucosal glands SG, and chronic inflammatory cells, may be permanently reduced.

As mentioned previously, the algorithms may be tailored to affect tissue to a pre-determined depth and/or to target specific types of cells within the airway wall. For instance, various algorithms may specifically target the mucus layer M, the epithelial layer E, the basement membrane BM, the lamina propria LP, the smooth muscle cells SM, the submucosa, submucosal glands SG, nerves N, or various combinations of these. In one embodiment, the algorithm is configured to generate energy that penetrates the epithelial layer E of the airway wall W up to the basement membrane BM. Within this embodiment, a variety of different cell types may be targeted. For example, the energy may be configured to target the ciliated pseudostratified columnar epithelial cells PCEC and goblet cells GC causing their removal while leaving the basal cells BC behind. In such embodiments, the airway wall W may have abnormal and non-functioning ciliated pseudostratified columnar epithelial cells PCEC and hyperplastic, abnormal goblet cells GC causing mucus hypersecretion. The delivered energy causes the abnormal ciliated pseudostratified columnar epithelial cells PCEC and goblet cells GC to be removed, such as by cell death or detachment, leaving the basal cells BC intact along the basement membrane BM. Recall, the ciliated pseudostratified columnar epithelial cells PCEC and goblet cells GC are connected to each other by tight junctions TJ and adherens junctions AJ. In addition, the ciliated pseudostratified columnar epithelial cells PCEC and goblet cells GC are connected to the basal cells BC by desmosomes D. In some embodiments, the energy is configured so as to overcome the tight junctions TJ and adherens junctions AJ, and additionally the desmosomes D, allowing removal of ciliated pseudostratified columnar epithelial cells PCEC and goblet cells GC. Likewise, the energy may be configured to allow preservation of the hemidesmosomes H which connect the basal cells BC to the basement membrane 126. Thus, the basal cells BC remain intact.

Removal of ciliated pseudostratified columnar epithelial cells PCEC and goblet cells GC can reduce mucus production and mucus secretion by a variety of mechanisms. For example, such removal can mute the signaling mechanisms that lead to the expression of proteins found in mucin, thereby reducing mucus production. In particular, Muc5ac is a protein found in the mucin in the airway goblet cells GC that is encoded by the MUC5AC gene. There are several ligands and transcription factors that are involved in Muc5ac expression. Interleukin-13 binds to a receptor that includes the interleukin-4Rα subunit, activating Janus kinase 1 (Jak1), leading to the phosphorylation of Stat6. There is no consensus Stat6 binding site in the MUC5AC and Muc5ac promoter, but Stat6 activation leads to increased expression of SPDEF (SAM pointed domain-containing Ets transcription factor), which up-regulates multiple genes involved in mucous metaplasia, and inhibits expression of Foxa2, which negatively regulates Muc5ac. Several ligands bind ErbB receptors, including epidermal growth factor, transforming growth factor α, amphiregulin, and neuregulin, activating mitogen-activated protein kinases (MAPK). Hypoxia-inducible factor 1 (HIF-1) also can be activated downstream of ErbB receptors, and there is a conserved HIF-1 binding site in the proximal MUC5AC and Muc5ac promoter. Complement C3 and β2-adrenergic-receptor signaling, also amplify Muc5ac production, whereas transcription factors such as Sox2, Notch, E2f4, and Math primarily regulate development.

In the case of removal of ciliated pseudostratified columnar epithelial cells PCEC and goblet cells GC, by cell death or detachment, the signaling mechanisms that lead to Muc5ac expression are muted. Therefore, mucus is not produced, resulting in a decrease in mucus in the airway. This leads to benefits in patients with COPD (chronic bronchitis, emphysema), asthma, interstitial pulmonary fibrosis, cystic fibrosis, bronchiectasis, acute bronchitis and other pulmonary diseases or disorders.

Removal of such epithelial cells can also reduce mucus secretion by a variety of mechanisms. In particular, removal of the mucus producing goblet cells GC leaves no cells to secrete mucus into the airway. Secretion of mucus is induced by the molecular mechanism of mucin exocytosis. A mucin-containing secretory granule is docked to the plasma membrane by the interaction of a granule-bound Rab protein with an effector protein that acts as a tether to Munc18, which binds the closed conformation of Syntaxin anchored to the plasma membrane. Secretion is triggered when ATP binds to P2Y2 purinergic receptors (P2Y2R) coupled to Gq, activating phospholipase C (PLC), which generates the second messengers diacylglycerol (DAG) and inositol triphosphate (IP3). DAG activates Munc1314 to open Syntaxin so it can form a four-helix SNARE (soluble N-ethylmaleimide-sensitive factor attachment protein receptor) complex with SNAP-23 (synaptosomal-associated protein 23) and VAMP (vesicle-associated membrane protein), drawing together the granule and plasma membranes. IP3 induces the release of calcium from IP3 receptors (IP3R) in the endoplasmic reticulum (ER), activating Synaptotagmin to induce final coiling of the SNARE complex, which results in fusion of the membranes and release of the mucins.

With the removal of these epithelial cells, the signaling mechanisms that lead to mucin exocytosis are muted. Therefore, less mucus is secreted, resulting in a decrease in mucus in the airway. This leads to benefits in patients with COPD (chronic bronchitis, emphysema), asthma, interstitial pulmonary fibrosis, cystic fibrosis, bronchiectasis, acute bronchitis and other pulmonary diseases or disorders.

In some embodiments, the basal cells BC left on the basement membrane BM are able to regenerate normal goblet cells GC and normal ciliated pseudostratified columnar epithelial cells PCEC, thereby inducing reverse remodeling of the disease to reduce the mucus hypersecretion. In some embodiments, ciliated pseudostratified columnar epithelial cells PCEC additionally repopulate by migration from surrounding areas of the airway wall W to assist in regeneration of healthy tissue in the target area. The goblet cells GC typically regenerate at a lower level as compared to mild, moderate, or severe goblet cell hyperplasia that is present before the application of energy. The newly regenerated goblet cells GC are significantly less productive of mucus and the newly regenerated ciliated pseudostratified columnar epithelial cells PCEC regrow normally functioning cilia C, which more easily expel mucus M. Thus, healthy new target tissue can be regenerated within days of the procedure. This dramatically reduces symptoms of cough and mucus hypersecretion in patients which results in fewer and less severe exacerbations and improvement in quality of life.

It may be appreciated that in other embodiments, the energy may be configured to target the abnormal goblet cells CG causing their removal, such as by cell death or detachment, leaving behind the ciliated pseudostratified columnar epithelial cells PCEC and the basal cells BC. Removal of the abnormal goblet cells CG can reduce mucus production and/or mucus secretion by many of the mechanisms described above. Likewise, the energy may be configured to target the abnormal ciliated pseudostratified columnar epithelial cells PCEC causing their removal, such as by cell death or detachment, leaving behind the goblet cells CG and the basal cells BC. Likewise, the energy may be configured to target the abnormal basal cells BC causing their removal, such as by cell death or detachment, leaving behind the ciliated pseudostratified columnar epithelial cells PCEC and goblet cells GC. In any of these combinations of cell removal, it may be appreciated that the remaining cells may be additionally modified or affected by the delivered energy or by energy delivered subsequently. For example, abnormal goblet cells CG left behind may be modified so as to reduce mucus production and/or mucus secretion while remaining intact. It may also be appreciated that cell populations may be partially removed wherein some cells of a particular cell type are removed by the delivered energy while some remain, optionally modified.

In other embodiments, the algorithm is configured to generate energy that penetrates the epithelial layer E of the airway wall W up to and including the basement membrane BM. In such embodiments, changes to the epithelial layer E may occur as described above. Additionally, the basement membrane BM may be affected by the delivered energy so as to assist in remodeling the airway wall W to a healthy state. In some embodiments, the basement membrane BM is altered so as to stabilize or reduce the thickness of the basement membrane BM. Basement membrane BM thickening is a feature of many pulmonary diseases, including chronic bronchitis and asthma. Thus, the delivered energy may target the basement membrane BM so as halt or reverse such thickening. In some embodiments, such altering of the basement membrane BM affects the ability of cells, such as neutrophils, and inflammatory molecules, such as cytokines, to cross the basement membrane BM, thus assisting in regeneration of a healthy airway wall W.

In some embodiments, the algorithm is configured to generate energy that penetrates the epithelial layer E of the airway wall W and beyond the basement membrane BM. The position of various layers of the airway wall W beyond the basement membrane BM may vary due to variations in the anatomy along the lung passageways. For example, the position of the smooth muscle layer SM may vary along the length of the lung passageway, ranging from adjacent to the basement membrane BM to below the lamina propria LP. Thus, energy delivery may be titrated to target select layers of the airway wall W for a particular lung passageway segment. For example, the algorithm may be chosen or adjusted to affect the smooth muscle layer SM at its particular location. Smooth muscle hypertrophy is a feature of many pulmonary diseases, including chronic bronchitis, asthma and several other airway diseases resulting in airway hyperreactivity. In some embodiments, the delivered energy induces cell death of smooth muscle cells. This may reduce airway hyperreactivity and cause desired bronchodilation.

In some embodiments, the algorithm is chosen or adjusted to affect the submucosal glands SG. Submucosal glands overproduce and hypersecrete mucus in diseased airways. In some embodiments, the delivered energy induces cell death of submucosal glands SG. A reduction in submucosal glands SG may lead to less mucus in the airways and improvement in patient outcomes.

In some embodiments, the algorithm is chosen or adjusted so that the delivered energy affects the lamina propria LP. The lamina propria LP is comprised of loose connective tissue. The connective tissue and matrix architecture of the lamina propria LP is very compressible and elastic which allows expansion of the lung passageways. In addition, the loose structure allows for the presence of many cell types. The cell population of the lamina propria LP is variable and can include, for example, fibroblasts, lymphocytes, plasma cells, macrophages, eosinophilic leukocytes, and mast cells. Patients with airway disease often have chronic inflammation, specifically increased populations of lymphocytes and macrophages. In some embodiments, the delivered energy reduces the quantity of inflammatory cells, particularly lymphocytes, macrophages and/or eosinophils, thus reducing inflammation. Such energy removes, such as by cell death, cells from the lamina propria LP while maintaining the extracellular matrix. By maintaining the matrix architecture, stem cells and/or other cells are able to repopulate the matrix forming a healthy tissue. This is in contrast to fibrosis or other scar forming mechanisms wherein the layers of the airway wall W, including the extracellular matrix, are permanently changed, such as by melting or collapsing the layers together. In addition, the cartilage layer CL is not injured so as to maintain the structural integrity of the airway and prevent collapse.

Thus, it may be appreciated that one or more algorithms may be used to provide energy to affect one or more layers of the airway wall W. The energy may penetrate to a particular depth within the airway wall W, affecting numerous layers extending from the surface of the wall W to the particular depth. Or, the energy may be configured to affect cells at a particular depth without affecting surrounding layers. The affects may include cell removal, such as by cell death or detachment, or modification of the cell, such as to change particular functioning of the cell. In some instances, only a portion of cells of the same type or in the same layer may be affected by the delivered energy. Optionally, additional energy, either utilizing the same or different algorithm, may be delivered to affect a larger portion or all of the cells of the same type or in the same layer. Or, additional energy, either utilizing the same or different algorithm, may be delivered to increase the affect. For example, additional energy may result in cell removal of previously modified cells. Still further, additional energy, either utilizing the same or different algorithm, may be delivered to affect a different portion or depth of the airway wall.

The actual mechanisms by which the cells are removed or modified may vary depending on the algorithm 152, energy delivery bodies 108, and patient anatomy, to name a few. In some embodiments, cells are removed (e.g. detached) by dielectrophoresis.

Dielectrophoresis describes the movement of particles under the influence of applied electric fields which are non-uniform. The dielectrophoretic motion is determined by the magnitude and polarity of the charges induced in a particle by the applied field. The dipole moment induced in a particle can be represented by the generation of equal and opposite charges at the particle boundary. Since this induced charge is not uniformly distributed over the particle surface, it creates a macroscopic dipole. Since the applied field is non-uniform, the local electric field and resulting force on each side of the particle will be different. Thus, depending on the relative polarizability of the particle with respect to the surrounding medium, it will be induced to move either towards the inner electrode and the high-electric-field region (positive dielectrophoresis) or towards the outer electrode, where the field is weaker (negative dielectrophoresis). The dielectrophoretic force is a function of cell volume and polarization, the conductivity and permittivity of the surrounding media, and the frequency and spatial gradients of the magnitude of the generated electric field.

In some embodiments, removal of the abnormal epithelial cells, such as ciliated pseudostratified columnar epithelial cells PCEC and goblet cells GC, is the result of dielectrophoresis induced by one or more energy pulses delivered by the energy delivery body 108. In particular, in some embodiments, the epithelial layer E is separated by the action of dielectrophoresis, wherein the abnormal ciliated pseudostratified columnar epithelial cells PCEC and goblet cells GC are pulled away from the anchored basal cells BC and removed from the airway wall W. Recall, the basal cells BC are connected to the basement membrane BM by hemidesmosomes H whereas the basal cells BC connect to the goblet cells GC and ciliated epithelial cells EC via desmosomes D. The energy parameters and electrode configuration can be designed such that the desmosomes connections D separate but the hemidesmosomes H remain intact, thereby removing the surface cells, leaving the basal cells BC substantially intact, and ready to regenerate epithelium.

Figure 19:
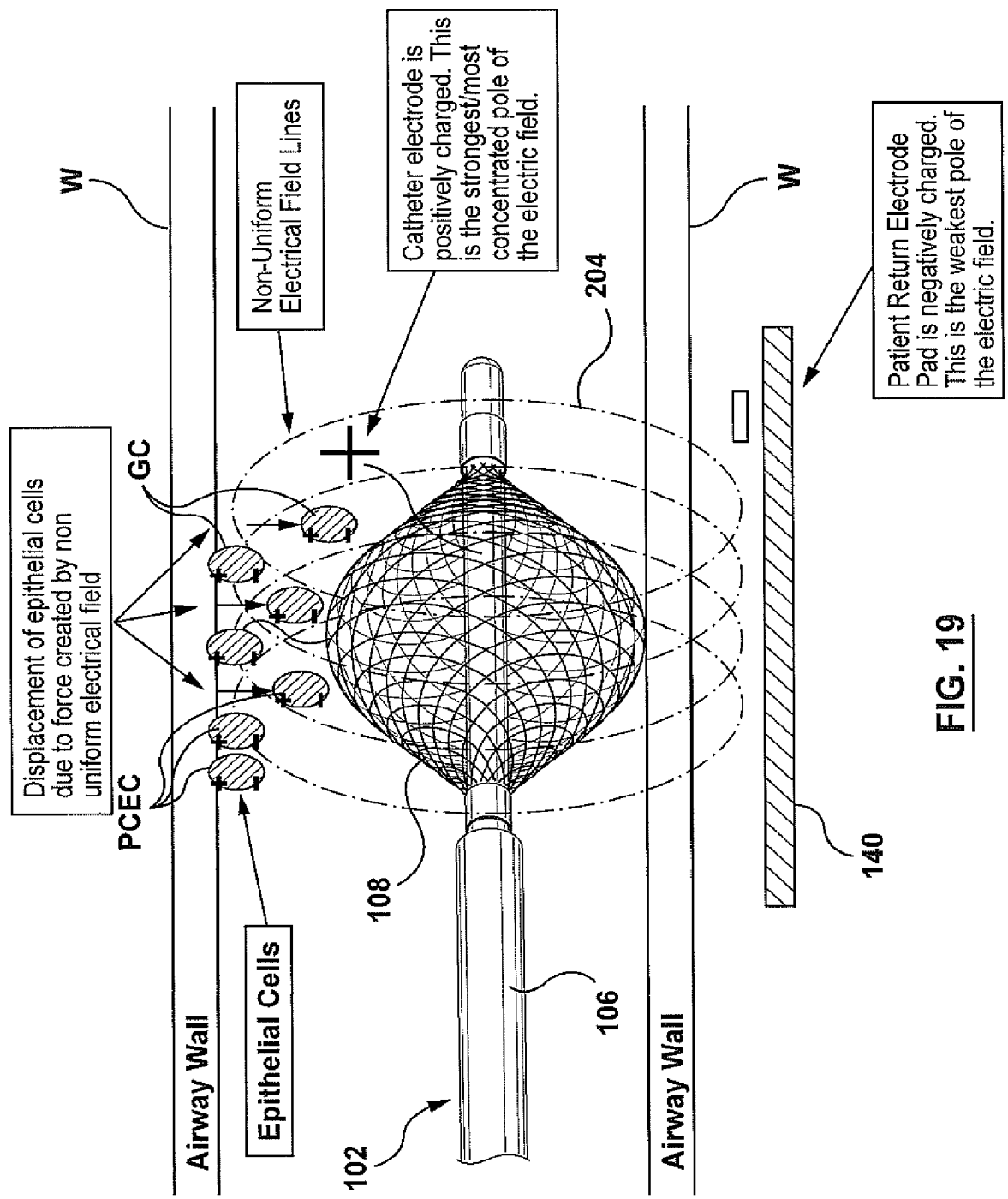
FIG. 19 schematically illustrates removal of epithelial cells by a dielectrophoresis effect.

FIG. 19 schematically illustrates removal of epithelial cells by a dielectrophoresis effect. Here, a distal portion of an embodiment of a catheter 102 having an energy delivery body 108 is illustrated positioned within a lung passageway. Energy 204 is delivered from the energy delivery body 108, as indicated by dashed electric field lines. The electric field is non-uniform due to the shape of the energy delivery body 108 and the placement of the return electrode 140 which is applied externally to the skin of the patient P. In this embodiment, the energy delivery body 108 is positively charged. This is the strongest/most concentrated pole of the electric field. The return electrode 140 is negatively charged and is the weakest pole of the electric field. Consequently, the non-uniform electric field causes detachment and displacement of the epithelial cells (e.g. ciliated pseudostratified columnar epithelial cells PCEC and goblet cells GC) from the airway walls W (as indicated by downward arrows). The epithelial cells are then removed by natural or induced mechanisms.

Alternatively or in addition to affecting tissue cells within the airway wall W, the delivered energy may affect pathogens resident in or near the airway wall W. Example pathogen types include without limitation bacteria (e.g., *Haemophilus influenzae, Streptococcus pneumoniae, Moraxella catarrhalis, Staphylococcus aureus, Pseudomonas aeruginosa, Burkholderia cepacia*, opportunistic gram-negatives, *Mycoplasma pneumoniae*, and *Chlamydia pneumoniae*), viruses (rhinoviruses, influenze/parainfluenza viruses, respiratory syncytial virus, coronaviruses, herpes simplex virus, adenoviruses), and other organisms (e.g., fungi).

In some embodiments, the pulmonary tissue modification system 100 may additionally or alternatively be useful for impacting pathogens found within a lumen of an airway (e.g. within the mucus layer M) or within tissue layers of the airway wall W of a patient such that infection is controlled, reduced, and/or eliminated. In some embodiments, the energy output from system 100 affects the mucus layer M and any pathogens that may be resident in or near the airway. The mucus layer M may become less viscous, thus making it easier for the patient to expel via coughing. The pathogens may be killed or programmed to die (e.g., apoptosis), thereby reducing or eliminating infection.

In some embodiments, the system 100 may assist the patient in developing antibodies or other commensal and supportive immune responses to targeted pathogens, improving future immunity and resistance to that pathogen in the future. Since the system 100 affects pathogens in a substantially non-thermal manner, leading to cell death, the cellular fragments still contain proteins. As these more intact proteins are released into the local environment and the circulation, the immune system develops new methods of surveillance, recognition and threat responses to these challenges, which can enhance host defense from those challenges or pathogens in the future.

As mentioned previously, it may be appreciated that the energy signal parameters may be manipulated to cause differing effects, such as differing depths of penetration. In some instances, the system 100 can be configured such that only the mucus layer M and any resident pathogens are affected. In some instances, the system can be configured such that cell death in the epithelial layer occurs. In some instances, the system can be configured such that the epithelial and submucosal cell death occurs via a single energy delivery algorithm. In some instances, the system can be configured such that the epithelial and submucosal cell death occurs and pathogens are affected, via a single energy delivery algorithm. In some instances, the separation of the epithelial layer E occurs. In some instances, the system 100 can be configured such that the epithelial layer E separation occurs, pathogens are affected, and/or deeper structures are affected via a single energy delivery algorithm. In some instances, the generator can have a variety of energy delivery algorithms stored within it, and the user can apply two or more of these algorithms to tailor therapy to an individual patient. This may be done in a single therapy session or multiple therapy sessions in order to address the needs of individual patients.

In some instances, it can be desirable to affect deeper cells including smooth muscle cells SM submucosal glands SG, and/or nerves N. A patient's pathology can be more complex than mucus hypersecretion caused by the epithelium E and therefore the procedural intent is to affect deeper structures. Airway smooth muscle cells SM are known to contribute to bronchial hyper-responsiveness, submucosal glands SG can contribute to severe mucus hypersecretion, and nerves N innervate both submucosal glands SG and airway smooth muscle SM. Alternatively, patients with mixed pathologies such as asthma and chronic obstructive pulmonary disease (COPD) (e.g. Asthma-COPD Overlap Syndrome) can benefit from a procedure that targets several mechanisms (e.g., mucus hypersecretion, smooth muscle hypertrophy, cilia dysfunction, and/or the like) and/or target tissues. The energy dose can be titrated (e.g., iteratively modified based on sensor and/or other feedback) to affect structures deep to the epithelium E. In some instances, as the energy dose is increased, the submucosal glands SG undergo a mild partial membrane lysis or a significant loss of structural integrity. Uniquely and unlike thermal energy, the lamina propria LP, which is a cell layer that sits between the epithelium E and submucosal glands SG, remains unchanged. A thermal energy source would cause significant changes in the structure of the extracellular matrix and cause fibrosis.

In addition to the submucosal glands SG, the smooth muscle SM can be affected depending on the dosing, ranging from focal changes to obliteration which causes removal of the epithelium E over days to weeks. The cartilage layer CL, the deepest structure in the airway wall, is unaffected by the energy and shows no signs of inflammation or necrosis, acting as an insulative barrier.

IV. Cell Targeting

In some embodiments, the energy delivery algorithms 152 are designed to target specific cells. Such targeting may be based on a variety of different aspects, including size, shape, location, type, function, and often a combination of these. In some embodiments, particular cell populations are targeted while other cell populations are avoided. It may be appreciated that such avoidance may or may not be complete, however avoidance involves minimization of affect. Such avoided cell populations may be considered collateral cell populations and they may be adjacent or nearby the targeted cell populations or at a distance. In some instances, particular cell populations are targeted due to their involvement in particular disease processes. The collateral cell populations are typically avoided either because these cell populations are not involved in the disease process or because these cell populations are beneficial for safety, recovery and/or improved outcomes. Thus, in some instances, collateral cells are simply benign bystanders but in other instances the collateral cells are critical-function cells whereby excessive damage to these cells would damage tissue functionality and cause harm to the patient.

In lung airways, the target cells may include goblet cells, dysfunctional pseudostratified columnar epithelial cells and submucosal glands while the collateral cells may include basal cells, chondrocytes and other more distant tissue cells not implicated in airway-centric disease processes such as mucus hypersecretion. A chondrocyte is a cell that has secreted the matrix of cartilage and has become embedded in it. Thus, chondrocytes construct and maintain the cartilaginous tissues that maintain the open orientation and structural integrity of the airways. Typically, chondrocytes are avoided in the treatment of mucus hypersecretion so as to maintain the airway structure via preserved cartilage form and the continued maintenance operations.

In pulmonary veins, target cells may include cardiomyocytes which are muscle cells (myocytes) that make up the cardiac muscle. In some embodiments, cardiac myocytes are targeted due to their association with ganglia which are implicated in aberrant cardiac arrhythmias. In such situations, collateral cells may include distant cells in the sinoatrial node or atrioventricular node that generate normal heart rhythms. In the esophagus, target cells may include precancerous cells, such as those involved in Barrett's esophagus. Collateral cells may include structural cells that maintain the extracellular matrix. In the colon, target cells may include precancerous cells, such as cells forming polyps. Collateral cells may include healthy mucosal and submucosal cells. Likewise, in the colon, target cells may include cells involved in the diseased epithelium of ulcerative colitis. Thus, collateral cells may include smooth muscle cells involved in peristalsis. Collateral cells may also include cells that are part of the host milieu in terms of commensal bacteria such as those that live in the gut and airways which can also be helpful, innocent bystanders.

Figure 20A:
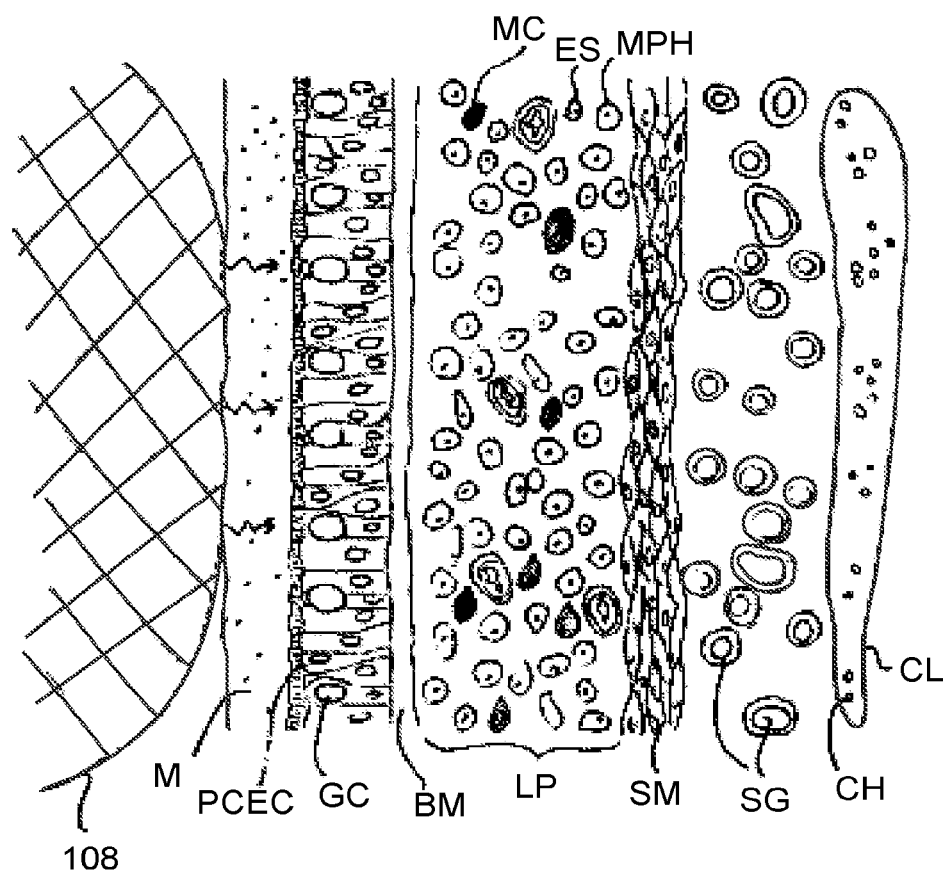
FIG. 20A illustrates a cross-section of a wall of a diseased lung airway along with an energy delivery body positioned thereon.

In the example of a lung airway, particular cell populations may be targeted based on a variety of aspects. FIG. 20A illustrates a cross-section of a wall W of a diseased lung airway along with an energy delivery body 108 positioned thereon. Here, the wall W is covered with a thick layer of mucus M. Below the layer of mucus M resides the pseudostratified columnar epithelial cells PCEC and goblet cells GC followed by the basement membrane BM. Below the basement membrane BM resides the lamina propria LP. The lamina propria LP is a layer of loose areolar connective tissue which constitutes part of the mucosa. In this example, the airway wall W is diseased and the lamina propria LP includes an abundance of mast cells MC, eosinophils ES and macrophages MPH. The lamina propria LP is bordered by a layer of smooth muscle cells SM and beyond the layer of smooth muscle cells SM resides the submucosal glands SG. The cartilage layer CL is beneath the smooth muscle cells CM and includes the chondrocytes CH.

In some embodiments, goblet cells GC and submucosal glands SG are targeted while chondrocytes CH are avoided. As mentioned previously, these epithelial cells and submucosal glands are often involved in the overproduction and accumulation of an excessive mucus layer M. Therefore, by modulating or eliminating these cells, such hypersecretion may be reduced or alleviated. Likewise, the cartilage layer CL is desired to be preserved due to its role in maintaining the matrix architecture of the airway, thereby preserving its structural integrity and preventing collapse. As illustrated in FIG. 20A, these cells are somewhat different in size, location and function, among other aspects. These differing aspects can be utilized in cell targeting. In some embodiments, the goblet cells GC and submucosal glands SG are selectively targeted due to their larger size while the chondrocytes CH are spared based on having a smaller size.

As shown in FIG. 20A, the targeted goblet cells GC are large columnar-shaped cells wherein their longest dimension or long axis is oriented perpendicular to the airway lumen. Since these cells are located closest to the energy delivery body 108, the electric field emanating therefrom is largely along the long axis of the goblet cells GC. In some embodiments, the size of goblet cells GC is approximately 20 µm along this long axis. The submucosal glands SG are roughly spherical having no clear orientation. Typical submucosal glands SG have a diameter of approximately 15 µm. Therefore, goblet cells GC and submucosal glands SG are somewhat similar in size along these dimensions. In contrast, chondrocytes CH are small ellipsoidal cells having their short axis oriented perpendicular the airway lumen. Along this axis, chondrocytes CH are typically approximately 5 μm in dimension. This is significantly smaller than the goblet cells GC and submucosal glands SG.

Figure 20B:
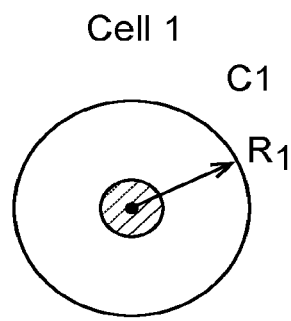
FIGS. 20B-20C schematically illustrate different sized cells.
Figure 20C:
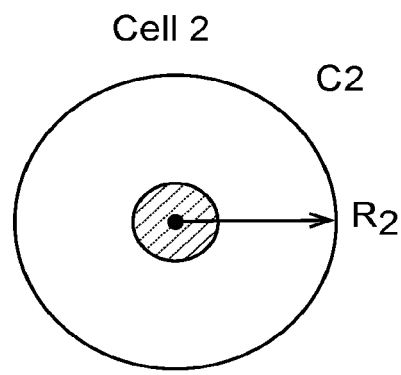
Figure 20D:
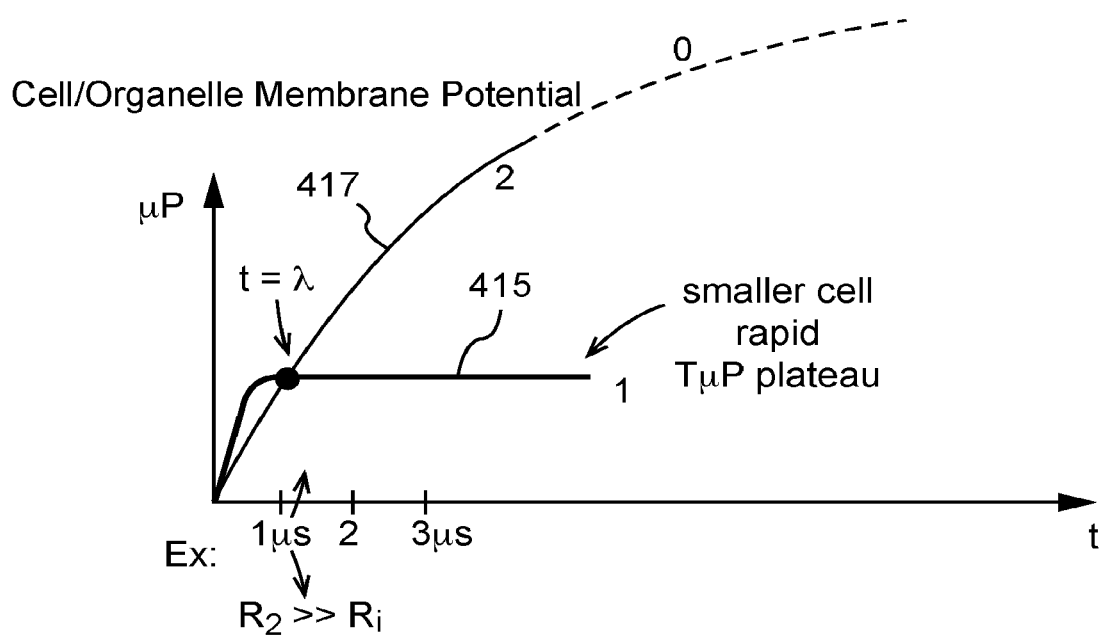
FIG. 20D illustrates an example of cell/organelle membrane potential in relation to time.

FIGS. 20B-20C schematically illustrate different sized cells. FIG. 20B shows a first cell C1 having a first radius R1 and FIG. 20C shows a second cell C2 having a second radius R2. In this example, the second cell C2 is larger than the first cell C1 such that R2>R1. The size of the cell affects how the electromotive force drives changes in transmembrane potential buildup. Changes in the transmembrane potential are used to exploit various electrochemical and biotransport characteristics in the cell causing modulation of the cell or cell death Small cells will charge faster since there is less distance for the charges to move within the cell. However, because there is less intracellular fluid in a smaller cell, there are fewer ions to be driven by such electrokinetic forces. Therefore, the cumulative charge buildup in the smaller cell will be less than that which occurs in the larger cells. These principles are illustrated in FIG. 20D which shows cell/organelle membrane potential in relation to time. A first curve 415 represents the membrane potential of the first cell C1 and a second curve 417 represents the membrane potential of the second cell C2. As shown, the membrane potential of the smaller first cell C1 rises quickly, ahead of the larger second cell C2, up to a transition time. However, the membrane potential of the smaller first cell C1 then plateaus while the membrane potential of the larger second cell C2 continues to increase. Thus, the membrane potential of the larger second cells reaches a greater level but it takes longer to achieve. It may be appreciated that principles described herein are not only applicable to spherical cells. Such principles are relevant to distance from the center of a cell or organelle to a boundary in the orientation of the electric field. Thus, as mentioned previously, the goblet cells GC and submucosal glands SG are considered larger than the chondrocytes CH and would follow the same principles as outlined in relation to spherical cells.

Figure 20E:
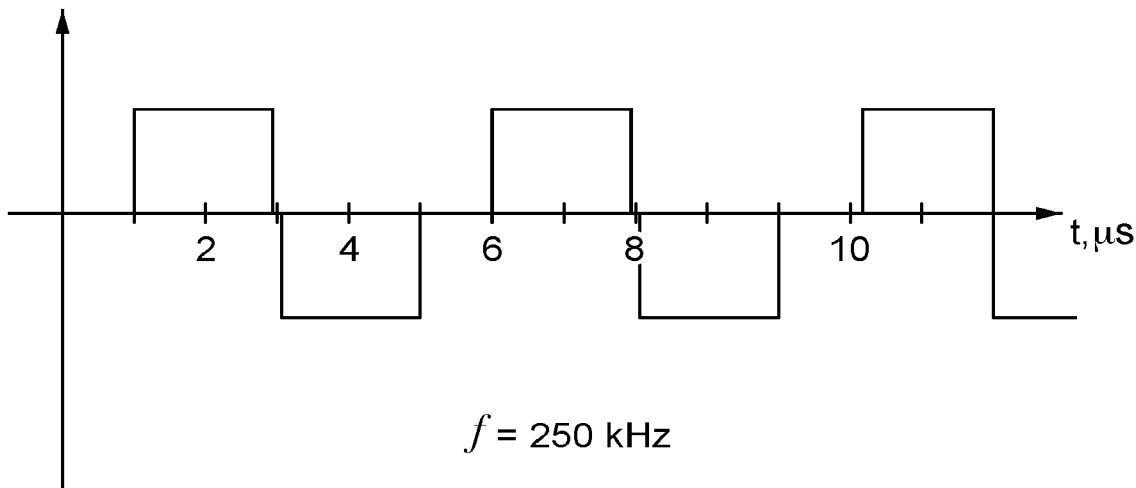
FIG. 20E illustrates a waveform having a lower frequency such as 250 kHz.
Figure 20F:
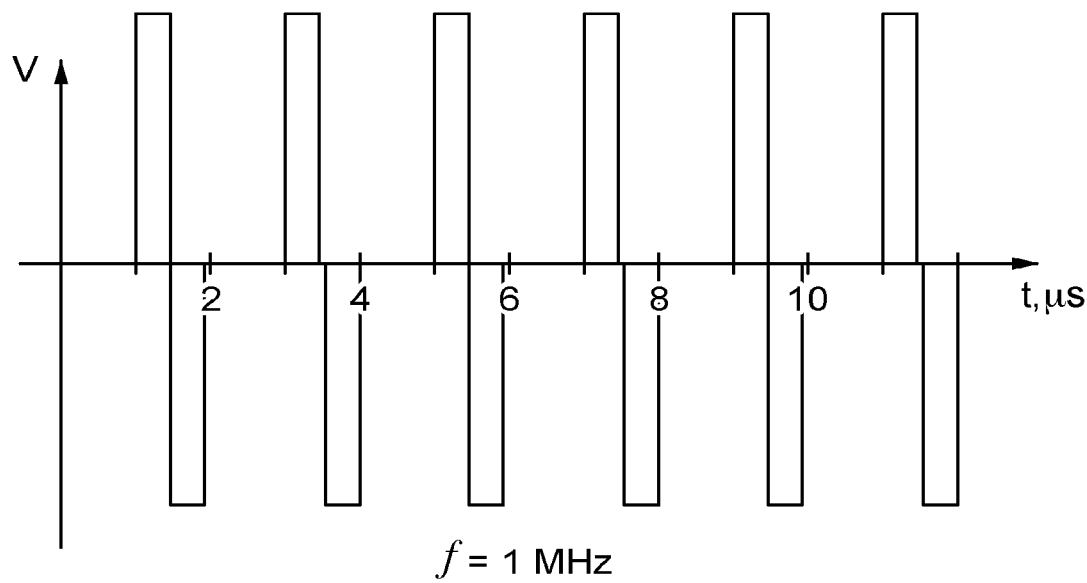
FIG. 20F illustrates a waveform having a higher frequency such as 1000 kHz.

The one or more energy delivery algorithms 152 specify electric signals which provide energy delivered to the airway walls W in the treatment of various conditions and diseases. In some embodiments, the frequency of the electric signals is modulated to ensure that the goblet cells GC and submucosal glands SG are affected based on their larger size in comparison to chondrocytes CH. This may be considered targeting in that the frequency is adjusted to ensure their destruction. It may be appreciated, that lower frequencies (e.g. toward 100 kHz or in the range of 100-300 kHz) results in cell death of all cell populations throughout the airway wall. This is because lower frequencies provide longer durations for charge buildup, allowing even the larger cells to respond. The frequency is low enough that pulse duration is greater than transition time FIG. 20E illustrates a waveform having a lower frequency such as 250 kHz. Higher frequencies (e.g. toward 1000 kHz) will not affect or kill any of these cells. This is because higher frequencies have shorter periods which translate into shorter durations for charge buildup. In this example, the frequencies are so high that even the smallest cells do not have time to respond. The frequency is high enough that pulse duration is less than transition time FIG. 20F illustrates a waveform having a higher frequency such as 1000 kHz.

Thus, in some embodiments, a frequency in the range of 400-800 kHz (e.g. 400 kHz, 450 kHz, 500 kHz, 550 kHz, 600 kHz, 650 kHz, 700 kHz, 750 kHz, 800 kHz) is used which provides a general degree of treatment effect to the targeted cell populations, while remaining within acceptable limits of chondrocyte effect. It may be appreciated that in some embodiments, frequencies in the range of 300-400 kHz may be used depending on the other parameter values.

Examples of applicable setting ranges, and selected specific combinations are provided in the following Table 1:

TABLE 1

| Voltage, V | Frequency, kHz | Packet Duration, μs | Packet Count, # |
|---|---|---|---|
| 500, 1000, 1500, 2000, 2500, 3000, 3500, 4000 | 300, 350, 400, 450, 500, 550, 600, 650, 700, 750, 800 | 10, 50, 100, 200, 500, 1000 | 1, 5, 10, 20, 50, 100, 200, 500, 1000 |
| 500 | 400 | 200 | 1000 |
| 500 | 300 | 1000 | 20 |
| 1000 | 400 | 500 | 1 |
| 2000 | 800 | 50 | 500 |
| 2500 | 600 | 1000 | 1 |
| 2500 | 600 | 100 | 5 |
| 2500 | 700 | 50 | 20 |
| 3000 | 700 | 100 | 5 |
| 3000 | 800 | 200 | 10 |
| 4000 | 300 | 10 | 50 |

It may be appreciated that frequency values in this desired range target the larger goblet cells GC and submucosal glands SG by ensuring a detrimental effect on these cells. Although the smaller chondrocytes CH are typically affected in this frequency range based on their size, other factors spare chondrocytes from destruction. For example, voltage of the electric signals used at these frequencies is chosen so that the electric field reaching the chondrocytes CH (which are further from the electrode body 108 as illustrated in FIG. 20A) is low enough to spare the chondrocytes CH. Thus, parameter values are chosen to target the goblet cells GC and submucosal glands SG based both on size and location within the airway.

In some embodiments, particular cells are targeted based on their ability to recover from injury. For example, in some embodiments the goblet cells GC and submucosal gland cells SC are targeted based on their superior ability to recover from injury in comparison to chondrocytes CH. Typically, chondrocytes CH are less able to recover from injury and therefore more susceptible to the effects of accumulation. Since chondrocytes CH are critical function cells, their survival is a guide as to the upper limit on the admissible dose and tissue injury that may be generated from treatment. This is due at least in part to the environment of the chondrocytes CH. Chondrocytes CH are immersed in cartilaginous matrix material which is an avascular tissue type. Therefore, chondrocytes CH are less able to access sources of energy and waste removal and rely on diffusion processes across large regions. This is evidenced by an increased lethal outcome for chondrocytes CH located near the center of the cartilage layer in comparison to those on the cartilage layer boundaries. In contrast, goblet cells GC and submucosal glands SG are more likely to recover from injury due to their well vascularized environments.

These differences can be exploited by varying the number of packets delivered by the electric signal. This is due to the various modes by which the electric signals alter cells and stimulate regeneration and resurfacing. In some instances, cellular effects are achieved right away due to the general intensity of the electric field produced by the electric signal. In these instances, delivery of additional packets will not affect the cell response. In other instances, the cellular effects are achieved after accumulation of several smaller effects, such as cumulative loss of homeostasis from cell or organelle leakage overwhelming the cell's ability to restore its native environment, resulting in dissolution of the cell or apoptosis. In these instances, the cumulative cell damage is the driving factor by which the cell dies, and thus subsequent packets will continue to compound the injury and/or effects of the earlier packets.

Therefore, in some embodiments, goblet cells GC and submucosal glands SG are targeted while sparing chondrocytes CH by delivering a low number of packets. In some embodiments, one packet is delivered and, in other embodiments, up to five packets are delivered. Such differences are due to a myriad of factors based on the individual patient, the other parameters and the type and position of the energy delivery body 108, to name a few. However, overall, delivering packets in the range of approximately one to five (e.g. with a frequency of 600 kHz, packet duration of 100 us and voltage of 2500-3000V) is a method to target goblet cells GC and submucosal glands SG while sparing chondrocytes CH in a lung airway. This is in contrast to targeting chondrocytes CH wherein, for example, 10 packets are delivered and in other embodiments up to 100 packets are delivered.

It may be appreciated that other signal parameters may be adjusted to assist or modify the effects of particular parameter choices. For example, at a given frequency, voltage may be modified to further control the cellular effects. Similarly, when a given number of packets are used, the voltage may also be modified to further control the cellular outcomes. For example, it may be appreciated that in some instances modifying the number of packets will affect all cell varieties to some extent. To counterbalance this, in some embodiments, the voltage is raised (e.g. from 2500V to 3000V for moving from 5 packets to 1 packet) to focus the energy on targeting the goblet cells GC and submucosal glands SG. This ensures adequate stimulation of these cells before the accumulation affects the chondrocytes CH.

In some embodiments, the goblet cells GC and submucosal glands SG are targeted based on their location and distribution in the airway wall W. This may be considered 'geographical targeting". As illustrated in FIG. 20A, the goblet cells GC and submucosal glands SG are located closer to the airway lumen and energy delivery body 108 in comparison to chondrocytes CH which are located deeper in the airway wall W. By titrating the overall intensity of the energy provided by the energy delivery algorithm 152, is it possible to affect cells at a desired depth with a rapid falloff in treatment effect before reaching the non-targeted cell populations. This titration of treatment effect will vary depending on the condition being treated and therefore the cells being targeted.

In summary, the goblet cells GC, other mucus producing cells and submucosal glands SG may be targeted for the treatment of mucus hypersecretion while avoiding chondrocytes CH in the cartilage layer CL by a variety of methods as described herein. It may also be appreciated that, in some embodiments, such targeting may also alter cell signaling in the local environment and thus can further reduce mucus production. In some embodiments this is achieved with an energy delivery algorithm 152 that provides an energy signal having a frequency of 600 kHz, a voltage of 3000 V and 10 packets wherein each packet has a duration of 200 µs. In other embodiments, this is achieved with an energy delivery algorithm 152 that provides an energy signal having a frequency of 550 kHz, a voltage of 2500 V and 5 packets wherein each packet has a duration of 100 µs. It may be appreciated that other combinations of parameters may be used, and combinations which include one or more of these parameter choices may be used. Such parameter choices may be based on a variety of factors, including treatment needs such as preventing tissue carbonization or stromal protein denaturation at the tissue-electrode interface. In some embodiments, this is achieved by using more packets, such as 20 or 50, or a lower frequency, such as 300 kHz or 400 kHz, with lower voltages, such as 2000 V or 1000 V, and/or shorter packet durations, such as 50 µs or 100 µs. Other treatment needs may include preventing unacceptable levels of muscle contraction. In some embodiments, this is achieved by using more packets at higher frequencies, lower voltages, or shorter packet durations. Other treatment needs may include avoiding taking too long to treat a particular area. In some embodiments, this is achieved by using fewer packets that are a greater voltage, lower frequency, or longer packet duration.

In some embodiments, mucus hypersecretion is treated by targeting cells in a lung airway wall W at an even shallower depth. In some embodiments, this is achieved with an energy delivery algorithm 152 that provides an energy signal using a higher frequency than described above such as 800 kHz, or a voltage lower than described above such as 2000 V, or fewer packets than described above such as 2 packets, or shorter packet durations than described above such as 50 µs. In some embodiments, this is achieved using an energy delivery algorithm 152 that provides an energy signal that combines all of these changes, thus having a frequency of 800 kHz, a voltage of 2000 V and 2 packets wherein each packet has a duration of 50 µs. It may be appreciated that other combinations of parameters may be used, and combinations which include one or more of these parameter choices may be used.

In some embodiments, a penetration to a deeper depth is desired, such as to affect smooth muscle cells SM in the treatment of asthma or other indications. In some embodiments, this is achieved with an energy delivery algorithm 152 that provides an energy signal using a lower frequency than described above such as 400 kHz, or a voltage higher than described above such as 3250 V, or more packets than described above such as 20 packets, or longer packet durations than described above such as 500 µs. In some embodiments, this is achieved using an energy delivery algorithm 152 that provides an energy signal that combines all of these changes, thus having a frequency of 400 kHz, a voltage of 3500V and 20 packets wherein each packet has a duration of 500 µs. It may be appreciated that such an algorithm 152 takes into consideration the aforementioned parameter considerations. For example, the smooth muscle cells SM are more resilient to the energy signal than chondrocytes CH and submucosal gland cells SG; therefore, additional energy is delivered to overcome the geographical placement of these target smooth muscle cells SM along with their higher effective thresholds. It may be appreciated that other combinations of parameters may be used, and combinations which include one or more of these parameter choices may be used.

It may be appreciated that these principles carry over to other anatomical locations and other types of cells. In addition, other disease types may additionally provide targeting features. For example, in some embodiments, cells are targeted based on their metabolic activity or energy demands. Cancer cells are cells which have a higher metabolic activity and energy demand than normal tissue cells. Such cells require more energy to remain functional in general. Likewise, these cells are more susceptible to compounding injury and accumulated loss of homeostasis from multiple energy packets than mature, differentiated or undifferentiated cells that exist in the same environmental region. This feature may be exploited in various clinical indications, such as in cancer treatments where the rapidly dividing and immature neoplastic cells are less resilient to injury.

In some embodiments, larger packet numbers preferentially increase the lethality of the applied electric fields to cancer cells relative to healthy cells exposed to the same electric field parameters. For example, cancer cells are generally less responsive to repeated accumulation of minor injury mechanisms, similar to chondrocytes. Therefore, preferential targeting of cancer cells may exploit this characteristic by subjecting them to 50 packets, or 100 packets, or 200 packets. This will result in a disproportionate increase in cancer cell death relative to the increased cell death that occurs to healthy, mature, differentiated cells. In the case of colon cancer, the cancer cells may be compared to healthy smooth muscle cells. Thus, in some embodiments, 10 packets are delivered, which treats some cancer cells but not the smooth muscle cells. In other embodiments, up to 100 packets are delivered, which treats many more cancer cells, and some smooth muscle cells. In still other embodiments, up to 1000 packets are delivered, treating even greater numbers of cancer cells, as well as additional smooth muscle cells. The number of packets used depends on the targeted tissue type, time permissible for the procedure, generator capacity, and muscle contraction constraints, to name a few. It may be appreciated that the muscle contraction constraints may limit the permissible applied voltage and increase the required frequency, reducing the effectiveness of an individual packet. It can thus be appreciated that this reduced efficacy can be compensated for by increasing the number of packets, resulting in reduced muscle contraction but with maintained treatment efficacy. In this example, the additional packets may contribute to longer procedure times.

V. Sensors

In some embodiments, one or more sensors 160 are included in the system 100 to measure one or more system or tissue parameters. Example sensors 160 include temperature sensors, impedance sensors, resistance sensors, surface conductance sensors, membrane potential sensors, capacitance sensors, and/or force/pressure sensors, or combinations thereof. Thus, parameters measured by sensors 160 can include impedance, membrane potential or capacitance, and/or temperature, to name a few. Sensors 160 can be used for (a) obtaining a baseline measure, (b) measuring a parameter during the delivery of energy, and/or (c) measuring a parameter following energy delivery, among others.

Sensors 160 can be positioned on energy delivery bodies 108, adjacent to energy delivery bodies 108, on the dispersive or return electrode 140, adjacent to the dispersive or return electrode 140 or in any suitable location along the catheter 102 or on the surface of the patient. The dispersive electrode may also contain its own sensors, which may be checked for by the system prior to treatment delivery to ensure the dispersive electrode is satisfactorily connected. The system may prohibit treatment delivery until these sensor requirements are satisfied. These may include one or multiple sensors on the dispersive electrode or the active electrode that can sense properties of the tissue to determine that it is properly connected to the tissue. Temperature sensors can monitor the temperature of an electrode and/or the electrode/tissue interface. Impedance sensors can monitor the impedance of the tissue across any two electrodes. In some embodiments, the impedance change can be sensed using a bipolar catheter sensor configuration, whereby local tissue property changes to impedance are evaluated. In another embodiment, the impedance change is sensed using a bipolar catheter sensor configuration, whereby local changes in system anatomical constituents, such as the excretion of mucus or edema into the airway is evaluated. Conductance sensors can monitor the transmission of electrical energy across any two electrodes. Force/pressure sensors can monitor the amount of force or pressure that the electrodes are placing on the tissue.

This sensor information can be used as feedback to the system in order to, as non-limiting examples, determine proper deployment of energy delivery bodies 108, drive a therapeutic algorithm 152, and/or stop energy delivery for safety reasons including to establish and confirm that the physical treatment system setup is satisfactory. Sensors 160 can also be used to sense when an adequate treatment is achieved. An algorithm 152 within the generator 104 can also use the sensed data to automatically titrate the therapeutic algorithm 152 such that the target tissue treatment is achieved. Said another way, one or more parameters and/or aspects of the therapeutic algorithm can be modified based on the sensor data in an iterative manner. For example, in some embodiments, the power and/or energy duration can be increased or decreased based on the sensor data.

The system can execute an algorithm using sensor data gained during therapeutic pulse delivery. In another embodiment, the system can execute an algorithm using sensor data gained from dedicated probing signals. In this embodiment, a dedicated probing signal can be a low voltage pulse or packet delivered before or between therapy pulses, or can be an AC signal at a dedicated frequency or over a range of frequencies. In these embodiments, the signal used to control the algorithm can be selected to target the optimal delivery of the energy.

It may be appreciated that there is a vast array of viable electrical signals that may perform monitoring and/or test pulsing to determine the desired system and patient conditions prior to or during procedure delivery. In some embodiments, the signals are delivered prior to commencement of the treatment therapy as a final-check on tissue conditions, which may also be used to guide any changes prior to beginning treatment delivery. For example, the signal may be delivered heartbeat prior, or delivered 1 ms prior, or delivered 500 ms prior (if done within/immediately prior to a procedure activation); or delivered 10 s up to 1000 s prior (if done at beginning of an EM activation or prior to an entire patient treatment). Alternatively, in some embodiments, the monitoring or test signals are delivered during the treatment algorithm, such as between packets of the delivered energy. This provides updated checks throughout the activation to ensure that the system conditions remain consistent with those needed for good therapeutic outcomes. In some embodiments, these monitoring or test signals are in the form of a brief pulse (e.g. 1 us, 100 us, 1 ms, 100 ms) which can be delivered in sequence with cardiac gating or independently of the patient ECG rhythm, which will partially depend on the type of signal and strength used. In addition, continuous waveform may be performed, such as delivery of a constant low-voltage DC signal (e.g. 0.5V, 1V, 5V, 10V, 50V; 500V) or continuous low-voltage AC waveform (e.g. 0.5V, 1V, 5V, 10V). The voltage for both of these would be kept low to prevent potential influence on procedure outcomes and reduce the risk for significant thermal damage or other conditions at the targeted and dispersive tissue sites, as well as to mitigate any potential influence on the heart. In any of these cases, the resulting impedance, or either its real or imaginary components may be used to derive and understand the characteristics of the electrical system for the patient. These conditions may be used to guide treatment parameter settings, such as voltage (e.g. 1000V, 2500V, 5000V, with deviations based on feedback on the order of 10 s, 100 s, or low-1000 s of V) or frequency (e.g. 600 kHz baseline, or 100 kHz, 500 kHz, 1000 kHz; with deviations in the 10 s and 100 s of kHz) or to indicate whether the system is correctly established and the treatment may be safely and effectively delivered. In some instances, various combinations of these test signals and signal frequencies may be collected and analyzed collectively to evaluate the desired tissue condition.

In some embodiments, the therapeutic pulses themselves are used to monitor the quality of the treatment system, whereby normal ranges or deviations from a baseline value are monitored and used as cutoffs to indicate good or poor quality of electrical contact and energy delivery. In other instances, a test pulse is performed that uses a lower voltage or energy than the therapeutic delivery. This test delivery may use the same waveform (e.g. square, roughly 500 kHz, roughly 2500V baseline) as the therapeutic energy dose, reducing deviations in tissue impedance response to due to permittivity characteristics of the tissue and dispersion frequency effects.

A. Impedance Sensors

1. Ensuring Proper Placement of Energy Delivery Bodies

In some embodiments, one or more impedance sensors are used to determine if the energy delivery bodies 108 are properly inserted and deployed in the airway of the lung. In some embodiments, a short duration, low voltage signal is delivered to the energy delivery bodies 108 during their placement and deployment/expansion within the targeted area of the airway. Based on measured electrical current feedback received by the generator 104 from the one or more impedance sensors, the generator's processor 154 performs a calculation using the set voltage and actual current to calculate the impedance. Calculated impedance is then compared to impedance values that are considered acceptable for the properly inserted and deployed energy delivery bodies 108. If the calculated impedance is outside of the range of acceptable impedances, the generator 104 displays a specific message and/or emits a specific sound alerting the operator. For example, if the energy delivery bodies 108 are still within the bronchoscope 112, the generator 104 may measure a very high impedance outside of the acceptable range. In such instances, the generator may then display a message (e.g., Check Electrode Position) until the operator repositions the energy delivery bodies 108 into the airway where the impedance is significantly lower and within the acceptable range. At this point, the message may change (e.g., Ready).

It may be appreciated that other types of sensors, such as temperature, force or pressure sensors may additionally or alternatively be used to verify electrode to tissue contact prior to initiation of treatment. It may also be appreciated that sufficient contact between electrodes and the walls of the airway is an important factor for effective treatment. Solid and consistent contact is desired to satisfactorily couple the energy from the electrode to the tissue and to achieve desired tissue effects.

2. Ensuring Proper Functioning of Catheter

In some embodiments, one or more impedance sensors are utilized to determine if the catheter 102 is functional or potentially defective. In such embodiments, a short duration, low voltage signal (e.g., a signal having a duration from 1-5 packets, and a voltage of about 50V or 100V or 500V) is delivered to the energy delivery bodies during their placement and deployment/expansion within the targeted area. Based on the measured electrical current feedback received by the generator 104, the generator's processor 154 performs a calculation using the set voltage and actual current to calculate the impedance. Calculated impedance is compared to the impedance values that are considered acceptable for a catheter that is functioning properly. If the calculated impedance is outside of the range of acceptable impedances, the generator 104 optionally displays a specific message and/or emits a specific sound alerting the operator. For example, if the catheter is defective, the impedance may be very high. In this embodiment, the generator 14 displays a message (e.g., 'Replace Catheter'). Once replaced, the generator 104 may then detect a much lower impedance within the acceptable range and display another message (e.g., 'Position Catheter'). Thus, impedance measurements can be used to avert a safety concern by detecting a malfunctioning catheter.

In some embodiments, such monitoring activities are accomplished by delivering electrical signals to independent active portions of a single energy delivery body 108, wherein one active portion acts as the affected electrode and another active portion acts as the dispersive electrode. Typically, unusually high impedances between the active portions indicate incomplete contact of the energy delivery body 108. For example, in some embodiments an impedance measurement outside 50-150Ω indicates poor contact. Likewise, in some embodiments, an impedance measurement of >200Ω indicates no contact, such as wherein the catheter 102 is receiving no electrical current, has broken connections, etc. In contrast, low impedances, such as <50Ω, between the active portions would indicate good electrical conduction between the active portions wherein the energy delivery body 108 has good tissue contact for its major contact area components. It may be appreciated that in some embodiments these active portions deliver energy independently to the tissue. Such delivery may become electrically congruous during therapy delivery or remain separate.

In some embodiments, the electrical environment conditions are measured between two or more electrodes, such as between an energy delivery body 108 in a catheter 102 and a dispersive pad electrode or between two separate energy delivery bodies 108 within the patient acting in a bipolar configuration. In some embodiments, an impedance measurement outside of 50-150Ω indicates poor contact of at least one of the energy delivery bodies 108. Likewise, in some embodiments, an impedance measurement of >200Ω indicates no contact of at least one of the energy delivery bodies 108, such as wherein the catheter 102 is receiving no electrical current, has broken connections, etc. It may be appreciated that such impedance values may vary depending on the anatomy. The above values are relevant to airways. Catheters positioned in other anatomical lumens may reference different impedance values for indication of sufficient contact. For example, typical impedance values in the colon (when measured in a monopolar configuration using a dispersive pad on the abdomen or leg) may be in the range of 30-75Ω. Likewise, typical impedance values in the heart may be in the range of 40-100Ω. And, typical impedance values in the esophagus may be in the range of 50-150Ω. Impedance values above these ranges may indicate poor contact or other problems related to energy delivery.

In some embodiments, unusually low impedance measurements (e.g. close to 0Ω when measuring between two points on the same electrode body or <50Ω when measuring between an electrode body and a dispersive pad) indicate other issues with the energy delivery system. In some situations, unusually low impedance measurements indicate that two energy delivery bodies 108 in a bipolar pair are too close together. In other situations, low impedance measurements indicate a short in the electrical system or generator. In still other situations, a low impedance measurement indicates electrical arcs. These conditions could risk ineffective treatment delivery via redistribution of energy delivery, danger to the patient due to the higher electric current flow and concentration which could induce electroporation or thermal damage or other non-targeted treatment outcome effects or could damage the electrical generator or other electrical/conductive components within the system.

Typically, impedance measurements from low voltage test pulses as described herein should correlate to impedance values measured during the delivery of treatment energy, particularly when using a monopolar configuration. This is because the broader whole-body system encompassed in the circuit will dominate the bulk tissue impedance, and thus any local changes will be muted and relatively non-contributory to the impedance of the overall system. This is contrary to other conventional procedures, where impedance change is a known treatment outcome that results from the reduced cell membrane dielectric capacity through the circuit.

3. Modifying the Energy Algorithm

In some embodiments, impedance measurements can be made prior to or after applying energy in order to define which energy delivery algorithm 152 to apply and/or the need to apply additional energy to the target location. In some embodiments, pre-treatment impedance measurements can be used to determine the settings of various signal parameters. In other embodiments, sensors can be used to determine if the energy-delivery algorithm should be adjusted.

In some embodiments, the impedance measurement is performed as follows. A short duration, low voltage signal is delivered to the energy delivery body 108 via a generator (e.g., the generator 104) once positioned at a targeted area within a lung passageway. Based on the measured electrical current feedback received by the generator 104, the generator 104 performs a calculation using the set voltage and actual current to calculate the impedance. The calculated impedance is compared to impedance values that are considered acceptable for the measured impedance. Then, the energy delivery algorithm 152 is modified or tailored based upon the measured impedance. Parameters that can be adjusted include, but are not limited to, voltage, frequency, rest period, cycle count, dead time, packet count or number of packets, or a combination thereof. Thus, a feedback control loop can be configured to modify a parameter of energy delivery based on the measured one or more system or tissue parameters.

In some embodiments, one or more impedance sensors are used to monitor the electrical properties of the tissue. Impedance values can be regarded as an indicator of tissue state. In some embodiments, impedance is measured at different frequencies to provide an impedance spectrum. This spectrum characterizes the frequency dependent, or reactive, component of impedance. Tissue has both resistive and reactive components; these are components of complex impedance. Reactance is the frequency dependent component of impedance that includes tissue capacitance and inductance. Changes in the state of the tissue can result in changes to overall impedance as well as to changes in the resistive or reactive components of complex impedance. Measurement of complex impedance involves the conduction of a low voltage sensing signal between two electrodes. The signal can include but not be limited to a sine wave. Changes in complex impedance, including changes in resistance or reactance, can reflect the state of treated tissue and therefore be used as indicators that treatment is affecting tissue, not affecting tissue, and or that treatment can be complete. In these embodiments, changes to impedance can be derived from the therapy pulses or from dedicated sensing signals to evaluate tissue properties when not simultaneously experiencing the therapy effects. Impedance values can also change depending on the contact conditions between the sensors and airway tissue. In this way, sensors can also be used to determine the state of contact between electrodes and the tissue.

In some instances, the generator 104 instructs the user that additional energy delivery at the target location is not needed. Optionally, the generator 104 displays a specific message and/or emits a specific sound alerting the operator as to which energy delivery algorithm 154 has been selected, or that treatment is complete at that target location. Thus, the generator 104 can be configured to automatically select the appropriate algorithm for a particular measured impedance or shut off the delivery of energy signals if the treatment is determined to be completed. Further, impedance or other sensors can be used to determine that a treatment should be automatically stopped due to a safety concern.

When using continuous monitoring of treatment conditions, it is possible to provide real-time feedback and immediate intervention into the treatment delivery if an aberrant condition is encountered. For instance, if a sudden change in impedance is found, it may indicate an arc to the tissue or the equipment, loss of electrode contact quality, or movement of one or more of the electrodes in the system, or some combination of these effects. For instance, if a rise or decrease in impedance of 50Ω is encountered, the generator may immediately interrupt and cease energy delivery, providing the user with a warning to check the system prior to proceeding. By interrupting the sequence when an aberrant condition is encountered, risk of injury or damage to the patient, operator, and equipment is reduced, as well as the risk of delivering an insufficient therapy, improving outcomes and reducing the time to deliver the procedure. This may be performed either with continuous monitoring for immediate response capability, or with intermittent or during therapy energy delivery, though the response rate for the pulsed monitoring conditions will be delayed due to the intermittent nature of the energy delivery.

In addition to interrupting the treatment, the monitoring and test pulse conditions may be used to determine the properties of the tissue in the electrical system and provide adjustments to the energy delivery algorithm. For instance, in some embodiments, if the impedance determined prior to energy delivery is 125Ω, voltage is set to 2500 V. However, in other embodiments, if impedance is measured as 175Ω, the voltage is set at 2700 V. Further, if the generator design encompasses system-based power-dependent components that vary the output as a function of the load, such as transformers, then this information could also be used to establish the "set voltage" to be targeted for delivery into the tissue. In instances that include transformers, for instance, the power-in is equal to power-out through the transformer, thus $i1V1=i2V2$, thus any change in output current due to impedance differences in the patient tissue system, will also result in compensatory changes in the delivered voltage. Where voltage is a dominant electrical parameter in energy delivery therapies, this change could significantly alter treatment outcomes as tissue conditions within, as well as between, patients changes. For example, in the above example, if the impedance is 175Ω instead of a calibrated load of 125Ω, then the set voltage may be adjusted to 2300 V, since the increased impedance will reduce the electrical current, providing a boost to the final output voltage from the generator, bringing it back to the 2500 V that is targeted for final delivery in the example clinical dose.

B. Temperature Sensors

In some embodiments, one or more temperature sensors are used to measure electrode and/or tissue temperature during treatment to ensure that energy deposited in the tissue does not result in clinically dangerous tissue heating. In some embodiments, the temperature measured at or near the electrodes is also used to determine the state of contact between the electrode and tissue prior to treatment. This can be achieved by applying energy at a level sufficient to generate heat but insufficient to cause substantial thermal injury dangerous to the patient or that region of tissue. The temperature may differ in its steady state value or in its variability depending upon whether the electrode is pressed against the airway wall, moving, or suspended in the airway lumen.

In some embodiments, one or more temperature sensors are disposed along the surface of one or more energy delivery bodies 108 so as to contact the tissue and ensure that the tissue is not being heated above a pre-defined safety threshold. Thus, the one or more temperature sensors can be used to monitor the temperature of the tissue during treatment. In one embodiment, temperature changes that meet pre-specified criterion, such as temperature increases above a threshold (e.g., 40° C., 45° C., 50° C., 60° C., 65° C.) value, can result in changes to energy delivery parameters (e.g. modifying the algorithm) in an effort to lower the measured temperature or reduce the temperature to below the pre-set threshold. Adjustments can include but not be limited to increasing the rest period or dead time, or decreasing the packet count, or decreasing the voltage or decreasing the number of cycles per packet. Such adjustments occur in a pre-defined step-wise approach, as a percentage of the parameter, or by other methods.

In other embodiments, one or more temperature sensors monitor the temperature of the tissue and/or electrode, and if a pre-defined threshold temperature is exceeded (e.g., 65° C.), the generator 104 alters the algorithm to automatically cease energy delivery. For example, if the safety threshold is set at 65° C. and the generator 104 receives the feedback from the one or more temperature sensors that the temperature safety threshold is being exceeded, the treatment can be stopped automatically.

C. Sensors to Monitor Electrode Contact or Properties Around an Electrode

In some embodiments, one or more sensors (e.g. temperature, impedance, force, pressure etc.) are placed in various locations, such as circumferentially, on the surface of the one or more energy delivery bodies 108. In such configurations, the sensors may be used to indicate if the contact between the surface of the one or more energy delivery bodies 108 and the bronchial airway wall surface is sufficient, such as suitably circumferential and/or stable. If sensors indicate that the contact is not sufficient, such as not circumferential (e.g., non-uniform temperature, impedance, force etc.) and/or stable (e.g., continuously changing temperature, impedance, force, etc.), the operator may adjust the level of the expansion for the one or more energy delivery bodies or choose a catheter 102 with different sized energy delivery bodies 108 that better match the internal diameter of the bronchus/bronchi that are being treated. In some embodiments, the generator 104 is configured to interpret the degree, quality, and/or stability of contact and provide the operator feedback to aid in the proper positioning of energy delivery bodies. For example, as the operator is in the process of positioning the one or more energy delivery bodies which is not in circumferential contact, the user interface 150 on the generator 104 may display a message such as "Poor Contact". In other embodiments where non-circumferential treatments are desired, the system can be used to confirm that only desired regions of the electrode are active and in contact with the targeted passageway regions.

It may be appreciated that such monitoring can detect potential user errors or failures in the electrical system which may prevent dangerous or detrimental treatment conditions. For instance, if no monitoring is performed of contact integrity for the electrodes used in the complete circuit or for the dispersive pad electrode itself, then there is a risk whereby treatment energy is deposited into the patient's tissue, but without a sink for the energy to dissipate into. In such instances, the electrical energy may find alternate pathways to complete a circuit, risking damage to the patient, the users/operators, or the equipment connected to the patient (including ECG systems, ventilator systems, life support systems, procedure tables, or other electrical/electrically conductive components and systems within the procedure suite).

In some embodiments, force or pressure sensors can be used to detect and measure the contact force between the energy delivery bodies and the walls of the airway and thereby determine the contact conditions between energy delivery bodies and tissue.

It may be appreciated that any of the system 100 embodiments disclosed herein can incorporate one or more sensors to monitor the application of the therapy.

VI. Cardiac Synchronization

Figure 21:
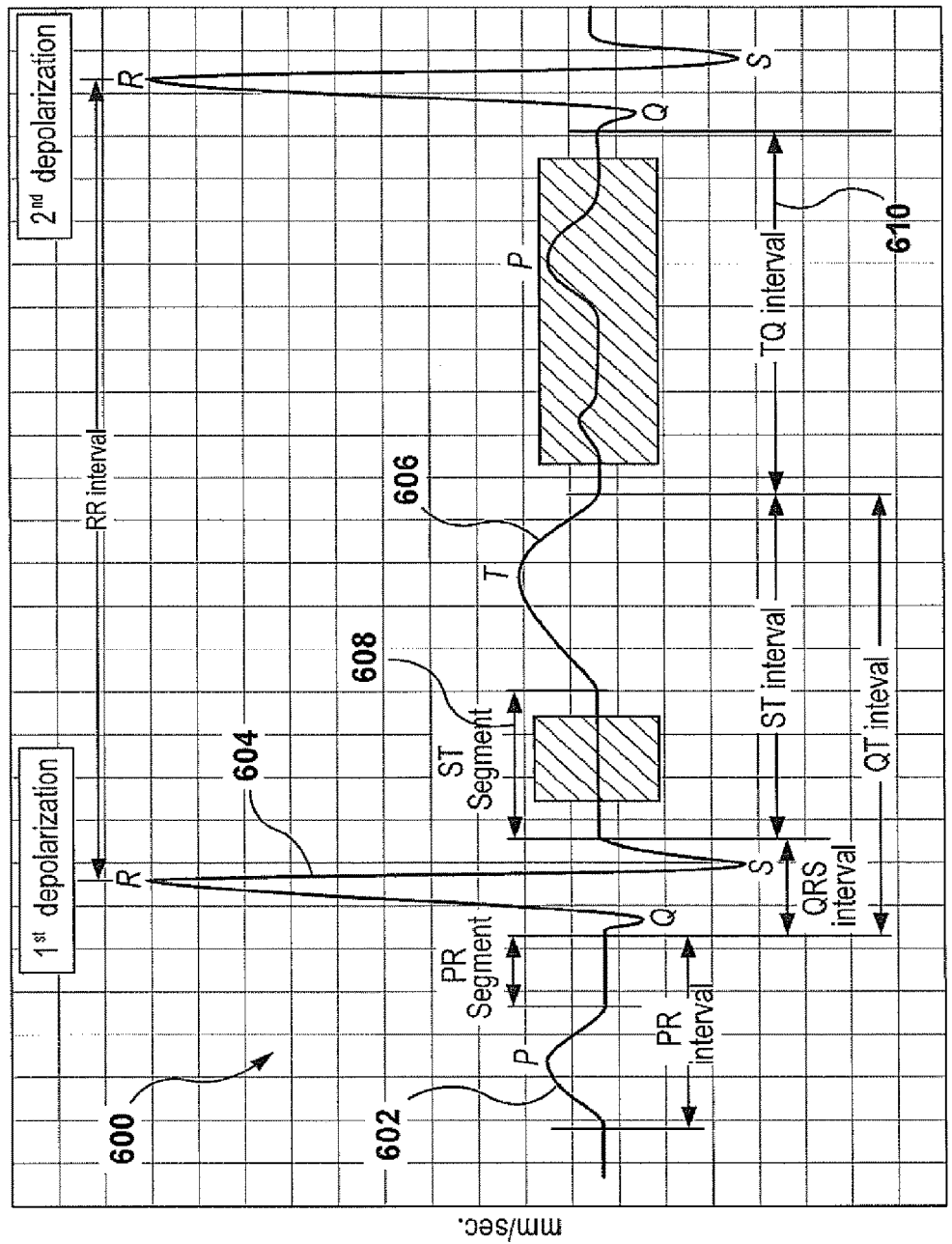
FIG. 21 is a graph illustrating portions of a sample electrocardiogram (ECG) trace of a human heart highlighting periods wherein it is desired to deliver energy pulses to the lung passageway via the energy delivery body.

In some embodiments, the energy signal is synchronized with the patient's cardiac cycle to prevent induction of cardiac arrhythmias. Thus, the patient's cardiac cycle is typically monitored with the use of an electrocardiogram (ECG). Referring to FIG. 21, a typical ECG trace 600 includes a repeating cycle of a P wave 602 representing atrial depolarization, a QRS complex 604 representing ventricular depolarization and atrial repolarization, and a T wave 606 representing ventricular repolarization. To safely deliver energy within the airway in close proximity to the heart, synchronization between energy delivery and the patient's cardiac cycle is employed to reduce the risk of cardiac arrhythmia. High voltage energy can trigger a premature action potential within the cardiac muscle as the delivered energy increases the cardiac muscle cell membrane permeability allowing ion transport, which can induce cardiac arrhythmias, especially ventricular fibrillation. To avoid cardiac arrhythmias, the electrical energy is delivered to the airway in a fashion that is outside the "vulnerable period" of the cardiac muscle. Within one cardiac cycle (heartbeat), the vulnerable period of the ventricular muscle is denoted on an ECG by the entire T wave 606. Typically, for ventricular myocardium, the vulnerable period coincides with the middle and terminal phases of the T wave 606. However, when high energy pulses are delivered in close proximity to the ventricle, the vulnerable period can occur several milliseconds earlier in the heartbeat. Therefore, the entire T wave can be considered to be within the vulnerable period of the ventricles.

The remaining parts of a cardiac cycle are the P wave 602 and the QRS complex 604, which both include periods when atrial or ventricular muscle is refractory to high voltage energy stimuli. If high voltage energy pulses are delivered during the muscle's refractory period, arrhythmogenic potential can be minimized. The ST segment 608 (interval between ventricular depolarization and repolarization) of the first cardiac cycle and the TQ interval 610 (interval including the end of the first cardiac cycle and the mid-point of the second cardiac cycle) are the periods where high voltage energy can be delivered without induction of cardiac arrhythmia due to the cardiac muscle depolarized state (refractory period). FIG. 20 includes shaded boxes that indicate example portions of the cardiac cycle during which energy can be applied safely.

Figure 21A:
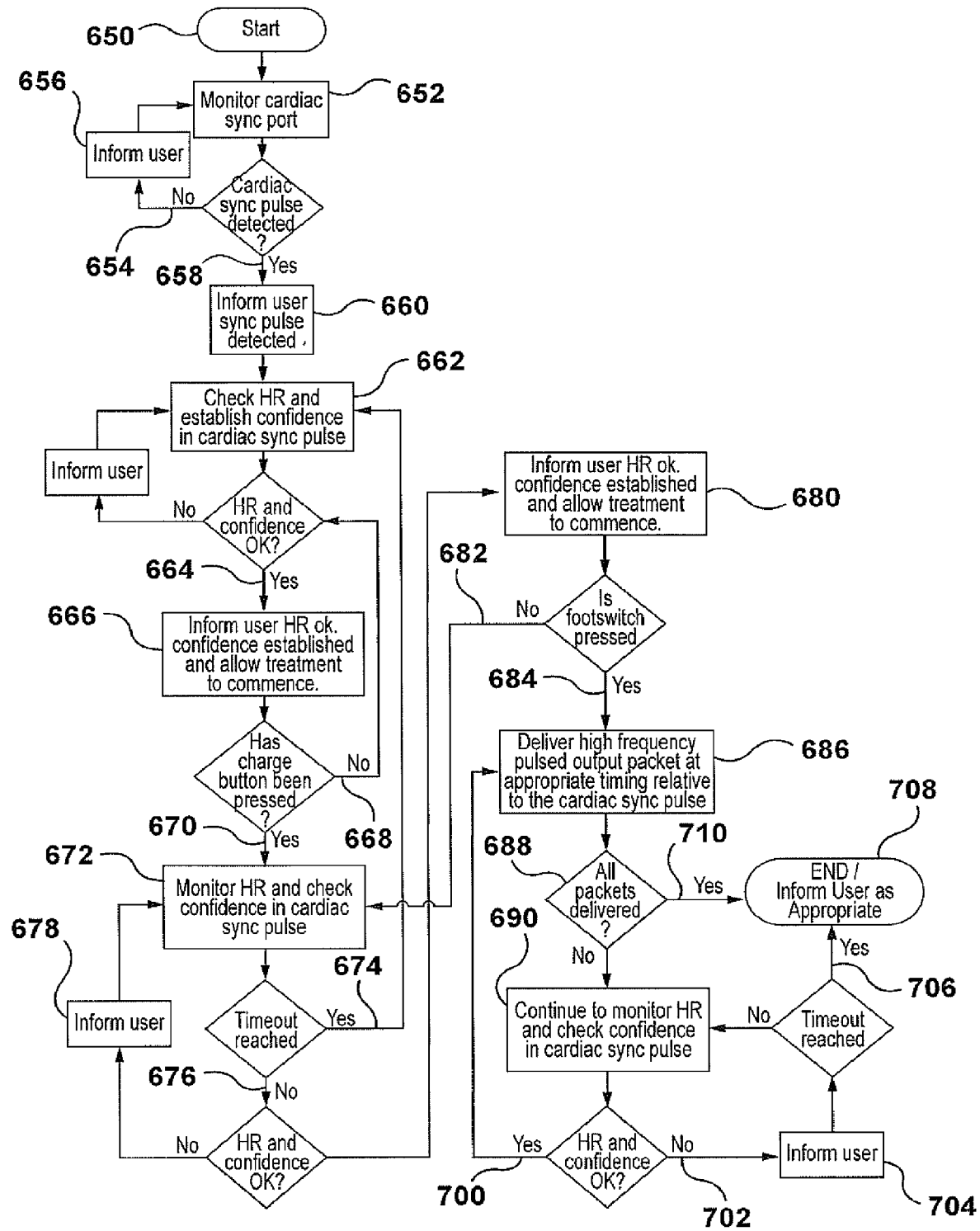
FIG. 21A is a flowchart depicting an embodiment of a method for synchronizing the delivery of energy with the cardiac cycle.

FIG. 21A is a flowchart depicting an embodiment of a method for synchronizing the delivery of energy with the cardiac cycle, according to some embodiments. In this embodiment, the electrocardiogram (ECG) is acquired by an external cardiac monitor 170 (such as the cardiac monitors available from AccuSync Medical Research Corporation) operatively connected to a communications port 167 on the energy producing generator 104, although it is understood that any suitable monitor may be employed. Here, the cardiac monitor 170 is used to continuously acquire the ECG, analyze one or more cardiac cycles, and identify the beginning of a time period where it is safe to apply energy. In some embodiments, when the cardiac monitor 170 detects this event/beginning (e.g., the R wave of an ECG trace), it sends a low voltage transistor to transistor logic (TTL) pulse (e.g., <5 V) to the communications port 167. At the start step 650, the processor 154 of the energy producing generator 104 monitors (at step 652) the communications port 167 to determine if the cardiac sync pulse is detected. If a TTL pulse is not detected (at step 654) by the generator 104, the user interface 150 is used to inform the user (at step 656). For example, the user interface 150 may display a solid red heart and/or any other suitable visual indicator. Once a cardiac sync pulse is detected (at step 658) by the generator 104, the user interface 150 is used to inform the user (at step 660). For example, the solid red heart may turn to a yellow blinking heart, turning on at the time the cardiac sync pulse is detected.

Because the external cardiac monitor 170 can send false TTL pulses and because the generator should not allow treatment to continue if the patient's heart rate is outside of the normal expected limits, is erratic, and/or has a widened QRS complex not associated with/different from the patient's baseline rhythm, the next step can involve checking the heart rate to establish confidence in the TTL pulse (i.e., cardiac sync pulse) (at step 662). In one embodiment, the processor 154 of the generator 104 is used to monitor the TTL pulses and calculate the time between each beat, referred to as $\Delta t1$, $\Delta t2$, $\Delta t3$, $\Delta t4$, $\Delta t5$. These values can be stored within the data storage module 156 of the generator 104 as a rolling buffer having the last five. At calculations. Next, the average of those five values can be calculated, referred to as $\Delta t$-ave. The next one or more TTL pulses detected can be used to calculate the next $\Delta t(s)$ (e.g., $\Delta t6$, $\Delta t7$, etc.), which can also be stored in the data storage module 156. For example, two TTL pulses can be utilized.

Next, the algorithms module 152 of the generator 104 is used to compare these values to a set of criteria that, if met, provide confidence that the patient's heart rhythm is normal/consistent and that the TTL pulse is reliable. For example, the heart rate can be calculated and checked to ensure it is between 40-150 beats per minute (bpm). In this example, $\Delta t6$ and $\Delta t7$ can also be compared to $\Delta t$-ave to verify that the heart rate is not erratic. In one embodiment, $\Delta t6$ and/or $\Delta t7$ can be within ±15% of $\Delta t$-ave in order to continue. In this example, both criteria must be met in order to confirm confidence (at step 664); however, in other embodiments, both criteria may not be required. Once confidence is confirmed, the user interface 150 can be used to inform the user that it is safe to continue (at step 666). For example, the yellow flashing heart on the user interface 150 can change to a green flashing heart. Next, the user interface 150 is used to direct the user to charge the high energy storage unit (e.g., one or more capacitors) of the generator 104. In one example, the user interface 150 displays a soft-key labeled 'Charge', which the user may press to charge the high energy storage unit. If the charge button has not been pressed (at step 668), the processor 154 continues to check heart rate and confidence in the TTL signals.

Once the processor 154 recognizes that the charge button has been pressed (at step 670), the processor 154 continues to check heart rate and confidence in the TTL signals (at step 672). During that time, if a predefined/predetermined amount of time has passed (e.g., about 30, 40, 50, 60, or up to 120 seconds, including all values and sub ranges in between) without verification that the heart rate and TTL confidence is established (at step 674), the system aborts the charging mode and reverts to the system status wherein it is checking heart rate and establishing confidence in the cardiac sync pulse (at step 662). If the timeout is not reached (step 676), the user interface 150 informs the user (at step 678) until confidence is established (at step 680). The user interface 150 can change such that the soft-key is now labeled 'Ready'. The system 100 is now waiting for the footswitch 168 to be pressed.

While the system 100 waits for the footswitch 168 to be pressed (at step 348), it continues to monitor heart rate and check for confidence (672). Another timeout can be predefined (e.g., about 30, 40, 50, 60, or up to 120 seconds, including all values and sub ranges in between), such that if the user does not press the footswitch 168 within that time (e.g., timeout is reached, as illustrated, at step 674), the system aborts being ready to deliver energy and returns to the system status wherein it is checking heart rate and establishing confidence in the TTL pulses (at step 662). Once the user presses the footswitch (at step 684), energy delivery can commence (at step 686). However, the generator 104 can be configured to wait until the next cardiac pulse is detected to further ensure that energy delivery occurs after the R-wave is detected. In one embodiment, the energy is not delivered until about 50 milliseconds after the leading edge of the TTL pulse is detected; however this value could range from about 0-300 milliseconds. The first energy packet can then be delivered (at step 686). The processor 104 then checks to determine if all packets have been delivered (at step 688). If not, the processor 154 continues to monitor heart rate and check confidence in the TTL pulses (at step 690) and energy delivery can continue once confidence in the cardiac sync pulse (at step 662) is re-established.

In some instances, it may be beneficial to ignore TTL pulses immediately following energy delivery, as they may be false triggers caused by the high voltage energy being delivered. For example, the processor 154 can ignore TTL pulses for about 400 ms after energy is delivered or about 450 ms after the leading edge of the last TTL pulse. In other situations, the TTL pulses can be ignored for about 50 ms-to about 1 second, including all values and sub ranges in between. Once the processor detects the next TTL pulse, the next $\Delta t$ can be calculated and compared against the criteria (at step 690) previously defined (i.e., based on a rolling average). Due to the potential for transient delays in the heart beat following energy delivery, if the next $\Delta t$ falls outside of the criteria, it is simply ignored. Then, the next $\Delta t$ can then be calculated and compared against the criteria previously defined. If the criteria are met (at step 700), the next packet is delivered (at step 686). If all packets have not been delivered, the system continues to monitor the heart rate and check for confidence in the cardiac sync pulse (at step 690) as previously described. If confidence is established (at step 700), the cycle continues. If confidence is not established (at step 702), the user is informed (at step 704), for example, by the heart turning yellow and flashing or turning solid red.

If the system 100 cannot determine acceptable confidence or no longer detects a TTL pulse within a certain amount of time (e.g., about 10, 20, 30, 40, 50, or 60 seconds), a timeout will be reached (at step 706), and the user interface 150 can be used to notify the user (at step 708). At this time, the cycle can end, and any remaining packets would not be delivered. The process then returns to start (at step 650). If the system can determine acceptable confidence (at step 700) within the set time limit, a timeout will not be reached (at step 688), and the cycle continues with continued monitoring of heart rate and checks for confidence (at step 690), as previously described. If confidence is gained (at step 700), the next energy packet is delivered (at step 686). Once all packets are delivered, the treatment is deemed complete (at step 710) and the user is informed of completion of treatment (at step 708). If the current associated with delivery of any of the high energy packets (at step 686) exceeds a set value (e.g., about 45 amps), the cycle can also end (at step 708).

It may be appreciated that in some embodiments, components for acquiring the electrocardiogram 170 are integrally formed with the generator 104. If the cardiac monitor is limited to acquiring up to a 5-lead ECG, and it may be beneficial to incorporate additional leads into the system. This would further eliminate the need to use the communications port 167 to receive cardiac sync pulses. Rather, the processor 154 can be configured to detect the R-waves directly and to assess the integrity of the entire QRS complex.

In some embodiments, the processor 154 may be configured to use either fewer or more than five Δt's to calculate Δt-ave. In some embodiments, the processor 154 may be configured to use between three and ten Δt's to calculate Δt-ave. Further, the processor 154 may be configured to use a Δt other than Δt6 and Δt7 to confirm confidence. For example, the processor 154 may be configured to use any subsequent Δt. The processor 154 may also be configured to allow heart rates beyond the 40-150 bpm described above. For example, the processor 154 may be configured to allow heart rates in the range of 30-160 bpm, including all values and sub ranges in between. The processor 154 may also be configured to allow Δt6 or Δt7 to be more or less than ±10%. For example, the processor 154 may be configured to allow Δt6 or other data point, including rolling averages, to be within ±3% to ±50%. User interface 150 examples provided herein are merely examples and should not be considered limiting.

Thus, it may be appreciated that generator can be configured to continuously monitor the patient's heart rate, and in case cardiac arrhythmias are induced, the treatment will be automatically stopped and an alarm can sound.

VII. Imaging

Methods associated with imaging that can be useful include: (a) detecting diseased target tissue, (b) identifying areas to be treated, (c) assessing areas treated to determine how effective the energy delivery was, (d) assessing target areas to determine if areas were missed or insufficiently treated, (e) using pre- or intra-procedural imaging to measure a target treatment depth and using that depth to choose a specific energy delivery algorithm to achieve tissue effects to that depth, (f) using pre or intra-procedural imaging to identify a target cell type or cellular interface and using that location or depth to choose a specific energy delivery algorithm to achieve tissue effects to that target cell type or cellular interface, and/or (g) using pre-, intra-, or post-procedural imaging to identify the presence or absence of a pathogen with or without the presence of inflamed tissue.

In some embodiments, confocal laser endomicroscopy (CLE), optical coherence tomography (OCT), ultrasound, static or dynamic CT imaging, X-ray, magnetic resonance imaging (MRI), and/or other imaging modalities can be used, either as a separate apparatus/system, or incorporated/integrated (functionally and/or structurally) into the pulmonary tissue modification system 100 by either incorporating into the energy delivery catheter 102 or a separate device. The imaging modality (or modalities) can be used to locate and/or access various sections of tissue as demonstrated by a thick area of epithelium, goblet cell hyperplasia, submucosal glands, smooth muscle, and/or other aberrancies relative to where the system is deployed in the chest. In some embodiments, the imaging can include CT performed immediately or considerably in advance of therapy administration, where the CT data is analyzed to determine best locations for delivering the therapy. In this embodiment, CT can be used to determine locations of mucus plugging prior to therapy delivery. CT scans may also be used to predict responsiveness. Patients with severe emphysema of the lung lobes may not respond to relief of mucus obstruction as compared to patients with less emphysema. Patients with low lung volumes, airway counts, or airway diameters at baseline may improve significantly. In some embodiments, pre-therapy CT scan analysis is performed on asthma patients. In some embodiments, the targeted depth of treatment can be measured and used to select a treatment algorithm 152 sufficient to treat to the targeted depth. At least one energy delivery body can then be deployed at the site of abnormal airway wall tissue and energy delivered to affect the target tissue. The imaging modality (or modalities) can be used before, during, between, and/or after treatments to determine where treatments have or have not been delivered or whether the energy adequately affected the airway wall. If it is determined that an area was missed or that an area was not adequately affected, the energy delivery can be repeated followed by imaging modality (or modalities) until adequate treatment is achieved. Further, the imaging information can be utilized to determine if specific cell types and or a desired depth of therapy was applied. This can allow for customization of the energy delivery algorithm for treating a wide variety of patient anatomies.

In some embodiments, imaging combined with the use of a fluorescent agent (e.g., fluorescein) can be performed to enhance recognition of pathogens that may be in the airway. The fluorescent agent can be chosen to directly tag certain pathogens (e.g., bacteria), indirectly tag cells associated with various infectious states (e.g., neutrophils), or indirectly or directly tag cells associated with autologous disease conditions (e.g., cancers which will then be visible. In some embodiments, such an imaging method/approach can include the steps of gaining access to the airway, delivering the fluorescent agent to within the airway, exciting the fluorescent agent by delivering an excitation signal into the airway, and assessing the presence or absence of fluorescence in response to the excitation signal.

A. Imaging for Access

In general, the methods, apparatuses, and systems disclosed herein can access pulmonary tissue or a target region (e.g., trachea, mainstem bronchi, lobar bronchi, segmental bronchi, sub-segmental bronchi, parenchyma) via a natural orifice route (e.g., from the mouth or nose), an artificially created orifice (e.g., via a tracheotomy, via a surgically created stoma, and/or any suitable intra-operative and/or surgical orifice), and/or via an artificially created orifice through the airway into other areas of the lung and/or tissue (e.g., parenchyma). The type of approach utilized can depend on factors such as a patient's age, comorbidities, need for other concomitant procedures, and/or prior surgical history.

Figure 22:
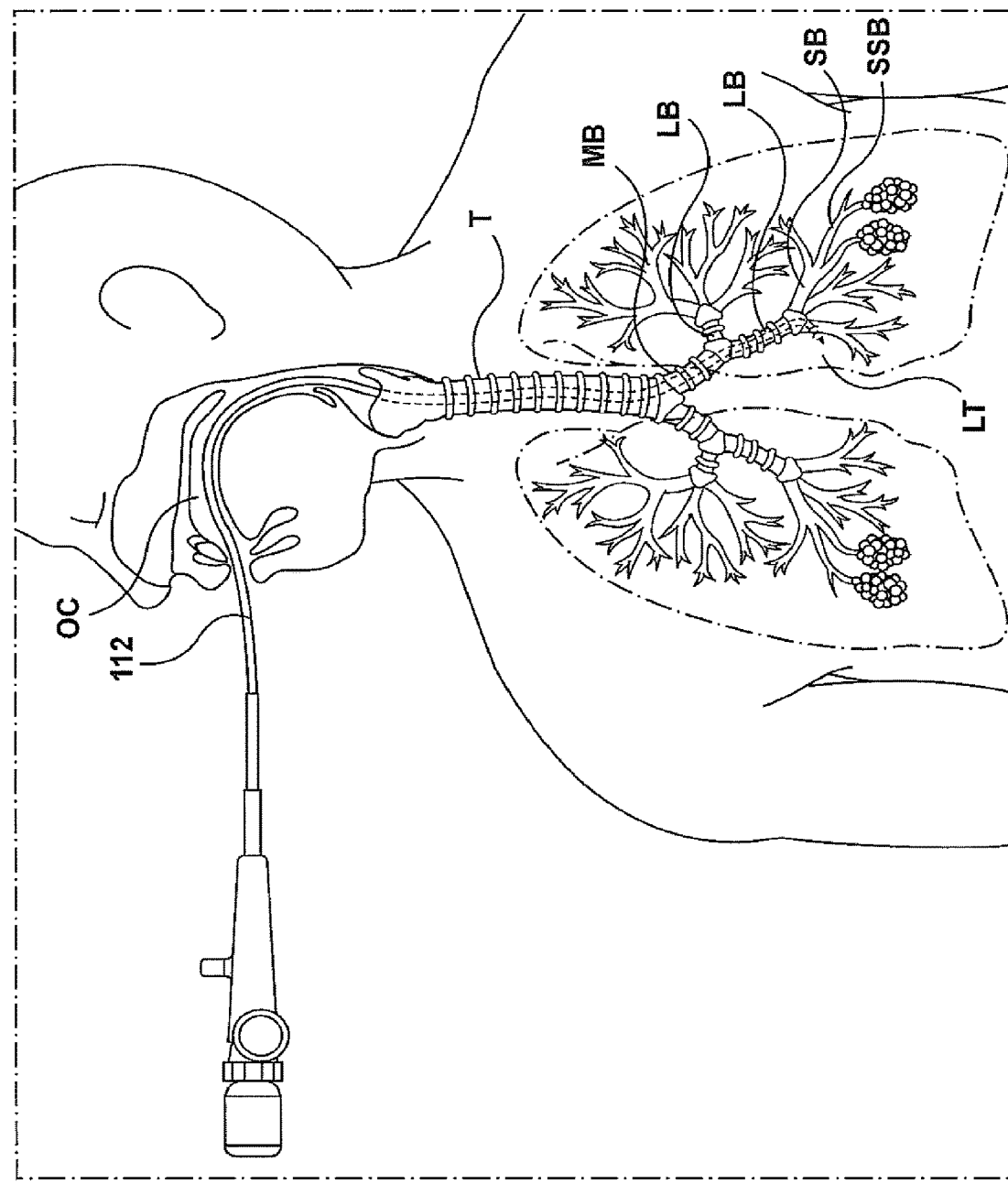
FIG. 22 illustrates accessing lung tissue, such as parenchyma, via the nose or mouth.

Methods for accessing the airway and/or other lung tissue (e.g., parenchyma) can include using the working channel of a bronchoscope delivered via the nose or mouth, into the trachea and/or more distal bronchi. As illustrated previously in FIGS. 8A-8B, a bronchoscope 112 may be inserted in the mouth or oral cavity OC of the patient P or other natural orifices such as the nose or nasal cavity NC. Similarly, other lung tissue LT, such as parenchyma, may be accessed by via the nose or mouth, as illustrated in FIG. 22. As shown, the distal end of the catheter 102 is advanced into the trachea T, the mainstem bronchi MB, and into the lobar bronchi LB crossing from an airway into the surrounding lung tissue LT. This may be achieved with a tool or catheter having a guidance system which allows for guidance outside of the lung passageway.

It may be appreciated that in some instances, direct visualization may not be necessary and/or desired, and the treatment catheter can be delivered directly into the airway via the nose or mouth.

Figure 23A:
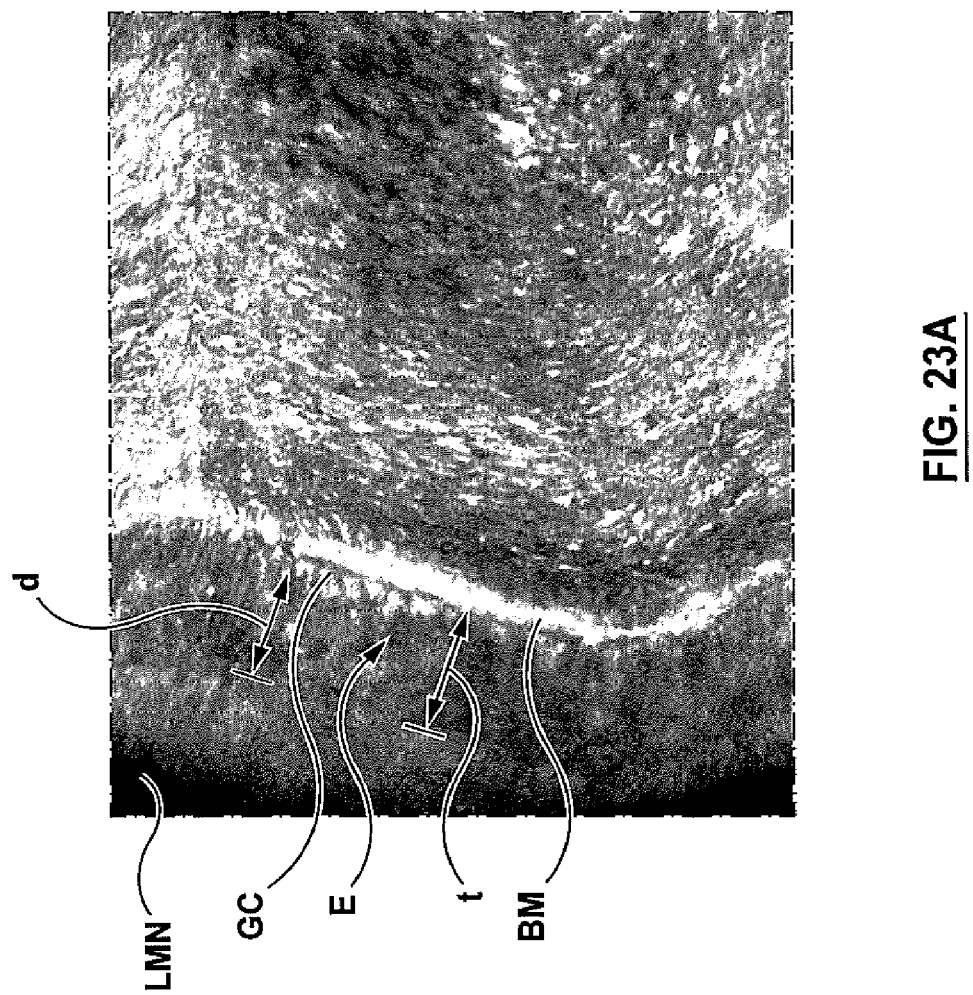
FIGS. 23A-23B depict example images of lung passageways obtainable using confocal laser endomicroscopy (CLE) and optical coherence tomography (OCT), respectively.
Figure 23B:
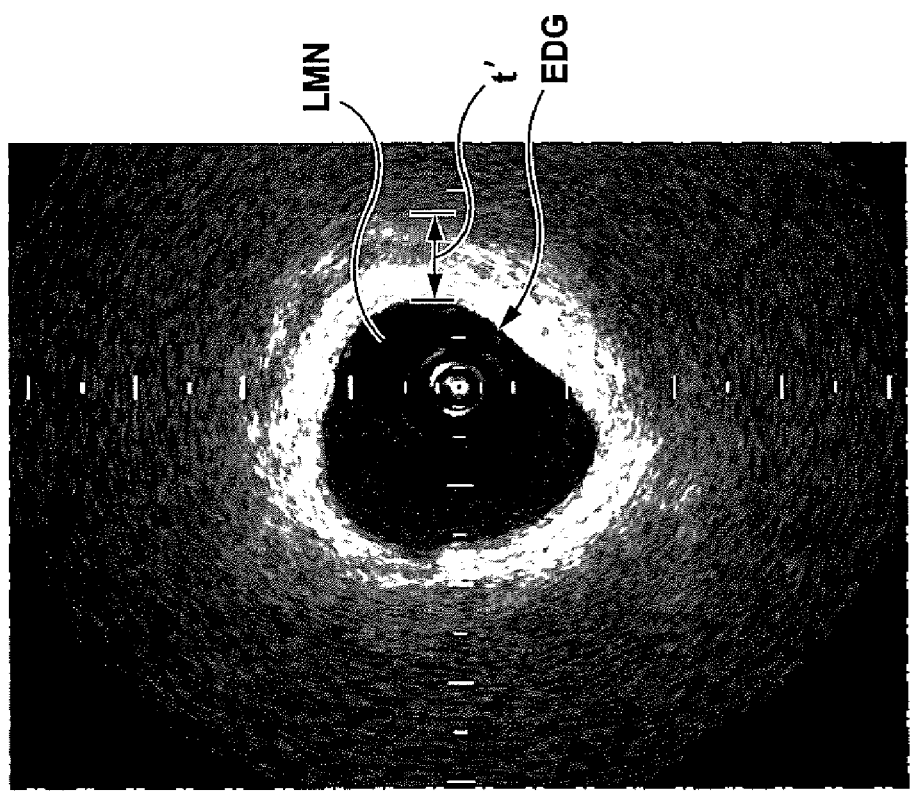

In other embodiments, accessing the airway and/or lung tissue (e.g., parenchyma) is achieved via other appliances inserted into the chest. Likewise, in some embodiments, one or more of a variety of imaging modalities (e.g., CLE, OCT) are used either along with direct visualization, or instead of direct visualization. As an example, a bronchoscope 112 can be delivered via the mouth to allow for direct visualization and delivery of the catheter 102, while an alternate imaging modality can be delivered via another working channel of the bronchoscope 112, via the nose, or adjacent to the bronchoscope via the mouth. In some embodiments, the imaging modality (e.g., direct visualization, CLE, and/or OCT) is incorporated into the catheter 102 with appropriate mechanisms to connect the imaging modality to either the system generator 104 or commercially available consoles. FIGS. 23A and 23B depict example images obtainable using CLE and OCT, respectively. These images can be used to guide delivery to a pre-determined location previously identified on CT scan using airway wall thickness (AWT) measurements, to target treatment based on visualization of cell structures, and/or to assess the effectiveness of treatment

B. Imaging for Treatment Planning

Methods associated with imaging can include using imaging pre-treatment to plan the procedure. Imaging can be used for detecting diseased target tissue, identifying areas to be treated, and/or for determining the appropriate energy delivery algorithm to achieve a desired depth of treatment. In some embodiments, imaging is used in the lung to determine areas of hyperinflation in patients suffering from emphysema. Such determinations can be used to plan treatment that will reduce or eliminate mucus plugging and restore expiratory respiration capacity. In other embodiments, imaging is used to determine regions of respiratory dysfunction, such as in particular cases of chronic bronchitis. In some embodiments, imaging, such as CT scans, are used to predict responsiveness. Patients with severe emphysema of the lung lobes may not respond to relief of mucus obstruction as compared to patients with less emphysema. Patients with air-trapping as a consequence of mucus inspissation or impaction may improve significantly. In some embodiments, pre-therapy CT scan analysis is performed on asthma patients.

In some embodiments, pre-treatment imaging is used to prioritize target segments when multiple treatment sessions are desired to cover an entire targeted region. For example, pre-treatment imaging may be used to determine which lung is the most diseased and therefore would benefit the most from therapy. Treating the more diseased lung first to obtain the best immediate benefit may also mitigate any risks incurred by transient induced injury to the treated lung. Such transient injury would cause the patient to rely more heavily on the untreated lung during the recovery period. Since the untreated lung is the healthier lung, subsequent morbidity and mortality implications may be reduced.

In some embodiments, an imaging scan, such as a CT scan, can be obtained preoperatively or intraoperatively, from which an AWT or Pi10 (theoretical airway wall thickness for an airway with an internal perimeter of 10 mm) measurement is obtained. Target zones can be identified using these metrics. Referring again to FIGS. 23A-23B, CLE or OCT can be used to measure a target treatment depth. The desired treatment depth can be based upon the thickness t of the epithelium E, as measured from the airway lumen LMN to the basement membrane BM; the distance d to a target cell type such as goblet cells GC, submucosal glands (not shown), or smooth muscle (not shown), and/or any other structure that the physician determines to be medically appropriate. FIG. 23B provides an example OCT image of a diseased airway. The thickness t' of the airway can be determined by measuring the distance from the airway lumen LMN to the outer edge EDG of the airway. Those measurements can then be used to choose a specific energy delivery algorithm 152 to achieve tissue effects to that depth. For example, the generator 104 can have a user interface 150 (such as a touch screen) that allows the selection of desired treatment depth. Once the operator chooses the desired depth, the system 100 can be configured to automatically select the appropriate energy delivery algorithm 152 to achieve that depth. Other anatomical assessments can also be made to help select target treatment sites. For example, using CLE, one can assess the size and/or density of goblet cells GC along with the distance d from the airway lumen LMN to the goblet cells GC to target both a treatment location and a target depth. These methods would allow for the therapy to be customized to each patient.

In some embodiments, the use of the bronchoscope 112 may allow for pre-procedural planning, wherein a sputum sample is acquired for analysis. If one or more pathogens are found, this information may be use for determining the appropriate energy delivery algorithm 152 to achieve a desired depth of treatment as a consequence of the initial data. In some cases, such as the combination of pathogen identification in conjunction with improved tissue imaging, it may be desirable to limit the treatment depth to merely the mucus layer M, where pathogens thrive; whereas, in other cases, it may be desirable to affect deeper airway structures. For planning the treatment, a sputum sample may be obtained and assessed to determine if an infection of the tracheobronchial tree may be present. If an infection is deemed to be present, the generator can be programmed to affect the mucus layer of the airway without substantially impacting other layers, which contains the pathogens causing the infection, or other pulmonary tissues. The method of performing sputum testing can also be used to assess the effect of the treatment. For assessing the effect of the treatment, additional sputum samples, as well as biopsies, can be taken following the energy-delivery procedure or at a later time. By comparing these samples and biopsies to the planning samples and each other, the effectiveness of the procedure can be determined. These data, combined with a clinical examination of the patient, can be used to further optimize therapy.

The method of performing one or more tissue biopsies can be used to plan treatment and/or assess the effect of the treatment. For planning the treatment, a biopsy can be performed and assessed microscopically to determine patient suitability (e.g., excessive mucus production, goblet cell density, goblet cell hypertrophy, epithelial thickness, inflammation, basement membrane thickening, submucosal inflammation, submucosal eosinophilia, submucosal gland thickening, smooth muscle hypertrophy, or other parameters) and/or degree of airway obstruction (e.g., thickness of epithelial and/or other layers). By measuring one or more of these parameters, the generator can be programmed to affect a certain depth of tissue, allowing for customization of the energy-delivery algorithm for each patient. For example, voltage can be increased for patients with thicker epithelial layers. For assessing the effect of the treatment, additional biopsies can be performed immediately following the energy-delivery procedure or at a later time. By comparing these biopsies to the planning biopsy and each other, the effectiveness of the procedure can be determined. For example, if the post treatment biopsy showed no change from the planning biopsy, either that location was not treated or insufficient energy was applied to affect the tissue. But, if the post treatment biopsy showed a reduction in epithelial thickness and/or structure (i.e., regeneration of healthy epithelium), the effectiveness of the energy delivery can be verified. This also applies to treatment to deeper tissue layers. By performing multiple biopsies along the airway, one could further assess whether or not a sufficient percentage of the total surface area was treated. These data, combined with a clinical examination of the patient can be used to further optimize therapy.

C. Imaging During Treatment

Use of a bronchoscope 112 allows for direct visualization of the target tissues and visual confirmation of catheter 102 placement and deployment. In some embodiments, direct visualization may not be necessary and the catheter 102 is delivered directly into the airway. Alternatively, a variety of imaging modalities (e.g., electromagnetic navigation, CLE, OCT) can be used either along with direct visualization or instead of direct visualization. As an example, a bronchoscope 112 can be delivered via the mouth to allow for direct visualization and delivery of the catheter 102, while an alternate imaging modality can be delivered via another working channel of the bronchoscope 112, via the nose, or adjacent to the bronchoscope via the mouth. In some embodiments, the imaging technology (e.g., direct visualization, CLE, and/or OCT) can be incorporated into the catheter with appropriate mechanisms to connect the imaging technology to either the system generator or commercially available consoles.

Such imaging during treatment can be used to guide initial placement of the catheter 102 and any further placements of the catheter 102, such as to specifically avoid overlapping of target segments or to specifically create overlapping target segments. In some embodiments, imaging studies provide both length and diameter of the airways in the targeted treatment zone. Thus, the clinician is able to determine the number of catheter placements or treatments that would cover the targeted treatment zone since the contact length of the energy delivery body is known at any given diameter. Such imaging can also be used to monitor the degree of overlap in various target segments. Further, such imaging can be used to monitor focal treatment, such as degree of rotation of the catheter 102 during various portions of the treatment. It may be appreciated that in some embodiments, tissue characteristics can be derived from the inherent OCT image itself to guide placement for focal targets. In some embodiments, fiducial markers can be used to guide delivery to the focal target.

Some focal targets, such as aberrant cell growths, may involve complicated guidance and targeting through a series of side-branches to reach the targeted region. These focal targets and their complicated access may benefit from advanced guidance to facilitate accurate catheter placement and treatment delivery. Examples of suitable guidance technologies include internal and external guidance. Internal guidance technologies may include direct visualization via bronchoscopy. Other methods may use alternate imaging approaches to navigate and also discern properties of the tissue, such as optical coherence tomography (OCT) or endoluminal ultrasound. In some embodiments, these techniques use the characteristics of the tissue itself to determine whether it is an appropriate area to deliver treatment, or if it is not of clinical concern, permitting the skipping over of non-clinically significant regions. External imaging methods to navigate through complex anatomical passageways to reach desired anatomical targets include external ultrasound, xrays/angiography, CT, MRI, electromagnetic guidance, or radiofrequency identification (RFID) determination of proximity. These external monitoring methods may be used with catheters specifically designed to enhance their visibility to these modalities, such as the inclusion of hyperechoic or hyperattenuating materials. In other systems, fiducial markers may also be used in conjunction with these imaging modalities to further guide the catheter electrodes to the targeted regions in three-dimensional space.

D. Imaging Post Treatment

In some embodiments, methods associated with imaging can include using imaging (e.g., using the imaging modality 169) to assess the effectiveness of the treatment that has been applied, either intra-operatively and/or post procedure. In some embodiments, during the procedure, the operator can use imaging to assess the treatment areas to determine if areas were missed or insufficiently treated. For example, if an area was missed, there may be an absence of rapid-onset or acute changes that are observed at the treated regions. In another example, if an area was insufficiently treated, the operator can observe that the target depth was not achieved. The operator can then re-measure the depth, select an appropriate treatment algorithm 152, and treat again in the same location. In some embodiments, if the generator 104 does not have a variety of pre-set algorithms based on desired depth, the same energy delivery algorithm can be used. Imaging can be also used post procedure to monitor the healing process and correlate tissue changes to clinical outcomes. The healing process can make it easier to visualize tissue changes and assess the effectiveness of the procedure. These data can further lead to the physician deciding to perform additional procedures to affect additional tissue.

E. Imaging Pre-Treatment and Post-Treatment Comparisons

In some embodiments, an image, such as a CT scan, is used pre-operatively or post-operatively to determine total airway count and airway volume. In another embodiment, pre- and post-treatment bronchoscopies are compared to evaluate improvement/depreciation in airway tissue condition, lumen diameter, or other characteristics of interest. In other embodiments, one or more images, such as CT scans, are compared between pre-operative and intra- or post-operative scans for total airway count and airway volume to evaluate changes in mucus plugging Similar techniques may also be employed to avoid encouraging the progression of hyperinflated regions of the tissue by guiding treatment to only the upper airways and branches that support healthy lung parenchymal regions. This technique may also be employed in combination with making efforts to acutely or chronically restore ventilation of the hyperinflated tissues in a manner that encourages expiration but does not foster or encourage further inspiration back into these regions. This will preserve more viable and properly performing lung parenchyma to occupy the pulmonary cavity, further compounding the benefits appreciated via improved ventilation to the healthy lung lobes and subsegments.

VIII. Mucus Plugging

A variety of methods, systems and devices are provided, among others, to control the type of treatment effect, the depth of the effect, and the coverage or area of the effect. Treatment outcomes include improving patient symptoms, both in the short and long term. In some embodiments, this includes reducing mucus hypersecretion, such as by eliminating or reducing mucus plugging of the airways which facilitates improved respiration during inhale and exhale processes, easing breathing ability. In addition to being uncomfortable and restricting general activity, mucus hypersecretion (with insufficient expectoration capacity) physically narrows the airway lumen available for airflow. When this is combined with patient conditions such as bronchiectasis, an inflammation of the airways, pneumonia, fluid in the lungs, or asthma, a transient-acute inflammation and bronchiole smooth muscle contraction, then the narrowing becomes exaggerated, severely limiting the usable lumen for airflow or occluding the airway from airflow entirely. In instances where airflow is entirely restricted in conjunction with mucus hypersecretion, it results in a mucus plug which imparts a number of morbidity implications for the downstream airways and lung parenchyma as well as the patient's overall mortality.

In some conditions, mucus plugging may result in respiratory acidosis. In other instances, the restricted airflow and particularly mucus plugging may further compound disease states in other vital anatomical functions and systems in the patient, such as poor circulatory function and pressure on the heart. Further, it is important to consider that mucus plugging not only prevents fresh air from entering the downstream airways and lungs, but it also prevents the expiration of the existing air contained within the downstream regions. COPD conditions such as emphysema are marked by hyperinflation of distal lung regions, with the inability to expire the trapped lung volume, decreasing the available space for the viable ventilated regions of the lung. Thus, by eliminating mucus plugging in the airways that feed hyperventilated lung tissues with trapped air, it may be possible to improve ventilation to the hyperventilated regions, permitting them to expire their trapped air and restore normal distributions of lung volumes, thus improving ventilation to the healthy portions of lung tissue.

In some embodiments, mucus hypersecretion is reduced to a point where hyperreactivity from bronchiolar smooth muscle cells during an asthma attack also does not cause mucus plugging of the airways, dramatically reducing the morbidity and mortality risks encountered during an asthma attack. With the elimination of mucus plugging via resurfacing and redistributing mucosal and submucosal airway cell populations, it is possible to restore proper ventilation to more of the lung. The presence of this outcome is clearly indicated by the increase in available airway counts and their respective diameters when comparing data pre- and post-therapy.

In addition, the elimination or reduction of mucus hypersecretion, especially the incidences of mucus plugging to healthy or diseased lung volumes will substantially increase the therapeutic efficacy of complementary treatments via inhaled medications. By improving access for inhaled medications to reach all targeted regions of the lung tissue, it is possible for them to most effectively treat the entire lung or any particular foci of disease regions.

In some instances, mucus plugging may be present prior to delivery of therapy. In these instances, an array of techniques may be employed to address the mucus plug. In the first condition, the mucus plug is left in situ and is harnessed as an electrical conduit to transfer the energy from the energy delivery body 108 into the tissue. In some instances, may dilute the concentration of the energy, and thus may require increased treatment protocol intensity to ensure adequate delivery. In some other approaches, the present mucus and mucus plugs may be agitated or removed via scrubbing with a brush, providing the patient inhaled saline to promote mucus secretion and coughing. In other instances, mucus and mucus plugs may be ignored, whereby the treatment simply skips performance in that region.

In another method, the mucus plugs are eliminated prior to delivering treatment as a part of attaining a standardized tissue environment prior to delivering therapy via the flushing of the airway(s) with one of several solutions including isotonic saline, hypertonic saline, calcium, or others. The fluid and mucus combination may then be removed as part of the broader lavage process via suctioning the flushing liquid. This method will reduce or eliminate the influence of mucus on diluting the energy and will likely provide a more stable and predictable initial environment for delivering therapies. This may result in more stabilized outcomes and improved refinement and optimization of the ideal clinical dose. This technique may be employed in the tissue prior to treatment as best practice regardless of the presence of visible mucus plugging.

IX. Catheter Embodiments

A variety of energy delivery catheter 102 embodiments are envisioned. Characteristics and features described herein can be used in any combination to achieve the desired tissue effects. Typically, such catheters 102 are sized and configured to treat lung passageways having a lumen diameter of approximately 3-20 mm Typically, energy delivery bodies 108 expand within the lung passageway lumen so as to reside near, against, in contact, or exerting pressure or force against the wall W of the lumen. In some embodiments, the energy delivery body 108 expands to a diameter of up to 22 mm, particularly 3-20 mm or 3-22 mm.

Figure 24:
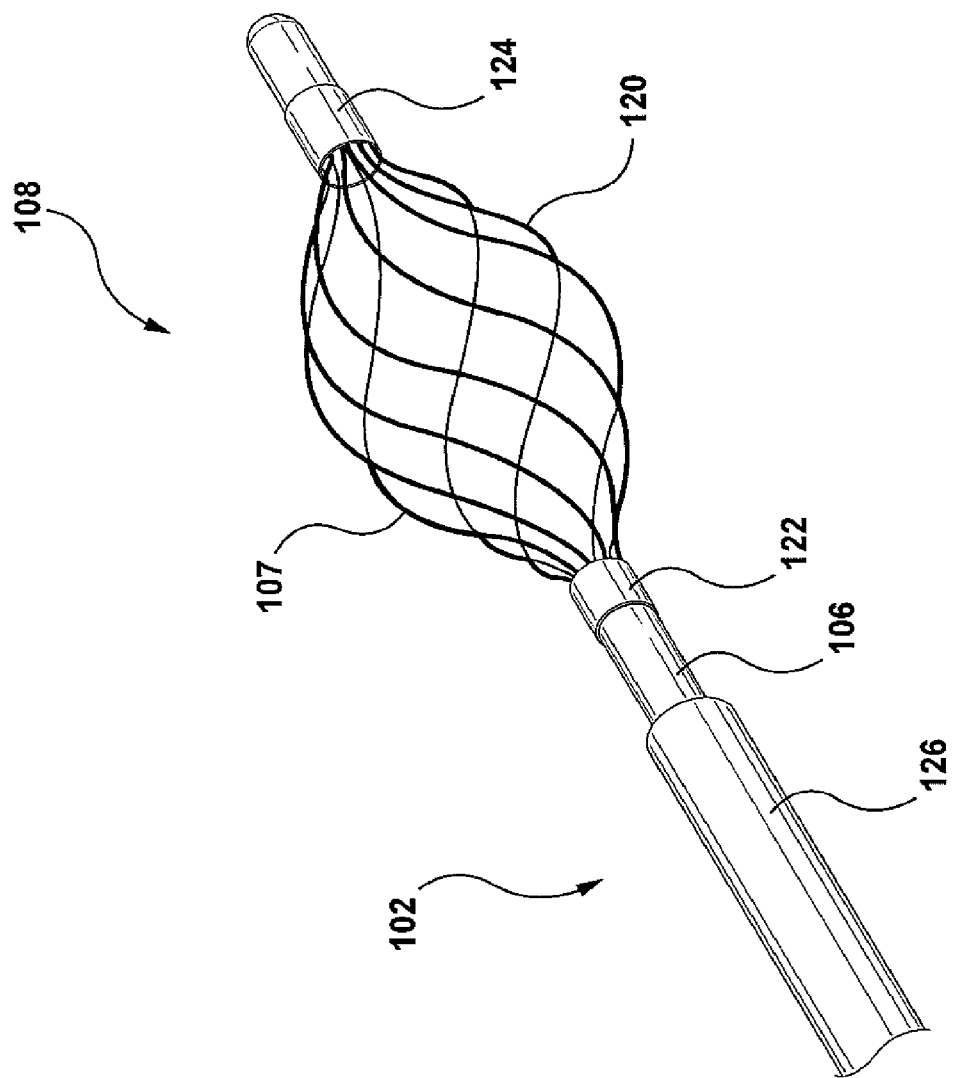
FIG. 24 depicts an embodiment of an energy delivery catheter having a single energy delivery body comprised of an electrode formed by a plurality of ribbons or wires forming a spiral-shaped basket.

FIG. 24 depicts an embodiment of an energy delivery catheter 102 having a single energy delivery body 108 comprised of at least two protrusions, each protrusion extending radially outwardly so as to contact an inner luminal wall of a lung passageway. It may be appreciated that although a single protrusion may be present, typically two protrusions are present to apply substantially opposing forces to the wall of the lung passageway to support the catheter therebetween. In this embodiment, the at least two protrusions comprise a plurality of ribbons or wires 120 which are constrained by a proximal end constraint 122 and a distal end constraint 124 forming a spiral-shaped basket. In this embodiment, the proximal end constraint 122 is attached to a shaft 106, and the shaft 106 does not pass through the energy delivery body 108. This allows the energy delivery body 108 to collapse upon itself without having the added dimension of the shaft 106 therein. The energy delivery body 108 is delivered to the targeted area in a collapsed configuration. This collapsed configuration can be achieved, for example, by placing a sheath 126 over the energy delivery body 108. In FIG. 24, since the shaft 106 terminates at the proximal end constraint 122, the distal end constraint 124 is essentially unconstrained and free to move relative to the shaft 106 of the catheter 102. Advancing a sheath 126 over the energy delivery body 108 allows the distal end constraint 124 to move forward, thereby lengthening/collapsing and constraining energy delivery body 108. Retraction of the sheath 126 allows the energy delivery body 108 to expand, such as through self-expansion. It may be appreciated that in an alternative embodiment, the ribbons or wires 120 are straight instead of formed into a spiral-shape (i.e., configured to form a straight-shaped basket). In still another embodiment, the energy delivery body 108 is laser cut from a tube.

In some embodiments, the energy delivery body 108 comprises a plurality of electrodes 107, wherein each wire 120 acts as a separate electrode 107 and is able fire separately using the wire next to it as a return electrode or using a dispersive electrode attached to the patient as a return electrode. In some instances, each wire 120 of the energy delivery body 108 can be electrically isolated from each other wire 120, and separate conductor wires can transmit the energy from the generator 104 to the wires 120 of the energy delivery body 108. In other instances, two or more wires 120 can be electrically connected to one another to form one or more sets of wires. The algorithm 152 of the generator 104 can perform the appropriate switching from one wire (or set of wires) to another as well as the alternation of the wire's function between active and return (ground) states.

Figure 25:
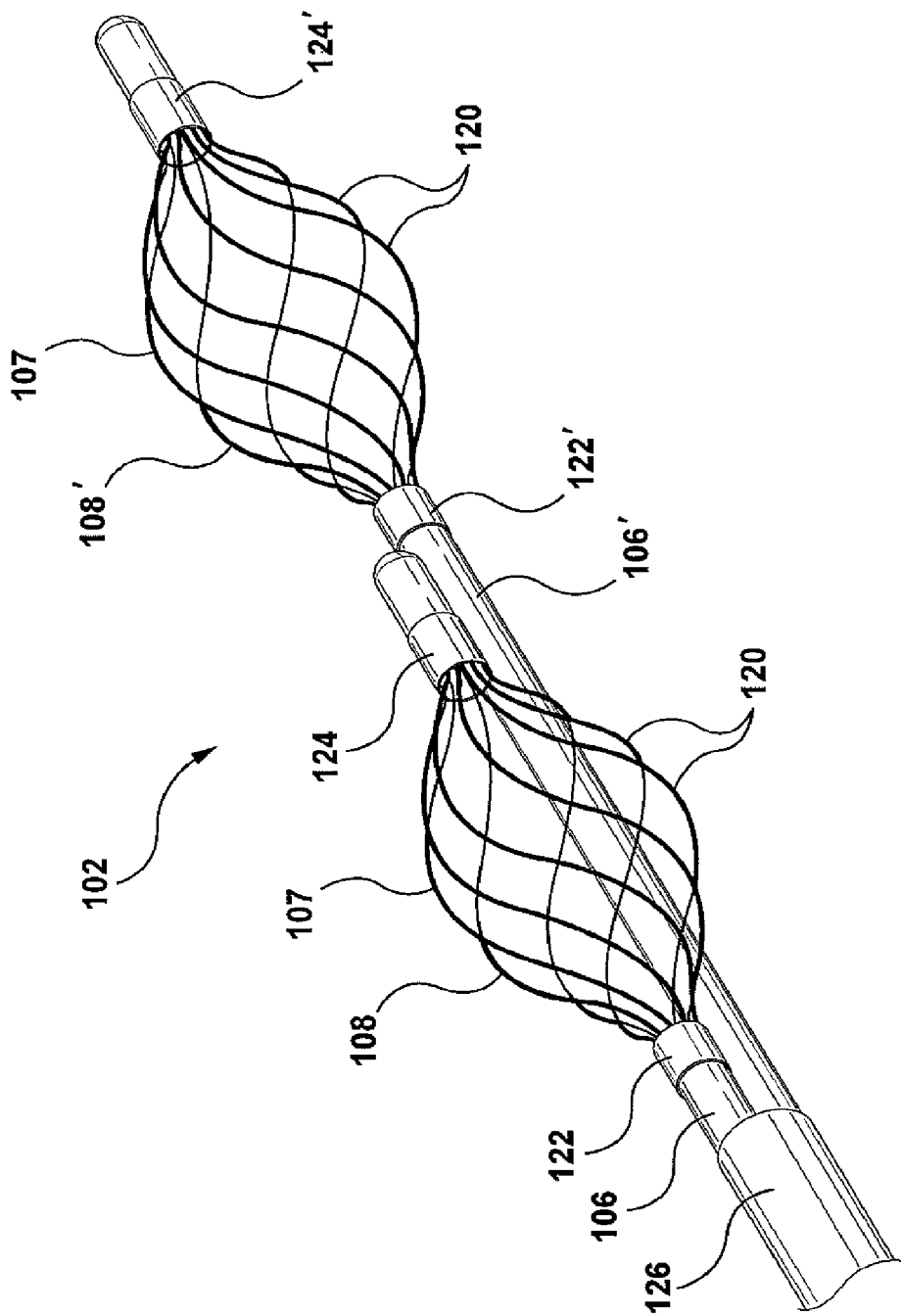
FIG. 25 depicts an embodiment wherein the energy delivery catheter includes two energy delivery bodies.

FIG. 25 depicts an embodiment wherein the energy delivery catheter 102 includes two energy delivery bodies, a first energy delivery body 108 and a second energy delivery body 108', wherein each body 108, 108' functions similarly to the embodiment of FIG. 24. In this embodiment, the first energy delivery body 108 is disposed along a distal end of a first shaft 106 and the second energy delivery body 108' is disposed along a distal end of second shaft 106'. As shown, the shafts 106,106' are aligned in parallel so that together they are passable through a sheath 126. In some embodiments, the shafts 106, 106' are fixed together so that they move in unison. In such embodiments, the shafts 106, 106' are typically arranged so that the energy delivery bodies 108, 108' are staggered, such as having the second energy delivery body 108' disposed more distally than the first energy delivery body 108, as shown in FIG. 25. In such arrangement, the energy delivery bodies 108, 108' may be separated by any suitable distance. Likewise, the energy bodies 108, 108' are arranged in relation to the shafts 106, 106' so that expansion of the energy bodies 108, 108' are not impinged by in any way. For example, in this embodiment, the energy delivery bodies 108, 108' are arranged so that the second shaft 106' does not interfere with the expansion of the first energy delivery body 108. Rather, the second shaft 106' passes through the basket-shaped energy delivery body 108, between the wires 120. In some embodiments, the shafts 106, 106' are not fixed together and are able to move in relation to each other, in particular the shafts 106, 106' are able to slide longitudinally in parallel to each other. In such embodiments, the shafts 106, 106' may be moved in relation to each other to increase or reduce the distance between the energy delivery bodies 108, 108'. Once a desired distance is achieved, the shafts 106, 106' may be fixed in place to maintain the desired distance between the energy delivery bodies 108, 108'.

In the embodiment illustrated in FIG. 25, each energy delivery body 108, 108' is comprised of a spiral-shaped basket made up of electrodes 107 in the form of wires 120. The energy delivery bodies 108, 108' can be activated in a bipolar fashion and/or a monopolar fashion. It may be appreciated that in alternative embodiments, the wires or ribbons 120 can be straight instead of formed into a spiral-shape (i.e., configured to form a straight-shaped basket). In some embodiments, the energy delivery bodies 108, 108' are laser cut from a tube. In this embodiment, the first shaft 106 terminates at the first proximal end constraint 122 of the first electrode body 108, leaving the first distal end constraint 124 essentially unconstrained. The second shaft 106' terminates at a second proximal end constraint 122' of the second electrode body 108' leaving the second distal end constraint 124' essentially unconstrained. Advancing a sheath 126 over the energy delivery bodies 108, 108' allows the distal end constraints 124, 124' to move forward, thereby collapsing, lengthening and constraining the energy delivery bodies 108, 108'. Retraction of the sheath 126 exposes the energy delivery bodies 108, 108' for expansion and delivery of energy.

Figure 26:
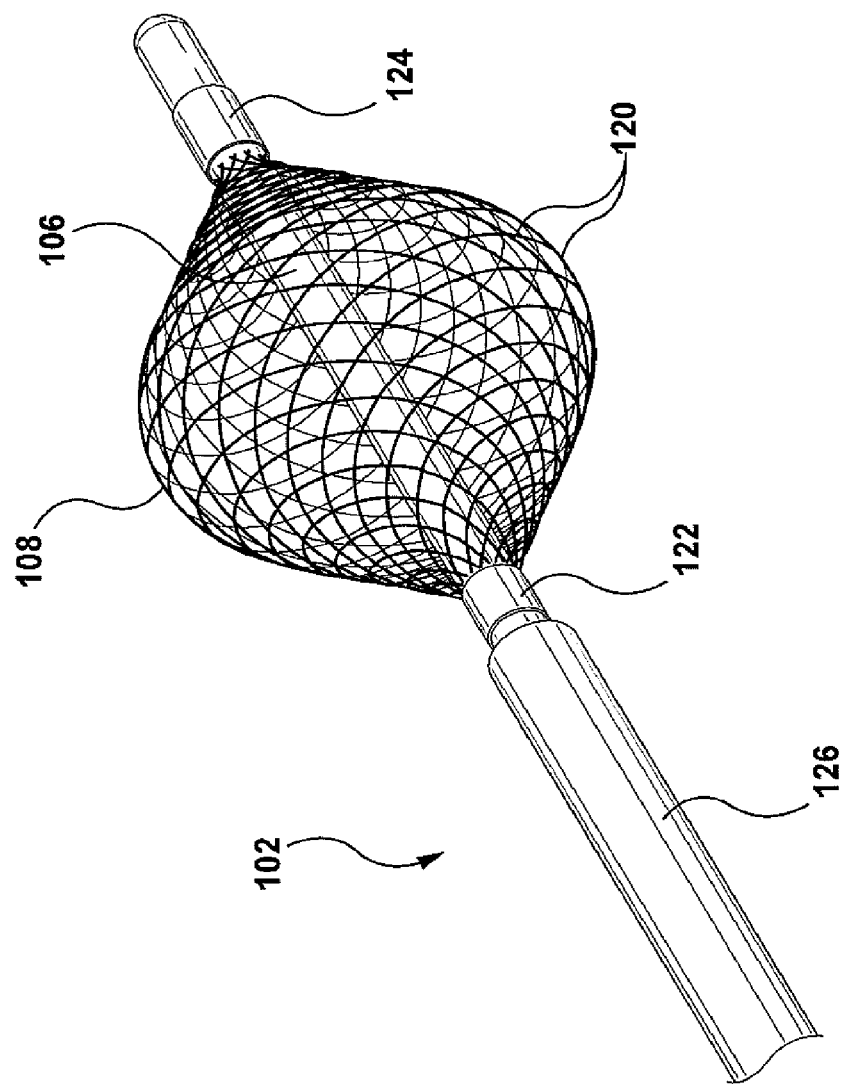
FIG. 26 depicts an embodiment of an energy delivery catheter having a single energy delivery body comprised, wherein the energy delivery body is mounted on a shaft which extends through the energy delivery body.

FIG. 26 depicts an embodiment of an energy delivery catheter 102 having a single energy delivery body 108 comprised of a monopolar electrode 107 formed by a plurality of ribbons or wires 120, wherein the energy delivery body 108 is mounted on a shaft 106 which extends through the energy delivery body 108. Again, the energy delivery body 108 has a basket shape constrained by a proximal end constraint 122 and a distal end constraint 124. In this configuration, in order for the energy delivery body 108 to collapse, either the proximal end constraint 122 or distal end constrain 124 slide freely on the shaft 106 while the other end is fixedly attached to the shaft 106. Upon the delivery of the energy delivery body 108 to the target treatment area, the sheath 126 is withdrawn by the operator via, for example, a lever or slider or plunger of the catheter's handle 110, which is operatively connected to the sheath 126. The withdrawal of the sheath 126 removes the restraint keeping the energy delivery body 108 collapsed, thus allowing its expansion leading to the wires 120 of the energy delivery body 108 contacting the bronchial wall.

In some embodiments, the collapsed configuration of the energy delivery body 108 can be achieved by mechanisms which restrict its expansion without the use of a sheath 126. For example, in some embodiments, a pull wire is attached to the proximal end constraint 122 of the energy delivery body 108 and extends down a lumen along the shaft 126 where it is operatively connected to a lever, slider, or plunger of the catheter's handle 110. In this embodiment, the distal end constraint 124 is fixedly attached to the shaft 106 and the proximal end constraint 122 is configured to slide freely on the shaft 106. While the pull wire is under pull force, the proximal end constraint 122 is positioned so that the energy delivery body 108 is collapsed. The pull wire can be maintained in this position by restraint within the handle 110. Release of the pull force, such as by reduction or removal of the restraint within the handle 110, allows the pull wire to move, thus freeing the proximal end constraint 122 and allowing it to travel closer to its distal end constraint 124 as self-expanding properties of the energy delivery body 108 cause expansion.

In other embodiments, the proximal end constraint 122 is affixed to the shaft 106 and the distal end constraint 124 is free to slide on the shaft 106. Further, a push rod (or tubing to achieve higher column strength) is attached to the distal end constraint 124 and extends down a lumen along the inner shaft 106 where it is operatively connected to mechanism such as a lever, slider, or plunger of the catheter's handle 110. When the push rod is pushed and subsequently restrained within the handle 110 of the catheter 102, the distal constraint 124 is moved away from the proximal end constraint 122 which causes the energy delivery body 108 to collapse. When the energy delivery body 108 is self-expanding, release of the push rod allows the energy delivery body 108 to expand. Alternatively, the push rod may be retracted, pulling the distal end constraint 124 toward the proximal end constraint 122 which causes the energy delivery body 108 to expand.

In the embodiment shown in FIG. 26, the energy delivery body 108 is formed b a braided metal tube constrained at both the proximal end constraint 122 and the distal end constraint 124 and configured to form a basket. The energy delivery body 108 can be controlled (i.e., collapsed, deployed) as described above. When the energy delivery body 108 comprises a braided metal tube, each wire in the braided tube is supported by multiple wires next to it as well as by the interwoven nature of the braid itself. This support and interwoven configuration can assure minimal variation in space between wires, otherwise known as pore or opening size of the braid. In addition, this support and interwoven configuration can allow constructing the braided tube from very small wires and yet have significant radial stability of the basket. This allows the use of many wires (e.g., 12, 16, 18, 20, 22, 24, etc.) while maintaining a relatively small profile of the energy delivery body 108 in the collapsed/constrained state and optimizing the opening size of the braided tube when electrode(s) is/are deployed/expanded. In this embodiment, the space between wires is rather small, leading to a treatment that is essentially continuous over 360 degrees of the inner lumen of a lung passageway.

Figure 27:
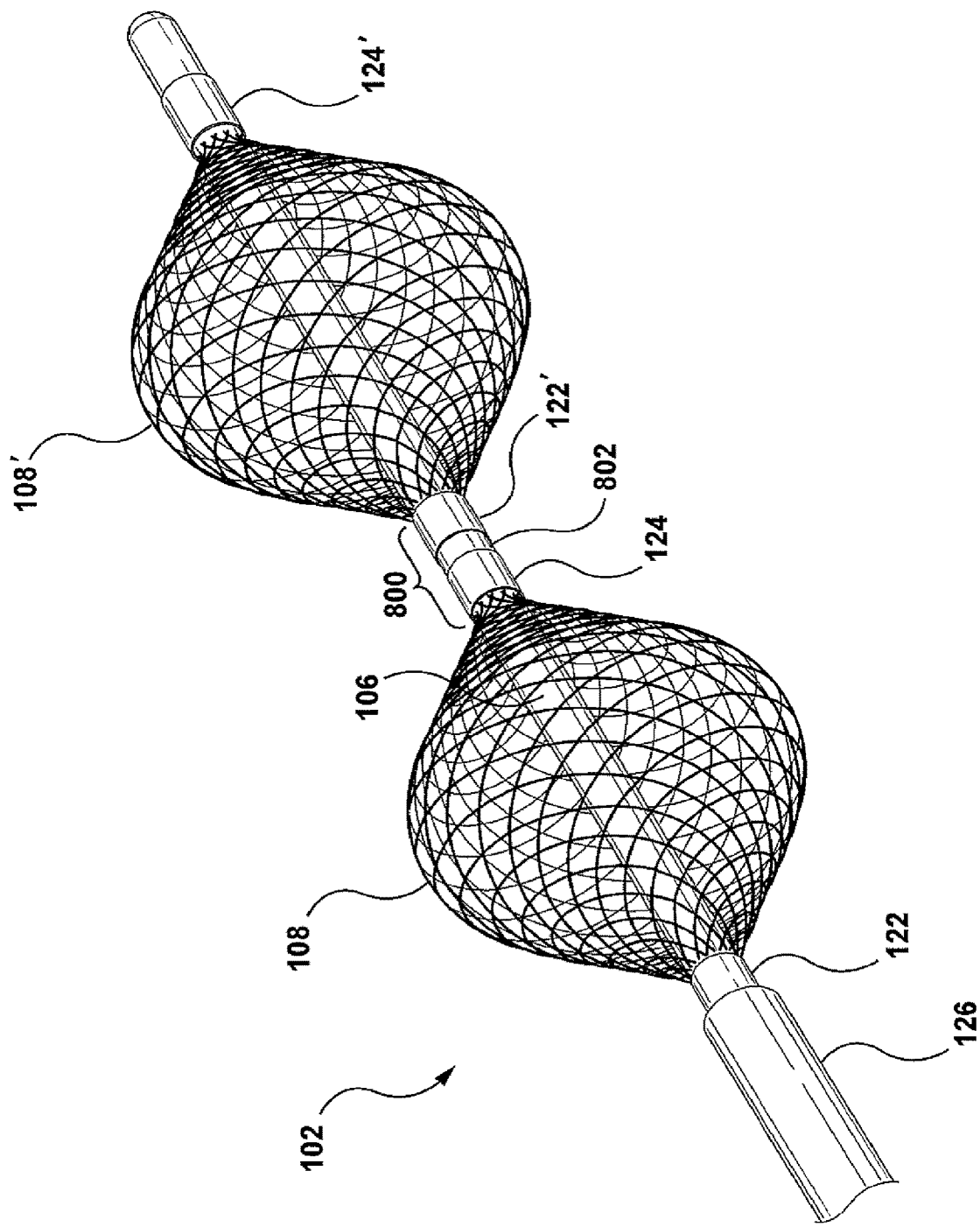
FIG. 27 illustrates an embodiment wherein both energy delivery bodies are carried on a single shaft.

FIG. 27 illustrates an embodiment wherein both energy delivery bodies 108, 108' are carried on a single shaft 106. In order for the energy delivery bodies 108, 108' to collapse, the first proximal end constraint 122 of the first energy delivery body 108 is fixedly attached to the catheter shaft 106. The other end constraints 122', 124, 124' are able to slide freely on the catheter shaft 106. The catheter is delivered with a sheath 126 constraining the energy delivery bodies 108, 108'. Upon delivery of the energy delivery bodies 108, 108' to the target area, the sheath 126 can be withdrawn by the operator via, for example, a mechanism such as a lever or slider or plunger of the catheter's handle 110. The withdrawal of the sheath 126 removes the restraint keeping energy delivery bodies 108, 108' collapsed, thus allowing their expansion leading to the surfaces of the energy delivery bodies 108, 108' contacting the bronchial wall. In addition, in some embodiments, the first distal end constraint 124 and the second proximal end constraint 122" are connected to each other via coupler 800. The coupler 800 is constructed using an electrically insulative material (e.g. polyether block amide (Pebax®) tubing, polyimide tubing, etc.) to provide an insulative gap 802 between energy delivery bodies 108, 108' to achieve electrical discontinuity between them. In some embodiments, this gap 802 is between 1 and 20 mm. This prevents arcing within the catheter shaft 106.

In some embodiments, the collapsed configuration of the energy delivery bodies 108, 108' can be achieved by restricting their expansion without the use of a sheath 126. For example, in one embodiment the distal end of a pull wire (not shown) is attached to the second distal end constraint 124' and the proximal end of the pull wire is attached to a mechanism of the handle 110 (for example plunger, slider or lever). The first proximal end constraint 122 is fixedly attached to the catheter shaft 106 and the other end constraints 124, 122', 124' slide freely over the catheter shaft 106. Such a configuration assumes that energy delivery bodies 108, 108' are in a collapsed configuration prior to initiating placement via a bronchoscope and require the operator to deploy/expand them. This deployment/expansion is achieved by the operator activating the mechanism of the handle 110 (e.g. lever, plunger or slider) which pulls the second distal end constraint 124' toward the first proximal end constraint 122, thus effectively deploying/expanding both energy delivery bodies 108, 108'. In another configuration, expansion can be achieved by employing two pull wires, one attached separately to each energy delivery body 108, 108'. In such embodiments, the operator can control the level of expansion of the energy delivery bodies 108, 108' separately.

Figure 28A:
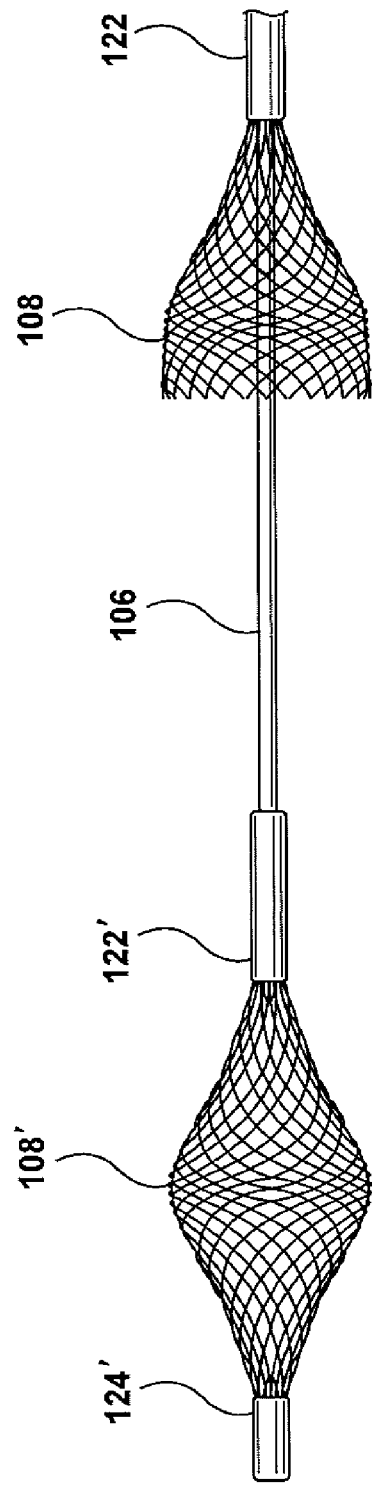
FIG. 28A illustrates an embodiment wherein one energy delivery body energy is unconstrained at one end forming a half-basket shape when expanded.

In some embodiments, the one or more energy delivery bodies 108, 108' are not constrained at both ends, rather one end is unconstrained creating a half-basket shape. FIG. 28A illustrates an embodiment wherein one energy delivery body energy 108' is unconstrained at one end forming a half-basket shape when expanded. In this embodiment, both the energy delivery bodies 108, 108' are comprised of braided metal wires. The distal-most energy delivery body 108' is constrained at both the second proximal end constraint 122' and the second distal end constraint 124' and configured to form a closed braided basket shape. The distal-most energy delivery body 108' is expandable so that typically at least the widest expansion diameter contacts the wall W of the lung passageway. The most proximal or first energy delivery body 108 is constrained at a first proximal end constraint 122 and configured to form an approximately half-open basket or half-basket shape when expanded, as shown. The proximal energy delivery body 108 is expandable so that typically at least the widest expansion diameter contacts the wall W of the lung passageway. The shaft 106 is fixedly attached to the first and second proximal end constraints, 122, 122'. The half basket shape of the proximal energy delivery body 108 allows its widest expansion diameter to be closer to that of the distal-most energy delivery body 108' than would otherwise be the case if the proximal energy delivery body 108 were whole shaped. Decreasing this distance between the energy delivery bodies 108, 108' allows for a treatment effect between the energy delivery bodies 108, 108' in addition to at the energy bodies 108, 108'. This ultimately creates a larger surface treatment effect given the effect between the bodies 108, 108'. In addition, the half basket shape may help avoid arcing.

The configuration depicted in FIG. 28A is delivered with the use of a sheath (not shown) as described in detail above, wherein both energy delivery bodies 108, 108' are self-expandable. In another embodiment, the second energy delivery body 108' is placed in a collapsed state prior to delivery into a bronchoscope and once positioned in a desired target area, deployed/expanded via a pull wire (not shown) connected to its second distal end constraint 124') and to a mechanism in the handle 110. This combination of full-basket (energy delivery body 108') and half-basket (energy delivery body 108) can be employed for bipolar or monopolar energy delivery. When electrodes are made of a braided metal wires, each wire is supported by multiple wires next to it as well as by the interwoven nature of the braid itself. This support and interwoven configuration can assure minimal variation in space between wires otherwise known as pore or opening size of the braid. In addition, this support and interwoven configuration allow constructing the braid from very small wires and yet have significant radial stability of the basket. This allows the use of many wires (for example 12, 16, 18, 20, 22, 24, etc.) while maintaining small profile of the energy delivery bodies 108, 108' in a collapsed or constrained state while optimizing the opening size of the braid when the energy delivery bodies 108, 108' are deployed or expanded. In this embodiment, the space between wires is rather small, leading to a treatment that is 360 degrees within a lung passageway.

Figure 28B:
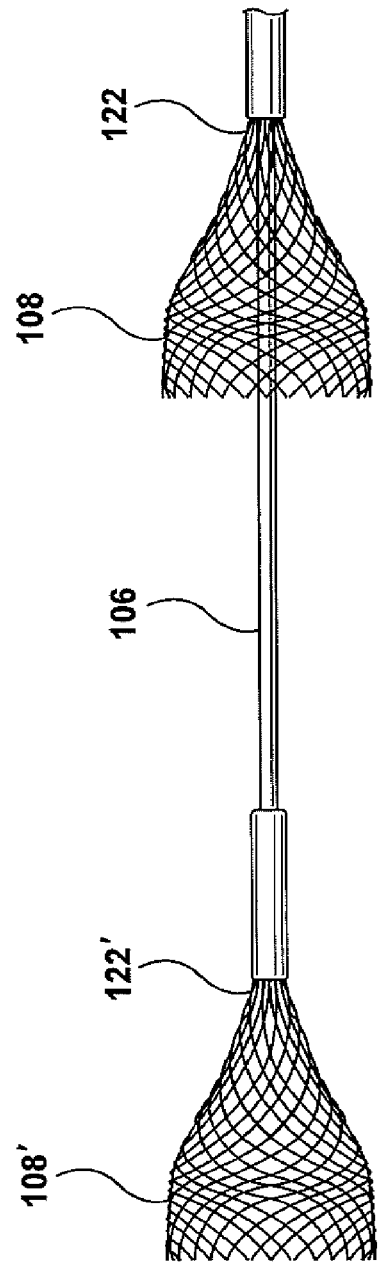
FIG. 28B illustrates an embodiment wherein both the energy delivery bodies are comprised of braided metal wires configured to form half-baskets when expanded.

FIG. 28B illustrates an embodiment wherein both the energy delivery bodies 108, 108' are comprised of braided metal wires with the proximal end constraints 122, 122' affixed to the shaft 106. In this embodiment, both energy delivery bodies 108, 108' are configured to form half-baskets. This configuration is sheath (not shown) may be delivered with the use of a sheath as described above, wherein the energy delivery bodies 108, 108' are self-expandable. This configuration of half-basket energy delivery bodies 108, 108' can be employed for bipolar and/or monopolar energy delivery.

Figure 29:
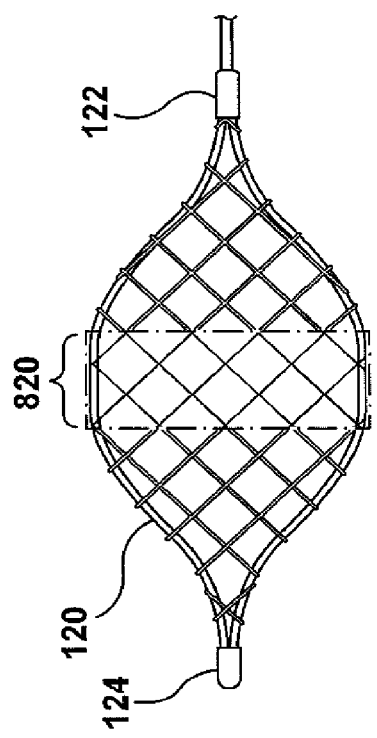
FIG. 29 illustrates a braided wire basket energy delivery body comprised of energizable wires wherein some of the wires are insulated with portions of the insulation removed to define an active area.

In some embodiments, the entire surface of the one or more energy delivery bodies 108 is energized by the energy signal for delivery to the target tissue. However, in other embodiments, an active surface area of the energy delivery body 108 is provided wherein the remaining portions are not active. In some embodiments, this is achieved by partially insulating one or more portions of the energy delivery body 108 leaving one or more active region(s). For example, FIG. 29 illustrates a braided wire basket energy delivery body 108 comprised of energizable wires 120 (acting as one or more electrodes) wherein some of the wires 120 are insulated with portions of the insulation removed to define an active area 820. In some embodiments, the insulation is removed from the outer (tissue contacting) surface of the wire 120. This approach can be useful, for example, if the measured impedance via the electrode wire 120 is affected by the amount of the exposed metal and if it is desirable for the measured impedance to represent the electrode-to-tissue interface. In other embodiments, the insulation can be removed on both the outer and inner surfaces of the electrode wire 120. One method for manufacturing an energy delivery body 108 with this configuration involves creating a braid using insulated wires, then using appropriate means (e.g., laser, mechanical) to remove the insulation to create one or more active areas 820. While this example depicts a single active area 820, a plurality of active areas is also envisioned in order to generate any treatment pattern. Similar techniques can also be employed for non-braided energy delivery bodies 108 described herein. In these embodiments, the insulation can be applied or removed as part of the manufacturing process to define any active area (or areas) 820 configuration desired to achieve various treatment patterns.

Figure 30:
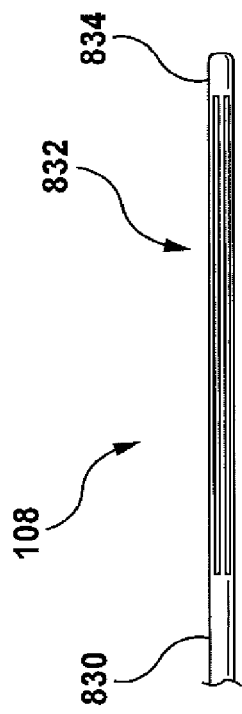
FIG. 30 illustrates another embodiment wherein a tube is laser cut to form a collapsed basket with both ends constrained via the tube itself.
Figure 31:
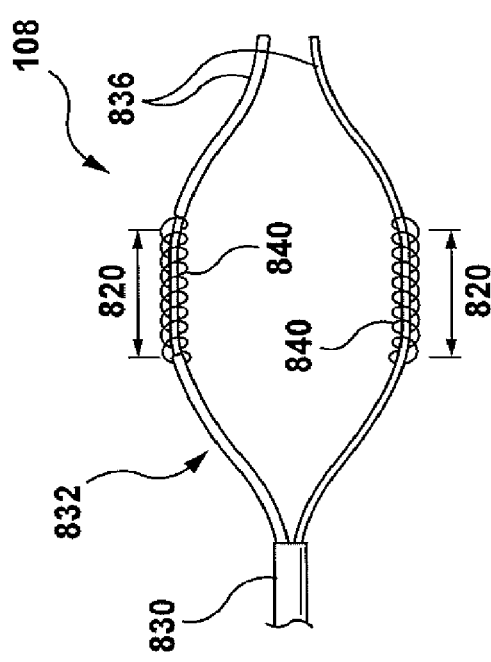
FIG. 31 illustrates an embodiment of an energy delivery body comprised of wires which are insulated and one or more separate additional electrodes (shown as coils) are connected to the insulated basket wires to form active areas.

FIG. 30 illustrates another embodiment wherein a metal (e.g. Nitinol) tube 830 is laser cut to form a collapsed basket 832 with both ends constrained via the tube 830 itself. The basket 832 can then be expanded and shape set, such that it can self-expand during use, so as to perform as the energy delivery body 108. Alternatively, push/pull mechanisms can be employed to expand/collapse the basket 832 for delivery and treatment. In some embodiments, one end 834 of the basket 832 is removed to create free ends 836, as illustrated in FIG. 31. Insulation (e.g., polymer tubing) can then be advanced over the free ends 836 and applied to portions of the basket 832. In some embodiments, the insulation is applied to proximal and distal portions of the basket, leaving one or more conductive/active areas 820 therebetween. In other embodiments, as shown in FIG. 31, the wires 120 of the basket 832 are insulated and one or more separate additional electrodes 840 (shown as coils) are connected to the insulated basket wires to form active areas 820. This assembly can then be affixed to a catheter 102 such that the energy delivery body 108 can be activated as a monopolar electrode with multiple pre-defined active areas 832.

Figure 32:
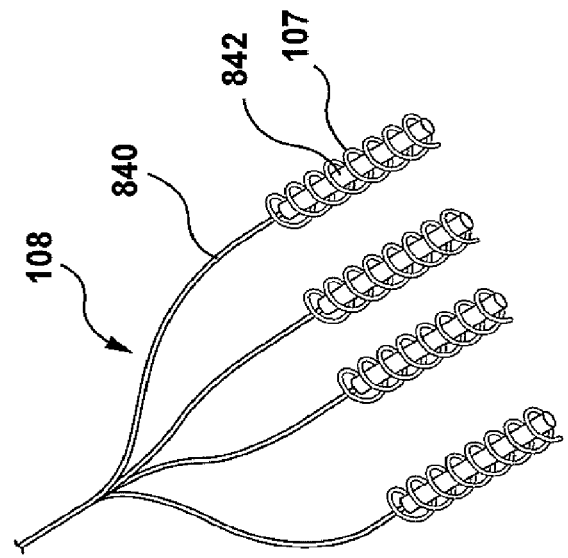
FIG. 32 illustrates an embodiment of an energy delivery body comprising a plurality of tines.

FIG. 32 illustrates another embodiment of an energy delivery body 108. In this embodiment, the body 108 comprises a plurality of tines 840, similar to the free ends 836 of FIG. 31. The tines 840 are able to expand outwardly so as to contact the lung passageway wall. In some embodiments, one or more of the tines 840 are insulated with insulation material 842. Electrodes 107 disposed along each tine 840, such as near the distal ends of each tine 840, can be created by removal of the insulation material 842 to expose an underlying energizable element or wire. Alternatively, a separate electrode 107 may be mounted on the insulation material 842, as depicted in FIG. 32. In some embodiments, the tines 840 are formed of polymer-covered wires, wherein the wire can act as structural support to self-expand the tines 840, can be energizable to deliver treatment energy and/or can be used to sense temperature and/or impedance. In some embodiments, the tines 840 are collapsible via a sheath 126 for delivery and allowed to expand into contact with the tissue upon retraction of the sheath 126. The electrodes can all fire simultaneously in a monopolar fashion, can fire independently in a monopolar fashion, and/or fire between one another in any pattern necessary to generate the desired treatment effect. The length of the electrodes can range from about 3 mm to about 5 cm, such as 3 mm, 5 mm, 1 cm, 2 cm, 3 cm, 4 cm or 5 cm. While depicted as all the same size in FIG. 32, the size (e.g., length, width) can vary.

Figure 33:
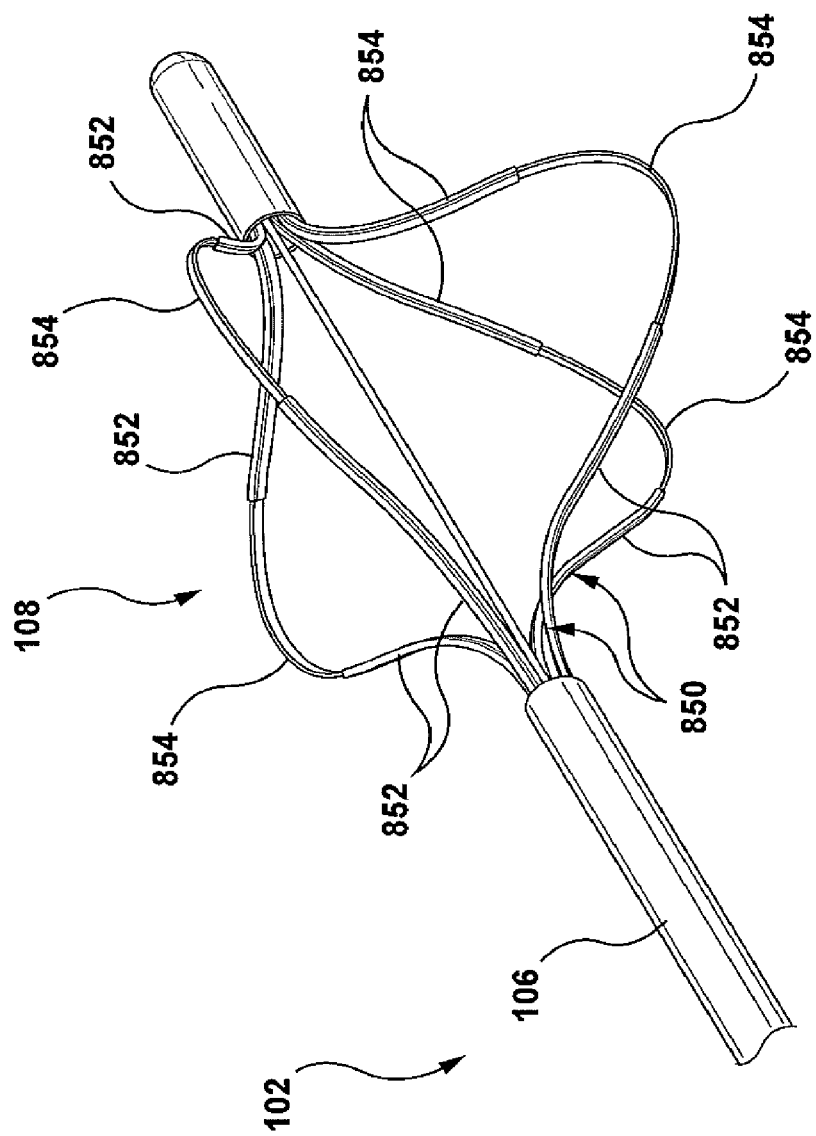
FIG. 33 illustrates an embodiment of an energy delivery body comprising one or more protrusions.

FIG. 33 illustrates another embodiment of an energy delivery body 108. In this embodiment, the energy delivery body 108 comprises one or more protrusions 850 rather than a basket weave. Each protrusion 850 is formed by a wire or ribbon 120 which acts as an electrode and bends radially outward from the longitudinal axis or shaft 106 of the catheter 102. In this embodiment, each protrusion 850 is electrically isolated from each of the other protrusions. The protrusions 850 may be comprised of a variety of suitable materials so as to act as an electrode, such as stainless steel, spring steel, or other alloys, and may be, for example, round wires or ribbon. Each protrusion 850 is insulated with a segment of insulation 852, such as a polymer (e.g., PET, polyether block amide, polyimide), over at least a portion of the proximal and distal ends of the energy delivery body 108. The exposed portion 854 of the wire or ribbon can then act as an electrode on each protrusion 850. In one embodiment, the exposed portions 854 of the protrusions 850 are completely free of insulation 852. In another embodiment, the insulation 852 is removed only from the outer surface of the protrusion 850 leaving the side of the protrusion 850 that does not come in contact with the tissue (e.g., an inner surface that faces the shaft 106 of the catheter 102) completely insulated. In one embodiment, each protrusion 850 is energized independently, with two protrusions 850 acting as neutral electrodes (return) and two protrusions 850 acting as active electrodes. Neutral and active electrodes can be positioned right next to each other. Neutral electrodes located 180 degrees from each other (opposite electrodes) can be electrically connected to each other and so can be the active electrodes. In this embodiment, only two conductive wires (power lines) are needed to connect two pairs of protrusions 850 to the generator 104. Further, pairs of protrusions 850 that are utilized in a bipolar fashion can further be multiplexed to allow for any combination or rotation of active versus neutral electrode. The generator 104 can be configured to have sufficient channels to support any of these approaches (i.e., 1 to 4 channels). This embodiment of the energy delivery body 108 can optionally be delivered in a collapsed configuration and expanded into tissue contact via a pullback wire and mechanism within the handle.

Figure 34:
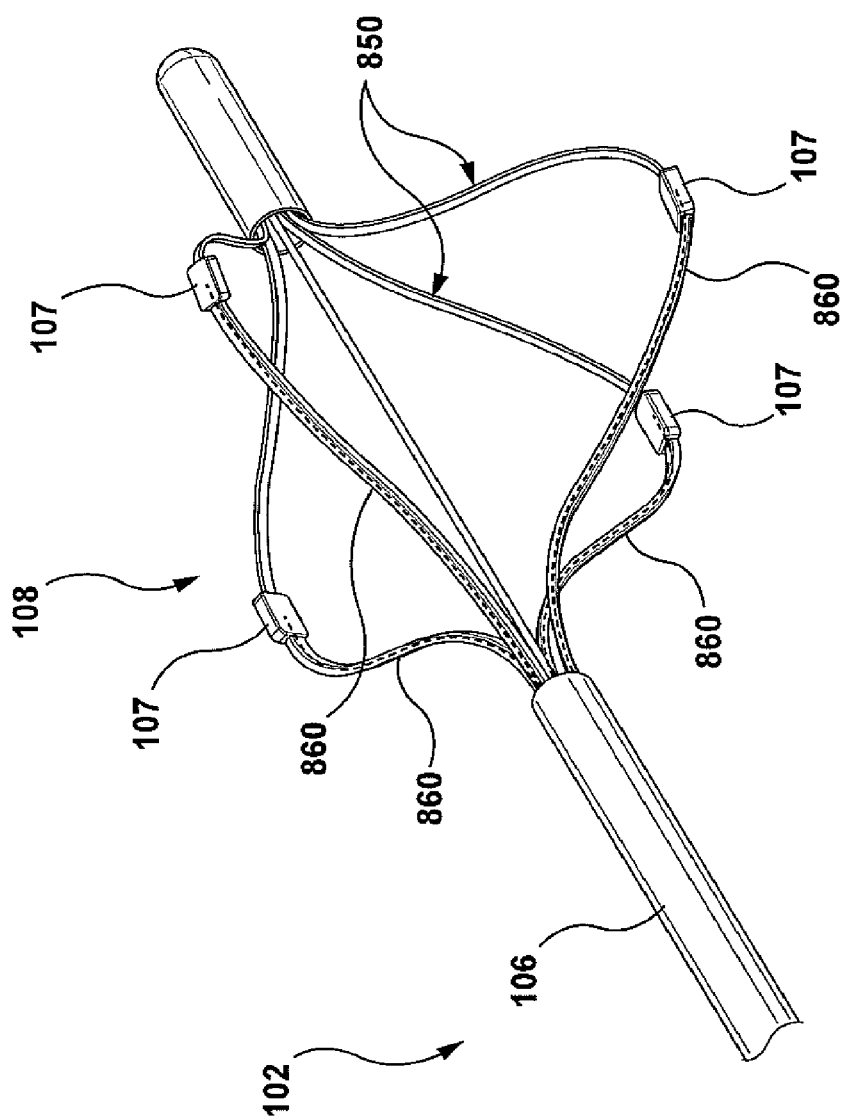
FIG. 34 illustrates an embodiment of energy delivery body comprising one or more protrusions wherein each protrusion is formed from a non-conductive material and carries, supports, and/or is otherwise coupled to a separate electrode.

FIG. 34 illustrates another embodiment of energy delivery body 108 comprising one or more protrusions 850 wherein each protrusion 850 bends radially outward from the longitudinal axis or shaft 106 of the catheter 102. However, in this embodiment, each protrusion 850 is formed from a non-conductive material and carries, supports, and/or is otherwise coupled to a separate electrode 107. Each electrode 107 has a conductive wire 860 connecting the electrode 107 to the generator 104. The protrusions 850 position said electrodes 107 against the tissue upon expansion, such as via a pull wire and mechanism within the handle. In this embodiment, each electrode 107 is placed over or adjacent each protrusion 850. If the protrusions 850 are comprised of a metal, insulation is provided to electrically isolate the electrodes 107 from the protrusions 850 themselves. If the protrusions 850 are comprised of a polymer or other non-conductive material, additional insulation would not be required. In some embodiments, the protrusions 850 are comprised of round wire or ribbon and configured to form a straight basket, as shown. In other embodiments (not shown), the protrusions 850 are configured in a spiral shape. It may be appreciated that separate electrodes 107 as depicted in FIG. 34 may likewise be applied to other embodiments, such as wherein the basket is comprised of a braided material Similar to the embodiment of FIG. 33, each electrode 107 may be energized in a variety of combinations. Furthermore, each protrusion 850 can carry the electrodes 107 that can be electrically connected to each other or electrically insulated from each other. To increase the surface area of the electrodes 107 each can be constructed from, for example, a metallic coil or in a form of a slotted (e.g. laser cut) tube. These configurations would allow for greater spatial coverage and yet maintain the flexibility of the electrodes 107 to allow the protrusions 850 of the basket to bend and straighten freely. As in FIG. 33, the surface of the protrusions 850 can be completely exposed or insulated over areas that do not come in contact with the tissue.

FIG. 35 illustrates another embodiment of a catheter 102 having at least one energy delivery body. In this embodiment, each energy delivery body comprises an expandable coil that can either act an electrode itself or can act as a carrier for separate electrodes mounted thereon. In this embodiment, the catheter 102 comprises two energy delivery bodies, a first energy delivery body 108 which is disposed proximally to a second energy delivery body 108'. Each energy delivery body 108, 108' has the shape of an expandable coil. A distal end 870 of the second energy delivery body 108' is coupled with or formed to an inner member 872, and a proximal end 874 of the first energy delivery body 108 is coupled with an outer member 876. The outer member 876 is rotatable relative to the inner member 872 to collapse and/or expand the energy delivery bodies 108, 108'. A coupler 878 attaches the energy delivery bodies 108, 108' together and provides insulation between them, if desired. The energy delivery bodies 108, 108' can be activated in a monopolar and/or bipolar fashion. The size of the energy delivery bodies 108, 108' can be the same or different, as described herein. The length of each expanded coil can range from about 5 mm to about 20 mm.

FIG. 36 depicts an energy delivery body 108 configured for more limited application of treatment energy, such as in a narrow region along the lung passageway wall or along a partial inner circumference of the lung passageway. In this embodiment, the energy delivery body 108 comprises a coil that limits the length of the active area. Such embodiments can be employed if very focal tissue effects are desired or if tissue effects extend beyond the active area in contact with tissue. In this embodiment, the energy delivery body 108 comprises a coil 880 having a width and a length, wherein the length of the coil 880 can be pre-shaped into a semi-circular or circular pattern, as shown. The treatment length LI is provided by the width of the coil 880 as it contacts the lung passageway wall W. This configuration can be activated in a monopolar configuration as depicted; however, it is further envisioned that two or more coils 880 can be employed to allow for bipolar and/or multiplexed energy delivery. Similarly, FIG. 37 illustrates an embodiment of an energy delivery body 108 comprising a rod 882 (such as shaft 106) having a width and a length, wherein the length of the rod 882 is pre-shaped into a semi-circular or circular pattern, as shown. The rod 882 includes one or more electrodes 107 disposed along its length. The one or more electrodes 107 may be embedded into or otherwise affixed to the rod 882. The treatment length LI is provided by the width of the one or more electrodes 107 which contact the lung passageway wall W. This embodiment allows for monopolar activation between all electrodes and a dispersive (neutral) electrode, bipolar activation between individual electrodes, and/or multiplexed activation between any combination of electrodes. It is further envisioned that two or more of these devices can be employed to allow for energy delivery between them. When the energy delivery bodies 108 are pre-shaped into the semi-circular or circular configuration, a sheath 126 can be used to collapse and constrain the energy delivery body 108 for self-expansion and/or a pull/push wire can be used to expand the energy delivery body 108. These methods for expanding and/or collapsing an energy delivery bodies 108 are described in detail within other examples provided.

Figure 38:
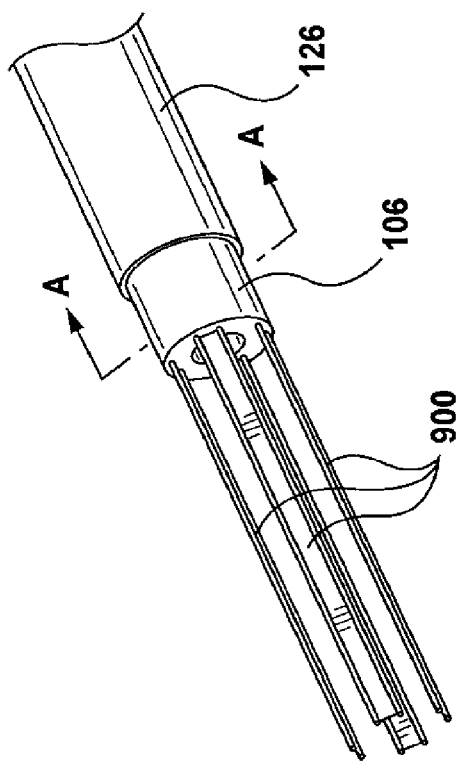
FIG. 38 illustrates an embodiment of a catheter having a sheath withdrawn proximally thus exposing one or more prongs.
Figure 38A:
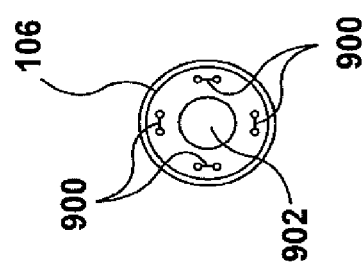
FIG. 38A is a cross-sectional illustration across A-A of FIG. 38.
Figure 39:
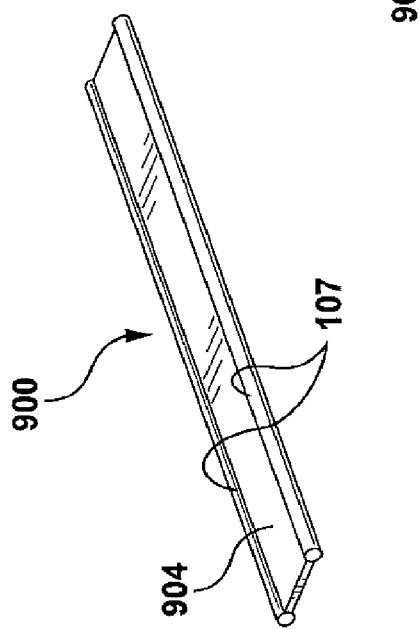
FIG. 39 illustrates an embodiment of a prong having two electrodes attached to an insulating substrate therebetween as a means to maintain distance between the electrodes.

The energy delivery body 108 can be optimized for situations in which force exerted onto the bronchial wall is desired to be more highly controlled. In this embodiment, the energy delivery body 108 is delivered into the bronchial lumen via a three-step process. First, as illustrated in FIG. 38, a sheath 126 is withdrawn proximally thus exposing one or more prongs 900 which act as protrusions. This embodiment includes four prongs 900 arranged symmetrically around a central lumen 902, as illustrated in the cross-sectional illustration of FIG. 38A. It may be appreciated that any number of prongs 900 may be present including one, two, three, four, five, six or more. Each prong 900 includes at least one electrode 107. FIG. 39 illustrates an embodiment of a prong 900 having two electrodes 107 having an elongate shape (such as wire) attached to an insulating substrate 904, such as a polymer substrate (e.g. ribbon, strip), therebetween as a means to maintain distance between the electrodes 107. It may be appreciated that the electrodes 107 may have a round or square/rectangular cross-section, and are typically affixed to the insulating substrate 904 such that the electrodes 107 are substantially parallel to one another. The manufacturing method of attaching the electrodes 107 to the insulating substrate 904 can employ (but is not limited to) co-extrusion, flexible circuits, deposition (printed electrodes), adhesive based bonding, and thermal bonding. The width of the insulting substrate 904 can vary.

Figure 40:
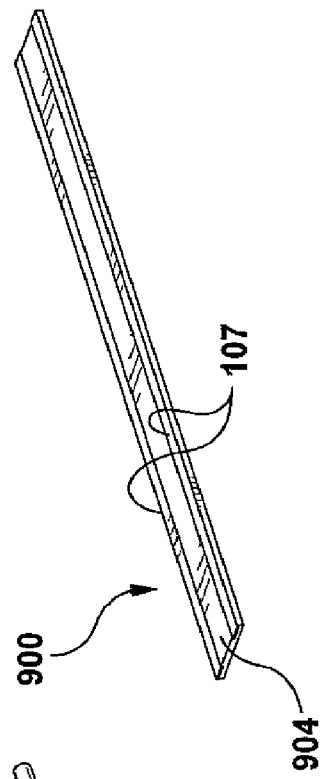
FIG. 40 illustrates an embodiment of a prong having a narrower insulating substrate than depicted in FIG. 36.

FIG. 40 illustrates an embodiment of a prong 900 having a narrower insulating substrate 904 than depicted in FIG. 39. Likewise, FIG. 41 illustrates an embodiment of a prong 900 having yet narrower insulating substrates 904 and greater than two electrodes 107. In particular, FIG. 41 illustrates five electrodes 107, however it may be appreciated that any number of electrodes 107 may be present, such as one, two, three, four, five, six, seven, eight or more. FIG. 42 illustrates a plurality of electrodes 107 mounted on a polymer substrate (e.g. ribbon, strip) wherein the electrodes 107 have an elongate shape (such as wire) and are positioned substantially in parallel to each other leaving a gap between each wire.

In some embodiments, the insulating substrate 904 with electrodes 107 is configured as a strip (FIGS. 39-42). Thus, the electrodes 107 are deployed as a linear strip positioned along a length of an airway. In other embodiments, the insulating substrate 904 with electrodes 107 is configured as a helix wherein the electrodes are deployed in a helical fashion. FIG. 43 illustrates the insulating substrate 904 with electrodes 107 as shown in FIGS. 39-40 configured as a helix. FIG. 44 illustrates the insulating substrate 904 with electrodes 107 as shown in FIG. 41 configured as a helix.

In some embodiments, a push-pull mechanism as described previously in relation to other embodiments can be employed to deploy the strip or ribbon. In case of the helix, the rotational mechanism can also be used. Electrodes 107 can be electrically connected to each other, can be insulated from each other or different patterns of electrical interconnection between electrodes depending on the energy application algorithm controlled by the generator.

Once the one or more prongs 900 are exposed, the second step of the three-step process involves introducing an expandable member 910, such as a balloon, by advancing the expandable member 910 from the lumen 902 while in an unexpanded state. The third step involves expanding the expandable member 901, such as inflating the balloon, as illustrated in FIGS. 45A-45B, until a desired interface between the prongs 900 (and therefore electrodes 107) and bronchial wall W is achieved. In another embodiment, the prongs 900 are positioned while the expandable member 910 is already disposed beneath the prongs 900 so their relative longitudinal position does not change. In this configuration, the withdrawal of the sheath 126 exposes both the expandable member 910 and the prongs 900 at the same time, thus eliminating the step of advancing the expandable member 910 out of the lumen 902. As described above, the expandable member 910 is subsequently expanded (e.g. inflated) until the desired interface between the prongs 900 and bronchial wall S is achieved. The size (e.g. length, width) of the prongs 900 can be the same or different. The number of prongs 900 can vary between 1 (monopolar configuration) and 100 (monopolar and/or bipolar) configuration. Energy application to the electrodes 107 can vary widely depending on the algorithm of the energy delivery apparatus (e.g. generator).

Figure 45C:
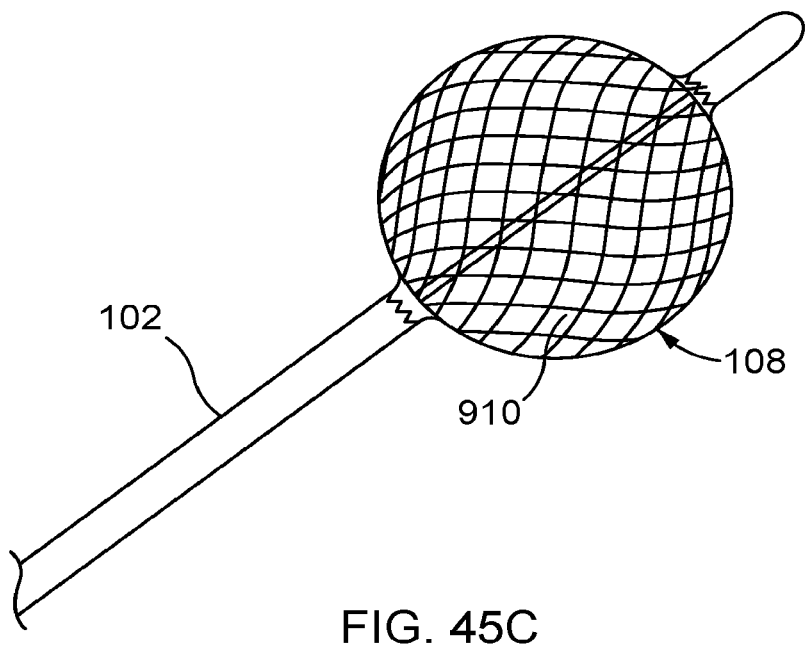
FIG. 45C illustrates an embodiment of a catheter having an energy delivery body comprising wires forming an expandable basket, wherein the energy delivery body transitions from a collapsed configuration to an expanded configuration due to expansion of an internal expandable member.
Figure 45D:
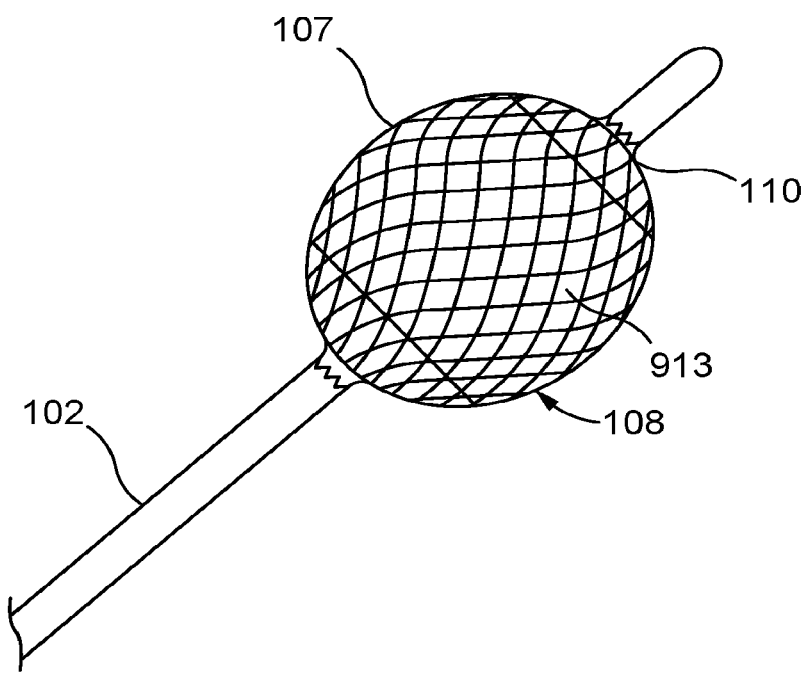
FIG. 45D illustrates an expandable member having a conductive surface.

It may be appreciated that other embodiments of energy delivery catheters 102 may also include portions that are expandable by an expandable member 910. For example, FIG. 45C illustrates an embodiment of a catheter 102 having an energy delivery body 108 comprising wires forming an expandable basket, wherein at least one of the wires acts as an electrode 107. In this embodiment, the energy delivery body 108 transitions from a collapsed configuration to an expanded configuration due to expansion of an internal expandable member 910, such as a balloon. In some embodiments, the expandable member 910 has a conductive surface 911, as illustrated in FIG. 45D.

Figure 45E:
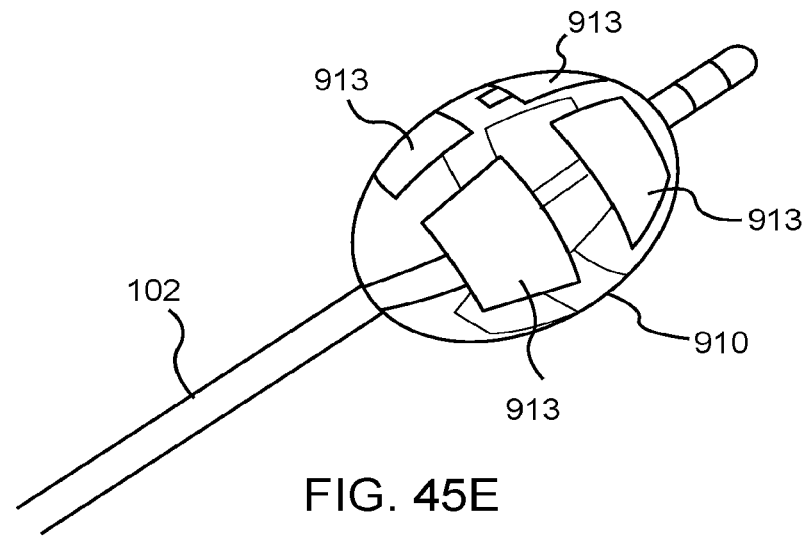
FIGS. 45E-45G illustrate a variety of energy delivery catheters having expandable members with printed electrodes.
Figure 45F:
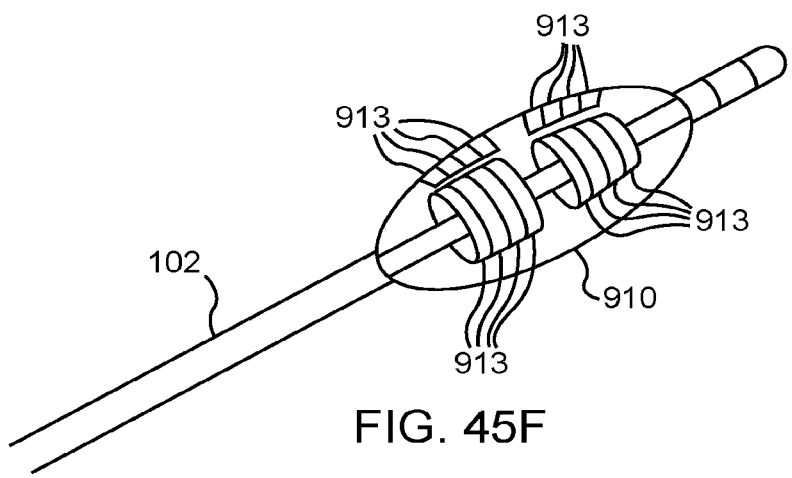
Figure 45G:
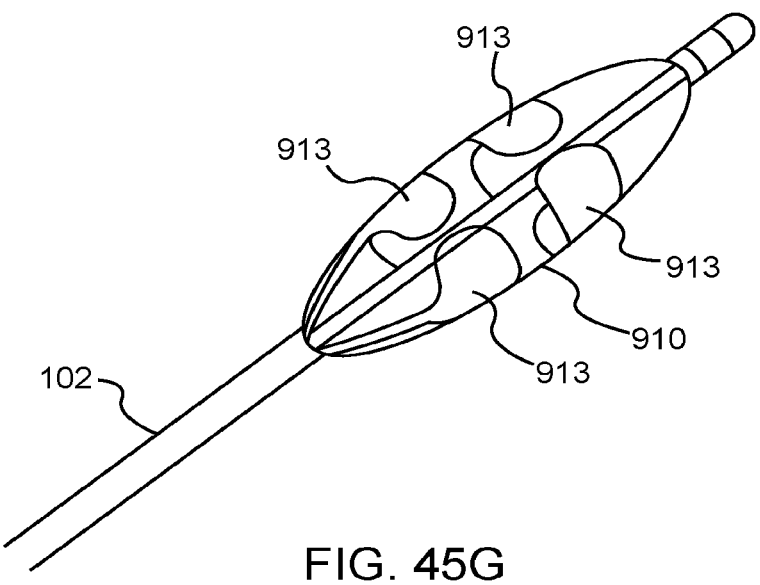

In some embodiments, the expandable member 910 includes one or more printed electrodes 913 which are disposed on the surface of the expandable member 910. FIGS. 45E-45G illustrate a variety of energy delivery catheters 102 having expandable members 910 with printed electrodes 913. It may be appreciated that the electrodes 913 may extend around the circumference of the expandable member 910, as shown, or may reside on a particular side of the expandable member 910. Electrodes 913 on a particular side may be used to provide focal treatment or the catheter 102 may be rotated to provide circumferential treatment. The electrodes 913 can be used in monopolar or bipolar modes.

Figure 45H:
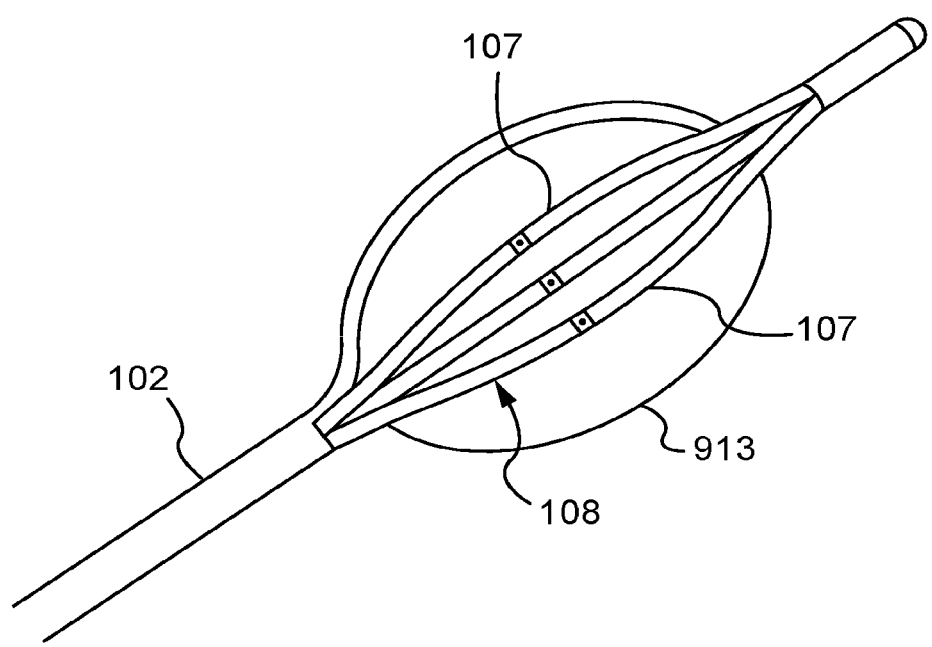
FIG. 45H illustrates an embodiment of an energy delivery catheter having an energy delivery body comprising two protrusions that are expandable by an expandable member.

FIG. 45H illustrates an embodiment of an energy delivery catheter 102 having an energy delivery body 108 comprising two protrusions that are expandable by an expandable member 910. In this embodiment, the two protrusions comprise wires which act as electrodes 107. It may be appreciated that in other embodiments, the electrodes 107 are comprised of printed electrodes 913 in the form of strips which are printed on the surface of the expandable member 913.

Figure 46:
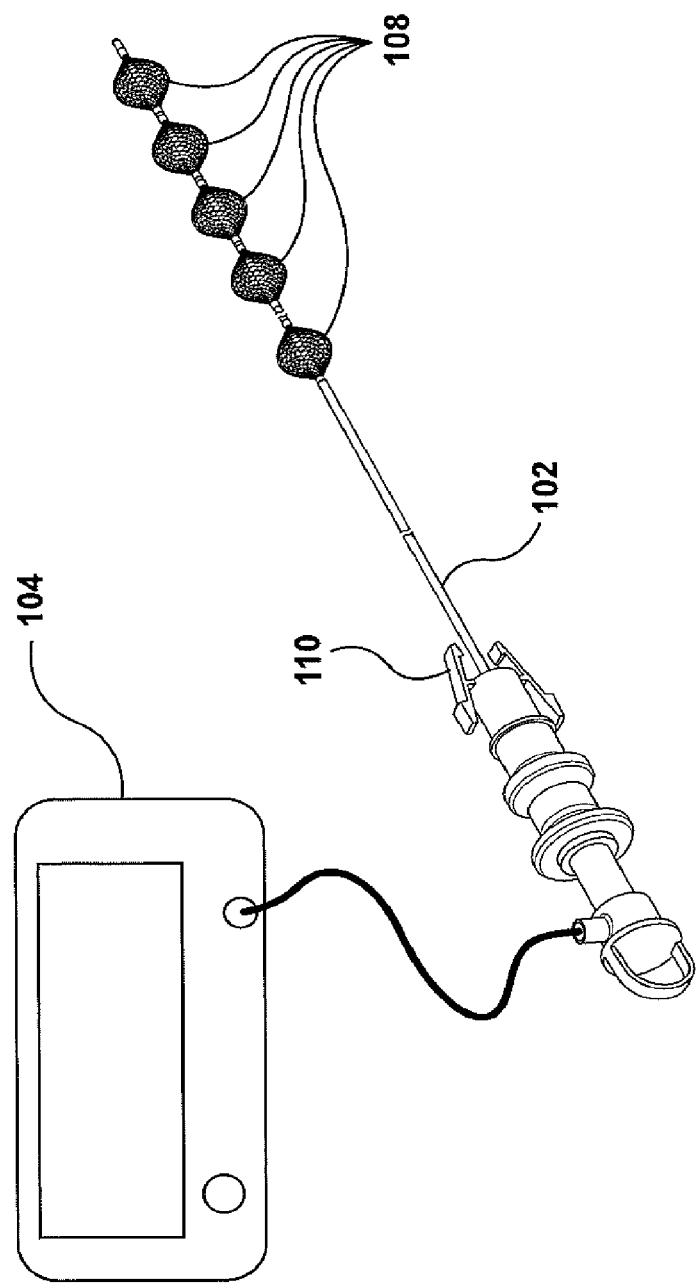
FIG. 46 illustrates an embodiment of an energy delivery catheter with four energy delivery bodies activatable in a bipolar/multiplexed fashion.

FIG. 46 illustrates an embodiment of an energy delivery catheter 102 with more than two energy delivery bodies 108 (four energy delivery bodies 108 are shown) activatable in a bipolar/multiplexed fashion. In this embodiment, the energy delivery bodies 108 are comprised of braided metal wires, wherein the wires serve as electrodes. Energy delivery bodies 108 can be activated in a bipolar fashion by cycling the power supplied by an external generator 104 between any pair of two energy delivery bodies 108, one of which is neutral. The combination between active and neutral energy delivery bodies 108 can be varied as well. For example, in one embodiment the energy can be applied to two or more energy delivery bodies 108 while one energy delivery body 108 serves as a neutral electrode. The combination of active energy delivery bodies 108 and neutral energy delivery bodies 108, the switching/cycling of the energy between active and neutral energy delivery bodies 108, the choice between activated and deactivated energy delivery bodies 108 is achieved through the energy delivery algorithm 152 of the generator 104. The algorithm 152 can apply and distribute energy between energy delivery bodies 108 based on a pre-defined approach, imaging data, and other factors determining the desired area and depth of treatment.

Figure 47:
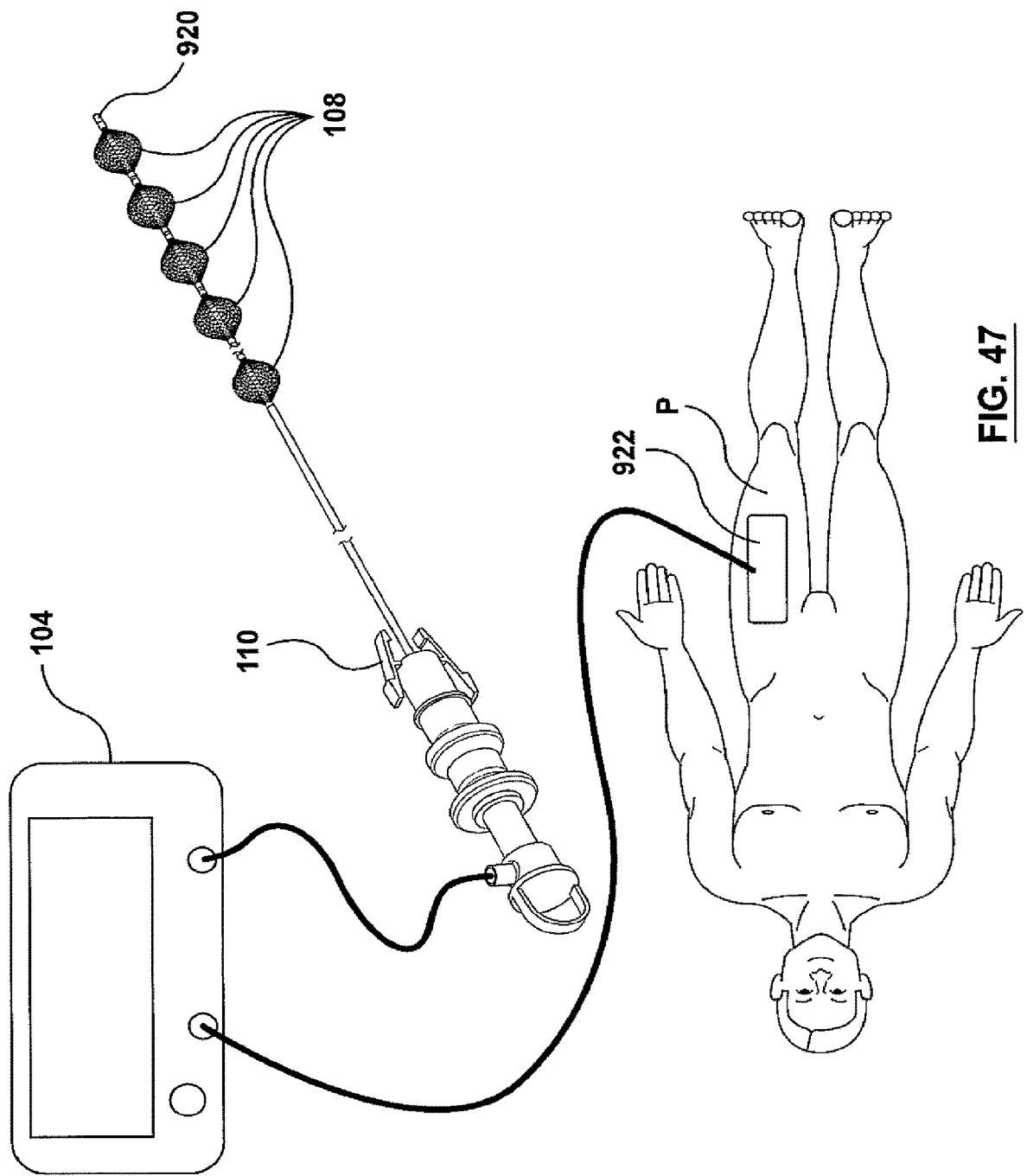
FIG. 47 illustrates monopolar energy delivery by supplying energy between the energy delivery bodies and a dispersive (return) electrode applied externally to the skin of the patient.

FIG. 47 illustrates another embodiment of an energy delivery catheter 102 having a multi-energy delivery body design. In this embodiment, the energy delivery bodies 108 are activated in a monopolar and/or bipolar multiplexed fashion. Monopolar energy delivery can be achieved by supplying energy between one or more energy delivery bodies 108 positioned near the distal end 920 of the catheter 102 and a dispersive (return) electrode 922 applied externally to the skin of the patient P. The combination of active energy delivery bodies 108, the switching/cycling of the energy between the active energy delivery bodies 108 and the dispersive electrode 922, and the choice between activated and non-activated energy delivery bodies 108 is achieved through the energy delivery algorithm 152 of the generator 102. The algorithm 152 can apply and distribute energy between energy delivery bodies 108 based on a pre-defined approach, imaging data and other factors determining the desired area and depth of treatment.

It may be appreciated that many of the figures herein depict energy delivery bodies 108 of essentially the same size (e.g., length, diameter) and shape for illustrative purposes, and should not be considered limiting. In some embodiments, the energy delivery bodies can vary in size in order to account for tapering of the airway lumen, better localize the energy field, and/or enhance treatment of the tissue. For example, if the desired catheter placement requires a distal energy delivery body to be in the lobar bronchi (about 9 mm-12 mm in diameter) and a proximal energy delivery body to be in the mainstem bronchi (about 12 mm-16 mm in diameter), the distal energy delivery body can be designed to expand to about 12 mm and the proximal energy delivery body to expand to about 16 mm. The energy delivery bodies can also be of different sizes to better localize the energy field. For example, if monopolar energy delivery is desired, it can be beneficial to have the dispersive (neutral) electrode incorporated into the catheter or another device (instead of placed on the outside of the patient, as shown in FIG. 47) in order to locate it closer to the treatment energy delivery body to better localize the energy. This can reduce the risk of causing muscle contractions or arrhythmias, as a lower voltage can be applied to generate the same electric field. The energy delivery bodies can also be of different sizes in order to enhance the ability to separate the tissue. In some embodiments, the active portion of the energy delivery body can be that area which is in contact with the airway. It is therefore possible that the area of contact for two different energy delivery bodies is nearly the same, for example, if two similarly-sized energy delivery bodies are placed into a similarly-sized airway and expanded approximately the same. However, if two similarly-sized energy delivery bodies are placed into different-sized airways and/or not expanded the same, the active portion of each energy delivery body can vary significantly. If one electrode is configured to have more contact area than the other, a non-uniform electric field can polarize the cells such that a greater force can be generated in an effort to separate the tissue. The energy delivery body can also be configured to bias the energy field normal to the epithelium or to create shear along the epithelium.

Figure 48:
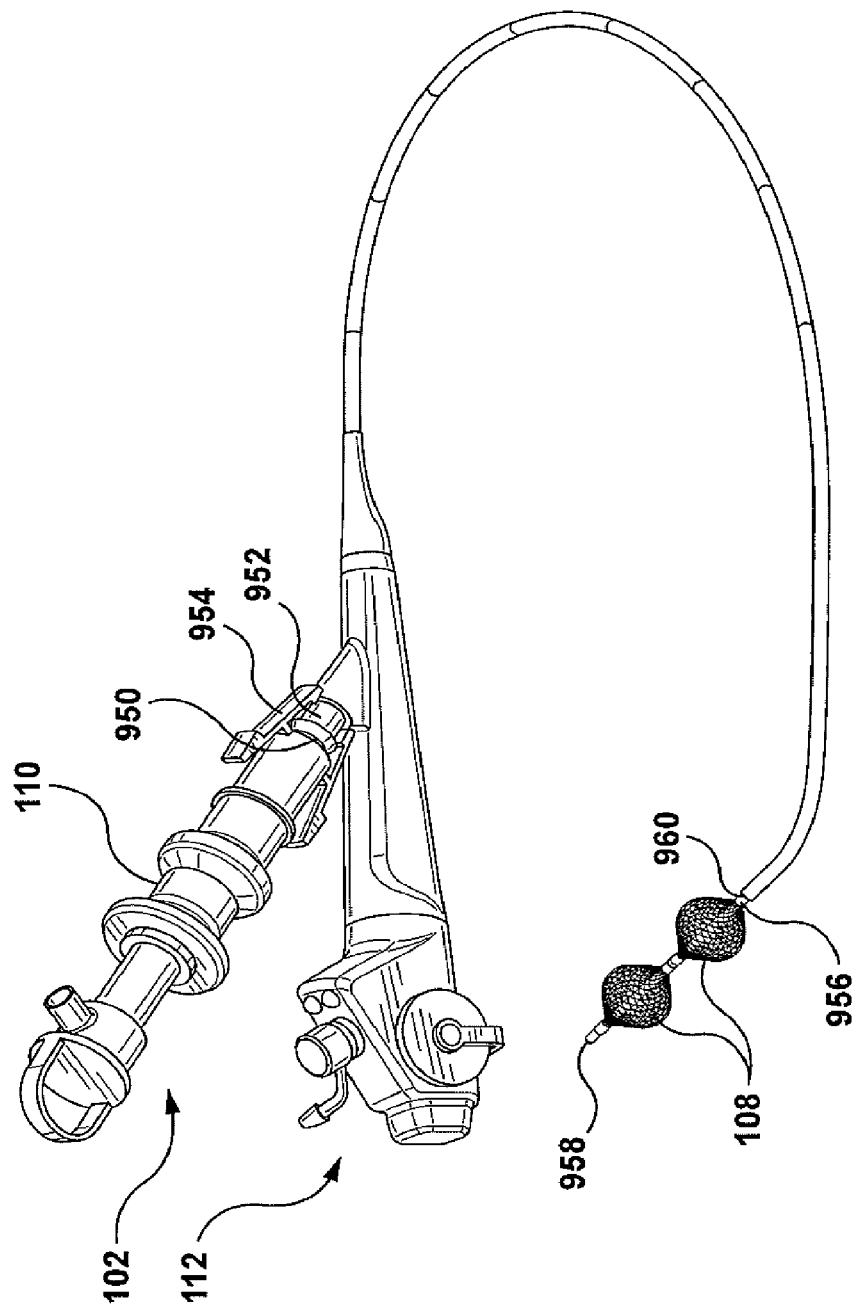
FIG. 48 illustrates an example catheter removably connected to a bronchoscope.

FIG. 48 depicts an example catheter 102 configured to removably connect to a bronchoscope 112. I this embodiment, a handle 110 of the catheter 102 includes a docking mechanism 950 that is removably connectable (e.g., snapped) to an external port 952 of a working channel of the bronchoscope 112. Such a docking mechanism 950 can make it easier for the operator to control both the bronchoscope 112 and the catheter 102 during the procedure. In another embodiment, the handle 110 is connectable to various bronchoscope attachments and/or accessories (e.g., valve, not shown) that are installable onto the external port 952 of the working channel of the bronchoscope 112. In yet another embodiment, the handle 110 does not have any mechanisms that connects to the external port or valve of the working channel of the bronchoscope 112. In such instances, the stability of the catheter 102 is achieved by means of friction between the shaft of the catheter 102 and accessories (for example valve) that are installed onto the external port 952 of the working channel of the bronchoscope 112.

In some embodiments, the length between a distal end 954 of the catheter handle 110 and the proximal end 956 of the most proximal energy delivery body 108 is tailored to be substantially equal to the length of the working channel of the bronchoscope 112, based on the distance between the proximal end of the working channel and the distal end of the working channel. When the catheter handle 110 is connected (e.g. snapped) to the external port 952 of the working channel of the bronchoscope 112, the energy delivery body or bodies 108 is/are introduced into the lung passageway. The step of positioning the one or more energy delivery bodies 108 within the target area of the lung passageway can be accomplished by moving the bronchoscope 112, and thereby moving the catheter 102 there attached. When the one or more energy delivery bodies 108 are successfully positioned within the target area and this position is visually assessed and confirmed by the operator (e.g. using visual bronchoscopy) the one or more energy delivery bodies can be expanded, deployed or otherwise positioned into tissue contact via a mechanism in the catheter handle 110 which is operatively connected to the one or more energy delivery bodies 108 (e.g. lever, slider, plunger, button operatively connected to the one or more energy delivery bodies 108 (via a pull wire or by other mechanisms) and ready for energy delivery.

In some embodiments, the length between the distal end 954 of the catheter handle 110 and the distal most distal end 958 of the one or more energy delivery bodies 108 is tailored to be substantially equal to the length of the working channel of the bronchoscope 112, based on the distance between the proximal end of the working channel 954 and the distal end of the working channel 960. When the catheter handle 110 is connected (e.g., snapped) to the external port 952 of the bronchoscope working channel, the one or more energy delivery bodies 108 are not yet introduced (FIG. 49A) into the bronchus lumen and are situated within the working channel of the bronchoscope 112. The step of introducing the one or more energy delivery bodies 108 into the bronchus lumen (FIG. 49B) can be achieved via a primary mechanism of the handle 112 (e.g. lever, slider, plunger, button). When one or more energy delivery bodies 108 are successfully positioned within the target area and this position is visually assessed and confirmed by the operator (e.g. using visual bronchoscopy) the electrodes can be expanded, deployed or otherwise positioned into tissue contact (FIG. 49C) via a secondary mechanism of the handle 112 (e.g. lever, slider, plunger, button) and ready for energy delivery. In one configuration, a secondary handle mechanism (e.g. lever, slider, plunger, button) is operatively connected (for example bonded or welded) to the proximal end of the catheter sheath. To deploy/expand one or more energy delivery bodies 108 the operator would move a secondary mechanism proximally thus moving the catheter sheath proximally which removes the constraint of the one or more energy delivery bodies 108 and allows them to expand. In another configuration, a secondary handle mechanism (e.g. lever, slider, plunger, button) is operatively connected (for example bonded or welded) to the proximal end of the pull or push wire/tubing. To deploy or expand the one or more energy delivery bodies 108 the operator would move a secondary mechanism proximally thus pulling the pull wire or tubing or distally thus pushing the push wire/tubing. In both embodiments depending on the specific configuration of the catheter and its deployment mechanism the action performed by the operator using a secondary handle mechanism will lead to the deployment or expansion of the one or more energy delivery bodies 108. In yet another configuration, there can be more than one secondary handle mechanism connected to more than one pull or push wires or tubings. In this scenario the expansion of one or more energy delivery bodies 108 can be controlled independently by activating different secondary handle mechanisms at different times and at different levels of magnitude.

In some embodiments, the length between the distal end of the catheter handle and the proximal end of the one or more energy delivery bodies 108 is tailored to be substantially longer than the length of the working channel. When one or more energy delivery bodies 108 are introduced into the lung passageway, the handle is not in contact with the external port of the bronchoscope working channel. The step of positioning one or more energy delivery bodies 108 within the target area can be accomplished by moving the bronchoscope or alternatively moving the catheter itself. In this case, the catheter is long enough that the catheter handle can be held by the operator or set down on or near the patient to allow the operator to hold the bronchoscope. When one or more energy delivery bodies 108 are successfully positioned within the target area and this position is visually assessed and confirmed by the operator (e.g. using visual bronchoscopy) the one or more energy delivery bodies 108 can be deployed or otherwise positioned into tissue contact via a mechanism in the catheter handle which is operatively connected to the one or more energy delivery bodies 108 (e.g. lever, slider, plunger, button) and ready for energy delivery.

According to embodiments described herein, which can partially or as a whole combine with other embodiments, the handle of the catheter can include a docking mechanism that can be removably connected (e.g., snapped) onto the external port of the bronchoscope working channel. In another embodiment, the handle can be connected to the various attachments and/or accessories (e.g., valve) that are installed onto the external port of the bronchoscope working channel. In yet another embodiment, the handle may not have any mechanisms that snap onto the external port of the bronchoscope working channel and the stability of the device is achieved by means of friction between the shaft of the catheter and accessories (e.g., valve) that are installed onto the external port of the bronchoscope working channel.

X. Treatment Patterns

It may be appreciated that a patient P may possess a single target zone for treatment or multiple target zones. A target zone is a contiguous area of a lung passageway that is targeted for treatment. A single lung passageway may include multiple target zones. Likewise, target zones may be located along separate lung passageways. Each target zone may include one or more target segments. A target segment is a portion of the lung passageway that is treatable by a single placement of the catheter 102 (i.e. single treatment). Thus, the target segment is defined by the outer area borders along the lung airway wall W within which the wall tissue has been treated by the one or more electrodes 108 of the catheter 102. It may be appreciated that different embodiments of the catheter 102 may cover differing sized areas of a lung passageway. Thus, the size of a target segment may vary based on catheter 102/system 100 design. In addition, the catheter 102 may be sequentially moved along a lung passageway to create multiple adjacent target segments, wherein adjacent target segments cover the target zone.

Thus, methods for treating the airway of a patient can include: (a) performing a single treatment at a target segment, (b) performing two or more treatments at adjacent target segments such that the overall treatment zone is generally continuous, and/or (c) performing two or more treatments spaced apart from one another. In some embodiments, proximal airways and side branches and more distal lobe targets are included in the targeted zone. In other embodiments, proximal airways and side branches or more distal lobe targets are excluded from the targeted zone. In some embodiments, the treatment areas are overlapped or applied as a discrete treatment at a target segment based on the disease state of the patient, such as the presence of isolated mucus plugging in a specific segment.

In some methods, the therapy is delivered over a series of independent treatment sessions. In one embodiment, therapy is only delivered to part of the targeted anatomy, with subsequent sessions to treat the remainder of the tissue. In another embodiment, therapy is delivered to the same anatomy at multiple sessions to intensify therapeutic effect. In another embodiment, therapy is delivered at multiple sessions to the same anatomy to re-induce the therapeutic effect if benefits to the patient decay over time. In another embodiment, therapy is delivered at multiple sessions with specific cell-type targeting for each independent session. In this embodiment, targeting can be achieved by selection of optimal pulsed electric field parameters for each cell type. In another embodiment, targeting is also be achieved with the administration of pre-conditioning or post-conditioning of the tissue. All multiple treatment session methods may be combined or performed independently.

Figure 51:
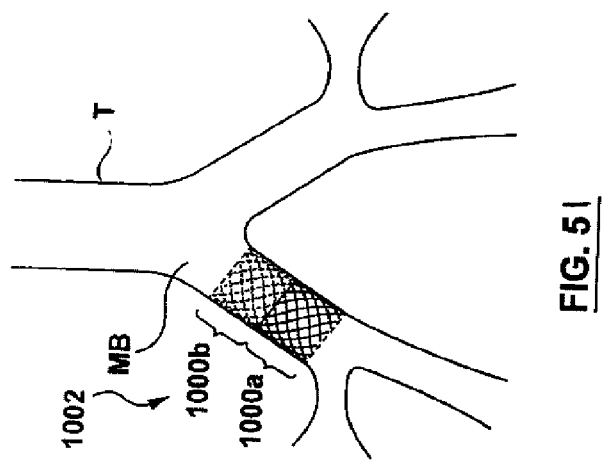
FIG. 51 is a schematic illustration of two target segments positioned adjacent to each other such that the overall target or treatment zone is generally contiguous.
Figure 50:
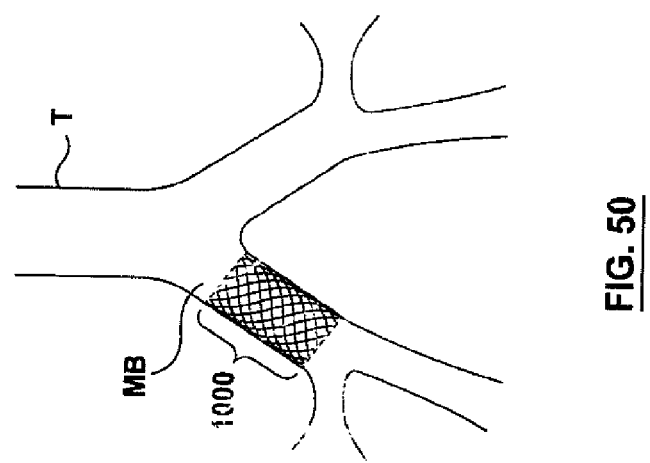
FIG. 50 is a schematic illustration of a single target segment within a mainstem bronchi of a lung.

FIG. 50 is a schematic illustration of a single target segment 1000 within a mainstem bronchi MB of a lung. In this embodiment, the target segment 1000 is treated by placement of the one or more energy delivery bodies 108 of the catheter 102 and delivery of treatment energy thereto. FIG. 51 is a schematic illustration of two target segments 1000a, 1000b positioned adjacent to each other such that the overall target or treatment zone 1002 is generally contiguous. Typically, the two target segments 1000a, 1000b are treated by first positioning the catheter 102 so as to treat the first target segment 1000a, then repositioning the catheter 102 so as to treat the second target segment 1000b. It may be appreciated that the various target segments may alternatively be treated with different catheters 102. It may also be appreciated that the target segments 1000a, 1000b may be treated in any order. It may also be appreciated that individual target segments 1000a, 1000b may be treated with different treatment parameters to invoke varying treatment effects optimally targeted to the desired outcome in each region. This may occur between a single pair of adjacent treatment applications or may continually progress along a pattern as the treatment proceeds through the broader length of the targeted length.

Likewise, in some embodiments, target segments overlap. FIGS. 51A-51D illustrate a method of generating two target segments 1000a, 1000b intentionally overlapped, where some overlapped region of tissue will receive the therapy more than once, so as to ensure complete contiguous treatment effects. FIG. 51A illustrates positioning of the catheter 102 within a lung passageway placing an energy delivery body 108 to create a first target segment 1000a, as illustrated in FIG. 51B. Energy is delivered by the energy delivery body 108 to the first target segment 1000a. FIG. 51C illustrates positioning the catheter 102 along the lung passageway so that the energy delivery body 108 is disposed in an adjacent location creating a second target segment 1000b that overlaps with the first target segment 1000a, as illustrated in FIG. 51D. Energy is delivered by the energy delivery body 108 to the second target segment 1000b. This results in an overlapped target segment 1000c.

The degree of overlap intensity and number of overlapping regions may be manipulated as a function of the energy delivery body 108 geometry and the geometry of the lung passageway or lumen. In particular, the degree of overlap is affected by the length of the energy delivery body 108 and the distance that the energy delivery body 108 is advanced. Examples of basic compensatory overlap, as well as compounding effect intensity overlap may be found in FIGS. 51E-51F. FIG. 51E illustrates the use of an energy delivery body 108 having a short length and therefore a minimal length of contact along the lumen wall, in this example the airway wall W. The energy delivery body 108 delivers energy to a first target segment 1000a creating a first tissue effect 1001a. The first energy effect 1001a has a boundary effect 1001a' indicated by dashed line. The energy delivery body 108 is then advanced along the lumen and delivers energy to a second target segment 1000b creating a second tissue effect 1001b. The second energy effect 1001b also has a boundary effect 1001b' indicated by dashed line. Thus, the overlap in tissue effects 1001c is largely by the boundary effects. FIG. 51F illustrates the use of an energy delivery body 108 having a longer length and therefore a longer length of contact along the lumen wall, in this example the airway wall W. The energy delivery body 108 delivers energy to a first target segment 1000a creating a first tissue effect 1001a. The first energy effect 1001a has a boundary effect 1001a' indicated by dashed line. The energy delivery body 108 is then advanced along the lumen and delivers energy to a second target segment 1000b creating a second tissue effect 1001b. The second energy effect 1001b also has a boundary effect 1001b' indicated by dashed line. Here, the overlap in tissue effects 1001c is much more significant and therefore intense.

Such overlapping may be desired for a variety of reasons. In some embodiments, such overlapping is desired to compensate for weaker regions at any given treatment segment. In some instances, portions of the energy delivery body 108 may have varying levels of contact with the lumen wall W. The treatment effect concentrates at the specific points of contact, such as the electrode braid wires, and is stronger in these areas along the contact length while being weaker in areas with less contact. By overlapping the treatment segments, the combined effect of the overlapped energy delivery compensates for the weaker regions of any given activation site zone. In other embodiments, such overlapping is desired to maintain an appropriate cadence of treatment activation delivery, whereby the user advances/withdraws the treatment delivery body along the target lumen length by an established distance following each activation. In some instances, this permits the assurance of complete adjacent treatment zones regardless of lumen diameter and electrode expansion and contact length. This method also ensures attaining complete lumen length coverage over variable diameter treatment zones where the electrode body is expanded to a larger diameter than anticipated, resulting in a shorter length than anticipated. This differential in contact length over the course of the treatment and adjacent treatment zones warrants ensuring contiguous treatment via erring on the overlap of treatment zone, and deliberately selecting shorter lengths of advancing/withdrawing the catheter electrode than the length of the catheter electrode itself.

In some embodiments, multiple branches are be treated during the same treatment session. It may be appreciated that in the lungs, and in various other lumens in the body, the main lumen deviates into progressively smaller segments and subsegments, referred as branches. In some embodiments, a portion of a lumen is treated along with a portion in a nearby branch FIG. 52 is a schematic illustration of two such target zones 1004, 1006 within a patient. In this embodiment, a first target zone 1004 is disposed within a mainstem bronchi MB and a second target zone 1006 is disposed within a lobar bronchi LB of a lung. Here, the first target zone 1004 is covered by a first target segment 1008 and the second target zone 1006 is covered by a second target segment 1010 wherein the first and second target segments 1008, 1010 are spaced apart from one another. Again, the two target segments 1008, 1010 may be treated by first positioning the catheter 102 so as to treat the first target segment 1008, then repositioning the catheter 102 so as to treat the second target segment 1010. It may be appreciated that the various target segments may alternatively be treated with different catheters 102. It may also be appreciated that the target segments 1008, 1010 may be treated in any order. It is understood that these figures provide example treatment patterns that can be used solely or in combination with one another to yield the desired outcome. Similarly, FIG. 52A illustrates a variety of target segments 1000 along various branching lung passageways, including within an ostium and along various smaller branches. This can be achieved with the repeated placement of a single catheter 102, placement of a plurality of catheters 102 or placement of a specialized catheter, such as having more than one energy delivery body 108. FIG. 52B illustrates treatment of differing lung passageways, such as branching from the same mainstem bronchi MB. In this embodiment, a single catheter 102 is used to treat two different lung passageways, each treated by a separate energy delivery body 108. It may be appreciated that the energy delivery bodies 108 may alternatively be provided by different catheters 102. The different catheters may be passed through the same bronchoscope or through different bronchoscopes. It may also be appreciated that, in some embodiments, subsegmental branches are targeted explicitly at the point of branch deviation so as to ensure contiguous treatment coverage.

In some instances, treating side branches poses particular challenges. Device designs accommodate these challenges so as to successfully treat a variety of different branching configurations. It may be appreciated that side branches pose a challenge for device designs in approximately four ways:

1) Distance:

Side branches are more distally located and may be beyond the reach that most scopes and probes are able to access and visualize well. Thus, to access branches for these distal targets, custom bronchoscopes may be used that are longer in length to reach these regions. In other cases, a standard long-shaft bronchoscope may be used in treating deep targets and deep subsegmental branches. In some instances, the bronchoscope is disposable.

Likewise, in some instances, catheters 102 having longer lengths are used to reach these regions. In some instances, the catheters 102 are 85 cm, 100 cm or 115 cm in length. In some instances, the catheter is disposable.

2) Diameter:

Side branches are narrower than upstream airways which may require narrower designed access devices and catheters 102. In such circumstances, new purpose-built or custom bronchoscopes may be desired to access such narrow-lumen airways. In some embodiments, the bronchoscope has a maximum diameter of 2.5 mm so as to access 3rd or 4th generation subsegments. In other embodiments, the bronchoscope has a maximum diameter of 2 mm to access 4th and 5th generation subsegments. In still other embodiments, the bronchoscope has a maximum diameter of 1.5 mm to access 5th and 6th generation subsegments. In some cases, the scopes are able to provide good visualization and can be deployed through the working channel of a shorter and broader standard-sized bronchoscope.

In addition to dedicated bronchoscopes designed to access the narrower subsegments, it may also be desired to employ dedicated small diameter catheters 102 to deliver the therapeutic energy. In some embodiments, the catheters 102 have their length reduced or increased to accommodate the desired concentration of energy delivered based on their contact surface area. In the cases of an energy delivery body 108 having an energy delivery body 108 comprising a braided basket electrode, the electrode may have a heat-set diameter that is inherently smaller.

Further, in some embodiments, some features of the catheters 102 are minimized or eliminated to facilitate access and deployment of the energy delivery bodies 108 into the deeper subsegmental targets that are beyond the reach of the bronchoscopes. In some embodiments, pull wires or any other actuating mechanics are eliminated from the deployment of the energy delivery body 108. For example, in some embodiments, the energy delivery body 108 comprises a self-expanding braided basket which is comprised of a memory alloy, such as nitinol. In such designs, the basket has a pre-set shape established to inherently produce the desired deployed configuration. The basket is retractable into a sheath or delivery catheter so as to collapse. In some embodiments, retraction causes the basket to fold upon itself in a collapsed configuration. For example, in some embodiments, the basket is retractable into a sheath so that the sheath shifts a widest portion of the basket to toward one end of catheter causing the widest portion to fold over an end of the basket. Thus, the basket forms a funnel shape in the collapsed configuration. Deployment is achieved by retracting the sheath or other constraining tool which allows the basket to self-expand. In some of these embodiments, the energy delivery body 108 has a maximum diameter of approximately 2.5 mm for accessing 3rd or 4th generation subsegments, a maximum diameter of approximately 2 mm for accessing 4th and 5th generation subsegments, a maximum diameter of approximately 1.5 mm for accessing 5th and 6th generation subsegments, or a maximum diameter of approximately 0.5 or 1.0 mm to access 6th and 7th generation subsegments.

3) Access

To reach some locations, the branches may include intricate or convoluted trajectories, including sharp angles and compound changes in direction. These angles or series of curves may make accessing the targeted region difficult through the use of standard bronchoscopes alone. Such targeted regions may be reached with the use of dedicated catheters 102 explicitly designed for such circumstances. In some embodiments, the catheter 102 comprises an elongate shaft 106 having pre-formed bends along its length, at least one energy delivery body 108 near its distal end and a handle 110 at its proximal end. The shaft 106 is pliable enough to be advanced through an access device (e.g. bronchoscope 112), but after extending beyond the working channel of the access device, the pre-formed bend is exposed allowing the shaft 106 to bend along its preformation. Higher degrees of preformation permit placement of the energy delivery body 108 into steeper-angled subsegments than the access device can access on its own.

In other embodiments, the catheter 102 comprises an elongate shaft 106 and at least one energy delivery body 108 near its distal end wherein the energy delivery body 108 has pre-formed bends. For example, in some embodiments, the energy delivery body 108 has an asymmetrical energy delivery body 108 or an energy delivery body 108 that deploys asymmetrically. In some embodiments, such asymmetries are provided by offset pull wires. In other embodiments, such asymmetries are provided by one or more dedicated supporting balloons configured to expand the energy delivery body 108 into the desired asymmetric shape. In still other embodiments, the energy delivery body 108 comprises a heat-set braided basket electrode. It may be appreciated that in some embodiments, the shaft 106 is hollow permitting advancement of a guidewire therethrough. Thus, the guidewire can be used to facilitate access into the difficult-to-reach angles and side branches, and the catheter 102 is then advanced along the guidewire with appropriate compliance of the catheter 102 to follow the guidewire course and enter the designated location for deployment and delivery of the therapy.

4) Number

In some instances, it is desired to treat a plurality of branches during a single treatment session to obtain a desired clinical effect. For example, when treating asthma, it is often desired to treat target segments near the terminal bronchiole deep subsegments which constrict in their inflammatory response and cause the acute attacks that induce asthma-associated morbidity and mortality. Since it is typically desired to treat many of these small airways to achieve a clinical benefit, techniques are employed that increase the speed of delivery to a given subsegmental branch or to treat multiple branches simultaneously.

In some embodiments, multiple side branches are treated simultaneously with the use of multiple catheters 102 using the same or multiple bronchoscopes. In some instances, custom-built bronchoscopes are designed with multiple lumens, permitting independent placement of each catheter 102. In other instances, a single catheter 102 is used to treat two different branches, each treated by a separate energy delivery body 108, as illustrated previously in FIG. 52B.

In some embodiments, the energy delivery bodies 108 act as bipolar pairs wherein the separate energy delivery bodies 108 deliver energy between each other in a closed-loop system. This dramatically focuses and intensifies the treatment effect to tissue between the different energy delivery bodies 108. Such an approach is particularly suitable for focal targets in the tissue, such as tumor nodules within the airways or lung parenchyma between airways. In delivering in this manner, the energy delivery bodies 108 have basket electrodes. FIG. 52C illustrates such an embodiment. Here, the catheter 102 has a Y-shaped distal end which splits into a first end having a first energy delivery body 108a and a second distal end having a second energy delivery body 108b. The catheter 102 is configured to position the first and second energy delivery bodies 108a, 108b into adjacent branches while the bronchoscope 112 or other access device remains in the ostium or larger, more proximal branch. In this example, the target tissue (e.g. tumor TU) is disposed between the adjacent branches, particularly between the first and second energy delivery bodies 108a, 108b. The first energy delivery body 108a receives energy so as to act as a positive electrode and the second energy delivery body 108b receives energy so as to act as a negative electrode. Thus, the first and second energy delivery bodies 102*a*, 102*b* act as a bipolar pair, focusing the treatment energy toward the target tissue therebetween.

In other embodiments, the energy delivery bodies 108 include one or more penetrating elements that are used to penetrate through the airway to reach greater proximity to an embedded targeted region or to enter an embedded targeted region directly. The closer the electrodes of the energy delivery body 108 are to the targeted region, the more intensely concentrated the energy will be and thus the stronger the treatment effect will be in that particular region. It may be appreciated that the one or more penetrating elements may act in a monopolar fashion communicating with a dispersive electrode pad, or they may act in a bipolar fashion communicating between each other.

Figure 52D:
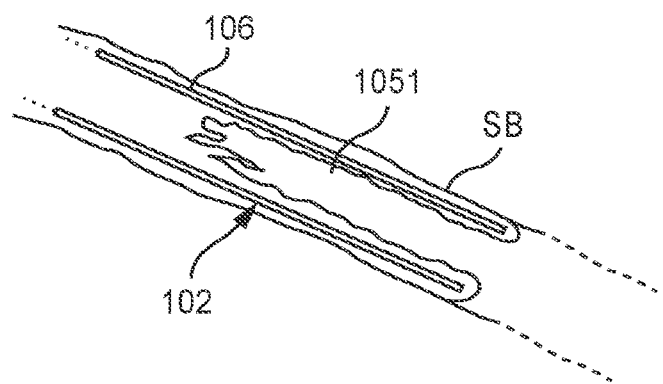
FIGS. 52D-52E illustrate an energy delivery body comprising an inflatable member which is closed at one end and attached to the distal end of the catheter at its other end.
Figure 52E:
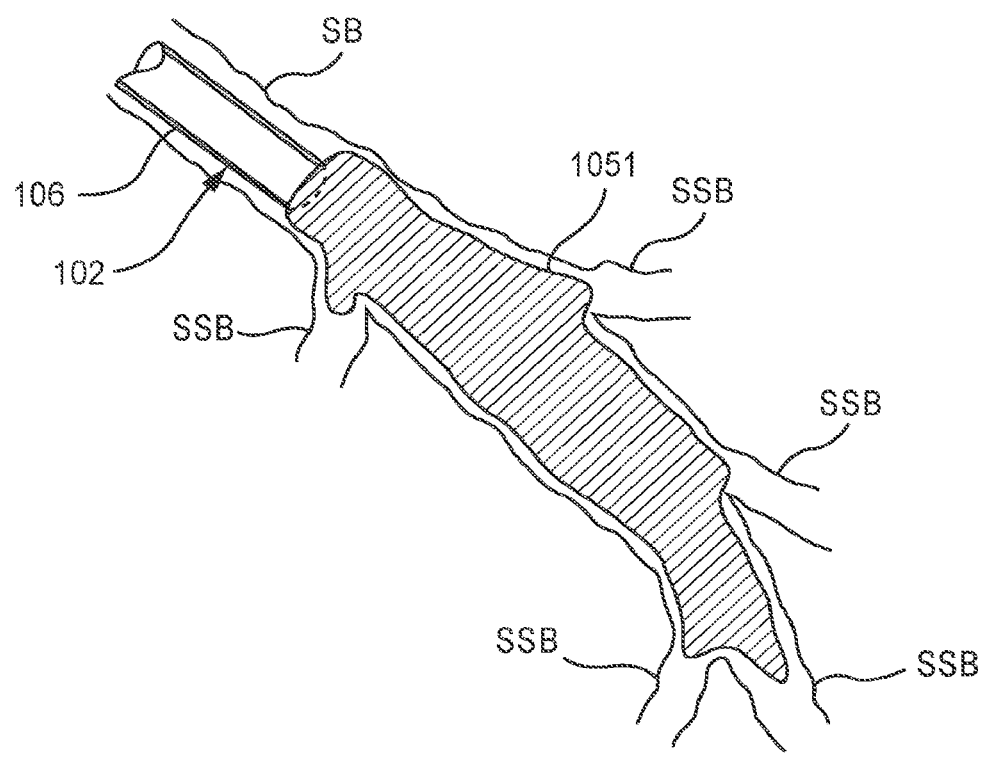

In some embodiments, the energy delivery body 108 comprises an inflatable member 1051 which is closed at one end and attached to the distal end of the catheter 102 at its other end, as illustrated in FIGS. 52D-52E. Thus, in some embodiments, the inflatable member 1051 appears as a continuous "balloon" having a single open end which is attached to the distal end of the catheter 102. FIG. 52D illustrates the inflatable member 1051 in an undeployed configuration. Here, the open end of the inflatable member 1051 is attached to the shaft 106 of the catheter 102 near its distal end. The inflatable member 1051 is tucked up into an internal lumen of the catheter 102 so that the catheter 102 can be advanced into the body lumen, such as a segmental bronchi SB. As shown, in this embodiment the inflatable member 1051 has an interior surface which faces a surface of the internal lumen of the catheter 102. Thus, the inflatable member is "inside out" when tucked up into the internal lumen of the catheter 102. Once the distal end of the catheter 102 is positioned within the body passageway, the inflatable member 1051 is deployed (e.g. pushed out of the distal end of the shaft 106), such as by filling of the catheter lumen with inflation medium. FIG. 52E illustrates the inflatable member 1051 in a deployed configuration. As shown, the inflatable member 1051 is sized and configured to extend along the airway, covering deeper branch take-offs, such as sub-segmental bronchi SSB. In some embodiments, the inflatable member 1051 extends into the take-offs so as to additionally treat portions of the deeper branches. This embodiment is particularly suitable for delivery to extended portions of airways or to portions of airways which are highly branched. It may be appreciated that the inflatable member 1051 may include a variety of different types of electrodes, such as thin electrode traces, for delivery of the energy.

Figure 52F:
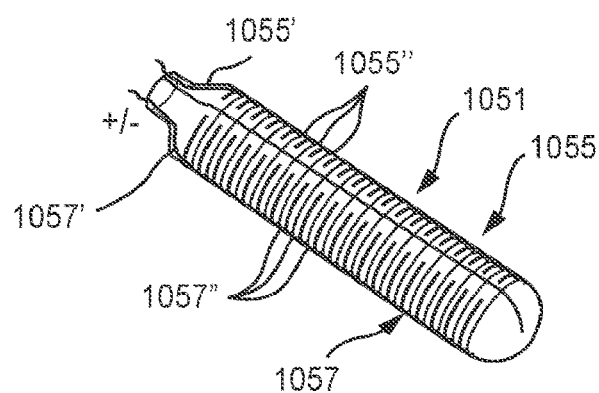
FIGS. 52F-52H illustrate an embodiment of an inflatable member having a plurality of electrodes wherein the plurality of electrodes has a two-pole design.
Figure 52G:
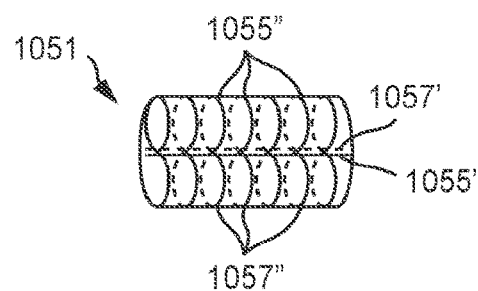
Figure 52H:
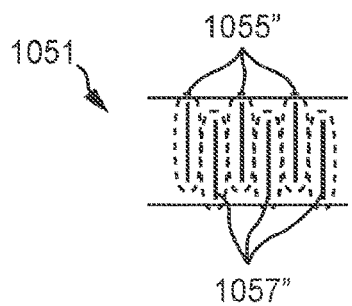

FIGS. 52F-52H illustrate an embodiment of an inflatable member 1051 having a plurality of electrodes 1053. In this embodiment, the plurality of electrodes 1053 has a two-pole design wherein the plurality of electrodes 1053 comprises a first set of electrodes 1055 having a first polarity and a second set of electrodes 1057 having a second polarity. Here, the first set of electrodes 1055 comprises a first center spine 1055' which extends longitudinally along the inflatable member 1051 and a first series of ribs 1055", each of which branch off from the center spine 1055' extending at least partially around the circumference of the inflatable member in a "rib cage" arrangement. Here, the second set of electrodes 1057 comprises a second center spine 1057' which extends longitudinally along the inflatable member 1051 and a second series of ribs 1057", each of which branch off from the second center spine 1057' extending at least partially around the circumference of the inflatable member in a "rib cage" arrangement. In this embodiment, the first center spine 1055' and the second center spine 1057' are disposed on opposite sides of the inflatable member 1051. Likewise, in this embodiment, the first series of ribs 1055" and the second series of ribs 1057" are offset from each other so as to interlace. FIG. 52G provides a closer view of a portion of the inflatable member 1057 of FIG. 52F. Here, the first center spine 1055' and the second center spine 1057' are shown as disposed on opposite sides of the inflatable member 1051. Likewise, the first series of ribs 1055" and the second series of ribs 1057" are shown interlacing wherein that the first series of ribs 1055" extend around the inflatable member 1057 in a C shape extending from the first center spine 1055' while the second series of ribs 1057" extend around the inflatable member 1057 in a C shape facing the opposite direction as it originates from the second center spine 1057' which is disposed on the opposite side of the inflatable member 1051. Thus, the ribs 1055", 1057" alternate in polarity, as illustrated in FIG. 52H, along the length of the inflatable member 1051. It may be appreciated that the energy delivered from the ribs 1055", 1057" may create overlapping treatment zones. In some instances, smaller zones that are added together to create a larger treatment area may give desired circumferential and longitudinal coverage while maintaining a desired depth of penetration, such as sufficient depth for treatment while avoiding involvement with the cartilage layer. It may also be appreciated that in such embodiments, the inflatable member 1051 is highly flexible so as to deploy as symmetrically as possible.

Figure 52I:
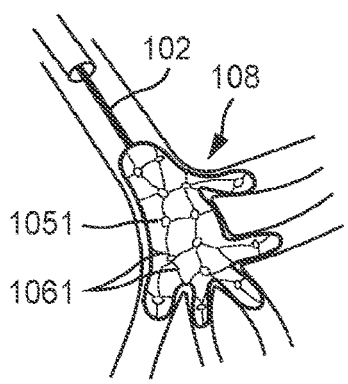
FIGS. 52I-52K illustrate additional embodiments of energy delivery body designs configured to treat multiple branches.
Figure 52J:
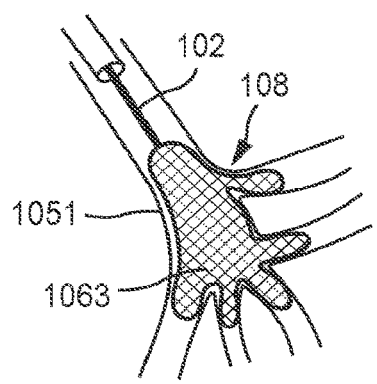
Figure 52K:
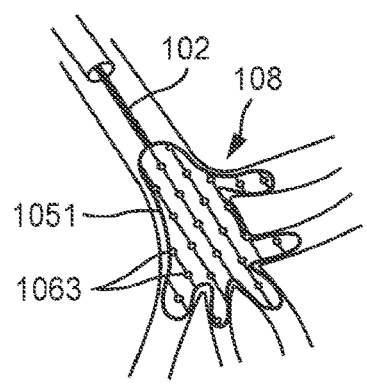

FIGS. 52I-52K illustrate additional embodiments of energy delivery body 108 designs configured to treat multiple branches. In each of these embodiments, the energy delivery body 108 comprises an inflatable member 1051 which is closed at one end and attached to the distal end of a catheter 102 at its other end. Thus, in these embodiments, the inflatable member 1051 appears as a continuous "balloon" having a single open end which is attached to the distal end of the catheter 102. In some embodiments, the inflatable member 1051 is configured to inflate in a manner which extends portions of the inflatable member 1051 into the side branches so as to create finger-like projections. In other embodiments, the inflatable member 1051 has formed finger-like projections which are positionable into the side branches. FIG. 52I illustrates an embodiment wherein the inflatable member 1051 includes very thin electrode traces which cross at activation points 1061 providing a "speckled" appearance. Here, the inflatable member 1051 is configured to be used in a monopolar arrangement. However, in other embodiments the inflatable member 1051 is arranged so that the activation points 1061 function in a bipolar manner or in a multipolar manner with the use of a dispersive external pad. FIG. 52J illustrates an embodiment wherein the inflatable member 1051 is surrounded by a compliant braid 1063 which acts as the electrode. In some instances, the compliant braid 1063 is embedded in the inflatable member 1051 and in other instances the compliant braid 1063 is separate wherein the inflatable member 1051 inflates to deploy the compliant braid 1063. FIG. 52K illustrates an embodiment wherein the inflatable member 1051 includes activation points 1061 arranged so as to function in a multi-polar manner.

In some embodiments, energy may be delivered to many deep subsegmental branches simultaneously with the use of a liquid electrode. In some embodiments, the liquid electrode is comprised of existing conductive solutions in the airways, such as mucus. In other embodiments, the liquid electrode is comprised of a conductive solution that is delivered to the airway, particularly into the targeted region. Typically, such a conductive solution comprises hypertonic saline, calcium, or other components and is delivered to an upstream segment so as to reach many of the downstream subsegmental branches. The treatment delivery would then be performed either via a catheter 102 having an energy delivery body 108 as described hereinabove or a catheter having a simple electrode configured to activate the conductive solution (e.g. a dull probe). In some embodiments, the conductive solution is then removed and in other embodiments the conductive solution is left behind to be resorbed. It may be appreciated that in some embodiments the conductive solution is comprised of a hypertonic solution, isotonic solution, or specialty conductive solution (e.g. calcium, silver, etc) that compounds the treatment effect.

In some embodiments, the liquid electrode is comprised of a conductive solution that is disposed within the energy delivery body 108. For example, in some embodiments, the energy delivery body 108 comprises a braided wire electrode forming a basket shape and a porous expandable member (e.g. a balloon with laser-drilled holes) that is disposed within the braided wire electrode basket. Inflation of the expandable member deploys the braided wire electrode basket and allows the conductive solution to weep from the porous expandable member. In a blood-filled environment, such as in the vasculature, blood circulating therearound will interact with the conductive solution weeping from the porous expandable member, thereby creating a virtual electrode. Thus, the conductive solution forms the second pole of the electrical circuit to create a bipolar electrode configuration. In another embodiment, a second pole electrode is added to the distal tip of the catheter to act as the return pole of the bipolar circuit. The second pole electrode may be comprised of any suitable conductive material, such as a platinum metal tip. In a blood-filled environment, such as in the vasculature, blood circulating therearound will interact with the second pole electrode thereby turning the local blood into a virtual electrode to complete the circuit. These embodiments allow for localized bipolar delivery of energy for treatment of tissue while diminishing affects on the integrity of adjacent structures and a need for cardiac synchronization.

To increase the speed of treatment delivery to facilitate treatment to many branches in a relatively short period of time, one or more energy delivery algorithms 152 may be chosen to fulfill these specific goals. In some embodiments, larger voltages, longer packets, or lower frequencies may be used to enable entire treatment to the targeted depth and intensity using a single packet. Such algorithms 152 may facilitate treatment immediately following placement of the one or more electrode bodies 108 when risks to cardiac arrythmias are properly controlled. When timing energy delivery to occur during the R-T interval, energy should be delivered within approximately 1 second of placement. When employing these techniques to expedite treatment delivery, the primary factor constraining the number of side branches and subsegments that may be targeted overall or within a given period of time thus becomes the operator's capacity to access and place the energy delivery body 108 at each targeted subsegment, and the maximum reasonable procedure time the clinician is willing to spend on treatment delivery.

It may also be appreciated that within a target segment, the lung passageway tissue may receive a variety of treatment patterns at any given cross-section. For example, some embodiments include treating the full circumference of the airway over a given length of the target segment and other embodiments include treating one or multiple discrete portions of the circumference of the airway over a given length of the target segment.

FIG. 53 is a schematic side view illustration of a portion of an energy delivery body 108 comprised of a braided basket. The braid is comprised of individual wires 120 which deliver energy. Between the wires are pores 1050. Depending on the degree of expansion (indicated by diameter 1052), the pore size will vary. FIG. 54 is a schematic cross-sectional view of the energy delivery body 108 of FIG. 53 positioned within a lung passageway having an airway wall W. Thus, the energy delivery body 108 is illustrated as a plurality of cross-sections of the wires 120 disposed against the inner lumen of the lung passageway (i.e. along the inner surface of the airway wall W). In some embodiments, treatment of a continuous full circumference (shading, 1054) of the airway W is achieved. Likewise, in some embodiments, continuous full circumference treatment along a length 1056 of the energy delivery body 108 is also achieved. This effect is illustrated in FIG. 55.

In some embodiments, in order to achieve substantially continuous, full circumference treatment over a given length, at least the applied electric field (V/cm) and the electrode design are taken into consideration. In one example, the electric field is applied in a monopolar fashion, wherein the field is applied to substantially the energy delivery body 108, and a dispersive (neutral) electrode is positioned either on the exterior of the patient or elsewhere within the body. The change and/or distribution of the magnitude of the field will depend on the applied voltage and the geometric relationship of the wires 120. In the example provided in FIGS. 53-55, the energy delivery body 108 in contact with the circumference and length of tissue to be treated is constructed from a metallic braid of wires 120. By having many wires 120 close together, the field between each wire 120 can be sufficient to cause the desired tissue effects continuously around the entire circumferential area of contact 1054. In this example, the diameter 1052 is designed to expand from approximately 2-3 mm in diameter when fully collapsed for delivery to about 10 mm, 12 mm, 15 mm, 18 mm, 20 mm, or 22 mm in diameter when fully expanded, including all values and subranges in between. Depending on the degree of expansion, the pore 1050 size will vary, but will generally be effective at generating a continuous tissue effect with pore sizes up to at least 10 $mm^2$. If the pore size becomes significantly larger, the same field applied can result in a discontinuous tissue effect (indicated by shading 1056), as depicted in FIG. 56. In this embodiment, the energy delivery body is comprised of four wires 120, wherein each wire 120 provides a tissue effect contributing to an overall discontinuous tissue effect. This can increase the speed of healing while still affecting a sufficient amount of tissue to provide a clinical benefit. A discontinuous lesion can also be achieved by reducing the applied electric field. In other embodiments, the length of the surface of the energy delivery body in contact with the tissue to deliver the therapy may be about 0.5 cm, 1 cm, 2 cm, or 10 cm, including all values and subranges in between.

In some embodiments, radially discontinuous effects may be desired. In these embodiments, focal targets for therapy delivery may be addressed. In other embodiments, radially discontinuous energizing of the energy delivery body may be done to decrease the contact surface area of the energy delivery body for a given placement to increase its local effects, whereby a radially continuous treatment zone may be generated by serially delivering the therapy to focal regions around the circumference of the targeted airway. In these embodiments, energy delivery bodies may be used which are not fully radially energized. In some embodiments, different radial regions of the energy delivery body may be independently energized, whereby radial treatment effect control can be driven by the system pulsed electric field generator. In another embodiment, the energy delivery body may not have electrically energizable surfaces distributed radially around the energy delivery body, whereby focal targeting of the treatment zone is achieved by deliberately placing the energy delivery body into contact at the specifically targeted focal region. In these embodiments, the number of radially energizable surfaces may be one. In other embodiments, the number of radially energizable surfaces may be approximately 2 to 10, including all numbers in between.

It may be appreciated that some embodiments have energy delivery bodies which include treating portions of the circumference ranging from about 25 to about 50%, from about 50% to about 75%, or from about 75% to about 100%, including all values and subranges in between. Some embodiments include treating lengths ranging from about 5 mm to about 20 mm, including all values and subranges in between, allowing for sufficient flexibility to treat a wide range of patient anatomies while minimizing the number of individual treatments to be performed.

XI. Conditioning

In some embodiments, cells targeted for treatment are conditioned so as to modify the behavior of the cells in response to the delivery of the energy signals. Such conditioning may occur prior to, during, or after delivery of the energy signals. In some embodiments, conditioning prior to energy delivery is considered pre-conditioning and conditioning after energy delivery is considered post-conditioning. Such differentiation is simply based on timing rather than on how the conditioning treatment affects the cells. In other embodiments, pre-conditioning relates to affecting what happens to the cells during energy delivery, such as how the cells uptake the energy, and post-conditioning relates to affecting what happens to the cells after energy delivery, such as how the cells behave after receiving the energy. Such differentiation may be less relevant to timing since in some instances conditioning may occur prior to energy delivery but only affect the cellular response following the energy delivery. Therefore, it may be appreciated that "conditioning" may be considered to apply to each of these situations unless otherwise noted.

Typically, conditioning is achieved by delivering a conditioning solution. The conditioning solution may be delivered via inhalants and aerosol materials. The conditioning solution may also be delivered via direct fluid injection of the conditioning solution into the targeted region. In some embodiments, the conditioning solution selectively alters the electrical properties of the target cells, such as to affect the way the pulsed energy delivery gets distributed. In other embodiments, the conditioning solution influences the activity of the target cells. For example, in the lung such conditioning solution may promote basal cell differentiation into ciliated cells and/or downregulate goblet cells and submucosal gland cells. In other embodiments, the conditioning solution increases the likelihood of the target cells to expire following pulsed energy delivery. In still other embodiments, the conditioning solution alters the responses of non-targeted cells to the pulsed electric fields. In alternate embodiments, conditioning is performed via non-solution-based exposure of the tissues. This includes radiation therapy, radiotherapy, proton beam therapy. In some embodiments, the conditioning will impact the enzymatic and energy-producing components of the cellular infrastructure.

The conditioning solution may be comprised of a variety of agents, such as drugs, genetic material, bioactive compounds, and antimicrobials, to name a few. For embodiments where the conditioning solution increases the likelihood of the target cells to expire following pulsed energy delivery, the conditioning solution may comprise chemotherapy drugs (e.g. doxorubicin, paclitaxel, bleomycin, carboplatin, etc), calcium, antibiotics, or toxins, to name a few. For embodiments where the conditioning solution alters the responses from non-targeted cells to the pulsed electric fields, the conditioning solution may comprise cytokines (e.g. immunostimulants, such as interleukins), genes, VEGF (e.g. to encourage more vessel growth into area) and/or cellular differentiating factors (e.g. molecules to promote conversion of goblet cells into ciliated cells).

In some embodiments, the conditioning solution includes cells, such as stem cells, autograft cells, allograft cells or other cell types. In these embodiments, the cells may be used to alter the tissue response to the pulsed electric fields. In other embodiments, the cells may be used to repopulate the affected area with healthy or desirable cells. For example, once target cells have been weakened or killed by the delivered pulsed energy treatment, the cells from the conditioning solution may move into the vacancies, such as a decellularized extracellular matrix. In some embodiments, the area is washed out to remove the dead cells, such as with a mild detergent, surfactant or other solution, prior to delivery of the conditioning solution containing the new cells. In other embodiments, mechanical stimulation, such as suction, debriding, or ultrasonic hydrodissection, is used to physically remove the dead cells prior to delivery of the conditioning solution containing the new cells.

In some embodiments, the conditioning provided may invoke a targeted immune response. The immune response may result in a number of factors that alter the treatment effect outcome. This may result in an increase in the systemic immunity upregulation using specific markers associated with some targeted tissue, such as a tumor or bacteria or virus associated with an infection. It may also result in an upregulation of the innate immunity that broadly affects the immune system functionality to detect general abnormal cells, bacteria, or other infectious organisms residing within the body, which may occur locally, regionally, or systemically.

In some embodiments, the conditioning solution is warmed or chilled to alter how the target cells respond. Generally, warmed solutions promote increased treatment effects (e.g. increased susceptibility to cell death), while chilled solutions would reduce the extent of treatment effect or increase cell survival after exposure to a reversibly-designed protocol. In some embodiments, a chilled conditioning solution comprised of genes and or drugs is used to precondition cells to survive energy delivery treatment, increasing the number of cells that survive the treatment. In some embodiments, the effects of the warmed/chilled conditioning solution is compounded with the general effects caused by the other agents in the solution (e.g. warmed calcium solution, chilled gene containing solution). In other embodiments, the warmed/chilled conditioning solution does not provide effects other than temperature changes. In such embodiments, the conditioning solution is typically comprised of isotonic saline, phosphate buffered solution or other benign solution.

It may be appreciated that such heating or cooling may alternatively be achieved by other methods that do not involve delivery of a conditioning solution. For example, the target tissue may be heated or cooled by contacting the tissue with a warmed/cooled device, deliberately warming/cooling the pulsed electric field delivery catheter, delivering mild cryotherapy, or delivering mild radiofrequency or microwave energy. As previously described, this could promote enhanced lethality or permeability effects to the tissue or it could provide protective aspects to the cells that enable them to survive the procedure and exude the desired change as was targeted for them as a result of the therapy.

Figure 56A:
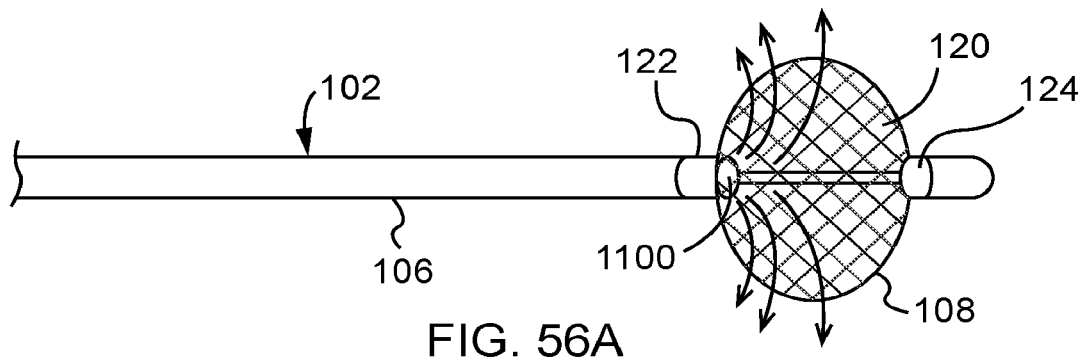
FIGS. 56A-56D illustrate embodiments of energy delivery catheters configured to deliver conditioning solution.

In some embodiments, a conditioning solution is delivered systemically, such as by intravenous injection, ingestion or other systemic methods. In other embodiments, the conditioning solution is delivered locally in the area of the targeted cells, such as through a delivery device or the energy delivery catheter 102 itself. FIGS. 56A-56D illustrate embodiments of energy delivery catheters 102 configured to deliver conditioning solution. FIG. 56A illustrates an embodiment of an energy delivery catheter 102 comprising an elongate shaft 106 having at least one energy delivery body 108 near its distal end and a handle 110 at its proximal end (not shown). In this embodiment, the energy delivery body 108 comprises a single monopolar delivery electrode, however it may be appreciated that other types, numbers and arrangements may be used. Here, the energy delivery body 108 is comprised of a plurality of wires or ribbons 120 constrained by a proximal end constraint 122 and a distal end constraint 124 forming a spiral-shaped basket serving as an electrode. In this embodiment, the shaft 106 is hollow or includes a lumen therethrough having an output 1100 at or near the energy delivery body 108. Thus, the conditioning solution is delivered through the shaft 106 and output 110 and flows outward toward the target tissue through the plurality of wires 120. This delivers the solution locally in the area of the energy delivery body 108 so that the tissue cells receiving the delivered energy will also receive the conditioning solution.

Figure 56B:
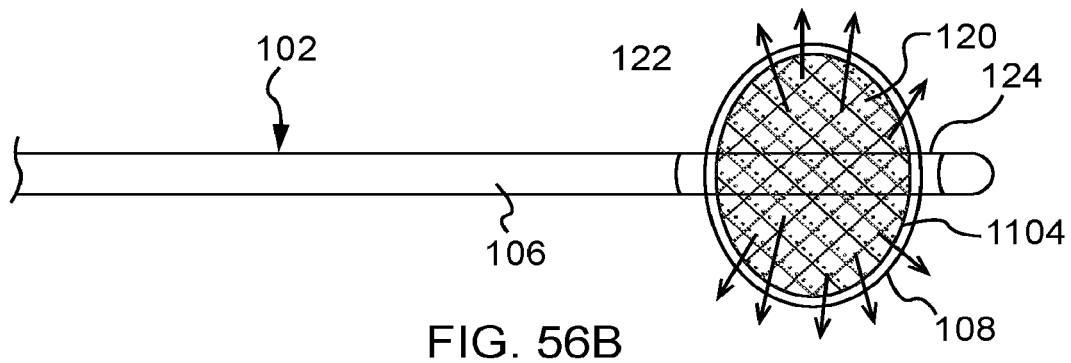

FIG. 56B illustrates another embodiment of an energy delivery catheter 102 configured to deliver conditioning solution. In this embodiment, the energy delivery catheter 102 comprises an elongate shaft 106 having at least one energy delivery body 108 near its distal end and a handle 110 at its proximal end (not shown). Again, the energy delivery body 108 comprises a single monopolar delivery electrode, however it may be appreciated that other types, numbers and arrangements may be used. Again, the energy delivery body 108 is comprised of a plurality of wires or ribbons 120 constrained by a proximal end constraint 122 and a distal end constraint 124 forming a spiral-shaped basket serving as an electrode. In addition, the energy delivery catheter 102 includes a weeping expandable member 1104, such as a balloon, which resides within the basket of the energy delivery body 108. In some embodiments, expansion of the expandable member 1104 expands the energy delivery body 108. In other embodiments, the energy delivery body 108 expands independently, such as by self-expansion or by actuating a mechanism such as a pull-wire.

In this embodiment, the shaft 106 is hollow or includes a lumen therethrough having an output 1100 within the expandable member 1104. Thus, the conditioning solution is delivered through the shaft 106 and output 110 and fills the expandable member 1104 so as to cause the expandable member 1104 to "weep" thus expelling or leaking the conditioning solution locally in the area of the energy delivery body 108 so that the tissue cells receiving the delivered energy will also receive the conditioning solution.

Figure 56C:
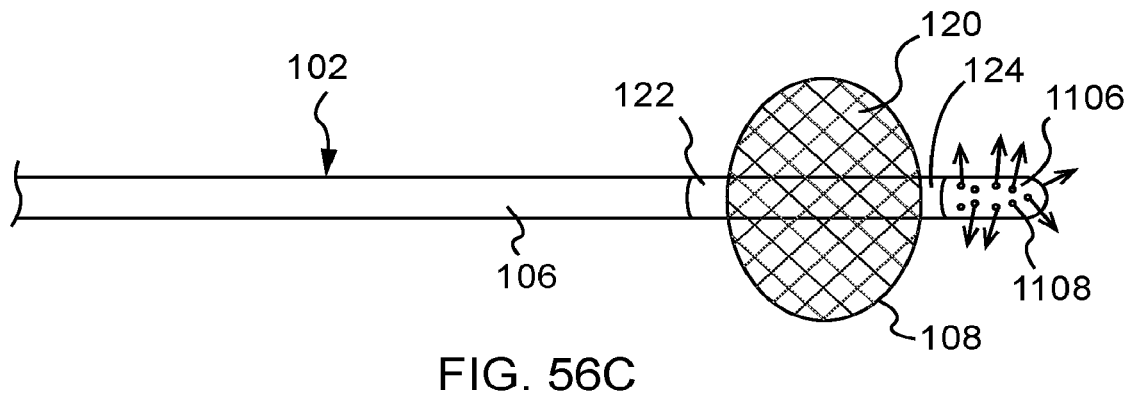

FIG. 56C illustrates an embodiment of an energy delivery catheter 102 configured to deliver conditioning solution through its distal tip 1106. In this embodiment, the energy delivery catheter 102 comprises an elongate shaft 106 having at least one energy delivery body 108 near its distal end and a handle 110 at its proximal end (not shown). Again, the energy delivery body 108 comprises a single monopolar delivery electrode, however it may be appreciated that other types, numbers and arrangements may be used. Again, the energy delivery body 108 is comprised of a plurality of wires or ribbons 120 constrained by a proximal end constraint 122 and a distal end constraint 124 forming a spiral-shaped basket serving as an electrode. In this embodiment, the energy delivery body 108 is disposed adjacent the distal tip 1106. The conditioning solution is delivered through the shaft 106 to its distal tip 1106, where the solution exits pores or holes 1108 in the distal tip 1106. In this embodiment, holes 1108 are arranged around the circumference of the distal tip 1106 and at the distal-most end forming an "open" tip. However, it may be appreciated that such holes 1108 may appear in a variety of arrangements, including or excluding circumferential holes or a hole at the distal-most end. Thus, the conditioning solution is delivered through the shaft 106 and exits the catheter 102 locally in the area of the energy delivery body 108 so that the tissue cells receiving the delivered energy will also receive the conditioning solution. It may be appreciated that in other embodiments, pores or holes 1108 may be located in other locations along the shaft 106 for delivery of conditioning solution therethrough, such as proximal to the energy delivery body 108 or both proximal and distal to the energy delivery body 108.

Figure 56D:
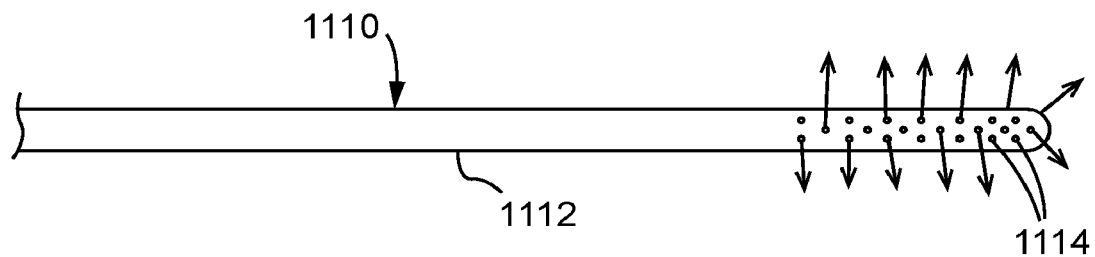

FIG. 56D illustrates embodiment of a delivery catheter 1110 configured to deliver conditioning solution through its distal tip 1106. Such a delivery catheter 1110 is used independently of the energy delivery catheter 102. Thus, it may be positioned near the target site prior to, during or after positioning of the energy delivery body 108. In this embodiment, the catheter 1110 comprises an elongate shaft 1112 having pores or holes 1114 near its distal tip 1116. The conditioning solution is delivered through the shaft 1112 to its distal tip 1116, where the solution exits the holes 1114 in the distal tip 1116. In this embodiment, holes 1114 are arranged around the circumference of the distal tip 1116. However, it may be appreciated that such holes 1114 may appear in a variety of arrangements, including or excluding circumferential holes or a hole at its distal-most end.

It may be appreciated that any of the above catheter design may also be used to suction and remove excess conditioning solution from the local area. Such suction may occur through the same lumen used for delivery of the conditioning solution or through a separate lumen. Likewise, a separate device may be used for removal of solution.

In some embodiments, the conditioning solution selectively alters the electrical properties of the target cells, such as to affect the way the pulsed energy delivery gets distributed. Thus, in these embodiments, the time of exposure and the volume of conditioning solution delivered can be adjusted according to diffusion constants of the active solutes in the conditioning solution and the anatomical regions delivered thereto.

In some embodiments, the time of exposure is calculated based on the desired depth of penetration by the conditioning solution and known diffusion constants. When penetrating a superficial layer, exposure time may be 5 seconds. When penetrating deeper layers, exposure time may be greater, such as 10-30 seconds for reaching the submucosal layer and greater than 1 minute for reaching the cartilage layer.

In some embodiments, the volume of conditioning solution delivered may also be based on diffusion rates. Sufficient volume is to be delivered to penetrate the tissue to the desired depth. In some embodiments, a predetermined volume of conditioning solution is delivered per activation (e.g. 2 ml), per airway (e.g. 5 ml), per lobe (e.g. 10 ml) or per lung (e.g. 25 ml delivered within the right or left mainstem bronchi and allowed to descend into the lobar bronchi, segmental bronchi, sub-segmental bronchi, and further branches. In other embodiments, a constant flow of conditioning solution is provided, such as throughout a procedure or during a predetermined period of time prior to or following an activation.

In some embodiments, conditioning solution is delivered to desired depths of penetration with the use of one or more microinjector needles. In some embodiments, one or more injector needles are disposed along an energy delivery catheter 102, particularly along an expandable member, such as a balloon, which resides within the basket of an energy delivery body 108. In such an embodiment, the expandable member may include an array of microinjector needles having a particular length to reach a predetermined depth. For example, the needles may have a length in the range of 0.1 to 2.0 mm which could be used to reach target cells in layers such as the submucosa. In other embodiments, one or more needles are used to penetrate to a particular depth, such as to deliver cells, the conditioning solution then disperses within the tissue, such as along the interstitial interface (e.g. mucosa/submucosa boundary). This activity is supported by the presence of connective tissue membranes that assist in separation of layers.

XII. General Embodiments

In some embodiments, placement and deployment of systems and devices described herein may be automated. In some embodiments, automated placement and deployment of the systems and devices may be performed by robotic bronchoscopy. In some embodiments, the robotic bronchoscopy is able to process data from imaging, such as a CT scan or intraoperative imaging (e.g. OCT), and automatically treat the diseased sites based on the processed data. Thus, algorithms are automatically chosen based on the processed data.

In some embodiments described herein, which can partially or as a whole be combined with other embodiments, a pulmonary tissue modification system for performing a pulmonary procedure can include an energy producing generator, an energy delivery catheter, accessories, and one or more imaging modalities.

In some embodiments, a bipolar catheter with two energy delivery bodies mounted near the distal end is connected to an energy producing generator outside of the body. The distal end of the catheter is passed through the mouth or nose and into the bronchial tree using a bronchoscope or other direct visualization system. The energy delivery bodies are deployed, expanded and/or otherwise positioned such that they contact the airway wall. The operator can then activate the generator via any suitable interface such as, for example, a foot switch, a button on the generator, a button on the catheter, or remote control, to deliver energy to airway tissue adjacent to and/or between the electrodes. In some embodiments, the operator can move the energy delivery bodies to another section of the diseased airway to deliver another treatment or elect to treat the entire surface of a section of the airway, or multiple sections of the airways. In some embodiments, more than one treatment can be applied to the same portion of the airway, depending on the desired depth of penetration. In some embodiments, two or more different energy delivery algorithms can be employed to affect the depth of penetration.

In some embodiments, a monopolar catheter, with a single energy delivery body mounted near the distal end, is connected to an energy producing generator outside of the body. The distal end of the catheter is passed through the mouth or nose and into the bronchial tree using a bronchoscope or other direct visualization system. The electrode is deployed, expanded and/or otherwise positioned such that it contacts the airway wall. A dispersive (neutral) or return electrode is affixed to another surface of the patient (e.g., an external location, such as the patient's skin), and is also connected to the electrical generator. The operator can then activate the generator via, for example, a foot switch, a button on the generator, a button on the catheter, or remote control to deliver energy to airway tissue via the electrode. The operator can move the energy delivery body to another section of the diseased airway to deliver a treatment or elect to treat the entire surface of a section of the airway, or multiple sections of the airways. In some embodiments, two or more monopolar energy delivery bodies can be incorporated into one or more catheters to enable treatment of multiple locations without repositioning the catheter(s). More than one treatment can be applied to the same portion of the airway, depending on the desired depth of penetration. In some embodiments, two or more different energy delivery algorithms can be employed to affect the depth of penetration. In some embodiments, a user interface on the generator can be used to select the desired treatment algorithm, while in other embodiments, the algorithm can be automatically selected by the generator based upon information obtained by one or more sensors.

In some embodiments, a catheter with a plurality of energy delivery bodies mounted near the distal end is connected to an energy producing generator outside of the body. The distal end of the catheter is passed through the mouth or nose and into the bronchial tree using a bronchoscope or other direct visualization system. The energy delivery bodies are deployed, expanded, or otherwise positioned such that they contact the airway wall. The operator can then activate the generator via, for example, a foot switch, a button on the generator, a button on the catheter, or remote control to deliver energy to airway tissue via the energy delivery bodies. In some embodiments, the energy delivery can be multiplexed across any one or more of the energy delivery bodies in any suitable pattern to affect the desired target tissue. In some embodiments, a dispersive (neutral) electrode can be affixed to another surface of the patient, such as the patient's skin, and also connected to the electrical generator to allow for monopolar energy delivery to any of the energy delivery bodies. More than one treatment can be applied to the same portion of the airway, depending on the desired depth of penetration. In some embodiments, two or more different energy delivery algorithms can be employed to affect the depth of penetration. The user interface on the generator can be used to select the desired treatment algorithm, or the algorithm can be automatically selected by the generator based upon information In some embodiments, the targeted treatment area can be identified and used to select a treatment algorithm sufficient to affect the pathogenic cells and/or deeper tissues. The electrode system can then be deployed at the site of pathogenic cells and/or abnormal airway wall tissue and energy delivered to affect the target tissue. The imaging modality (or modalities) can be used before, during, between, and/or after treatment(s) to determine where treatment(s) have or have not been delivered and/or whether the energy adequately affected the airway wall. If it is determined that a target treatment area was missed or that a target treatment area was not adequately affected, the energy delivery can be repeated followed by imaging as described herein until adequate treatment is achieved. Further, the imaging information can be utilized to determine if specific cell types and or a desired depth of therapy was applied. This can allow for customization of the energy delivery algorithm for treating a wide variety of patient anatomies.

In some embodiments, any of the apparatuses and/or systems described herein can be used in methods for treating diseased airways, and/or other lung tissue (e.g., parenchyma), which can generally include accessing the airway, and optionally performing pre-, intra-, and/or post-procedural imaging to plan, guide and/or verify treatment. In some embodiments, the methods can further include one or more of treating a sufficient treatment zone with each energy application, treating a sufficient overall treatment area, treating to a sufficient depth, treating a pre-defined cell type or types, customizing therapy based on imaging and/or sensor information, and combinations thereof.

EXAMPLES

The following examples further illustrate embodiments of the systems and methods disclosed herein, and should not be construed in any way as limiting their scope.

Example 1: Circumferential Treatment and Tissue Effect with a Bipolar System

A non-thermal energy delivery apparatus having bipolar expandable energy delivery bodies was developed. The apparatus included two energy delivery bodies, each comprised of nitinol, braided, expanding electrodes mounted concentrically on a catheter shaft with a mechanism to expanded and contract both energy delivery bodies (e.g., see FIG. 27). The expanded energy delivery body diameters ranged from about 5 mm to about 20 mm. The energy delivery bodies were substantially equal in length at about 3 cm each, and were spaced along the longitudinal axis of the catheter shaft about 2.5 cm apart from edge to edge. To evaluate the effect of pulsed high-voltage energy on epithelial and submucosal tissue layers within the airway, the apparatus was introduced into the left and/or right bronchi of live, anesthetized pigs and energy was delivered in the form of bipolar, square-wave pulses at a pulse frequency of about 300 kHz, pulse amplitude of about 4000V, and total energy delivery duration of about 415 microseconds (83 microseconds per packet, 5 packets).

Following the procedure, the animals were recovered, then subsequently euthanized after approximately twenty-four hours. The airways were then dissected out and fixed in formalin for about forty-eight hours. The airways were then sectioned at approximately 5 mm increments and processed for histology in typical fashion. Sections of both treated and untreated areas were processed for comparison purposes. Slides were prepared using a hematoxylin and eosin (H&E) stain.

Figure 57A:
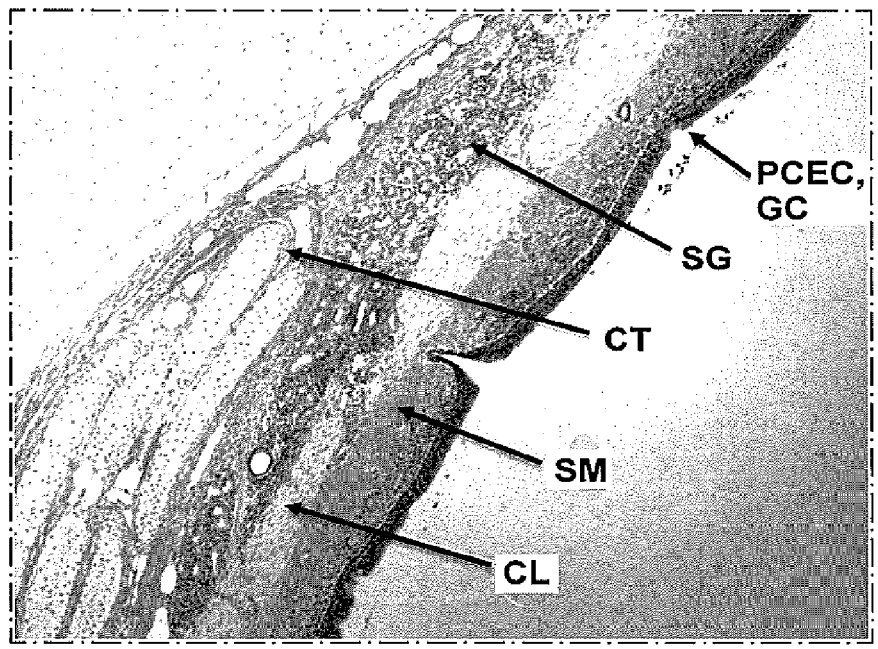
FIGS. 57A-57B illustrate histology example (Lab 6, Animal 1-10085)
Figure 57B:
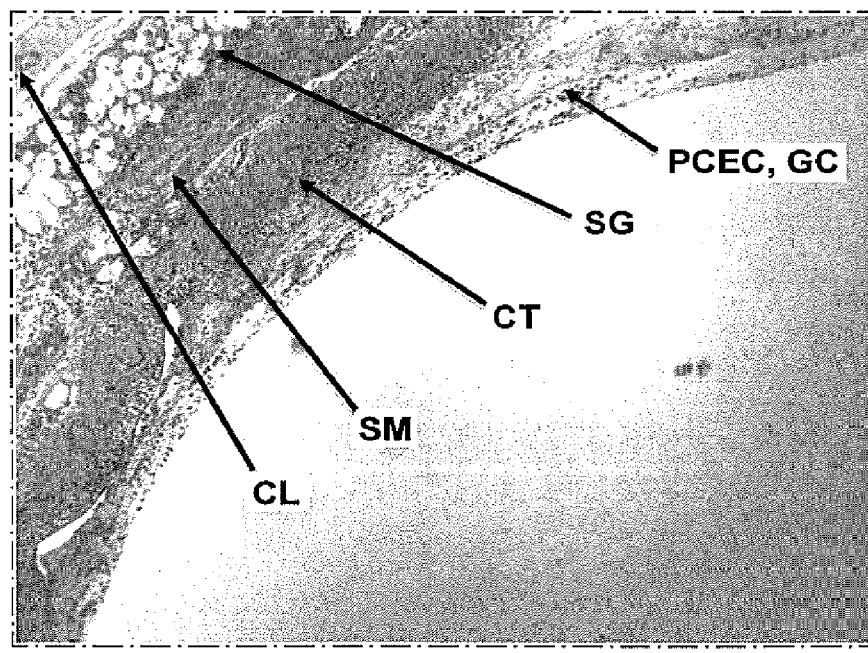

FIG. 57A shows a typical section of healthy, untreated airway, and FIG. 57B shows a typical section of treated airway, 24 hrs post energy delivery. In the untreated airway (FIG. 57A), ciliated epithelium E with pseudostratified columnar epithelial cells PCEC and goblet cells GC and intact submucosal structures, including submucosal glands SG, connective tissue CT, smooth muscle SM, and cartilage CL can be observed. In the treated airway (FIG. 57B), epithelial E with pseudostratified columnar epithelial cells PCEC and goblet cells GC have been substantially removed or destroyed, leaving only cellular remnants and the basement membrane. Further, the submucosal structures have been affected; most notably, submucosal gland cells SG are mostly absent, and extra-cellular gland structures have been disrupted. Smooth muscle SM and connective tissue layers CT also show signs of cellular damage and disruption while the cartilage CL was left unaffected.

Example 2: Circumferential Treatment and Tissue Effect with a Monopolar System

A non-thermal energy delivery apparatus having a monopolar expandable energy delivery body was developed. The apparatus included a single energy delivery body comprised of nitinol, braided, expanding electrode mounted concentrically on a catheter shaft with a mechanism to expanded and contract the energy delivery body (e.g., see FIG. 26). The expanded energy delivery diameter ranged from about 5 mm to about 20 mm. To evaluate the effect of pulsed high-voltage energy on epithelial and submucosal tissue layers within the airway, the apparatus was introduced into the left and/or right bronchi of live, anesthetized pigs and energy was delivered in the form of bipolar, square-wave pulses at a pulse frequency of 300 kHz, pulse amplitude of 4000V and total energy delivery duration of 415 microseconds (83 microseconds per packet, 5 packets).

Following the procedure, the animals were recovered, then subsequently euthanized after approximately twenty-four hours. The airways were then dissected out and fixed in formalin for about forty-eight hours. The airways were then sectioned at approximately 5 mm increments and processed for histology in typical fashion. Sections of both treated and untreated areas were processed for comparison purposes. Slides were prepared using a hematoxylin and eosin (H&E) stain.

Figure 58A:
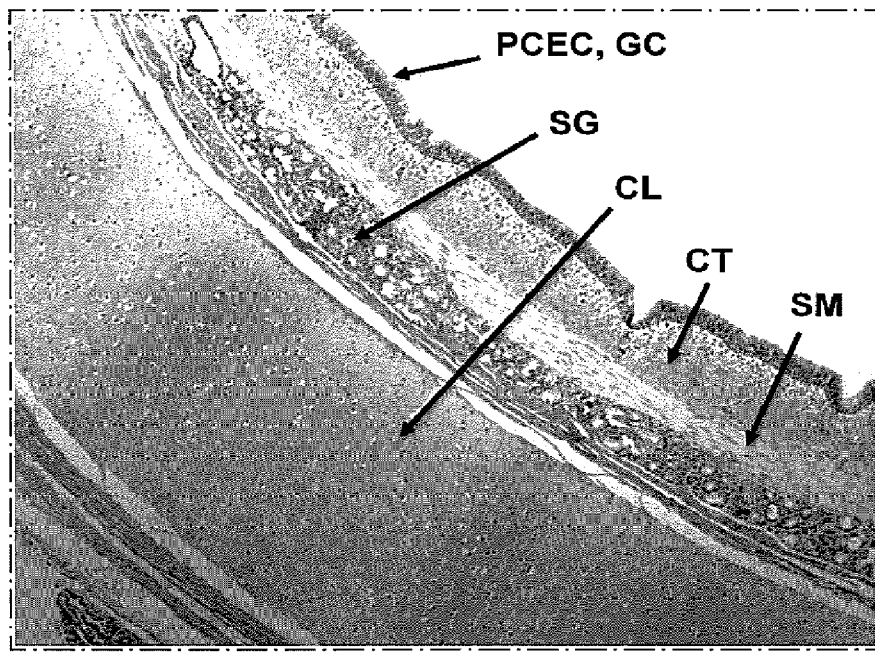
FIGS. 58A-58B illustrate another histology example (Lab 6, Animal 1-10085)
Figure 58B:
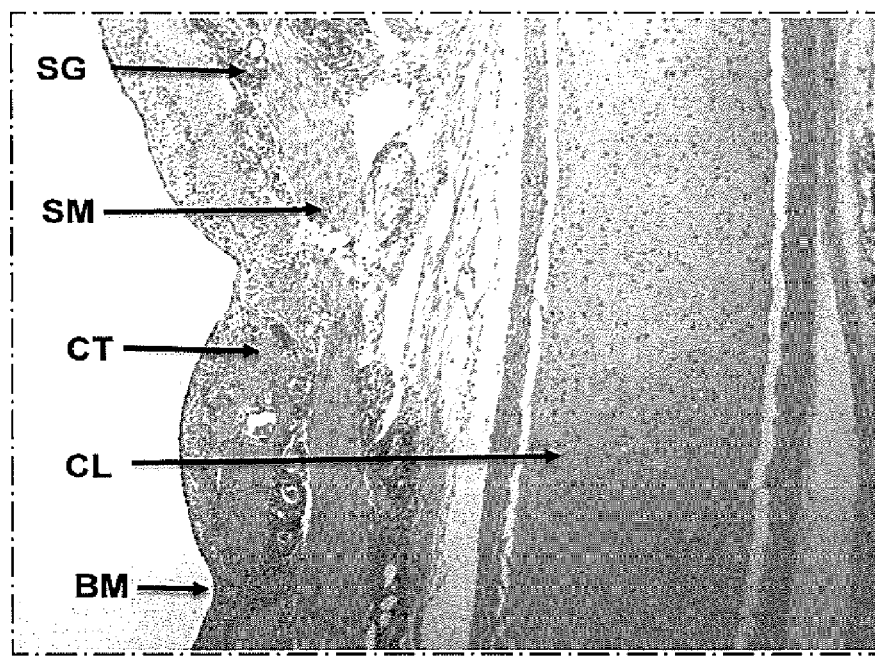

FIG. 58A shows a typical section of healthy, untreated airway and FIG. 58B shows a typical section of treated airway 24 hrs post energy delivery. In the untreated airway (FIG. 58A), ciliated epithelium E with pseudostratified columnar epithelial cells PCEC and goblet cells GC and intact submucosal structures, including submucosal glands SG, connective tissue CT, cartilage CL and smooth muscle SM can be observed. In the treated airway (FIG. 58B) epithelial E and goblet cells GC have been substantially removed or destroyed, leaving only cellular remnants and the basement membrane BM. Further, the submucosal structures have been affected; most notably, submucosal gland cells SG are absent in some locations. In this example, extra-cellular gland structures, including smooth muscle SM and connective tissue layers CT have been left largely unaffected. The cartilage CL was left unaffected. The treatment affects are similar using either the bipolar or monopolar systems, with tissue changes noted where the electrode is in contact with the airway.

As used herein, the terms "about" and/or "approximately" when used in conjunction with numerical values and/or ranges generally refer to those numerical values and/or ranges near to a recited numerical value and/or range. In some instances, the terms "about" and "approximately" can mean within ±10% of the recited value. For example, in some instances, "about 100 [units]" can mean within ±10% of 100 (e.g., from 90 to 110). The terms "about" and "approximately" can be used interchangeably.

While preferred embodiments have been shown and described herein, it will be obvious to those skilled in the art that such embodiments are provided by way of example only. Numerous variations, changes, and substitutions will now occur to those skilled in the art without departing from the scope of the present disclosure. It should be understood that various alternatives to the embodiments described herein may be employed in practice.

What is claimed is:

1. A method for treating a portion of tissue within a patient comprising:
    delivering a conditioning solution to the patient so as to affect or invoke an immune response in the patient;
    advancing a portion of a catheter having an energy delivery body into a body lumen within the patient, wherein the energy delivery body functions in a monopolar manner with a remote dispersive return electrode;
    positioning the remote dispersive return electrode on or in the patient at a distance from the energy delivery body so that the energy delivery body functions in a monopolar manner with the remote dispersive return electrode; and
    transmitting non-thermal pulsed electric field energy from an external generator through the energy delivery body to at least a wall of the body lumen to treat a target tissue within the portion of tissue within the patient for a duration in a range of 0.5 to 100 milliseconds wherein at least a portion of the target tissue is treated below a threshold for thermal ablation so as to leave an extracellular matrix of the body lumen intact, wherein together the immune response and the transmitting step cause the portion of tissue to expire,
    wherein the non-thermal pulsed electric field energy is generated from a waveform provided by the external generator, wherein the waveform has a fundamental frequency in a range of 10 kHz-10 MHz and comprises at least two packets of biphasic cycles separated by a rest period transmitted during the duration.

2. A method as in claim 1, wherein the target tissue comprises a tumor.

3. A method as in claim 2, wherein the immune response results in an increase in systemic immunity upregulation using specific markers associated with the tumor.

4. A method as in claim 2, wherein the immune response results in an upregulation of an innate immunity that affects immune system functionality to detect abnormal cells.

5. A method as in claim 1, wherein the target tissue comprises a bacteria or a virus.

6. A method as in claim 1, wherein the conditioning solution comprises a drug, a chemotherapy drug, a bioactive compound, a cytokine, an immunostimulant, an interleukin, calcium, an antibiotic, an antimicrobial or a toxin.

7. A method as in claim 1, wherein the conditioning solution comprises at least one agent comprising genetic material, a gene, VEGF or a cellular differentiating factor.

8. A method as in claim 1, wherein the conditioning solution comprises at least one cell.

9. A method as in claim 1, wherein the rest period is in a range of 0.001 seconds to about 10 seconds.

10. A method as in claim 1, wherein each packet includes at least one positive pulse peak that is asymmetric with at least one negative pulse peak.

11. A method as in claim 1, wherein each packet comprises a plurality of pulses which are unbalanced.

* * * * *